US012180299B2

(12) United States Patent
Baruah et al.

(10) Patent No.: US 12,180,299 B2
(45) Date of Patent: Dec. 31, 2024

(54) MULTISPECIFIC ANTIBODY ANALOGS COMPRISING A COMMON LIGHT CHAIN, AND METHODS OF THEIR PREPARATION AND USE

(71) Applicant: Adimab, LLC, Lebanon, NH (US)

(72) Inventors: Hemanta Baruah, Lebanon, NH (US); Robert Mabry, Lebanon, NH (US)

(73) Assignee: Adimab, LLC, Lebanon, NH (US)

( * ) Notice: Subject to any disclaimer, the term of this patent is extended or adjusted under 35 U.S.C. 154(b) by 699 days.

(21) Appl. No.: 16/738,221

(22) Filed: Jan. 9, 2020

(65) Prior Publication Data

US 2020/0223939 A1 Jul. 16, 2020

Related U.S. Application Data

(63) Continuation of application No. 15/300,764, filed as application No. PCT/US2015/023888 on Apr. 1, 2015, now abandoned.

(60) Provisional application No. 61/973,830, filed on Apr. 1, 2014.

(51) Int. Cl.
*C07K 16/32* (2006.01)
*C07K 16/28* (2006.01)
*C07K 16/46* (2006.01)

(52) U.S. Cl.
CPC .......... *C07K 16/32* (2013.01); *C07K 16/2863* (2013.01); *C07K 16/468* (2013.01); *C07K 2317/21* (2013.01); *C07K 2317/24* (2013.01); *C07K 2317/31* (2013.01); *C07K 2317/35* (2013.01); *C07K 2317/515* (2013.01); *C07K 2317/522* (2013.01); *C07K 2317/524* (2013.01); *C07K 2317/526* (2013.01); *C07K 2317/53* (2013.01); *C07K 2317/55* (2013.01); *C07K 2317/56* (2013.01); *C07K 2317/565* (2013.01); *C07K 2317/567* (2013.01); *C07K 2317/64* (2013.01); *C07K 2317/92* (2013.01)

(58) Field of Classification Search
CPC .............. C07K 16/468; C07K 2317/56; C07K 2317/567
USPC ...................................... 424/133.1
See application file for complete search history.

(56) References Cited

U.S. PATENT DOCUMENTS

| | | | |
|---|---|---|---|
| 5,731,168 A | 3/1998 | Carter et al. | |
| 7,183,076 B2 | 2/2007 | Arathoon et al. | |
| 7,262,028 B2 | 8/2007 | Van Berkel et al. | |
| 7,642,228 B2 | 1/2010 | Carter et al. | |
| 7,695,936 B2 | 4/2010 | Carter et al. | |
| 7,919,257 B2 | 4/2011 | Hoogenboom et al. | |
| 7,927,834 B2 | 4/2011 | Van Berkel et al. | |
| 7,932,360 B2 | 4/2011 | Van Berkel et al. | |
| 7,951,917 B1 | 5/2011 | Arathoon et al. | |
| 8,216,805 B2 | 7/2012 | Carter et al. | |
| 8,337,841 B2* | 12/2012 | Kojima | C07K 16/005 435/7.1 |
| 8,679,785 B2 | 3/2014 | Carter et al. | |
| 8,765,412 B2 | 7/2014 | Arathoon et al. | |
| 8,921,281 B2* | 12/2014 | Fischer | C12N 15/66 506/26 |
| 9,354,228 B2* | 5/2016 | Vasquez | C40B 40/08 |
| 10,787,500 B2* | 9/2020 | Nett | B01D 15/3847 |
| 2006/0159673 A1 | 7/2006 | Kojima | |
| 2007/0178552 A1 | 8/2007 | Arathoon et al. | |
| 2010/0003254 A1 | 1/2010 | Hattori et al. | |
| 2011/0250642 A1 | 10/2011 | Ji et al. | |
| 2012/0107326 A1 | 5/2012 | Horowitz et al. | |
| 2012/0128671 A1 | 5/2012 | Horowitz et al. | |
| 2012/0264647 A1 | 10/2012 | Horowitz et al. | |
| 2015/0203591 A1* | 7/2015 | Yancopoulos | C07K 16/468 530/387.3 |
| 2017/0022291 A1* | 1/2017 | Baruah | C07K 16/468 |
| 2018/0249687 A1* | 9/2018 | Harriman | C12N 15/8509 |
| 2020/0148787 A1* | 5/2020 | Wang | A61P 7/04 |
| 2020/0262926 A1* | 8/2020 | Amaral | A61P 37/00 |
| 2021/0047387 A1* | 2/2021 | Nett | C07K 16/00 |
| 2022/0025037 A1* | 1/2022 | Baruah | C07K 16/28 |
| 2022/0119534 A1* | 4/2022 | Baruah | A61P 35/02 |

FOREIGN PATENT DOCUMENTS

| | | |
|---|---|---|
| EP | 1605058 A1 | 12/2005 |
| EP | 1 876 236 | 1/2008 |
| JP | H10-504970 A | 5/1998 |
| WO | WO-95/09917 A1 | 4/1995 |
| WO | WO-96/07754 A1 | 3/1996 |
| WO | WO-1998/50431 A2 | 11/1998 |
| WO | 2006109592 | 10/2006 |
| WO | WO-2011/131746 A2 | 10/2011 |
| WO | WO-2012/023053 A2 | 2/2012 |
| WO | WO-2012/123949 A1 | 9/2012 |
| WO | WO-2013/063702 A1 | 5/2013 |

(Continued)

OTHER PUBLICATIONS

Vajda et al., (Current Opinion in Structural Biology, 67 pp. 226-231 (2021)).*
Marks et al., (J. Biol. Chem. 295(29) 9823-9837 (2020)).*
Akbar et al., (Cell Reports 34, 108856, Mar. 16, 2021).*
Lo et al., (BMC Genomics vol. 22, Article No. 116 (2021)).*
Krah et al. (New Biotechnology Oct. 25, 2017;39(Pt B): 167-173; Epub Jan. 27, 2017).*
Hui et al. Cancer Research, (Jul. 2021) vol. 81, No. 13 SUPPL. Abstract No. 1861. Meeting Info: AACR Annual Meeting 2021. Philadelphia, PA, United States. May 17, 2021-May 21, 2021).*
Bebbington, CR et al., High-level expression of a recombinant antibody from myeloma cells using a glutamine synthetase gene as an amplifiable selectable marker, Biotechnology (NY), 10(2):169-75 (1992).

(Continued)

*Primary Examiner* — Lynn A Bristol
(74) *Attorney, Agent, or Firm* — Robin L. Teskin; Baker, Donelson, Bearman, Caldwell & Berkowitz PC

(57) ABSTRACT

Multispecific antibody analogs that co-engage at least two different antigens or epitopes, which may also be referred to as targets as used interchangeably throughout, said analogs comprising a common light chain, are provided, as well as methods for their production and use.

10 Claims, 15 Drawing Sheets

Specification includes a Sequence Listing.

(56) References Cited

FOREIGN PATENT DOCUMENTS

| WO | WO-2013/177101 A2 | 11/2013 |
|---|---|---|
| WO | WO-2014/012085 A2 | 1/2014 |

OTHER PUBLICATIONS

Carter, Paul, Bispecific human IgG by design, Journal of Immunological Methods, 248:7-15 (2001).
Coloma, M. and Morrison, S., Design and production of novel tetravalent bispecific antibodies, Nat Biotechnol., 15(2):159-63 (1997).
Hoogenboom, H. and Winter, G., By-passing immunisation. Human antibodies from synthetic repertoires of germline VH gene segments rearranged in vitro, J Mol Biol., 227(2):381-8 (1992).
Huse, WD et al., Generation of a large combinatorial library of the immunoglobulin repertoire in phage lambda, Science, 246(4935):1275-81 (1989).
Kang, AS et al., Linkage of recognition and replication functions by assembling combinatorial antibody Fab libraries along phage surfaces, Proc Natl Acad Sci USA, 88(10):4363-6 (1991).
Mccafferty, J. et al., Phage antibodies: filamentous phage displaying antibody variable domains, Nature, 348(6301):552-4 (1990).
Miller, K. et al., Design, construction, and in vitro analyses of multivalent antibodies, J Immunol., 170(9):4854-61 (2003).
Nissim, A. et al., Antibody fragments from a 'single pot' phage display library as immunochemical reagents, EMBO J., 13(3):692-8 (1994).
Xiang, JH et al., Production of murine V-human Cr1 chimeric anti-TAG72 antibody using V region cDNA amplified by PCR, Mol Immunol., 27(8):809-17 (1990).
Hoogenboom, Hennie R., Selecting and screening recombinant antibody libraries, Nature Biotechnology, 23(9):1105-1116 (2005).
International Search Report for PCT/US2015/23888, 4 pages (Jul. 28, 2015).
Mazor, Y. et al., E-clonal antibodies: selection of full-length IgG antibodies using bacterial periplasmic display, Nature Protocols, 3(11):1766-1777 (2008).
Schubert, I. et al., Dual-Targeting for the Elimination of Cancer Cells with Increased Selectivity, Antibodies, 1:2-18 (2012).
Written Opinion for PCT/US2015/23888, 12 pages (Jul. 28, 2015).
Sharkey, Beth, et al. "Purification of common light chain IgG-like bispecific antibodies using highly linear pH gradients." MAbs. vol. 9. No. 2. Taylor & Francis, 2017.
Van Blarcom, Thomas, et al. "Productive common light chain libraries yield diverse panels of high affinity bispecific antibodies." MAbs. vol. 10. No. 2. Taylor & Francis, 2018.
De Nardis, Camilla, et al. "A new approach for generating bispecific antibodies based on a common light chain format and the stable architecture of human immunoglobulin G1." Journal of Biological Chemistry 292.35 (2017):14706-14717.
Krah, Simon, et al. "Engineering bispecific antibodies with defined chain pairing." New biotechnology 39 (2017):167-173.
Krah, Simon, et al. "Generation of human bispecific common light chain antibodies by combining animal immunization and yeast display." Protein Engineering, Design and Selection 30.4 (2017): 291-301.
Merchant, A M et al. "An efficient route to human bispecific IgG." Nature biotechnology vol. 16,7 (1998): 677-81. doi:10.1038/nbt0798-677.
Vaughan TJ, Williams AJ, Pritchard K, Osbourn JK, Pope AR, Earnshaw JC, McCafferty J, Hodits RA, Wilton J, Johnson KS. Human antibodies with sub-nanomolar affinities isolated from a large non-immunized phage display library. Nature biotechnology. Mar. 1, 1996;14:309-14.

* cited by examiner

MULTISPECIFIC ANTIBODY ANALOGS COMPRISING A COMMON LIGHT CHAIN, AND METHODS OF THEIR PREPARATION AND USE

CROSS REFERENCE TO RELATED APPLICATIONS

This application is a continuation application of U.S. application Ser. No. 15/300,764, filed Sep. 29, 2016, which is a U.S. Nat'l Phase Appl. of Int'l Appl. No. PCT/US2015/023888, filed Apr. 1, 2015, which claims the benefit of U.S. Provisional Application No. 61/973,830, filed Apr. 1, 2014, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 20, 2015, is named 2009186-0115_SL.txt and is 207,538 bytes in size.

FIELD OF THE INVENTION

The present invention relates, inter alia, to multispecific antibody analogs that comprise a common light chain, and methods of making and using the same.

BACKGROUND OF THE INVENTION

All references cited herein, including patents, patent applications, and non-patent publications referenced throughout are hereby expressly incorporated by reference in their entireties for all purposes.

Antibodies and antibody-based molecules represent attractive candidates as diagnostic tools and therapeutics. To date more than 30 therapeutic monoclonal antibodies have been approved for and successfully applied in diverse indication areas including cancer, organ transplantation, autoimmune and inflammatory disorders, infectious disease, and cardiovascular disease.

However, the majority of these antibodies are monospecific antibodies, which recognize a single epitope and can be selected to either activate or repress the activity of a target molecule through this single epitope. Many physiological responses, however, require crosslinking, "cross-talk" or co-engagement of or between two or more different proteins or protein subunits to be triggered. An important example is the activation of heteromeric, cell-surface receptor complexes. For these receptor complexes, activation is normally achieved through ligand interaction with multiple domains on different proteins resulting in proximity-associated activation of one or both receptor components.

A desire to address and therapeutically exploit some of these more complex physiological processes, and disease states associated therewith, has stimulated significant effort towards generating multispecific antibodies that can co-engage multiple epitopes or antigens. One avenue that has received much attention is the engineering of additional and novel antigen binding sites into antibody-based drugs such that a single inventive multispecific antibody analog molecule co-engages two or more different antigen targets (or distinct epitopes on one or more antigens). Such multispecific antibody analogs offer the ability of consolidating the specificity of two epitopes into one molecule. Within a therapeutic context, multispecific Abs may offer additivity or synergy of efficacy depending upon the mechanism of action and the nature of the target biology. However, several concerns have surfaced related to manufacturing, and the ability to produce multispecific molecules that possess biophysical properties similar to approved or clinically validated mAbs has plagued reduced the momentum of these molecules from entering the clinic. To address these concerns, several strategies have been proposed that may overcome issues related to aggregation and stability. However, these strategies do not offer options related to valency and may be limited in biological activity as a mechanism of cross-linking receptors. Alternative strategies that create constructs able to engage two arms per target (tetravalent) may offer superior potency.

Tailoring valency for multispecific antibodies, such as bispecific antibodies (bsAbs), facilitates the identification of formats that can match with preferred targeting strategies. There exists a wide array of constructs that comprise different architectures which can have a significant impact on engagement with selected targets. Several bispecific constructs focus on the ability to engage each target with one arm of the antibody (monovalent), which may be essential for targeting certain cell populations without activating the target pathway. However, engagement with two arms for each target (bivalent) may the preferred method to bind to cell types in an avid state. This generally increases with affinity of the antibody to the target cell and frequently increases the potency of antibodies. Bispecific antibodies that bind two targets bivalently are typically constructed as tetravalent constructs by fusing variable regions together in a number of formats. Single-chain antibodies (scFvs) have been applied in this manner by fusing to IgGs to construct tetravalent bsAbs. While there are successful reports of such constructs in which affinity and potency of the parental antibodies are retained, expression and biophysical properties are frequently impacted and create obstacles for drug development. Protein engineering techniques have been applied to overcome these obstacles, yet this is very labor intensive and not always successful. While scFvs permit the ability to tailor valency with bispecifics, an alternative strategy to create tetravalent molecules that do suffer from production and stability issues would be advantageous.

Fab fragments serve as an alternative source for adding specificity and tailoring valency. Fabs frequently exhibit production levels and stability similar to parental IgG and do not fall victim to the obstacles observed with scFvs. However, Fabs are larger molecules typically expressed as two chains and are not connected with a linker as present with scFvs. As a result, generating bispecifics with Fabs can be challenging depending on the format. Several reports in the literature provide opportunities to utilize the heterodimeric interface between VH:VL and CL:CH1, however, these molecules can be limited give the absence of an Fc region that provides extended PK properties and effector function attributed a glycosylated CH2 region.

The generation of multispecifics, such as bispecifics, containing Fabs and an Fc region has been achieved by several parties. To achieve high levels of pure major product, two engineering obstacles must be addressed: heavy chain and light chain promiscuity. IgG1 heavy chains dimerize via the Fc region to form homodimers. To improve the pairing of two different heavy chains containing VH regions specific to two different targets or epitopes, several groups have generated bispecific antibodies by modifying the CH3 domain to generate heterodimeric Fc constructs. Employed strategies include substituting amino acids at the CH3 interface (Genentech, Amgen, Zymeworks), fusions with other IgG isotypes (EMD Serono), or substituting amino acids to modify Protein A binding for purification of Fc-heterodimer bispecifics (see, e.g., U.S. Pat. Nos. 5,731,168; 7,6423,228; 7,695,936; 8,216,805; 8,679,785; 8,765,412; 7,951,917; 7,183,076; WO 2013/0363702; WO 2014/012085). These constructs facilitate the generation of bispecifics in novel ways but do not address promiscuity of the light chains. This issue has been termed the "light chain problem". Several reports offer solutions by substituting amino acids at the CL:CH1 and/or VH:VL interface. While early reports hold promise, a modular approach for screening bispecifics with germline diversity remains to be seen. As an alternative, several groups have identified two VH regions that bind to two different targets or epitopes yet share the same light chain (see, e.g., U.S. Pat. Nos. 5,731,168; 7,6423,228; 7,695,936; 8,216,805; 8,679,785; 8,765,412; 7,951,917; 7,183,076). This strategy reduces the number of lights chains from two to one and reduces the number of chains for assembly from four to three. However, the identification of VH regions that can share the same light chain is not trivial. Issues related to compromise in affinity and epitopic diversity are limiting factors to this approach.

Currently, there are several options for the identification of VH regions that share the same light chain. Fixed light chain repertoires are available that offer the discovery of VH regions against different targets. However, this strategy requires the discovery against two targets and may not be amenable to scenarios in which one existing antibody (HC and LC) is suited to be paired with another specificity. The ability to generate VH diversity surrounding any given light chain (rather than a pre-selected LC or an LC from a fixed light chain repertoire, as described in, e.g., 7,919,257; U.S. Pat. Nos. 7,262,028; 7,927,834; 7,932,360; US 2011/0250642; Merchant et al., Nature Biotechnol., 1998, 16: 677-681; Nissim et al., "Antibody fragments from a 'single pot' phage display library as immunochemical reagents," EMBO J., 1994, 13: 692-698; Hoogenboom and Winter, J. Mol. Biol., 1992, 227, 381-388; Hoogenboom and Winter, "By-passing Immunisation," J. Mol. Biol., 1992, 227: 381-388) would provide more opportunity to pair new specificities with antibodies that have already been validated (preclinical/clinical). In addition, the ability to bypass full-scale naïve discovery efforts or generate large diversities to minimize time and labor would provide an attractive alternative.

Others have reported yet further multispecific antibody analog formats and methods for generating them (see, e.g., WO 2012/023053; WO 95/09917; WO 2013/177101; Miller et al., J. Immunol., Vol. 170, pages 4854-4861 (2003); Coloma et al., Nature Biotechnology, Vol. 15, pages 159-163 (1997); WO 2011/131746; WO 2012/123949).

There remains, therefore a need for multispecific antibody analogs that, for example, minimize some of the expression and production shortcomings described above and herein throughout. There also remains a need for multivalent and multispecific antibody analogs that allow for greater flexibility in the number, orientation, and attachment points antigen binding sites in the context of a multispecific antibody analog format.

SUMMARY OF THE INVENTION

Applicants have discovered, inter alia, multispecific antibody analogs and methods of making such, (referred to interchangeably throughout as "analogs" or "antibody analogs"), including bispecific, trispecific, tetraspecific, pentaspecific antibody analogs, and the like. Certain multispecific antibody analogs in accordance with the invention may advantageously correspond to an IgG or IgG-like format, which format comprises a first polypeptide comprising a first heavy chain having specificity for a first antigen; second polypeptide comprising a second heavy chain having specificity for a second antigen; and a common light chain. Certain other multispecific antibody analogs in accordance with the invention may advantageously comprise at least two copies of a first polypeptide and at least two copies of a second polypeptide, wherein the first polypeptide comprises a variable heavy domain (VH) with specificity for one antigen (also referred interchangeably throughout as "target" or "targets") of interest as well as a VH with specificity for a second antigen of interest, and wherein the second polypeptide comprises a light chain variable domain that is compatible with both VHs and can for an antigen 1 binding region and an antigen 2 binding regions when associated with the first VH and the second VH, respectively.

Accordingly, in certain embodiments provided are methods of obtaining or identifying one or more common light chains for use in preparing a multispecific antibody or multispecific antibody analog, the method comprising:
  i) performing a first selection against a first antigen from a first library and obtaining one or more light chains from the output that has specificity for the first antigen;
  ii) performing a second selection against a second antigen from a second library and obtaining heavy chains from the output that has specificity for the second antigen;
  iii) generating a restricted library comprising the one or more light chains obtained in step i) and the heavy chains obtained in step ii);
  iv) performing a third selection against the first antigen from the restricted library generated in step iii) and obtaining one or more antibodies form the output of the third selection, wherein the one or more antibodies comprise one or more light chains that each have specificity for the first antigen and the second antigen;
  thereby obtaining or identifying the one or more common light chains.

In certain embodiments, a) the first library comprises a naïve library; b) the second library comprises a naïve library; or c) the first library comprises a naïve library and the second library comprises a naïve library. In further embodiments, such methods further comprise:
  a) performing a subsequent selection against the first antigen from a maturation library;
  b) performing a subsequent selection against the second antigen from a maturation library; or
  c) performing a subsequent selection against the first antigen from a maturation library and performing a subsequent selection against the second antigen from a maturation library;
  after performing:
  a) step i;
  b) step ii
  c) step iii; and/or
  d) step iv.

In certain other embodiments methods are provided for making a multispecific antibody analog comprising contacting the one or more common light chains obtained or identified according to any one the embodiments provided herein and throughout, wherein: a first polypeptide comprising a heavy chain that has specificity for the first antigen; and a second polypeptide comprising a heavy chain that has specificity for the second antigen. In certain of these embodiments, the one or more common light chains, the first polypeptide, and the second polypeptide are expressed by host cells. In certain of these embodiments, the one or more common light chains, the first polypeptide, and the second polypeptide are expressed by the same host cell.

In certain other embodiments are provided a multispecific antibody analog comprising a common light chain obtained or identified by performing a method as disclosed herein and throughout.

In certain other embodiments provided are methods of making a multispecific antibody analog comprising at least two first antigen binding regions and at least two second antigen binding regions, said first and second antigen binding regions having a common light chain, wherein first antigen binding regions have a different antigen specificity than the second antigen binding regions, the method comprising;
  i) obtaining at least one light chain from a first antigen binding region having specificity for the first antigen, wherein the first antigen binding region comprises said at least one light chain and a heavy chain;
  ii) obtaining heavy chains from the output of a selection performed from a naïve library against a second antigen;
  iii) preparing a restricted library comprising heavy chains obtained in step ii) and the at least one light chain obtained in step i);
  iv) performing a second selection against the second antigen from the library prepared in step iii);
  v) obtaining an multispecific antibody comprising the second antigen binding region from the selection performed in step iv), wherein the second antigen binding region comprises the at least one light chain obtained in step i);
  vi) incorporating the first antigen binding region and the second antigen binding region into a multispecific antibody format, wherein the format comprises:
  an IgG moiety comprising either:
    a) the first antigen binding region; or
    b) the second antigen binding region; and
  two Fab moieties, wherein each Fab moiety comprises either:
    a) the second antigen binding region; or
    b) the first antigen binding region;
  wherein the N-terminus of the heavy chain of one Fab moiety is linked to the C-terminus of the Fc region of one heavy chain of the IgG moiety via a linker moiety, and the N-terminus of the heavy chain of the other Fab moiety is linked to the C-terminus of the Fc region of the other heavy chain of the IgG moiety via a linker moiety; thereby generating the multispecific antibody analog.

In certain embodiments, optionally in combination with any of the preceding or following embodiments, each linker moiety independently comprises a peptide from 1 to 75 amino acids in length, inclusive. In certain embodiments, one or more of the linker moieties independently comprises at least one of the 20 naturally occurring amino acids. In other embodiments, optionally in combination with any of the preceding or following embodiments, one or more of the linker moieties independently comprises at least one non-natural amino acid incorporated by chemical synthesis, post-translational chemical modification or by in vivo incorporation by recombinant expression in a host cell. In certain other embodiments, optionally in combination with any of the preceding or following embodiments, one or more of the linker moieties independently comprises one or more amino acids selected from the group consisting of serine, glycine, alanine, proline, asparagine, glutamine, glutamate, aspartate, and lysine. In other embodiments, optionally in combination with any of the preceding or following embodiments, one or more of the linker moieties independently comprises a majority of amino acids that are sterically unhindered. In other embodiments, optionally in combination with any of the preceding or following embodiments, one or more of the linker moieties independently comprises one or more of the following: an acidic linker, a basic linker, and a structural motif. In other embodiments, optionally in combination with any of the preceding or following embodiments, one or more of the linker moieties independently comprises: polyglycine, polyalanine, poly(Gly-Ala), or poly(Gly-Ser). In other embodiments, optionally in combination with any of the preceding or following embodiments, one or more of the linker moieties independently comprises: a polyglycine selected from the group consisting of: $(Gly)_3$ (SEQ ID NO: 1), $(Gly)_4$ (SEQ ID NO: 2), and $(Gly)_5$ (SEQ ID NO: 3). In other embodiments, optionally in combination with any of the preceding or following embodiments, one or more of the linker moieties independently comprises $(Gly)_3Lys(Gly)_4$ (SEQ ID NO: 4); $(Gly)_3AsnGlySer(Gly)_2$ (SEQ ID NO: 5); $(Gly)_3Cys(Gly)_4$ (SEQ ID NO: 6); and GlyProAsnGlyGly (SEQ ID NO: 7). In other embodiments, optionally in combination with any of the preceding or following embodiments, one or more of the linker moieties independently comprises a combination of Gly and Ala. In other embodiments, optionally in combination with any of the preceding or following embodiments, one or more of the linker moieties independently comprises a combination of Gly and Ser. In other embodiments, optionally in combination with any of the preceding or following embodiments, one or more of the linker moieties independently comprises a combination of:

Gly and Glu; or Gly and Asp. In other embodiments, optionally in combination with any of the preceding or following embodiments, one or more of the linker moieties independently comprises a combination of Gly and Lys.

In other embodiments, optionally in combination with any of the preceding or following embodiments, one or more of the linker moieties independently comprises a sequence selected from group consisting of: [Gly-Ser]n (SEQ ID NO: 8); [Gly-Gly-Ser]n (SEQ ID NO: 9); [Gly-Gly-Gly-Ser]n (SEQ ID NO: 10); [Gly-Gly-Gly-Gly-Ser]n (SEQ ID NO: 11); [Gly-Gly-Gly-Gly-Ser-Gly-Gly-Gly-Gly]n (SEQ ID NO: 12); [Gly-Gly-Gly-Gly-Ser-Gly-Gly-Gly-Gly-Ser-Gly-Gly-Gly-Gly]n (SEQ ID NO: 13); [Gly-Gly-Gly-Gly-Ser-Gly-Gly-Gly-Gly-Ser-Gly-Gly-Gly-Gly-Ser-Gly-Gly-Gly-Gly]n (SEQ ID NO: 14); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 15); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 16); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 17); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

In other embodiments, optionally in combination with any of the preceding or following embodiments, one or more of the linker moieties independently comprises a sequence selected from the group consisting of: [Gly-Glu]n (SEQ ID NO: 18); [Gly-Gly-Glu]n (SEQ ID NO: 19); [Gly-Gly-Gly- Glu]n (SEQ ID NO: 20); [Gly-Gly-Gly-Gly-Glu]n (SEQ ID NO: 21); [Gly-Asp]n (SEQ ID NO: 22); [Gly-Gly-Asp]n (SEQ ID NO: 23); [Gly-Gly-Gly-Asp]n (SEQ ID NO: 24); [Gly-Gly-Gly-Gly-Asp]n (SEQ ID NO: 25); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

In other embodiments, optionally in combination with any of the preceding or following embodiments, at least one of the first and second antigen binding regions comprises at least one humanized variable heavy domain or at least one humanized variable light domain. In other embodiments, optionally in combination with any of the preceding or following embodiments, at least one of the first and second antigen binding regions comprises at least one complimentary determining region CDR that is derived from a non-human multispecific antibody or multispecific antibody fragment.

In other embodiments, optionally in combination with any of the preceding or following embodiments, at least one of the first and second antigen binding regions binds an epitope from a tumor associated antigen, a hormone receptor, a cytokine receptor, chemokine receptor, a growth factor receptor, an immune activating receptor, a hormone, a cytokine, a chemokine, a growth factor, a G protein-coupled receptor, or a transmembrane receptor. In other embodiments, optionally in combination with any of the preceding or following embodiments, least one of the first and second antigen binding regions binds a target associated with an autoimmune disorder, an inflammatory disorder, an oncological disorder, neuromuscular disorder, a neurodegenerative disorder, a metabolic disorder, or an infectious disease.

In other embodiments, optionally in combination with any of the preceding or following embodiments the multispecific antibody analog binds at least two different targets. In other embodiments, optionally in combination with any of the preceding or following embodiments, the multispecific analog binds at least three different targets. In other embodiments, optionally in combination with any of the preceding or following embodiments, the multispecific antibody analog binds at least four different targets. In other embodiments, optionally in combination with any of the preceding or following embodiments the multispecific antibody analog binds at least one target monovalently. In other embodiments, optionally in combination with any of the preceding or following embodiments, the multispecific antibody analog binds at least two targets monovalently. In other embodiments, optionally in combination with any of the preceding or following embodiments, the multispecific antibody analog binds at least three targets monovalently. In other embodiments, optionally in combination with any of the preceding or following embodiments, the multispecific antibody analog binds at least four targets monovalently.

In other embodiments, optionally in combination with any of the preceding or following embodiments, at least one of the antigen binding regions comprises or is derived from a non-human species. In other embodiments, optionally in combination with any of the preceding or following embodiments, at least one of the antigen binding sites comprises a humanized variable domain or a humanized CDR.

In other embodiments, optionally in combination with any of the preceding or following embodiments, at least one VH comprises a VH CDR1, a VH CDR2, and a VH CDR3 each independently selected from the following: a VH CDR1 amino acid sequence selected from the group consisting of: GSVSSGSYYWS (SEQ ID NO: 26); GSISSGGYYWS (SEQ ID NO: 27); GSINSSSYYWQ (SEQ ID NO: 28); FTLSGDWIH (SEQ ID NO: 29); FNIKDTYIH (SEQ ID NO: 30); FSLTNYGVH (SEQ ID NO: 31); GSISSGGDYWQ (SEQ ID NO: 32); a VH CDR2 amino acid sequence selected from the group consisting of: YIYYSGSTNYNPSLKS (SEQ ID NO: 33); IIYYSGWTNYNPSLKS (SEQ ID NO: 34); EIAYSGSTYYNPSLKS (SEQ ID NO: 35); EISAAGGYTDYADSVKG (SEQ ID NO: 36); RIYPTNGYTRYADSVKG (SEQ ID NO: 37); VIWSGGNTDYNTPFTSR (SEQ ID NO: 38); and a VH CDR3 selected from the group consisting of: ARTNLYSTPFDI (SEQ ID NO: 39); ARGVGPDFWSGYSYSSYFDL (SEQ ID NO: 40); ARGQQWAAFDI (SEQ ID NO: 41); ARESRVSFEAAMDY (SEQ ID NO: 42); SRWGGDGFYAMDY (SEQ ID NO: 43); RALTYYDYEFAYW (SEQ ID NO: 44).

In other embodiments, optionally in combination with any of the preceding or following embodiments, at least one VL comprises a VL CDR1, a VL CDR2, and a VL CDR3 each independently selected from the following: a VL CDR1 amino acid sequence selected from the group consisting of: RASQDISSWLA (SEQ ID NO: 45); RASQAISSWLA (SEQ ID NO: 46); RASQNIATDVA (SEQ ID NO: 47); RASQDVNTAVA (SEQ ID NO: 48); RASQSIGTNIH (SEQ ID NO: 49); a VL CDR2 amino acid sequence selected from the group consisting of: AASSLQS (SEQ ID NO: 50); DASSLES (SEQ ID NO: 51); AASSLQS (SEQ ID NO: 52); SASFLYS (SEQ ID NO: 53); YASESIS (SEQ ID NO: 54); and a VL CDR3 amino acid sequence selected from the group consisting of: QQEHDFPWT (SEQ ID NO: 55); HQYQSYSWT (SEQ ID NO: 56); QQEHDFPWT (SEQ ID NO: 57); QQSEPEPYT (SEQ ID NO: 58); QQHYTTPPT (SEQ ID NO: 59); QQNNNWPTT (SEQ ID NO: 60).

In other embodiments, optionally in combination with any of the preceding or following embodiments, the multispecific antibody analog comprises at least one heavy chain framework region that corresponds to or is derived from VH1-46, VH3-23, VH4-39, or VH4-61, and wherein at least one light chain framework region that corresponds to or is derived from VK1-05, VK1-12, or VK3-11.

In other embodiments, optionally in combination with any of the preceding or following embodiments, the multispecific antibody analog comprises a VH region that comprises an amino acid sequence selected from the group consisting of:

```
                                          (SEQ ID NO: 61)
VQLQESGPGLVKPSETLSLTCTVSGGSVSSGSYYWSWIRQPPGKGLEWIGY

IYYSGSTNYNPSLKSRVTISVDTSKNQFSLKLSSVTAADTAVYYCARTNLY

STPFDIWGQGTMVTVSS;

(SEQ ID NO: 62)
QVQLQESGPGLVKPSETLSLTCTVSGGSISSGGYYWSWIRQPPGKGLEWIG

IIYYSGWTNYNPSLKSRVTISVDASRNQFSLKLSSVTAADTAVYYCARGVG

PDFWSGYSYSSYFDLWGRGTLVTVSS;

(SEQ ID NO: 63)
QLQLQESGPGLVKPSETLSLTCTVSGGSINSSSYYWQWIRQPPGKGLEWIG

EIAYSGSTYYNPSLKSRVTISVDTSKNQFSLKLSSVTAADTAVYYCARGQQ

WAAFDIWGQGTMVTVSS;
```

```
                                                   (SEQ ID NO: 64)
EVQLVESGGGLVQPGGSLRLSCAASGFTLSGDWIHWVRQAPGKGLEWVGEI

SAAGGYTDYADSVKGRFTISADTSKNTAYLQMNSLRAEDTAVYYCARESRV

SFEAAMDYWGQGTLVTVSS;

(SEQ ID NO: 65)
EVQLVESGGGLVQPGGSLRLSCAASGFNIKDTYIHWVRQAPGKGLEWVARI

YPTNGYTRYADSVKGRFTISADTSKNTAYLQMNSLRAEDTAVYYCSRWGGD

GFYAMDYWGQGTLVTVSS;

(SEQ ID NO): 66)
QVQLKQSGPGLVQPSQSLSITCTVSGFSLTNYGVHWVRQSPGKGLEWLGVI

WSGGNTDYNTPFTSRLSINKDNSKSQVFFKMNSLQSDDTAIYYCARALTYY

DYEFAYWGQGTLVTVSS;
and (SEQ ID NO: 67)
QLQLQESGPGLVKPSETLSLTCTVSGGSISSSGGDYWQWIRQPPGKGLEWIG

EIAYSGSTYYNPSLKSRVTISVDTSKNQFSLKLSSVTAADTAVYYCARGQQ

WAAFDIWGQGTMVTVSS.
```

In other embodiments, optionally in combination with any of the preceding or following embodiments, the multispecific antibody analog comprises a VL region that comprises an amino acid sequence selected from the group consisting of:

```
                                                   (SEQ ID NO: 68)
DIQLTQSPSSVSASVGDRVTITCRASQDISSWLAWYQQKPGKAPKLLIYAA

SSLQSGVPSRFSGSGSGTDFTLTISSLQPEDFATYYCQQEHDFPWTFGGGT

KVEIK;

(SEQ ID NO: 69)
DIQLTQSPSTLSASVGDRVTITCRASQAISSWLAWYQQKPGKAPKLLIYDA

SSLESGVPSRFSGSGSGTEFTLTISSLQPDDFATYYCHQYQSYSWTFGGGT

KVEIK;

(SEQ ID NO: 70)
DIQLTQSPSSVSASVGDRVTITCRASQDISSWLAWYQQKPGKAPKLLIYAA

SSLQSGVPSRFSGSGSGTDFTLTISSLQPEDFATYYCQQEHDFPWTFGGGT

KVEIK;

(SEQ ID NO: 71)
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIK;

(SEQ ID NO: 72)
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIK;
and (SEQ ID NO: 73)
DILLTQSPVILSVSPGERVSFSCRASQSIGTNIHWYQQRTHGSPRLLIKYA

SESISGIPSRFSGSGSGTDFTLSINSVESEDIADYYCQQNNNWPTTFGAGT

KLELK.
```

In other embodiments, optionally in combination with any of the preceding or following embodiments, the multispecific antibody analog comprises a polypeptide comprising, from N-terminus to C-terminus, a first VH region, a CH1, a hinge region, a CH2 region, a CH3 region, a second VH region, and a CH1 region, the amino acid sequence of which comprises an amino acid sequence selected from the group consisting of:

```
                                                   (SEQ ID NO: 74)
QVQLQESGPGLVKPSETLSLTCTVSGGSVSSGSYYWSWIRQPPGKGLEWIG

YIYYSGSTNYNPSLKSRVTISVDTSKNQFSLKLSSVTAADTAVYYCARTNL

YSTPFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGKGGGGSGGGG

SGGGGSQLQLQESGPGLVKPSETLSLTCTVSGGSINSSSYYWQWIRQPPGK

GLEWIGEIAYSGSTYYNPSLKSRVTISVDTSKNQFSLKLSSVTAADTAVYY

CARGQQWAAFDIWGQGTMVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKKVEPKSC;

(SEQ ID NO: 75)
QVQLQESGPGLVKPSETLSLTCTVSGGSVSSGSYYWSWIRQPPGKGLEWIG

YIYYSGSTNYNPSLKSRVTISVDTSKNQFSLKLSSVTAADTAVYYCARTNL

YSTPFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGKGGGGSGGGG

SGGGGSQVQLQESGPGLVKPSETLSLTCTVSGGSISSGGYYWSWIRQPPGK

GLEWIGIIYYSGWTNYNPSLKSRVTISVDASRNQFSLKLSSVTAADTAVYY

CARGVGPDFWSGYSYSSYFDLWGRGTLVTVSSASTKGPSVFPLAPSSKSTS

GGTAALGCLVKDYFPEPVTVSWNSGALTSGVHTFPAVLQSSGLYSLSSVVT

VPSSSLGTQTYICNVNHKPSNTKVDKKVEPKSC;

(SEQ ID NO: 76)
QVQLQESGPGLVKPSETLSLTCTVSGGSISSGGYYWSWIRQPPGKGLEWIG

IIYYSGWTNYNPSLKSRVTISVDASRNQFSLKLSSVTAADTAVYYCARGVG

PDFWSGYSYSSYFDLWGRGTLVTVSSASTKGPSVFPLAPSSKSTSGGTAAL

GCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREP
```

-continued

```
                                                  (SEQ ID NO: 77)
QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGKG

GGGSGGGGSGGGGSQVQLQESGPGLVKPSETLSLTCTVSGGSVSSGSYYWS

WIRQPPGKGLEWIGYIYYSGSTNYNPSLKSRVTISVDTSKNQFSLKLSSVT

AADTAVYYCARTNLYSTPFDIWGQGTMVTVSSASTKGPSVFPLAPSSKSTS

GGTAALGCLVKDYFPEPVTVSWNSGALTSGVHTFPAVLQSSGLYSLSSVVT

VPSSSLGTQTYICNVNHKPSNTKVDKKVEPKSC;

(SEQ ID NO: 77)
QLQLQESGPGLVKPSETLSLTCTVSGGSINSSSYYWQWIRQPPGKGLEWIG

EIAYSGSTYYNPSLKSRVTISVDTSKNQFSLKLSSVTAADTAVYYCARGQQ

WAAFDIWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFL

YSKLTVDKSRWQQGNVFSCSVMHEALHNHYTQKSLSLSPGKGGGGSGGGGS

GGGGSQVQLQESGPGLVKPSETLSLTCTVSGGSVSSGSYYWSWIRQPPGKG

LEWIGYIYYSGSTNYNPSLKSRVTISVDTSKNQFSLKLSSVTAADTAVYYC

ARTNLYSTPFDIWGQGTMVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKKVEPKSC.
```

In other embodiments, optionally in combination with any of the preceding or following embodiments, the multispecific antibody analog comprises four copies of a polypeptide comprising, from N-terminus to C-terminus, a VL region, and a CK region, and wherein said polypeptide heterodimerizes with compatible VH regions of the multispecific antibody analog, the amino acid sequence of which comprises an amino acid sequence selected from the group consisting of:

```
                                                  (SEQ ID NO: 78)
DIQLTQSPSSVSASVGDRVTITCRASQDISSWLAWYQQKPGKAPKLLIYAA

SSLQSGVPSRFSGSGSGTDFTLTISSLQPEDFATYYCQQEHDFPWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 79)
DIQLTQSPSTLSASVGDRVTITCRASQAISSWLAWYQQKPGKAPKLLIYDA

SSLESGVPSRFSGSGSGTEFTLTISSLQPDDFATYYCHQYQSYSWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 80)
DIQMTQSPSSLSASVGDRVTITCRASQNIATDVAWYQQKPGKAPKLLIYSA

SFLYSGVPSRFSGSRSGTDFTLTISSLQPEDFATYYCQQSEPEPYTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 81)
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;
and
                                                  (SEQ ID NO: 82)
DILLTQSPVILSVSPGERVSFSCRASQSIGTNIHWYQQRTHGSPRLLIKYA

SESISGIPSRFSGSGSGTDFTLSINSVESEDIADYYCQQNNNWPTTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.
```

In other embodiments, optionally in combination with any of the preceding or following embodiments, the multispecific antibody analog has binding specificity for an oncology target. In other embodiments, optionally in combination with any of the preceding or following embodiments, the multispecific antibody analog has binding specificity for one or more targets selected from the group consisting of: EGFR, HER2, and HER3. In other embodiments, optionally in combination with any of the preceding or following embodiments, the multispecific antibody analog has binding specificity for EGFR and HER2. In other embodiments, optionally in combination with any of the preceding or following embodiments, the polypeptide multispecific antibody analog has binding specificity for EGFR and HER3. In other embodiments, optionally in combination with any of the preceding or following embodiments, the multispecific antibody analog has binding specificity for EGFR, HER2, and HER3.

In other embodiments, optionally in combination with any of the preceding or following embodiments, the multispecific antibody analog is selected from the group consisting of the multispecific antibody analogs described in the Examples.

In other embodiments, optionally in combination with any of the preceding or following embodiments, the multispecific antibody analog is expressed by a prokaryotic host cell or a eukaryotic host cell. In other embodiments, optionally in combination with any of the preceding or following embodiments, the multispecific antibody analog is expressed by a eukaryotic host cell. In other embodiments, optionally in combination with any of the preceding or following embodiments, the multispecific antibody analog is expressed by a eukaryotic host cell selected from the group consisting of: yeast cells; *Saccharomyces cerevisiae* cells; *Pichia* cells; mammalian cells; Chinese hamster ovary (CHO) cells; human embryonic kidney (HEK) cells; insect cells; Sf9 cells; and Sf21 cells.

In other embodiments, optionally in combination with any of the preceding or following embodiments, provided are multispecific antibody analogs prepared by performing a method according to any of the preceding or following embodiments.

As the artisan will understand, any and all of the embodiments disclosed above and throughout may be practiced in any combination and, accordingly, all such combinations are contemplated, and are hereby disclosed and encompassed within the scope of the invention.

DETAILED DESCRIPTION OF THE INVENTION

Figure 1:
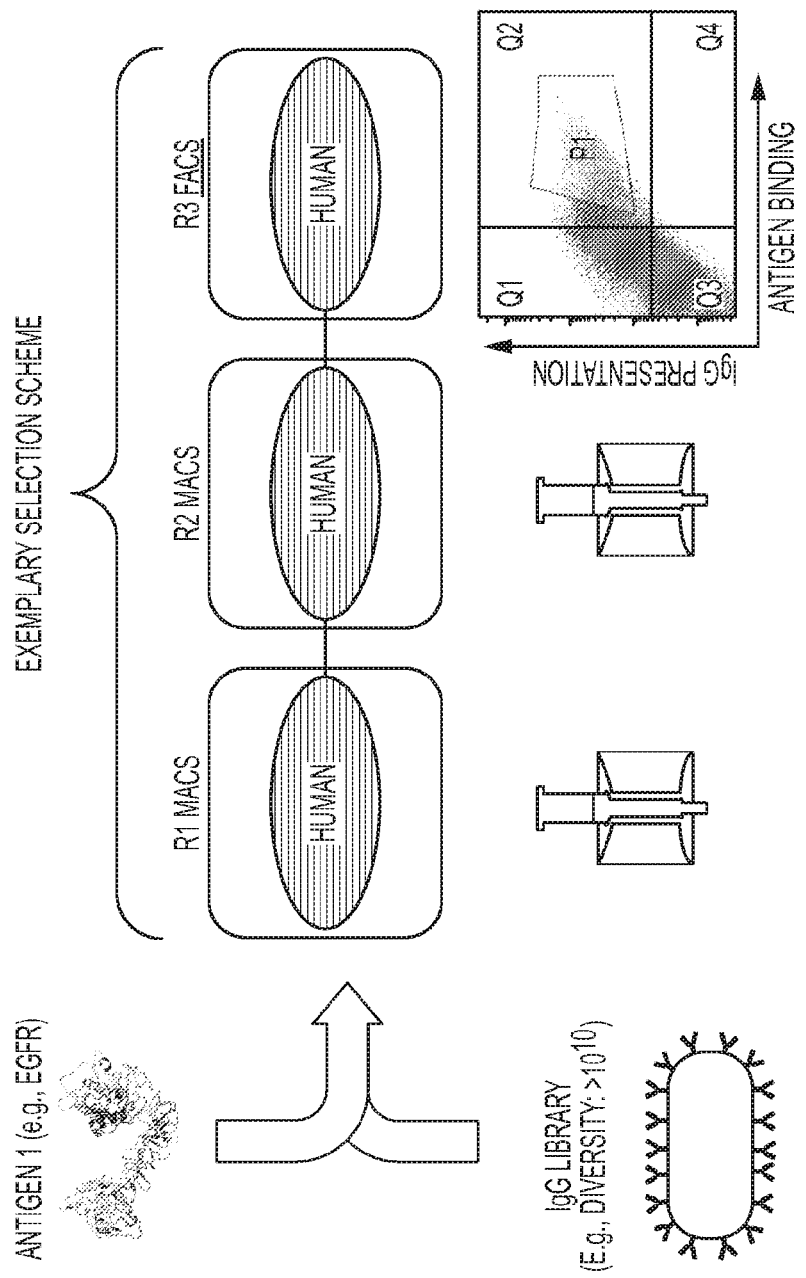
FIG. 1 provides a schematic representation of an exemplary naïve library antigen selection scheme for identifying antibodies with specificity for Antigen.
Figure 2:
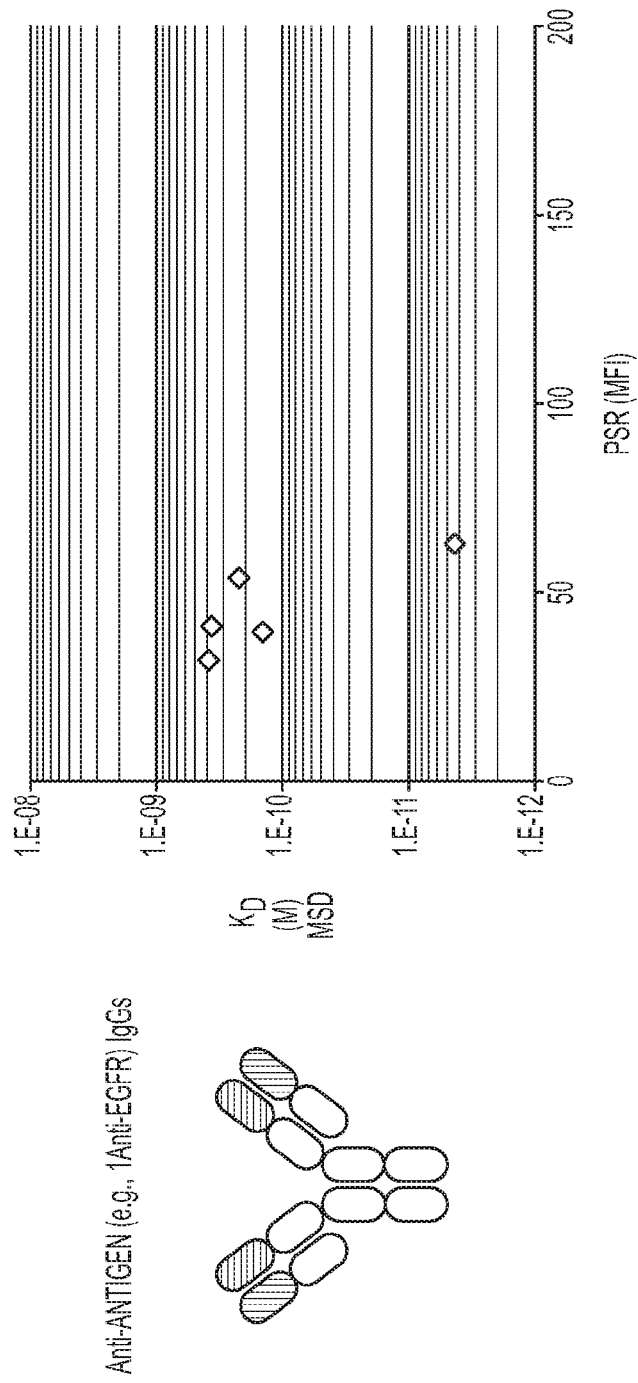
FIG. 2 provides the dissociation constants ($K_D$) measured using a Meso Scale Discovery® (MSD®)-based assay (see, e.g., Estep et al., *MAbs*, Vol. 5(2), pp. 270-278 (2013)) for five IgG antibodies that were isolated by performing a selection, as illustrated in FIG. 1, for EGFR binders using a naïve library. M=molar.

The present invention provides, inter alia, multispecific antibody analogs (referred to interchangeably throughout as "multispecific analogs", "analogs" or "antibody analogs"), including bispecific, trispecific, tetraspecific, pentaspecific antibody analogs, and the like, which advantageously comprise at least two copies of a first polypeptide and at least two copies of a second polypeptide, wherein such multispecific analogs have specificity for more than one antigen (also referred interchangeably throughout as a "target" or in the plural sense "targets").

As would be understood by those of ordinary skill in the art, the term "antibody" is used herein in the broadest sense and specifically encompasses at least monoclonal antibodies, polyclonal antibodies, multi-specific antibodies (e.g., bispecific antibodies), multispecific antibody analogs, chimeric antibodies, humanized antibodies, human antibodies, antibody fragments, and derivatives thereof. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. An "antibody" also refers to an immunoglobulin molecule, a fragment of an immunoglobulin molecule, or a derivative thereof, which has the ability to specifically bind to an antigen, which may be, for example: a protein; a polypeptide; peptide; a hormone; a cytokine; a chemokine; a growth factor; a neurotransmitter; a carbohydrate-containing biological molecule; a lipid or fatty acid-containing biological molecule; or other biological molecule; via an epitope present on such antigen. An "antibody analog" or "antibody analogs" refers to variants, of an antibody or antibody format. Such antibody analogs may comprise variants or variations with regard to the format, structure, or amino acid composition, or antibodies, as describes herein and throughout.

Multispecific antibody analogs that may be generated or used in accordance with the invention may correspond to a variety of different formats. In certain embodiments, multispecific analogs may comprise antibodies that comprise or otherwise correspond to an Ig-like format, such as an IgG, IgA, IgD, or IgM format. In embodiments in which the multispecific analogs comprise or otherwise correspond to, for example, an IgG format, such antibody analogs comprise: a first polypeptide comprising a first heavy chain having specificity for a first antigen (also referred interchangeably throughout as an "antigen 1"); a second polypeptide comprising a second heavy chain having specificity for a second antigen (also referred interchangeably throughout as an "antigen 2"); and a third polypeptide comprising a common light chain. In certain of these embodiments, the first polypeptide comprises a first variable heavy domain (VH) with specificity for the first antigen of interest; the second polypeptide comprises a second variable heavy domain (VH) with specificity for the second antigen of interest; and the third polypeptide comprises a light chain variable domain that is compatible with both VHs and can form a first antigen binding region and a second antigen binding region when associated with the first VH and the second VH, respectively.

Also provided herein are methods by which one or more common light chains may be obtained or identified for use in preparing multispecific antibody analogs in accordance with the invention, which comprise: i) performing a first selection against a first antigen from a first library and obtaining one or more light chains from the output that has specificity for the first antigen; ii) performing a second selection against a second antigen from a second library and obtaining heavy chains from the output that has specificity for the second antigen; iii) generating a restricted library comprising the one or more light chains obtained in step i) and the heavy chains obtained in step ii); iv) performing a third selection against the first antigen from the restricted library generated in step iii) and obtaining one or more antibodies form the output of the third selection, wherein the one or more antibodies comprise one or more light chains that each have specificity for the first antigen and the second antigen; thereby obtaining or identifying the one or more common light chains. In certain embodiments, the first library comprises a naïve library; the second library comprises a naïve library; or the first library comprises a naïve library and the second library comprises a naïve library.

As will be understood by the artisan and as disclosed throughout, an antigen may comprise one or more epitopes. An "epitope" refers to a region, structure, or motif on an antigen which is recognized by an antibody and to which the antibody binds. Thus, antibodies may be obtained or identified which have specificity for more than one epitope on the same antigen. "Epitopic coverage", "epitope coverage", and like terms refer to the extent to which such antibodies are collected, isolated, and/or identified when performing a selection or library interrogation process that collectively have specificities for number of epitopes that approximate the full repertoire, or diversity, of available epitopes of the antigen of interest.

As will be understood by the artisan and as disclosed throughout, "specificity" refers to the property of an antibody which enables to react with one or more antigenic determinants, such as one or more epitopes, of an antigen of interest, and not with other epitopes of the antigen of interest or with other antigens of interest. As understood in the art, antibody specificity is dependent on chemical composition, physical forces, energetic favorability, steric hindrance, and molecular structure or topology of the binding site of the epitope and/or the antibody.

As will be understood by the artisan and as disclosed throughout, "affinity" refers to the strength, or stability of an antibody-epitope interaction. Antibodies with better affinity for an epitope bind relatively tightly and/or stably with the epitope, whereas antibodies with poorer affinity for an epitope bind relatively weakly and or less stably. Although not always the case, it is often found that antibodies having greater specificity for an antigen of interest of an epitope of interest relative to another antibody has better affinity for that antigen or epitope relative to the other antibody.

As will be understood by the artisan and as disclosed throughout, "obtaining" or "identifying" antibodies or components of antibodies (such as common light chains, heavy chains, or antigen binding regions) having specificity for (an) epitope(s) of an antigen of interest refers to distinguishing (or distinguished) antibodies that have such specificity from those antibodies that do not have such specificity. Obtaining or identifying antibodies having specificity for an antigen or epitope of interest need not require physical separation of antibodies from those antibodies that do not have such specificity in order for them to be distinguished. However, in certain embodiments, obtaining or identifying antibodies having specificity for an antigen or epitope of interest comprises physically separating such antibodies from those antibodies that do not have such specificity. Exemplary methods and means for obtaining or identifying antibodies are known in the art, and include, for example, flow cytometry, florescence activated cell sorting (FACS), magnetic activated cell sorting (MACS®), enzyme-linked immunosorbent assay (ELISA), and the like, and combinations thereof.

Any means for determining such specificity in the art may be employed for determining such specificity in accordance with the methods disclosed throughout, and include, for example, labelling such antibodies with a detectable label; detecting a detectable label; detecting a functional consequence of antibody binding to antigen or epitope on an antigen, such as competition with another antibody known to have specificity for such epitope(s); modulation of protein-protein or protein-ligand interaction between the antigen of interest and a known protein interaction partner or ligand.

As will be understood by the artisan and as disclosed throughout, "plurality" and "pluralities" refer to, in the broadest sense, two or more members of a group of items. In certain embodiments of the invention some or all of the members of such a plurality may be essentially identical. In certain other embodiments of the invention, many, most, or all of the members of a plurality of items, while each possessing similar characteristics that merit their inclusion in the plurality, are nonetheless different in some discernible way and possess different properties.

As will be appreciated by the artisan, the terms "plurality" and "library" (and "pluralities" and "libraries") may be readily used interchangeably. However, in the context of the inventions disclosed throughout, whereas a "plurality" of items, such as antibodies, nucleic acid encoding antibodies, or host cells, may comprise many or most members that are essentially identical, a "library" of items, such as antibodies, nucleic acid encoding antibodies, or host cells comprise members many or most members that are unique.

In the context of antibodies that are employed in practicing the disclosed inventions, a library (or plurality) of such antibodies will comprise many or most members that each possess a unique primary acid sequence; however, such libraries (or pluralities) may also include members that have identical amino acid sequences. In certain embodiments, the variable regions of such members will comprise many of the differences in amino acid sequence between such members.

In the context of host cells that are employed in practicing the disclosed inventions, a plurality (or library) of such host cells will comprise host cell members, many of which that each express a unique antibody; however, such host cell pluralities (or libraries) may also include members that express identical antibody sequences. In certain embodiments, such host cells will also harbor nucleic acid that collectively encodes the antibody libraries that are collectively expressed by the host cells.

As will be understood by the artisan and as disclosed throughout, "diversity" refers to a variety or a noticeable heterogeneity. The term "sequence diversity" refers to a variety of sequences which are collectively representative of several possibilities of sequences, for example, those found in natural human antibodies. For example, heavy chain CDR3 (CDRH3) sequence diversity may refer to a variety of possibilities of combining the known human DH and H3-JH segments, including the N1 and N2 regions, to form heavy chain CDR3 sequences. The light chain CDR3 (CDRL3) sequence diversity may refer to a variety of possibilities of combining the naturally occurring light chain variable region contributing to CDRL3 (i.e., L3-VL) and joining (i.e., L3-JL) segments, to form light chain CDR3 sequences. As used herein, H3-JH refers to the portion of the IGHJ gene contributing to CDRH3. As used herein, L3-VL and L3-JL refer to the portions of the IGLV and IGL genes (kappa or lambda) contributing to CDRL3, respectively.

As will be understood by the artisan and as disclosed throughout antibody libraries suitable for use in accordance with the disclosed methods may be designed and prepared by any method available in the art as disclosed, for example, in WO2009036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

It is often desirable to include one more maturation library selections as part of an antibody discovery process. Such maturation library selections, such as affinity maturation library selections, may be advantageously incorporated into the methods disclosed herein. In such embodiments the methods disclosed herein further comprise: a) performing a subsequent selection against the first antigen from a maturation library; b) performing a subsequent selection against the second antigen from a maturation library; or c) performing a subsequent selection against the first antigen from a maturation library and performing a subsequent selection against the second antigen from a maturation library; after performing: a) step i; b) step ii; c) step iii; and/or d) step iv.

A "naive library" refers to a library of polynucleotides (or polypeptides encoded by such polynucleotides) that has not been interrogated for the presence of antibodies having specificity a particular antigen. A "naïve library" also refers to a library that is not restricted to, or otherwise biased or enriched for, antibody sequences having specificity for any group of antigens, or for a particular antigen. A naïve library is thus distinct from a "restricted library" and "maturation library (such as, for example, an "affinity maturation library"), both of which are described below.

A naïve library may also comprise a "preimmune" library, which refers to a library that has sequence diversity and length diversity similar to naturally occurring antibody sequences, such as human antibody sequences, before such naturally occurring sequences have undergone negative selection and/or somatic hypermutation. Such preimmune libraries may be designed and prepared so as to reflect or mimic the pre-immune repertoire, and/or may be designed and prepared based on rational design informed by the collection of human V, D, and J genes, and other large databases of human heavy and light chain sequences (e.g., publicly known germline sequences; sequences from Jackson et al, J. Immunol Methods, 2007, 324: 26, incorporated by reference in its entirety; sequences from Lee et al., Immunogenetics, 2006, 57: 917, incorporated by reference in its entirety; and sequences compiled for rearranged VK and VX). Additional information may be found, for example, in Scaviner et al., Exp. Clin. Immunogenet., 1999, 16: 234; Tomlinson et al, J. Mol. Biol, 1992, 227: 799; and Matsuda et al, J. Exp. Med., 1998, 188: 2151, each incorporated by reference in its entirety. In certain embodiments of the invention, cassettes representing the possible V, D, and J diversity found in the human repertoire, as well as junctional diversity (i.e., N1 and N2), are synthesized de novo as single or double-stranded DNA oligonucleotides. In certain embodiments of the invention, oligonucleotide cassettes encoding CDR sequences are introduced into yeast along with one or more acceptor vectors containing heavy or light chain chassis sequences. No primer-based PCR amplification or template-directed cloning steps from mammalian cDNA or mRNA are employed. Through standard homologous recombination, the recipient yeast recombines the cassettes (e.g., CDR3s) with the acceptor vector(s) containing the chassis sequence(s) and constant regions, to create a properly ordered synthetic, full-length human heavy chain and/or light chain immunoglobulin library that can be genetically propagated, expressed, displayed, and screened. One of ordinary skill in the art will readily recognize that the chassis contained in the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector. In certain embodiments, the invention provides a synthetic, preimmune human antibody repertoire comprising about 10⁷ to about 10²⁰ antibody members, wherein the repertoire comprises:

(a) selected human antibody heavy chain chassis (i.e., amino acids 1 to 94 of the heavy chain variable region, using Kabat's definition); (b) a CDRH3 repertoire, designed based on the human IGHD and IGHJ germline sequences, the CDRH3 repertoire comprising the following:
  (i) optionally, one or more tail regions;
  (ii) one or more N1 regions, comprising about 0 to about 10 amino acids selected from the group consisting of fewer than 20 of the amino acid types preferentially encoded by the action of terminal deoxynucleotidyl transferase (TdT) and functionally expressed by human B cells;
  (iii) one or DH segments, based on one or more selected IGHD segments, and one or more N- or C-terminal truncations thereof;
  (iv) one or more N2 regions, comprising about 0 to about 10 amino acids selected from the group consisting of fewer than 20 of the amino acids preferentially encoded by the activity of TdT and functionally expressed by human B cells; and (v) one or more H3-JH segments, based on one or more IGHJ segments, and one or more N-terminal truncations thereof (e.g., down to XXWG);
(c) one or more selected human antibody kappa and/or lambda light chain chassis; and
(d) a CDRL3 repertoire designed based on the human IGLV and IGL germline sequences, wherein "L" may be a kappa or lambda light chain.

Exemplary such preimmune libraries, and the design and composition of polynucleotide sequences (and polypeptide sequences encoded by them) comprising them, are further described in, for example, Lee et al. (Immunogenetics, 2006, 57: 917); Martin et al., Proteins, 1996, 25:130; WO 2009/036379; and WO 2012/09568.

A "maturation library" refers to a library that is designed to enhance or improve at least one characteristic of an antibody sequence that is identified upon interrogation of a library, such as a naïve library or a preimmune library, for the presence of antibody sequences having specificity for the antigen. Such maturation libraries may be generated by incorporating nucleic acid sequences corresponding to: one or more CDRs; one or more antigen binding regions; one or more VH or VL regions; and/or one or more heavy chains or light chains; obtained from or identified in an interrogation of a naïve library (herein referred to as "antibody leads") into libraries designed to further mutagenize in vitro or in vivo to generate libraries with diversity introduced in the context of the initial antibody leads. Such maturation libraries and methods of making them are provided in, for example, WO 2009/036379 (for example, at pages 75 through 77); and WO 2012/09568 (for example pages 69 to 72), and include: maturation libraries in which variegation is performed in which a CDRH3 of interest remains unaltered, and heavy chain framework regions, CHRH1, and/or CHDH2 regions are variegated; libraries in which a CDRL3 of interest remains unaltered, and light chain framework regions, CHRL1, and/or CHDL2 regions are variegated; libraries in which premade, diverse, light chains are combined with one or more heavy chains of interest.

In certain embodiments of the invention, antibody libraries, whether naïve libraries, maturation libraries, or restricted libraries, are designed to be small enough to chemically synthesize and physically realize, but large enough to encode antibodies with the potential to recognize any antigen. In certain embodiments, an antibody library comprises about 10⁷ to about 10²⁰ different antibodies and/or polynucleotide sequences encoding the antibodies of the library. In some embodiments, the libraries are designed to include 10³, 10⁴, 10⁵, 10⁶, 10⁷, 10⁸, 10⁹, 10¹⁰, 10¹¹, 10¹², 10¹³, 10¹⁴, 10¹⁵, 10¹⁶, 10¹⁷, 10¹⁸, 10¹⁹, or 10²⁰ different antibodies and/or polynucleotide sequences encoding the antibodies. In certain embodiments, the libraries may comprise or encode about 10³ to about 10⁵, about 10⁵ to about 10⁷, about 10⁷ to about 10⁹, about 10⁹ to about 10¹¹, about 10¹¹ to about 10¹³, about 10¹³ to about 10¹⁵, about 10¹⁵ to about 10¹⁷, or about 10¹⁷ to about 10²⁰ different antibodies. In certain embodiments, the diversity of the libraries may be characterized as being greater than or less than one or more of the diversities enumerated above, for example greater than about 10³, 10⁴, 10⁵, 10⁶, 10⁷, 10⁸, 10⁹, 10¹⁰, 10¹¹, 10¹², 10¹³, 10¹⁴, 10¹⁵, 10¹⁶, 10¹⁷, 10¹⁸, 10¹⁹, or 10²⁰ or less than about 10³, 10⁴, 10⁵, 10⁶, 10⁷, 10⁸, 10⁹, 10¹⁰, 10¹¹, 10¹², 10¹³, 10¹⁴, 10¹⁵, 10¹⁶, 10¹⁷, 10¹⁸, 10¹⁹, or 10²⁰. In certain other embodiments of the invention, the probability of an antibody of interest being present in a physical realization of a library with a size as enumerated above is at least about 0.0001%, 0.001%, 0.01%, 0.1%, 1%, 5%, 10%, 20%, 30%, 40%, 50%, 60%, 70%, 80%, 85%, 90%, 95%, 99%, 99.5%, or 99.9%

A "common light chain" refers to a an antibody light chain that: can combine with a first heavy chain having specificity for a first antigen; and can combine with a second heavy chain having specificity for a second antigen; such that an antigen binding region is formed which has specificity for the first antigen and an antigen binding region is formed which has specificity for the second antigen. Accordingly, a multispecific antibody analog may be generated comprising: the first heavy chain; the second heavy chain; and the common light chain.

A "restricted library" refers to a library that comprises: one or more unique heavy chains, one or more unique light chains, or one or more unique heavy chains and one or more unique light chains; that have been obtained or identified by performing a selection from, for example, a naive library for antigen binding regions having specificity for one antigen of interest; and is used to obtain or identify antigen binding regions having specificity for another antigen of interest. Such restricted libraries typically comprise a number of either heavy chains or light chains that is in far excess of the number of light chains or heavy chains, respectively. In certain embodiments, the number of unique heavy chains is at least 10⁵, at least 10⁶, at least 10⁷, 10⁸, or at least 10⁹ or greater and the number of unique light chains is one, two, three, four, five, ten, 15, 20, 50, 100, 200, 500, or 1000. In certain embodiments, the number of unique heavy chains is between 10⁷ and 10⁸, and the number of unique light chains is less than 10, preferably approximately 5.

Multispecific antibody analogs may also comprise antibodies comprise at least two copies of a first polypeptide and at least two copies of a second polypeptide, wherein each copy of the first polypeptide comprises a variable heavy domain (VH) with specificity for one antigen of interest as well as a VH with specificity for a second antigen of interest; and wherein each copy of the second polypeptide comprises a light chain variable domain that is compatible with both VHs and can form a first antigen (also referred interchangeably throughout as an "antigen 1") binding region and a second antigen (also referred interchangeably throughout as an "antigen 2") binding region when associated with the first VH and the second VH, respectively In certain of such embodiments, each copy of the second polypeptide comprises a copy of a common light chain. Accordingly, because such inventive analogs comprise two copies of one heavy chain-containing polypeptide species and two copies of one light chain-containing polypeptide species, such antibody analogs afford greatly streamlined production characterized by greatly diminished, if not essentially eliminated, generation of undesired oligomeric species (i.e., homo dimeric heavy chain specific, mis-pairing of light chains, etc.) that is characteristic of prior methods and analogs which require at least two different VH polypeptide-containing specifies and/or at least two light chain-containing polypeptide species as disclosed in, for example (see, e.g., U.S. Pat. Nos. 5,731, 168; 5,807,706; 5,821,333; 7,183,076; 7,642,228; 7,695, 936; U.S. Ser. No. 11/536,951, U.S. Pat. Nos. 8,216,805, and 7,951,917). As a result, the herein disclosed and claimed analogs and methods of their preparation afford correspondingly augmented yields of relatively pure amounts of the desired multispecific antibody analog.

The inventive methods by which the disclosed multispecific antibody analogs are generate comprise, for example: obtaining or identifying one or more light chains from one or more first antigen binding regions having specificity for a first antigen of interest; performing a first selection from, for example, a naïve library for antigen binding regions having specificity for a second antigen of interest; obtaining heavy chains from the output of the selection against the second antigen and mixing them with one or more light chains thereby generating a restricted library; performing second selection against the second antigen of interest with the restricted library; obtaining or identifying from the output of restricted library selection one or more antigen binding regions having specificity for the second antigen of interest, wherein the one or more antigen binding regions comprises the one or more light chains; and incorporating the antigen binding region having specificity for the first antigen of interest and the one or more antigen binding regions having specificity for the second antigen of interest into a multispecific antibody analog comprising: an IgG moiety comprising either:

a) the first antigen binding region; or
b) the second antigen binding region; and two Fab moieties, wherein each Fab moiety comprises either:

a) the second antigen binding region; or
b) the first antigen binding region;

wherein the N-terminus of the heavy chain of one Fab moiety is linked to the C-terminus of the Fc region of one heavy chain of the IgG moiety via a linker moiety, and the N-terminus of the heavy chain of the other Fab moiety is linked to the C-terminus of the Fc region of the other heavy chain of the IgG moiety via a linker moiety; thereby generating the multispecific antibody analog.

In certain embodiments, the one or more light chains from the first antigen binding regions is obtained or identified from the output of a selection performed with for example, a naïve library for antigen binding regions against the first antigen of interest.

By "Fab" or "Fab region" as used herein is meant the polypeptides that comprise the VH, CH1, VL (also known as VK, used interchangeably throughout), and CL (also known as CK, used interchangeably throughout) immunoglobulin domains. Typically, the VH and CH1 domains comprise one polypeptide and the VL and CL domains comprise another polypeptide, wherein the two polypeptides are linked to one another via at least one inter-polypeptide disulfide bond. Fab may refer to this region in isolation, or this region in the context of a full length antibody or antibody fragment.

By "protein" or "polypeptide" as used herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptides.

By "scFv" as used herein is meant a polypeptide consisting of two variable regions connected by a linker sequence; e.g., VH-linker-VL, VH-linker-VL, VK-linker-VL, or VL-linker-VH. "Linkers" (also referred to a "linker moieties", used interchangeably throughout), are described in more detail below.

By "position" as used herein is meant a location in the sequence of a protein or nucleic acid. Protein positions may be numbered sequentially, or according to an established format, for example the Kabat index for antibody variable regions or the EU index for antibody constant regions. For example, position 297 is a position in the human antibody IgG1. Corresponding positions are determined as outlined above, generally through alignment with other parent sequences.

By "residue" as used herein is meant a position in a protein and its associated amino acid identity. For example, Asparagine 297 (also referred to as Asn297, also referred to as N297) is a residue in the human antibody IgG1. In some embodiments it can also refer to nucleic acid bases.

Antibodies (used interchangeably with "immunoglobulins", or "immunoglobulin molecules") can be monomeric, dimeric, trimeric, tetrameric, pentameric, etc., and comprise a class of structurally related proteins consisting of two pairs of polypeptide chains: one pair of light chains (LC) and one pair of heavy chains (HC), all of which are inter-connected by disulfide bonds. The structure of immunoglobulins has been well characterized. See for instance Fundamental Immunology Ch. 7 (Paul, W., ed., 2nd ed. Raven Press, N.Y. (1989)).

Traditional natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa), which are referred to herein as a "light chain" and "heavy chain", respectively. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. The distinguishing features between these antibody classes are their constant regions, although subtler differences may exist in the variable region.

Each of the light and heavy chains is made up of two distinct regions, referred to as the variable and constant regions. The IgG heavy chain is composed of four immunoglobulin domains linked from N- to C-terminus in the order VH-CH1-CH2-CH3, referring to the "variable heavy domain" (also referred to as a "heavy chain variable domain", used interchangeably throughout), heavy chain constant domain 1, heavy chain constant domain 2, and heavy chain constant domain 3 respectively (also referred to as VH-Cγ1-Cγ2-Cγ3, referring to the variable heavy domain, constant gamma 1 domain, constant gamma 2 domain, and constant gamma 3 domain respectively). The IgG light chain is composed of two immunoglobulin domains linked from N- to C-terminus in the order VL-CL, referring to the "variable light domain" (also referred to as a "light chain variable domain", used interchangeably throughout) and the light chain constant domain respectively. The constant regions show less sequence diversity, and are responsible for binding a number of natural proteins to elicit important biochemical events. The structure that constitutes the natural biological form of an antibody, including the variable and constant regions, is referred to herein as a "full length antibody". In most mammals, including humans and mice, the full length antibody of the IgG isotype is a tetramer and consists of two identical pairs of two immunoglobulin chains, each pair having one light chain and one heavy chain, each light chain comprising a VL and a CL, and each heavy chain comprising a VH, CH1, a CH2, and a CH3. In some mammals, for example in camels and llamas, IgG antibodies may consist of only two heavy chains, each heavy chain comprising a variable domain attached to the Fc region.

The heavy chain constant region typically is comprised of three domains, CH1, CH2, and CH3, and the CH1 and CH2 domains are connected by a hinge region. Each light chain typically is comprised of a light chain variable domain (abbreviated herein as "VL" or "VL") and a light chain constant domain. The VH and VL domains may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. Typically, the numbering of amino acid residues in this region is performed by the method described in Kabat (see, e.g., Kabat et al, in "Sequences of Proteins of Immunological Interest," 5th Edition, U.S. Department of Health and Human Services, 1992). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of VH CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "variable", "variable domain", or "variable region" each interchangeably refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

The term "framework region" refers to the art-recognized portions of an antibody variable region that exist between the more divergent (i.e., hypervariable) CDRs. Such framework regions are typically referred to as frameworks 1 through 4 (FRMI, FRM2, FRM3, and FRM4) and provide a scaffold for the presentation of the six CDRs (three from the heavy chain and three from the light chain) in three dimensional space, to form an antigen-binding surface. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al, Nature, 1989, 342: 877; Martin and Thornton, J. Mol. Biol, 1996, 263: 800. Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al, in "Sequences of Proteins of Immunological Interest," 5th Edition, U.S. Department of Health and Human Services, 1992). The Kabat numbering scheme is a widely adopted standard for numbering the amino acid residues of an antibody variable domain in a consistent manner. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

By "Fc" or "Fc region", as used herein is meant the polypeptide comprising the constant region of an antibody excluding the first constant region immunoglobulin domain. Thus "Fc region" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Accordingly, and without departing from the above, "Fc region" may also be defined as comprising a "CH2 domain or a variant thereof" and a "CH3 domain or a variant thereof". Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

A variable light chain (VL) and corresponding variable heavy domain (VH) of the inventive multispecific antibody analogs comprise a binding domain, also referred to interchangeably throughout as an "antigen binding site" that interacts with an antigen. Such antigen binding sites (or binding regions, used interchangeably throughout), are optionally provided and employed in the context of either an IgG or a Fab of the present invention. Thus, a "first variable light domain" and a "first variable heavy domain" of the inventive multispecific antibody analogs together form a "first antigen binding site". Similarly, a "second variable light domain" and a "second variable heavy domain" of the inventive multispecific antibody analogs together form a "second antigen binding site". A "third variable light domain" and a "third variable heavy domain" of the inventive multispecific antibody analogs together form a "third antigen binding site", and so on. Accordingly, the inventive multispecific antibody analogs may comprise an IgG comprising two antigen binding regions, to which has been attached two Fabs, wherein such Fabs are each attached to the C-terminus of each CH3 region of the IgG via a linker moiety.

The antigen binding sites for use in accordance with the invention, including the VHs, VLs, and/or CDRs that comprise such, may be obtained or derived from any source of such, as will be understood by the artisan. Accordingly, such antigen binding sites, VHs, VLs, and/or CDRs may be obtained or derived from hybridoma cells that express antibodies against a target recognized by such; from B cells from immunized donors, which express antibodies against a target recognized by such; from B-cells that have been stimulated to express antibodies against a target recognized by such; and or from identification of antibodies or antibody fragments that have been identified by screening a library comprising a plurality of polynucleotides or polypeptides for antigen binding antibodies (or antigen binding fragments thereof). With regard to the design, preparation, display, and implementation of such libraries for use in identifying and obtaining antigen binding sites for use in accordance with the invention, see, e.g., WO 2009/036379; WO2012009568; WO2010105256; U.S. Pat. Nos. 8,258,082; 6,300,064; 6,696,248; 6,165,718; 6,500,644; 6,291,158; 6,291,159; 6,096,551; 6,368,805; 6,500,644; and the like.

Any one or more of the antigen binding sites, VHs, VLs, or CDRs, and combinations thereof, of the inventive multispecific antibody analogs, may comprise sequences from a variety of species. In some embodiments, such antigen binding sites, VHs, VLs, or CDRs, and combinations thereof may be obtained from a nonhuman source, including but not limited to mice, rats, rabbits, camels, llamas, and monkeys. In some embodiments, the scaffold and/or framework regions can be a mixture from different species. As such, a multispecific antibody analog in accordance with the invention may comprise a chimeric antibody and/or a humanized antibody. In general, both "chimeric antibodies" and "humanized antibodies" refer to antibodies in which regions from more than one species have been combined. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally in a humanized antibody the entire antibody, except the CDRs, is encoded by a polynucleotide of human origin or is identical to such an antibody except within its CDRs. The CDRs, one, some, or all of which are encoded by nucleic acids originating in a non-human organism, are grafted into the framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (see, e.g., U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing, reshaping, and resurfacing non-human antibodies are well known in the art (See Tsurushita & Vasquez, 2004, Humanization of Monoclonal Antibodies, Molecular Biology of B Cells, 533-545, Elsevier Science (USA), and references cited therein). In certain variations, the immunogenicity of the antibody is reduced using a method described in Lazar et al., 2007, Mol Immunol 44:1986-1998 and U.S. Ser. No. 11/004,590, entitled "Methods of Generating Variant Proteins with Increased Host String Content and Compositions Thereof", filed on Dec. 3, 2004.

Accordingly, any one or more of the antigen binding sites, or one or more VHs, VLs, CDRs, or combinations thereof, which comprise the inventive multispecific antibody analogs disclosed herein may be derived from a non-human species and/or result from humanization of a non-human antibody or antibody fragment. Such VHs, VLs, and/or CDRs obtained or derived from non-human species, when included in the inventive multispecific antibody analogs disclosed herein, are referred to as "humanized" such regions and/or domains.

The inventive antibody analogs disclosed herein preferably comprise first and second polypeptides that each comprise a hinge region, wherein each hinge region comprises at least one thiol group that is capable of participating in an intermolecular disulfide bond such that the first and the second polypeptide are covalently linked as a result of formation of the disulfide bond. As is understood in the art, chemical modification may be introduced into (or onto) certain residues within such hinge regions which effect the introduction of such thiol groups for disulfide bond formation. Alternatively, the thiol groups may be provided by a cysteine residue that is present within the hinge region. Such cysteines may be provided by native hinge polypeptide sequence, or may be introduced by mutagenesis into nucleic acid encoding the hinge region. As used herein, whereas a "hinge" or a "hinge region" of the inventive antibody analogs may comprise or constitute a natural or native hinge region as found in, for example, immunoglobulins such as IgGs, IgMs, IgAs, IgEs, and the like, such a hinge or hinge region may also comprise or constitute a substitutes form thereof. Further, such a hinge or hinge region may, in certain embodiments comprise or constitute a "linker moiety" as disclosed throughout. In other embodiments, a hinge or hinge region may comprise both a natural or native hinge region as disclosed above and a linker moiety as disclosed throughout.

In certain embodiments, the inventive antibody analogs disclosed herein comprise one or more linkers or linker moieties. Such linkers or linker moieties may comprise a peptidic linker moiety or a non-peptidic linker moiety. The terms "linker" and "linker moiety" and the like, means a divalent species (-L-) covalently bonded in turn to a polypeptide having a valency available for bonding and to an amino acid that comprises the inventive multispecific antibody analogs, which amino acid has a valency available for bonding. The available bonding site may conveniently comprise a side chain of an amino acid (e.g., a lysine, cysteine, or aspartic acid side chain, and homologs thereof). In some embodiments, the available bonding site in the analog is the side chain of a lysine or a cysteine residue. In some embodiments, the available bonding site in the analog is the N-terminal amine of a polypeptide comprising the analog. In some embodiments, the available bonding site in the analog is the C-terminal carboxyl of a polypeptide comprising the analog. In some embodiments, the available bonding site in the analog is a backbone atom (e.g., a c-alpha carbon atom) of a polypeptide comprising the analog.

Preferably, a linker moiety is employed to covalently attach a VH or a VL to the C-terminus of a CH3 domain of an antibody analog. A linker moiety may also be employed to covalently attach a first VH or a first VL to a second VH or a second VL, respectively. A linker moiety may also be employed to covalently attach a first VH or a first VL to a second VL or a second VH, respectively. A linker moiety may also be employed to covalently attach a VH of a single chain antigen binding site, such as an scFv, to the VL of such a single chain antigen binding site, and vice versa. A linker moiety may also be employed to attach the VH or the VL of such a single chain antigen binding site, such as an scFv, to a C-terminus of a CH3 domain or variant thereof. A linker moiety may also be employed to attach a VH to the N-terminus of a CL domain or to the N-terminus of a CH2. A linker moiety may also be employed to attach a VL to the N-terminus of a CL domain or to the N-terminus of a CH2 domain. As will be appreciated, combinations and/or multiples of the foregoing may be employed in order to prepare any of the multispecific antibody analogs disclosed herein, such that a plurality of antigen binding sites may be included in such analogs, optionally with a multiple of specificities. Accordingly, a multispecific antibody analog may be generated by employing one or more linkers to covalently attach one, two, three, four, five, six, seven, or more VLs, VHs, and/or single chain antigen binding sites, such as scFvs to the first polypeptide, the second polypeptide, a VH, or a VL attached to the first polypeptide or the second polypeptide, and the like, so as to generate an antibody analog having bi-, tri-, tetra-, pent-, hexa-, hepta-, or octa-valency, and so on, and/or bi-, tri-, tetra-, pent-, hexa-, hepta-, or octa-specificity, and so on.

In certain embodiments, the VH region of a Fab is attached to the CH3 region of each heavy chain of an IgG in order to generate the inventive multispecific antibody analogs.

In certain embodiments the linker moieties comprise amino acids that are selected from glycine, alanine, proline, asparagine, glutamine, lysine, aspartate, and glutamate. In a further embodiment the linker moiety is made up of a majority of amino acids that are sterically unhindered, such as glycine, alanine and/or serine. In certain embodiments the linker moiety is comprises a sequence selected from the group Gly-Ser]n (SEQ ID NO: 8); [Gly-Gly-Ser]n (SEQ ID NO: 9); [Gly-Gly-Gly-Ser]n (SEQ ID NO: 10); [Gly-Gly-Gly-Gly-Ser]n (SEQ ID NO: 11); [Gly-Gly-Gly-Gly-Ser-Gly-Gly-Gly-Gly]n (SEQ ID NO: 12); [Gly-Gly-Gly-Gly-Ser-Gly-Gly-Gly-Gly-Ser-Gly-Gly-Gly-Gly]n (SEQ ID NO: 13); [Gly-Gly-Gly-Gly-Ser Gly-Gly-Gly-Gly-Ser-Gly-Gly-Gly-Gly-Ser-Gly-Gly-Gly-Gly]n (SEQ ID NO: 14); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 15); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 16); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 17); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Such linkers may comprise: an acidic linker, a basic linker, and a structural motif, or combinations thereof; a polyglycine, a polyalanine, poly(Gly-Ala), or poly(Gly-Ser); (Gly)3 (SEQ ID NO: 1), (Gly)4 (SEQ ID NO: 2), or (Gly)5 (SEQ ID NO: 3); (Gly)3Lys(Gly)4 (SEQ ID NO: 4), (Gly)3AsnGlySer(Gly)2 (SEQ ID NO: 5), (Gly)3Cys(Gly)4 (SEQ ID NO: 6), or GlyProAsnGlyGly (SEQ ID NO: 7), [Gly-Ser]n (SEQ ID NO: 8), [Gly-Gly-Ser]n (SEQ ID NO: 9), [Gly-Gly-Gly-Ser]n (SEQ ID NO: 10), [Gly-Gly-Gly-Gly-Ser]n (SEQ ID NO: 11), [Gly-Gly-Gly-Gly-Ser-Gly-Gly-Gly-Gly]n (SEQ ID NO: 12), [Gly-Gly-Gly-Gly-Ser-Gly-Gly-Gly-Gly-Ser-Gly-Gly-Gly-Gly]n (SEQ ID NO: 13), [Gly-Gly-Gly-Gly-Ser Gly-Gly-Gly-Gly-Ser-Gly-Gly-Gly-Gly-Ser-Gly-Gly-Gly-Gly]n (SEQ ID NO: 14), [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 15), [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 16), or [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 17); [Gly-Glu]n (SEQ ID NO: 18), [Gly-Gly-Glu]n (SEQ ID NO: 19), [Gly-Gly-Gly-Glu]n (SEQ ID NO: 20), [Gly-Gly-Gly-Gly-Glu]n (SEQ ID NO: 21), [Gly-Asp]n (SEQ ID NO: 22); [Gly-Gly-Asp]n (SEQ ID NO: 23), [Gly-Gly-Gly-Asp]n (SEQ ID NO: 24), [Gly-Gly-Gly-Gly-Asp]n (SEQ ID NO: 25); where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

In certain embodiments, charged linker moieties are employed. Such charges linker moieties may contain a significant number of acidic residues (e.g., Asp, Glu, and the like), or may contain a significant number of basis residues (e.g., Lys, Arg, and the like), such that the linker moiety has a pi lower than 7 or greater than 7, respectively. As understood by the artisan, and all other things being equal, the greater the relative amount of acidic or basic residues in a given linker moiety, the lower or higher, respectively, the pI of the linker moiety will be. Such linker moieties may impart advantages to the multispecific antibody analogs disclosed herein, such as improving solubility and/or stability characteristics of such polypeptides at a particular pH, such as a physiological pH (e.g., between H 7.2 and pH 7.6, inclusive), or a pH of a pharmaceutical composition comprising such analogs, as well as allowing for optimization of characteristics such as rotational and translational flexibility of the domains and/or regions of the analog that are attached via the linker moiety. Such characteristics may advantageously be optimized and tailored for any given multispecific antibody analog by the artisan.

For example, an "acidic linker" is a linker moiety that has a pI of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker moiety that has a pI of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group consisting of [Gly-Glu]n (SEQ ID NO: 18); [Gly-Gly-Glu]n (SEQ ID NO: 19); [Gly-Gly-Gly-Glu]n (SEQ ID NO: 20); [Gly-Gly-Gly-Gly-Glu]n (SEQ ID NO: 21); [Gly-Asp]n (SEQ ID NO: 22); [Gly-Gly-Asp]n (SEQ ID NO: 23); [Gly-Gly-Gly-Asp]n (SEQ ID NO: 24); [Gly-Gly-Gly-Gly-Asp]n (SEQ ID NO: 25); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75. In certain embodiments, a basic linker will contain a sequence that is selected from the group consisting of [Gly-Lys];[Gly-Gly-Lys]n (SEQ ID NO: 83); [Gly-Gly-Gly-Lys]n (SEQ ID NO: 84); [Gly-Gly-Gly-Gly-Lys]n (SEQ ID NO: 85); [Gly-Arg]n (SEQ ID NO: 86); [Gly-Gly-Arg]n (SEQ ID NO: 87); [Gly-Gly-Gly-Arg]n (SEQ ID NO: 88); [Gly-Gly-Gly-Gly-Arg]n (SEQ ID NO: 89); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Additionally, linker moieties may be employed which possess certain structural motifs or characteristics, such as an alpha helix. For example, such a linker moiety may contain a sequence that is selected from the group consisting of [Glu-Ala-Ala-Ala-Lys]n (SEQ ID NO: 90), where n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75: for example, [Glu-Ala-Ala-Ala-Lys]3 (SEQ ID NO: 91), [Glu-Ala-Ala-Ala-Lys]4 (SEQ ID NO: 92), or [Glu-Ala-Ala-Ala-Lys]5 (SEQ ID NO: 93), and so on.

In still further embodiments the each linker moiety employed in the disclosed multispecific antibody analogs independently comprises: polyglycine, polyalanine, poly (Gly-Ala), or poly(Gly-Ser), (Gly)3 (SEQ ID NO: 1), (Gly)4 (SEQ ID NO: 2), and (Gly)5 (SEQ ID NO: 3), (Gly)3Lys (Gly)4 (SEQ ID NO: 4), (Gly) 3AsnGlySer(Gly)2 (SEQ ID NO: 5), (Gly)3Cys(Gly)4 (SEQ ID NO: 6), and Gly-ProAsnGlyGly (SEQ ID NO: 7), a combination of Gly and Ala, a combination of Gly and Ser, a combination of, Gly and Glu, a combination of Gly and Asp, a combination of Gly and Lys, or combinations thereof.

It is understood in the art that, for many prior multispecific antibody analogs and methods of preparing them, there has been a requirement to engineer or design certain motifs into the Fc region, for example the CH3 domain of heavy chains in order to favor heterodimerization of different heavy chains—as opposed to homodimerization of identical heavy chains—in order to generate meaningful quantities and purities of the desired multispecific analog (see, e.g., U.S. Pat. Nos. 5,731,168; 5,807,706; 5,821,333; 7,183,076; 7,642,228; 7,695,936; U.S. Ser. No. 11/536,951, U.S. Pat. Nos. 8,216,805, and 7,951,917). Such engineering, while burdensome, may also introduce untoward antigenicity and/or immunogenicity characteristics to any potential antibody-based therapeutic, as well as other downstream formulation complications that may not be realized until relatively late in development. Advantageously, the herein disclosed and claims multispecific antibody analogs, and methods of their making, eliminate the requirement to engineer such heterodimerization motifs, and thus negate such concerns or complications. Indeed, because the VH domains for two or more targets (antigens) of interest are present on the same polypeptide in the herein disclosed analogs, there is only one VH-containing polypeptide that needs to be expressed, along with a single light chain specific. Accordingly, as there are only two different species of polypeptide chains that are expressed and that are required to associate in order to generate the inventive multispecific antibody analogs, the generation of contaminating, undesired oligomeric species is almost non-existent, or at least greatly diminished. Accordingly, there exists essentially only one four-chain specifies that is possible to be formed in accordance with the herein disclosed methods, and the natural dimerization motifs found in the Fc, CH1-CK, and VH-VL domains are sufficient to promote efficient yield and recovery of properly associated and properly folded, four-chain (two heavy chain-containing, two light chain-containing) comprising multispecific antibody analogs as disclosed and claimed herein.

Thus, whereas it is understood that the inventive multispecific antibody analogs do not require the design or engineering of heterodimerization motifs in order to obtain meaningful quantities and purities of the desired analog, the methods and analogs disclosed herein are nonetheless amenable to the inclusion of such motifs. In certain embodiments, the inventive multispecific antibody analogs comprise, for example, a CH2 domain variant and/or a CH3 domain variant, wherein such variants each independently comprise at least one different amino acid substitution such that a heterodimeric domain pair is generated such that heterodimerization of the first and second polypeptides of the inventive multispecific antibody analogs favored over homodimerization.

With regard to a "variant" of a domain or region of a multispecific antibody analog as used herein throughout, such a variant refers a polypeptide sequence that comprises such a domain or region, and that differs from that of a parent polypeptide sequence by virtue of at least one amino acid modification. The parent polypeptide sequence may be a naturally occurring or wild-type (WT) polypeptide sequence, or may be a modified version of a WT sequence. Preferably, the variant has at least one amino acid modification compared to the parent polypeptide, region, or domain, e.g. from about one to about ten amino acid modifications, and preferably from about one to about five amino acid modifications compared to the parent. The variant polypeptide sequence herein will preferably possess at least about 80% homology with a parent sequence, and most preferably at least about 90% homology, more preferably at least about 95% homology.

By "parent polypeptide", "parent polypeptide sequence", "parent protein", "precursor polypeptide", or "precursor protein" as used herein is meant an unmodified polypeptide or polypeptide sequence that is subsequently modified to generate a variant polypeptide or polypeptide sequence. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it.

By "Fc polypeptide variant" or "variant Fc polypeptide" as used herein is meant an Fc polypeptide that differs from a parent Fc polypeptide by virtue of at least one amino acid modification. By "Fc variant antibody" or "antibody Fc variant" as used herein is meant an antibody that differs from a parent antibody by virtue of at least one amino acid modification in the Fc region.

By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

As mentioned above, although the inventive multispecific antibody analogs do not require the design or engineering of heterodimerization motifs in order to obtain meaningful quantities and purities of the desired analog, the methods and analogs disclosed herein are nonetheless amenable to the inclusion of such motifs. Interaction between heterodimeric pairs or disclosed multispecific antibody analogs comprising such heterodimeric pairs may be promoted at the heterodimeric pair interface by the formation of protuberance-into-cavity complementary regions at such interfaces; the formation of non-naturally occurring disulfide bonds at such interfaces; leucine zipper at such interfaces; hydrophobic regions at such interfaces; and/or hydrophilic regions at such interfaces. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). Where a suitably positioned and dimensioned protuberance or cavity exists at the interface of either the first or second polypeptide, it is only necessary to engineer a corresponding cavity or protuberance, respectively, at the adjacent interface. Non-naturally occurring disulfide bonds are constructed by replacing on the first polypeptide a naturally occurring amino acid with a free thiol-containing residue, such as cysteine, such that the free thiol interacts with another free thiol-containing residue on the second polypeptide such that a disulfide bond is formed between the first and second polypeptides. Exemplary heterodimerization pairs and methods for making such in accordance with the present invention are available in the art, and are disclosed, for example, in US 2011/0054151; US 2007/0098712; and the like.

In certain embodiments, the heterodimeric pairs are contained within the Fc region of the inventive multispecific antibody analogs. Fc regions that contain such heterodimeric pairs are referred to as "heterodimeric Fc regions".

Accordingly, in certain embodiments, multispecific antibody analogs comprise a CH2 and/or a CH3 domain variant, wherein either: a) the CH2 domain variant and the CH3 domain variant each independently comprises a at least one protuberance in either the CH2 domain or the CH3 domain of the first polypeptide and at least one corresponding cavity in the CH2 domain or the CH3 domain of the second; or the CH2 domain variant and the CH3 domain variant each independently comprises at least one cavity in either the CH2 domain or the CH3 domain of the first polypeptide and at least one corresponding protuberance in the CH2 domain or the CH3 domain of the second polypeptide. In certain other embodiments, the multispecific antibody analogs comprise a CH2 and/or a CH3 domain variant, wherein either: a) the CH2 domain variant and the CH3 domain variant each independently comprises at least one substituted negatively-charged amino acid in either the CH2 domain or the CH3 domain of the first polypeptide and at least one corresponding positively-charged amino acid in either the CH2 domain or the CH3 domain of the second polypeptide; or b) the CH2 domain variant and the CH3 domain variant each independently comprises at least one substituted positively-charged amino acid in either the CH2 domain or the CH3 domain of the first polypeptide and at least one corresponding substituted negatively-charged substituted amino acid in either the CH2 domain or the CH3 domain of the second polypeptide.

With regard to Fc function in "natural" antibodies (i.e., those antibodies generated in vivo via native biological antibody synthesis by native B-cells), the Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class is the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65). The FcγRs bind the IgG Fc region with different affinities. The extracellular domains of FcγRIIIa and FcγRIIIb are 96% identical; however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge.

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-76). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A particular feature of the Fc region of "natural" antibodies is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins.

In some embodiments, the inventive multispecific antibody analogs disclosed herein comprise an Fc variant. An Fc variant comprises one or more amino acid modifications relative to a parent Fc polypeptide, wherein the amino acid modification(s) provide one or more optimized properties. Fc variants further comprise either a CH2 domain variant, a CH3 domain variant, or both a CH2 domain variant and a CH3 domain variant. By "modification" herein is meant an alteration in the physical, chemical, or sequence properties of a protein, polypeptide, antibody, inventive multispecific antibody analog, or immunoglobulin. An amino acid modification can be an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution Y349T refers to a variant polypeptide, in this case a constant heavy chain variant, in which the tyrosine at position 349 is replaced with threonine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

An Fc variant disclosed herein differs in amino acid sequence from its parent by virtue of at least one amino acid modification. The inventive multispecific antibody analogs disclosed herein may have more than one amino acid modification as compared to the parent, for example from about one to fifty amino acid modifications, e.g., from about one to ten amino acid modifications, from about one to about five amino acid modifications, etc. compared to the parent. Thus the sequences of the Fc variants and those of the parent Fc polypeptide are substantially homologous. For example, the variant Fc variant sequences herein will possess about 80% homology with the parent Fc variant sequence, e.g., at least about 90% homology, at least about 95% homology, at least about 98% homology, at least about 99% homology, etc. Modifications disclosed herein also include glycoform modifications. Modifications may be made genetically using molecular biology, or may be made enzymatically or chemically.

Fc variants disclosed herein are defined according to the amino acid modifications that compose them. Thus, for example, the substitution Y349T refers to a variant polypeptide, in this case a constant heavy chain variant, in which the tyrosine at position 349 is replaced with threonine. Likewise, Y349T/T394F defines an Fc variant with the substitutions Y349T and T394F relative to the parent Fc polypeptide. The identity of the WT amino acid may be unspecified, in which case the aforementioned variant is referred to as 349T/394F. It is noted that the order in which substitutions are provided is arbitrary, that is to say that, for example, 349T/394F is the same Fc variant as 394F/349T. Unless otherwise noted, constant region and Fc positions discussed herein are numbered according to the EU index or EU numbering scheme (Kabat et al., 1991, Sequences of Proteins of Immunological Interest, 5th Ed., United States Public Health Service, National Institutes of Health, Bethesda). The EU index or EU index as in Kabat or EU numbering scheme refers to the numbering of the EU antibody (Edelman et al., 1969, Proc Natl Acad Sci USA 63:78-85).

In certain embodiments, the Fc variants disclosed herein are based on human IgG sequences, and thus human IgG sequences are used as the "base" sequences against which other sequences are compared, including but not limited to sequences from other organisms, for example rodent and primate sequences. Immunoglobulins may also comprise sequences from other immunoglobulin classes such as IgA, IgE, IgD, IgM, and the like. It is contemplated that, although the Fc variants disclosed herein are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first immunoglobulin are defined. Alignment of conserved residues may conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm, after alignment. In another embodiment, equivalent residues are within about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered as disclosed herein may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants disclosed herein to other parent IgGs.

Fc variants that comprise or are CH3 domain variants as described above may comprise at least one substitution at a position in a CH3 domain selected from the group consisting of 349, 351, 354, 356, 357, 364, 366, 368, 370, 392, 394, 395, 396, 397, 399, 401, 405, 407, 409, 411, and 439, wherein numbering is according to the EU index as in Kabat. In a preferred embodiment, CH3 domain variants comprise at least one CH3 domain substitution per heavy chain selected from the group consisting of 349A, 349C, 349E, 349I, 349K, 349S, 349T, 349W, 351 E, 351K, 354C, 356K, 357K, 364C, 364D, 364E, 364F, 364G, 364H, 364R, 364T, 364Y, 366D, 366K, 366S, 366W, 366Y, 368A, 368E, 368K, 368S, 370C, 370D, 370E, 370G, 370R, 370S, 370V, 392D, 392E, 394F, 394S, 394W, 394Y, 395T, 395V, 396T, 397E, 397S, 397T, 399K, 401 K, 405A, 405S, 407T, 407V, 409D, 409E, 411 D, 411 E, 411K, and 439D. Each of these variants can be used individually or in any combination for each heavy chain Fc region. As will be appreciated by those in the art, each heavy chain can comprise different numbers of substitutions. For example, both heavy chains that make up the Fc region may comprise a single substitution, one chain may comprise a single substitution and the other two substitutions, both can contain two substitutions (although each chain will contain different substitutions), etc.

In some embodiments, the CH2 and/or CH3 domain variants are made in combinations, that is, two or more variants per heavy chain Fc domain, selected from the group outlined above.

Other CH2 and/or CH3 domain variants that favor heterodimerization that may be employed in the design and preparation of the inventive multispecific antibody analogs of the invention are provided in, for example, Ridgeway et al., 1996, Protein Engineering 9[7]:617-621; U.S. Pat. No. 5,731,168; Xie et al., 2005, J Immunol Methods 296:95-101; Davis et al., 2010, Protein Engineering, Design & Selection 23[4]:195-202; Gunasekaran et al., 2010, J Biol Chem 285[25]:1937-19646; and PCT/US2009/000071 (published as WO 2009/089004).

The Fc variants disclosed herein may be optimized for improved or reduced binding to Fc receptors or Fc ligands. By "Fc receptor" or "Fc ligand" as used herein is meant a molecule, preferably a polypeptide, from any organism that binds to the Fc region of an antibody to form an Fc-ligand complex. Fc ligands include but are not limited to FcγRs, (as described above, including but not limited to FcγRIIIa, FcγRIIa, FcγRIIb, FcγRI and FcRn), C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs. Fc ligands may include undiscovered molecules that bind Fc.

The inventive multispecific antibody analogs may be designed to optimize properties, including but are not limited to enhanced or reduced affinity for an Fc receptor. By "greater affinity" or "improved affinity" or "enhanced affinity" or "better affinity" than a parent Fc polypeptide, as used herein, is meant that an Fc variant binds to an Fc receptor with a significantly higher equilibrium constant of association (KA or Ka) or lower equilibrium constant of dissociation (KD or Kd) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, by the binding methods disclosed herein, including but not limited to BIA-CORE® methods, by one skilled in the art. Accordingly, by "reduced affinity" as compared to a parent Fc polypeptide as used herein is meant that an Fc variant binds an Fc receptor with significantly lower KA or higher KD than the parent Fc polypeptide. Greater or reduced affinity can also be defined relative to an absolute level of affinity.

In one embodiment, particularly useful Fc modifications for the present invention are variants that reduce or ablate binding to one or more FcγRs and/or complement proteins, thereby reducing or ablating Fc-mediated effector functions such as ADCC, ADCP, and CDC. Such variants are also referred to herein as "knockout variants" or "KO variants". Variants that reduce binding to FcγRs and complement are useful for reducing unwanted interactions mediated by the Fc region and for tuning the selectivity of the inventive multispecific antibody analogs. Preferred knockout variants are described in U.S. Ser. No. 11/981,606, filed Oct. 31, 2007, entitled "Fc Variants with Optimized Properties". Preferred modifications include but are not limited substitutions, insertions, and deletions at positions 234, 235, 236, 237, 267, 269, 325, and 328, wherein numbering is according to the EU index. Preferred substitutions include but are not limited to 234G, 235G, 236R, 237K, 267R, 269R, 325L, and 328R, wherein numbering is according to the EU index. A preferred variant comprises 236R/328R. Variants may be used in the context of any IgG isotype or IgG isotype Fc region, including but not limited to human IgG1, IgG2, IgG3, and/or IgG4 and combinations thereof. Preferred IgG Fc regions for reducing FcγR and complement binding and reducing Fc-mediated effector functions are IgG2 and IgG4 Fc regions. Hybrid isotypes may also be useful, for example hybrid IgG1/IgG2 isotypes as described in US 2006-0134105. Other modifications for reducing FcγR and complement interactions include but are not limited to substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Fc modifications that improve binding to FcγRs and/or complement are also amenable to incorporation in the design and preparation of the inventive multispecific antibody analogs disclosed herein. Such Fc variants may enhance Fc-mediated effector functions such as ADCC, ADCP, and/or CDC. Preferred modifications for improving FcγR and complement binding are described in, e.g., U.S. Pat. No. 8,188,231 and US 2006-0235208. Preferred modifications comprise a substitution at a position selected from the group consisting of 236, 239, 268, 324, and 332, wherein numbering is according to the EU index. Preferred substitutions include but are not limited to 236A, 239D, 239E, 268D, 267E, 268E, 268F, 324T, 332D, and 332E. Preferred variants include but are not limited to 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, ibid.

In one embodiment, the inventive multispecific antibody analogs disclosed herein may incorporate Fc variants that enhance affinity for an inhibitory receptor FcγRIIb. Such variants may provide the inventive multispecific antibody analogs herein with immunomodulatory activities related to FcγRIIb+ cells, including for example B cells and monocytes. In one embodiment, the Fc variants provide selectively enhanced affinity to FcγRIIb relative to one or more activating receptors. Modifications for altering binding to FcγRIIb are described in U.S. Pat. No. 8,063,187, filed May 30, 2008, entitled "Methods and Compositions for Inhibiting CD32b Expressing Cells". In particular, Fc variants that improve binding to FcγRIIb may include one or more modifications at a position selected from the group consisting of 234, 235, 236, 237, 239, 266, 267, 268, 325, 326, 327, 328, and 332, according to the EU index. Preferable substitutions for enhancing FcγRIIb affinity include but are not limited to 234D, 234E, 234W, 235D, 235F, 235R,235Y, 236D, 236N, 237D, 237N, 239D, 239E, 266M, 267D, 267E, 268D, 268E, 327D, 327E, 328F, 328W, 328Y, and 332E. More preferably, substitutions include but are not limited to 235Y, 236D, 239D, 266M, 267E, 268D, 268E, 328F, 328W, and 328Y. Preferred Fc variants for enhancing binding to FcγRIIb include but are not limited to 235Y/267E, 236D/267E, 239D/268D, 239D/267E, 267E/268D, 267E/268E, and 267E/328F.

In some embodiments, the inventive multispecific antibody analogs disclosed herein may incorporate Fc variants that improve FcRn binding. Such variants may enhance the in vivo pharmacokinetic properties of the inventive multispecific antibody analogs. Preferred variants that increase binding to FcRn and/or improve pharmacokinetic properties include but are not limited to substitutions at positions 259, 308, 428, and 434, including but not limited to for example 259I, 308F, 428L, 428M, 434S, 434H, 434F, 434Y, 434M, 428L/434S, 259I/308F and 259I/308F/428L (and others described in U.S. Ser. No. 12/341,769, filed Dec. 22, 2008, entitled "Fc Variants with Altered Binding to FcRn"). Other variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/ 256E, 433K/434F/436H, 308T/309P/311S (Dall'Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671.

The inventive multispecific antibody analogs disclosed herein can incorporate Fc modifications in the context of any IgG isotype or IgG isotype Fc region, including but not limited to human IgG1, IgG2, IgG3, and/or IgG4. The IgG isotype may be selected such as to alter FcγR- and/or complement-mediated effector function(s). Hybrid IgG isotypes may also be useful. For example, US 2006-0134105 describes a number of hybrid IgG1/IgG2 constant regions that may find use in the particular invention. In some embodiments of the invention, inventive multispecific antibody analogs may comprise means for isotypic modifications, that is, modifications in a parent IgG to the amino acid type in an alternate IgG. For example, an IgG1/IgG3 hybrid variant may be constructed by a substitutional means for substituting IgG1 positions in the CH2 and/or CH3 region with the amino acids from IgG3 at positions where the two isotypes differ. Thus a hybrid variant IgG antibody may be constructed that comprises one or more substitutional means, e.g., 274Q, 276K, 300F, 339T, 356E, 358M, 384S, 392N, 397M, 4221, 435R, and 436F. In other embodiments of the invention, an IgG1/IgG2 hybrid variant may be constructed by a substitutional means for substituting IgG2 positions in the CH2 and/or CH3 region with amino acids from IgG1 at positions where the two isotypes differ. Thus a hybrid variant IgG antibody may be constructed that comprises one or more substitutional means, e.g., one or more of the following amino acid substations: 233E, 234L, 235L, −236G (referring to an insertion of a glycine at position 236), and 327A.

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide normally consists of GlcNAc2Man3GlcNAc, with differing numbers of outer residues.

The inventive multispecific antibody analogs herein may also comprise carbohydrate moieties, which moieties will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of inventive multispecific antibody analogs disclosed herein occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at residue 297.

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)2 typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the α1,4 mannose of the mature core carbohydrate structure. The bisecting GlcNAc can be enzymatically attached to the mature core carbohydrate structure by a α(1,4)-N-acetylglucosaminyltransferase III enzyme (GnTIII). CHO cells do not normally express GnTIII (Stanley et al., 1984, J. Biol. Chem. 261:13370-13378), but may be engineered to do so (Umana et al., 1999, Nature Biotech. 17:176-180).

Described herein are multispecific antibody analogs that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In one embodiment, the inventive multispecific antibody analogs disclosed herein are modified to control the level of fucosylated and/or bisecting oligosaccharides that are covalently attached to the Fc region.

A variety of methods are well known in the art for generating modified glycoforms (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Ser. No. 12/434,533). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α-1,6-fucosyltranserase] and/or I31-4-N-acetylglucosaminyltransferase III [GnTIII]), by modifying carbohydrate(s) after the IgG has been expressed, or by expressing antibody in the presence of fucose analogs as enzymatic inhibitors. Other methods for modifying glycoforms of the inventive multispecific antibody analogs disclosed herein include using glycoengineered strains of yeast (Li et al., 2006, Nature Biotechnology 24(2):210-215), moss (Nechansky et al., 2007, Mol Immunol 44(7):1826-8), and plants (Cox et al., 2006, Nat Biotechnol 24(12):1591-7). The use of a particular method to generate a modified glycoform is not meant to constrain embodiments to that method. Rather, embodiments disclosed herein encompass inventive multispecific antibody analogs with modified glycoforms irrespective of how they are produced.

In one embodiment, the inventive multispecific antibody analogs disclosed herein are glycoengineered to alter the level of sialylation. Higher levels of sialylated Fc glycans in immunoglobulin G molecules can adversely impact functionality (Scallon et al., 2007, Mol. Immunol. 44(7):1524-34), and differences in levels of Fc sialylation can result in modified anti-inflammatory activity (Kaneko et al., 2006, Science 313:670-673). Because antibodies may acquire anti-inflammatory properties upon sialylation of Fc core polysaccharide, it may be advantageous to glycoengineer the inventive multispecific antibody analogs disclosed herein for greater or reduced Fc sialic acid content.

"Engineered glycoform" typically refers to the different carbohydrate or oligosaccharide; thus for example an immunoglobulin may comprise an engineered glycoform. In one embodiment, a composition disclosed herein comprises a glycosylated inventive multispecific antibody analog having an Fc region, wherein about 51-100% of the glycosylated antibody, e.g., 80-100%, 90-100%, 95-100%, etc. of the antibody in the composition comprises a mature core carbohydrate structure which lacks fucose. In another embodiment, the antibody in the composition both comprises a mature core carbohydrate structure that lacks fucose and additionally comprises at least one amino acid modification in the Fc region. In an alternative embodiment, a composition comprises a glycosylated inventive multispecific antibody analog having an Fc region, wherein about 51-100% of the glycosylated antibody, 80-100%, or 90-100%, of the antibody in the composition comprises a mature core carbohydrate structure which lacks sialic acid. In another embodiment, the antibody in the composition both comprises a mature core carbohydrate structure that lacks sialic acid and additionally comprises at least one amino acid modification in the Fc region. In yet another embodiment, a composition comprises a glycosylated inventive multispecific antibody analog having an Fc region, wherein about 51-100% of the glycosylated antibody, 80-100%, or 90-100%, of the antibody in the composition comprises a mature core carbohydrate structure which contains sialic acid. In another embodiment, the antibody in the composition both comprises a mature core carbohydrate structure that contains sialic acid and additionally comprises at least one amino acid modification in the Fc region. In another embodiment, the combination of engineered glycoform and amino acid modification provides optimal Fc receptor binding properties to the antibody.

The inventive multispecific antibody analogs disclosed herein may comprise one or more modifications that provide additional optimized properties. Said modifications may be amino acid modifications, or may be modifications that are made enzymatically or chemically. Such modification(s) likely provide some improvement in the inventive multispecific antibody analog, for example an enhancement in its stability, solubility, function, or clinical use. Disclosed herein are a variety of improvements that may be made by coupling the inventive multispecific antibody analogs disclosed herein with additional modifications.

In one embodiment, at least one variable region of multispecific antibody analog disclosed herein may be affinity matured, that is to say that amino acid modifications have been made in the VH and/or VL domains to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Inventive multispecific antibody analogs disclosed herein may comprise one or more modifications that provide reduced or enhanced internalization of an inventive multispecific antibody analog.

In other embodiments, modifications are made to improve biophysical properties of the inventive multispecific antibody analogs disclosed herein, including but not limited to stability, solubility, and oligomeric state. Modifications can include, for example, substitutions that provide more favorable intramolecular interactions in the inventive multispecific antibody analog such as to provide greater stability, or substitution of exposed nonpolar amino acids with polar amino acids for higher solubility. Other modifications to the inventive multispecific antibody analogs disclosed herein include those that enable the specific formation or homodimeric or homomultimeric molecules. Such modifications include but are not limited to engineered disulfides, as well as chemical modifications or aggregation methods.

In further embodiments, the inventive multispecific antibody analogs disclosed herein comprise modifications that remove proteolytic degradation sites. These may include, for example, protease sites that reduce production yields, as well as protease sites that degrade the administered protein in vivo. In one embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains, acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO, HEK, COS, NIH LT3, Saos, and the like), yeast cells, bacterial cells, and plant cells. Additional modifications include modifications that remove or reduce the ability of heavy chains to form inter-chain disulfide linkages. Additional modifications include modifications that remove or reduce the ability of heavy chains to form intra-chain disulfide linkages.

The inventive multispecific antibody analogs disclosed herein may comprise modifications that include the use of unnatural amino acids incorporated using, including but not limited to methods described in Liu & Schultz, 2010, Annu Rev Biochem 79:413-444. In some embodiments, these modifications enable manipulation of various functional, biophysical, immunological, or manufacturing properties discussed above. In additional embodiments, these modifications enable additional chemical modification for other purposes.

Other modifications are contemplated herein. For example, the inventive multispecific antibody analogs may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the inventive multispecific antibody analogs. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the inventive multispecific antibody analogs disclosed herein.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody disclosed herein.

Covalent modifications are included within the scope of inventive multispecific antibody analogs disclosed herein, and are generally, but not always, done post-translationally. For example, several types of covalent modifications can be introduced into the molecule by reacting specific amino acid residues with an organic derivatizing agent that is capable of reacting with selected side chains or the N- or C-terminal residues. In some embodiments, the covalent modification of the inventive multispecific antibody analogs disclosed herein comprises the addition of one or more labels. The term "labeling group" means any detectable label. In some embodiments, the labeling group is coupled to the inventive multispecific antibody analog via spacer arms of various lengths to reduce potential steric hindrance. Various methods for labeling proteins are known in the art and may be used in generating inventive multispecific antibody analogs disclosed herein.

In certain embodiments, the inventive multispecific antibody analogs disclosed herein comprise "fusion proteins", also referred to herein as "conjugates". The fusion partner or conjugate partner can be proteinaceous or non-proteinaceous; the latter generally being generated using functional groups on the inventive multispecific antibody analog and on the conjugate partner. Conjugate and fusion partners may be any molecule, including small molecule chemical compounds and polypeptides. For example, a variety of conjugates and methods are described in Trail et al., 1999, Curr. Opin. Immunol. 11:584-588. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the multispecific antibody analogs. Thus, for example, the conjugation of a toxin to a multispecific antibody analog targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment disclosed herein. Rather, these terms are used to convey the broad concept that any multispecific antibody analogs disclosed herein may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to inventive multispecific antibody analog, or binding of a radionuclide to a chelating agent that has been covalently attached to the inventive multispecific antibody analog. Additional embodiments utilize calicheamicin, auristatins, geldanamycin, maytansine, and duocarmycins and analogs. Antibody-drug conjugates are described in Alley et al., 2010, Curr Opin Chem Biol 14[4]:529-37.

In certain embodiments, the inventive multispecific antibody analogs disclosed herein are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, cytokines may be fused to an inventive multispecific antibody analog to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In further embodiments, the inventive multispecific antibody analogs disclosed herein may be conjugated to a "receptor" (such streptavidin) for utilization in tumor pretargeting wherein the analog-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the inventive multispecific antibody analog is conjugated or operably linked to an enzyme in order to employ Antibody Dependent Enzyme Mediated Prodrug Therapy (ADEPT). ADEPT may be used by conjugating or operably linking the inventive multispecific antibody analog to a prodrug-activating enzyme that converts a prodrug (e.g. a peptidyl chemotherapeutic agent.

Also disclosed herein are methods for producing and experimentally testing the inventive multispecific antibody analogs. The disclosed methods are not meant to constrain embodiments to any particular application or theory of operation. Rather, the provided methods are meant to illustrate generally that one or more multispecific antibody analogs of the invention may be produced and experimentally tested to obtain inventive multispecific antibody analogs. General methods for antibody molecular biology, expression, purification, and screening are described in Antibody Engineering, edited by Kontermann & Dubel, Springer, Heidelberg, 2001; and Hayhurst & Georgiou, 2001, Curr Opin Chem Biol 5:683-689; Maynard & Georgiou, 2000, Annu Rev Biomed Eng 2:339-76.

In one embodiment disclosed herein, nucleic acids are created that encode the inventive multispecific antibody analogs, and that may then be cloned into host cells, such as yeast cells or mammalian cells, expressed and assayed, if desired. Thus, nucleic acids, and particularly DNA, may be made that encode each protein sequence. These practices are carried out using well-known procedures. For example, a variety of methods that may find use in generating inventive multispecific antibody analogs disclosed herein are described in Molecular Cloning-A Laboratory Manual, 3rd Ed. (Maniatis, Cold Spring Harbor Laboratory Press, New York, 2001), and Current Protocols in Molecular Biology (John Wiley & Sons). There are a variety of techniques that may be used to efficiently generate DNA encoding inventive multispecific antibody analogs disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode inventive multispecific antibody analogs.

The inventive multispecific antibody analogs disclosed herein may be produced by culturing a host cell transformed with nucleic acid, e.g., expression vectors containing nucleic acid encoding the first and second polypeptides of inventive multispecific antibody analogs, under the appropriate conditions to induce or cause expression of the polypeptides. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast cells, and plant cells. For example, a variety of cell lines that may find use in generating inventive multispecific antibody analogs disclosed herein are described in the ATCC® cell line catalog, available from the American Type Culture Collection.

In certain embodiments, the inventive multispecific antibody analogs are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NS0 cells and variants thereof. In an alternate embodiment, library proteins are expressed in bacterial cells. Bacterial expression systems are well known in the art, and include Escherichia coli (E. coli), Bacillus subtilis, Streptococcus cremoris, and Streptococcus lividans. In alternate embodiments, inventive multispecific antibody analogs are produced in insect cells (e.g. Sf21/Sf9, Trichoplusia ni Bti-Tn5b1-4) or yeast cells (e.g. S. cerevisiae, Pichia, etc.). In an alternate embodiment, inventive multispecific antibody analogs are expressed in vitro using cell free translation systems. In vitro translation systems derived from both prokaryotic (e.g. E. coli) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the inventive multispecific antibody analogs may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the first and second polypeptides of inventive multispecific antibody analogs disclosed herein may be incorporated into one or more expression vectors, as appropriate, in order to express the encoded polypeptides. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in generating inventive multispecific antibody analogs disclosed herein include but are not limited to those which enable protein expression in mammalian cells, bacteria, insect cells, yeast cells, and in vitro systems. As is known in the art, a variety of expression vectors are available, commercially or otherwise, that may find use for expressing inventive multispecific antibody analogs disclosed herein.

Expression vectors typically comprise a protein or polypeptide to be expressed, which is operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the inventive multispecific antibody analog, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

The first and second polypeptides of the invention may each be independently operably linked to a fusion partner to enable targeting of the expressed polypeptide and/or multispecific antibody analog, purification, screening, display, and the like. Fusion partners may be linked to the inventive multispecific antibody analog sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS (SEQ ID NO: 94). A fusion partner may be a targeting or signal sequence that directs inventive multispecific antibody analog and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ (SEQ ID NO: 95) and $H_{10}$ (SEQ ID NO: 96) or other tags for use with Immobilized Metal Affinity Chromatography (IMAC) systems (e.g. Ni+2 affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an inventive multispecific antibody analog may be purified using a His-tag by immobilizing it to a Ni+2 affinity column, and then after purification the same His-tag may be used to immobilize the antibody to a Ni+2 coated plate to perform an ELISA or other binding assay (as described below). A fusion partner may enable the use of a selection method to screen inventive multispecific antibody analogs (see below). Fusion partners that enable a variety of selection methods are well-known in the art.

For example, by fusing the members of an inventive multispecific antibody analog library to the gene 11 protein, phage display can be employed. Fusion partners may enable inventive multispecific antibody analogs to be labeled. Alternatively, a fusion partner may bind to a specific sequence on the expression vector, enabling the fusion partner and associated inventive multispecific antibody analog to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In certain embodiments, the multispecific antibody analogs are purified or isolated after expression. The multispecific antibody analogs may be isolated or purified in a variety of ways known to those skilled in the art. Purification may be particularly useful in the invention for separating heterodimeric heavy chain species from homodimeric heavy chain species, as described herein. Standard purification methods include chromatographic techniques, including ion exchange, hydrophobic interaction, affinity, sizing or gel filtration, and reversed-phase, carried out at atmospheric pressure or at high pressure using systems such as FPLC or HPLC. Purification methods also include electrophoretic, isoelectric focusing, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of inventive multispecific antibody analogs disclosed herein. For example, the bacterial proteins A and G bind to the Fc region. Likewise, the bacterial protein L binds to the Fab region of some antibodies, as of course does the antibody's target antigen. Purification can often be enabled by a particular fusion partner. For example, inventive multispecific antibody analogs may be purified using glutathione resin if a GST fusion is employed, Ni+2 affinity chromatography if a His-tag is employed, or immobilized anti-flag antibody if a flag-tag is used. For general guidance in suitable purification techniques, see, e.g. Protein Purification: Principles and Practice, 3rd Ed., Scopes, Springer-Verlag, NY, 1994. The degree of purification necessary will vary depending on the screen or use of the inventive multispecific antibody analogs. In some instances no purification is necessary. For example in one embodiment, if the inventive multispecific antibody analogs are secreted, screening may take place directly from the media. As is well known in the art, some methods of selection do not involve purification of proteins.

Virtually any antigen may be targeted by the inventive multispecific antibody analogs disclosed herein, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CAI25, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PG12, PGJ2, PIN, PLA2, placental alkaline phosphatase (FLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular FLAP-like alkaline phosphatase, TfR, TGF, TGF-alpha, TGF-beta, TGF-beta Pan Specific, TGF-beta RI (ALK-5), TGF-beta RII, TGF-beta RII, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1Apo-2, DR4), TNFRSF10B (TRAIL R2DRS, KILLER, TRICK-2A, TRICK-B), TNFRSF10C (TRAIL R3DcRI, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2TNFRH2), TNFRST23 (DcTRAIL RITNFRHI), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRILT-ALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

Exemplary antigens that may be targeted specifically by the multispecific antibody analogs of the invention include but are not limited to: CD20, CD19, Her2, EGFR, EpCAM, c-MET, CD3, FcγRIIIa (CD16), FcγRIIa (CD32a), FcγRIIb (CD32b), FcγRI (CD64), Toll-like receptors (TLRs) such as TLR4 and TLR9, cytokines such as IL-2, IL-5, IL-13, IL-12, IL-23, and TNFα, cytokine receptors such as IL-2R, chemokines, chemokine receptors, growth factors such as VEGF and HGF, and the like.

The choice of suitable target antigens and co-targets depends on the desired therapeutic application. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. The choice of co-targets will depend on the detailed biology underlying the pathology of the indication that is being treated.

Monoclonal antibody therapy has emerged as an important therapeutic modality for cancer (Weiner et al., 2010, Nature Reviews Immunology 10:317-327; Reichert et al., 2005, Nature Biotechnology 23[9]:1073-1078). For anticancer treatment it may be desirable to target one antigen (antigen-1) whose expression is restricted to the cancerous cells while co-targeting a second antigen (antigen-2) that mediates some immunological killing activity. For other treatments it may be beneficial to co-target two antigens, for example two angiogenic factors or two growth factors that are each known to play some role in proliferation of the tumor. Exemplary co-targets for oncology include but are not limited to HGF and VEGF, IGF-1R and VEGF, Her2 and VEGF, CD19 and CD3, CD20 and CD3, Her2 and CD3, CD19 and FcγRIIIa, CD20 and FcγRIIIa, Her2 and FcγRIIIa. An inventive multispecific antibody analog of the invention may be capable of binding VEGF and phosphatidylserine; VEGF and ErbB3; VEGF and PLGF; VEGF and ROBO4; VEGF and BSG2; VEGF and CDCP1; VEGF and ANPEP; VEGF and c-MET; HER-2 and ERB3; HER-2 and BSG2; HER-2 and CDCP1; HER-2 and ANPEP; EGFR and CD64; EGFR and BSG2; EGFR and CDCP1; EGFR and ANPEP; IGF1R and PDGFR; IGF1R and VEGF; IGF1R and CD20; CD20 and CD74; CD20 and CD30; CD20 and DR4; CD20 and VEGFR2; CD20 and CD52; CD20 and CD4; HGF and c-MET; HGF and NRP1; HGF and phosphatidylserine; ErbB3 and IGF1R; ErbB3 and IGF1,2; c-Met and Her-2; c-Met and NRP1; c-Met and IGF1R; IGF1,2 and PDGFR; IGF1,2 and CD20; IGF1,2 and IGF1R; IGF2 and EGFR; IGF2 and HER2; IGF2 and CD20; IGF2 and VEGF; IGF2 and IGF1R; IGF1 and IGF2; PDGFRa and VEGFR2; PDGFRa and PLGF; PDGFRa and VEGF; PDGFRa and c-Met; PDGFRa and EGFR; PDGFRb and VEGFR2; PDGFRb and c-Met; PDGFRb and EGFR; RON and c-Met; RON and MTSP1; RON and MSP; RON and CDCP1; VGFR1 and PLGF; VGFR1 and RON; VGFR1 and EGFR; VEGFR2 and PLGF; VEGFR2 and NRP1; VEGFR2 and RON; VEGFR2 and DLL4; VEGFR2 and EGFR; VEGFR2 and ROBO4; VEGFR2 and CD55; LPA and S1 P; EPHB2 and RON; CTLA4 and VEGF; CD3 and EPCAM; CD40 and IL6; CD40 and IGF; CD40 and CD56; CD40 and CD70; CD40 and VEGFR1; CD40 and DR5; CD40 and DR4; CD40 and APRIL; CD40 and BCMA; CD40 and RANKL; CD28 and MAPG; CD80 and CD40; CD80 and CD30; CD80 and CD33; CD80 and CD74; CD80 and CD2; CD80 and CD3; CD80 and CD19; CD80 and CD4; CD80 and CD52; CD80 and VEGF; CD80 and DR5; CD80 and VEGFR2; CD22 and CD20; CD22 and CD80; CD22 and CD40; CD22 and CD23; CD22 and CD33; CD22 and CD74; CD22 and CD19; CD22 and DR5; CD22 and DR4; CD22 and VEGF; CD22 and CD52; CD30 and CD20; CD30 and CD22; CD30 and CD23; CD30 and CD40; CD30 and VEGF; CD30 and CD74; CD30 and CD19; CD30 and DR5; CD30 and DR4; CD30 and VEGFR2; CD30 and CD52; CD30 and CD4; CD138 and RANKL; CD33 and FTL3; CD33 and VEGF; CD33 and VEGFR2; CD33 and CD44; CD33 and DR4; CD33 and DR5; DR4 and CD137; DR4 and IGF1,2; DR4 and IGF1R; DR4 and DR5; DR5 and CD40; DR5 and CD137; DR5 and CD20; DR5 and EGFR; DR5 and IGF1,2; DR5 and IGFR, DR5 and HER-2, and EGFR and DLL4. Other target combinations include one or more members of the EGF/erb-2/erb-3 family.

Other targets (one or more) involved in oncological diseases that the multispecific antibody analogs disclosed herein may bind include, but are not limited to those selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, I1L12A, IL1A, IL1B, 1L2, INHA, TGFA, TGFB1, TGFB2, TGFB3, VEGF, CDK2, FGF10, FGF18, FGF2, FGF4, FGF7, IGF1R, IL2, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFBIII, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR113, NR2F6, NR4A3, ESR1, ESR2, NROB1, NROB2, NR1D2, NR1H2, NR1H4, NR112, NR2C1, NR2C2, NR2E1, NR2E3, NR2F1, NR2F2, NR3C1, NR3C2, NR4A1, NR4A2, NR5A1, NR5A2, NR6 μl, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFBIII, AGR2, AIG1, AKAP1, AKAP2, CANT1, CAVI, CDH12, CLDN3, CLN3, CYB5, CYC1, DAB21P, DES, DNCL1, ELAC2, ENO2, ENO3, FASN, FU12584, FU25530, GAGEBI, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33 μl, SLC43 μl, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDCI, STAB 1, VEGF, VEGFC, ANGPTL3, BA11, COL4A3, IL8, LAMA5, NRP1, NRP2, STAB 1, ANGPTL4, PECAMI, PF4, PROK2, SERPINFI, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL1A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MK167 (Ki-67), NGFB (GF), NGFR, NME1 (M23A), PGR, PLAU (uPA), PTEN, SERPINB5 (maspin), SERPINE1 (PAl-1), TGFA, THBS1 (thrombospondin-1), TIE (Tie-1), TNFRSF6 (Fas), TNFSF6 (FasL), TOP2A (topoisomerase IIa), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, 1D2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-111), MUC1 (mucin), PTGS2 (COX-2), RAC2 (p21Rac2), S100A2, SCGBID2 (lipophilin B), SCGB2A1 (mammaglobin 2), SCGB2A2 (mammaglobin 1), SPRR1B (Spr1), THBS1, THBS2, THBS4, and TNFAIP2 (B94), RON, c-Met, CD64, DLL4, PLGF, CTLA4, phophatidylserine, ROBO4, CD80, CD22, CD40, CD23, CD28, CD80, CD55, CD38, CD70, CD74, CD30, CD138, CD56, CD33, CD2, CD137, DR4, DR5, RANKL, VEGFR2, PDGFR, VEGFR1, MTSP1, MSP, EPHB2, EPHA1, EPHA2, EpCAM, PGE2, NKG2D, LPA, SIP, APRIL, BCMA, MAPG, FLT3, PDGFR alpha, PDGFR beta, ROR1, PSMA, PSCA, SCD1, and CD59.

Monoclonal antibody therapy has become an important therapeutic modality for treating autoimmune and inflammatory disorders (Chan & Carter, 2010, Nature Reviews Immunology 10:301-316; Reichert et al., 2005, Nature Biotechnology 23[9]:1073-1078). Many proteins have been implicated in general autoimmune and inflammatory responses, and thus may be targeted by the inventive multispecific antibody analogs of the invention. Autoimmune and inflammatory targets include but are not limited to C5, CCL1 (1-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (1P-10), CXCL11 (1-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, 10, 1L13, 1L17C, IL1A, IL1B, IL1F10, 1L1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, I11, IL12RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFBII1, TGFB2, TGFB3, TGFB1, TGFBR1, TGFBR2, TGFB3, TH1L, TNF, TNFRSF1A, TNFRSF1B, TNFRSF7, TNFRSF8, TNFRSF9, TNFRSFIIA, TNFRSF21, TNFSF4, TNFSF5, TNFSF6, TNFSFII, VEGF, ZFPM2, and RNF110 (ZNF144).

Exemplary co-targets for autoimmune and inflammatory disorders include but are not limited to IL-1 and TNFalpha, IL-6 and TNFalpha, IL-6 and IL-1, IgE and IL-13, IL-1 and IL-13, IL-4 and IL-13, IL-5 and IL-13, IL-9 and IL-13, CD19 and FcγRIIb, and CD79 and FcγRIIb.

Multispecific antibody analogs of the invention with specificity for the following pairs of targets to treat inflammatory disease are contemplated: TNF and IL-17A; TNF and RANKL; TNF and VEGF; TNF and SOST; TNF and DKK; TNF and alphaVbeta3; TNF and NGF; TNF and IL-23p19; TNF and IL-6; TNF and SOST; TNF and IL-6R; TNF and CD-20; IgE and IL-13; IL-13 and IL23p19; IgE and IL-4; IgE and IL-9; IgE and IL-9; IgE and IL-13; IL-13 and IL-9; IL-13 and IL-4; IL-13 and IL-9; IL-13 and IL-9; IL-13 and IL-4; IL-13 and IL-23p19; IL-13 and IL-9; IL-6R and VEGF; IL-6R and IL-17A; IL-6R and RANKL; IL-17A and IL-1 beta; IL-1 beta and RANKL; IL-1beta and VEGF; RANKL and CD-20; IL-1alpha and IL-1 beta; IL-1 alpha and IL-1beta.

Pairs of targets that the multispecific antibody analogs described herein can bind and be useful to treat asthma may be determined. In an embodiment, such targets include, but are not limited to, IL-13 and IL-1 beta, since IL-1 beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-13; IL-13 and LHR agonist; IL-13 and CL25; IL-13 and SPRR2a; IL-13 and SPRR2b; and IL-13 and ADAMS. The inventive multispecific antibody analogs herein may have specificity for one or more targets involved in asthma selected from the group consisting of CSF1 (MCSF), CSF2 (GM-CSF), CSF3 (GCSF), FGF2, IFNA1, IFNB1, IFNG, histamine and histamine receptors, ILiA, IL1 B, IL2, IL3, IL4, IL5, IL6, IL7, IL8, IL9, I10, I11, IL12A, IL12B, IL13, IL14, IL15, IL16, IL17, I18, IL19, KITLG, PDGFB, IL2RA, IL4R, IL5RA, IL8RA, IL8RB, IL12RB1, IL12RB2, IL13RA1, IL13RA2, IL18R1, TSLP, CCLi, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCLi, CCR2, CCR3, CCR4, CCR5, CCR6, CCR7, CCR8, CX3CR1, GPR2, XCR1, FOS, GATA3, JAK1, JAK3, STATE, TBX21, TGFB1, TNF, TNFSF6, YY1, CYSLTR1, FCER1A, FCER2, LTB4R, TB4R2, LTBR, and Chitinase.

Pairs of targets involved in rheumatoid arthritis (RA) may be co-targeted by the invention, including but not limited to TNF and IL-18; TNF and IL-12; TNF and IL-23; TNF and 1L-1beta; TNF and MIF; TNF and IL-17; and TNF and IL-15.

Antigens that may be targeted in order to treat systemic lupus erythematosus (SLE) by the inventive multispecific antibody analogs herein include but are not limited to CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGSI, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, I11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, ILIR2, ITGA2, ITGA3, MS4A1, ST6GALI, CDIC, CHSTIO, HLA-A, HLA-DRA, and NT5E.; CTLA4, B7.1, B7.2, BlyS, BAFF, C5, IL-4, IL-6, IL-10, IFN-α, and TNF-α.

The inventive multispecific antibody analogs herein may target antigens for the treatment of multiple sclerosis (MS), including but not limited to IL-12, TWEAK, IL-23, CXCL13, CD40, CD40L, IL-18, VEGF, VLA-4, TNF, CD45RB, CD200, IFNgamma, GM-CSF, FGF, C5, CD52, and CCR2. An embodiment includes co-engagement of anti-IL-12 and TWEAK for the treatment of MS.

One aspect of the invention pertains to inventive multispecific antibody analogs capable of binding one or more targets involved in sepsis, in an embodiment two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL-10, IL-1B, NFκB1, PROC, TNFRSFIA, CSF3, CCR3, ILIRN, MIF, NFκB1, PTAFR, TLR2, TLR4, GPR44, HMOX1, midkine, IRAK1, NFκB2, SERPINA1, SERPINE1, and TREM1.

In some cases, inventive multispecific antibody analogs herein may be directed against antigens for the treatment of infectious diseases.

The inventive multispecific antibody analogs may be screened using a variety of in vitro methods, including but not limited to those that use binding assays, cell-based assays, and selection technologies. Automation and high-throughput screening technologies may be utilized in the screening procedures. Screening may employ the use of a fusion partner or label. The use of fusion partners has been discussed above. By "labeled" herein is meant that the inventive multispecific antibody analogs disclosed herein have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In certain embodiments, the functional and/or biophysical properties of the inventive multispecific antibody analogs are screened in an in vitro assay. In vitro assays may allow a broad dynamic range for screening properties of interest. Particularly relevant for the present invention, the inventive multispecific antibody analogs may be tested for their affinity for one or more antigens. Properties that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of inventive multispecific antibody analogs to a protein or nonprotein molecule that is known or thought to bind the inventive multispecific antibody analog. In one embodiment, the screen is a binding assay for measuring binding to the target antigen. In an alternate embodiment, the screen is an assay for binding of inventive multispecific antibody analogs to an Fc ligand, including but are not limited to the family of FcγRs, the neonatal receptor FcRn, the complement protein C1q, and the bacterial proteins A and G. Said Fc ligands may be from any organism. In one embodiment, Fc ligands are from humans, mice, rats, rabbits, and/or monkeys. Binding assays can be carried out using a variety of methods known in the art, including but not limited to FRET (Fluorescence Resonance Energy Transfer) and BRET (Bioluminescence Resonance Energy Transfer)-based assays, ALPHASCREEN® assay (Amplified Luminescent Proximity Homogeneous Assay), Scintillation Proximity Assay, ELISA (Enzyme-Linked Immunosorbent Assay), SPR (Surface Plasmon Resonance, also known as BIACORE® assay), isothermal titration calorimetry, differential scanning calorimetry, gel electrophoresis, and chromatography including gel filtration. These and other methods may take advantage of some fusion partner or label of the inventive multispecific antibody analog. Assays may employ a variety of detection methods including but not limited to chromogenic, fluorescent, luminescent, or isotopic labels.

The biophysical properties of the inventive multispecific antibody analogs, for example stability and solubility, may be tested using a variety of methods known in the art. Protein stability may be determined by measuring the thermodynamic equilibrium between folded and unfolded states. For example, inventive multispecific antibody analogs disclosed herein may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an inventive multispecific antibody analog may be quantitatively or qualitatively determined using a wide range of methods that are known in the art. Methods which may find use for characterizing the biophysical properties of inventive multispecific antibody analogs disclosed herein include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an inventive multispecific antibody analog could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the inventive multispecific antibody analog's stability and solubility.

In certain embodiments, the inventive multispecific antibody analogs may be tested using one or more cell-based or in vitro assays. For such assays, inventive multispecific antibody analogs, purified or unpurified, are typically added exogenously such that cells are exposed to inventive multispecific antibody analogs described herein. These assays are typically, but not always, based on the biology of the ability of the inventive multispecific antibody analog to bind to the target antigen and mediate some biochemical event, for example effector functions like cellular lysis, phagocytosis, ligand/receptor binding inhibition, inhibition of growth and/or proliferation, inhibition of calcium release and/or signaling, apoptosis and the like. Such assays often involve monitoring the response of cells to inventive multispecific antibody analog, for example cell survival, cell death, cellular phagocytosis, cell lysis, change in cellular morphology, or transcriptional activation such as cellular expression of a natural gene or reporter gene. For example, such assays may measure the ability of inventive multispecific antibody analogs to elicit cell killing, for example ADCC, ADCP, and CDC. Assays that measure cellular killing that is mediated by co-engagement of antigens are particularly relevant for the invention. For some assays additional cells or components, that is in addition to the target cells, may need to be added, for example serum complement, or effector cells such as peripheral blood monocytes (PBMCs), NK cells, macrophages, T cells, and the like. Such additional cells may be from any organism, e.g., humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In one embodiment, the DELFIA® EuTDA-based cytotoxicity assay (PERKINELMER®, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an inventive multispecific antibody analog. Cell types for such assays may be prokaryotic or eukaryotic, and a variety of cell lines that are known in the art may be employed. Alternatively, cell-based screens are performed using cells that have been transformed or transfected with nucleic acids encoding the inventive multispecific antibody analogs.

The biological properties of the inventive multispecific antibody analogs disclosed herein may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the inventive multispecific antibody analogs disclosed herein, a particular challenge arises when using animal models to evaluate the potential for in-human efficacy of candidate polypeptides—this is due, at least in part, to the fact that inventive multispecific antibody analogs that have a specific effect on the affinity for a human Fc receptor may not have a similar affinity effect with the orthologous animal receptor. These problems can be further exacerbated by the inevitable ambiguities associated with correct assignment of true orthologues (Mechetina et al., 2002, Immunogenetics 54:463-468), and the fact that some orthologues simply do not exist in the animal. Therapeutics are often tested in mice, including but not limited to nude mice, Rag-deficient mice, SCID mice, xenograft mice, and transgenic mice (including knockins and knockouts). For example, an inventive multispecific antibody analog of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the drug to reduce or inhibit cancer growth and metastasis. Therapeutic inventive multispecific antibody analogs herein can be tested in mouse strains NZB, NOD, BXSB, MRL/lpr, K/BxN and transgenics (including knockins and knockouts). Such mice can develop various autoimmune conditions that resemble human organ specific, systemic autoimmune or inflammatory disease pathologies such as systemic lupus erythematosus (SLE) and rheumatoid arthritis (RA). For example, an inventive multispecific antibody analog disclosed herein intended for autoimmune diseases may be tested in such mouse models by treating the mice to determine the ability of the inventive multispecific antibody analog to reduce or inhibit the development of the disease pathology. Because of the incompatibility between the mouse and human Fcy receptor system, an alternative approach is to use a murine SCID model in which immune deficient mice are engrafted with human PBLs or PBMCs (huPBL-SCID, huPBMC-SCID) providing a semi-functional human immune system with human effector cells and Fc receptors. Other organisms, e.g., mammals, may also be used for testing. For example, because of their genetic similarity to humans, monkeys can be suitable therapeutic models, and thus may be used to test the efficacy, toxicity, pharmacokinetics, or other property of the inventive multispecific antibody analogs disclosed herein. Tests of the inventive multispecific antibody analogs disclosed herein in humans are ultimately required for approval as drugs, and thus of course these experiments are contemplated. Thus the inventive multispecific antibody analogs disclosed herein may be tested in humans to determine their therapeutic efficacy, toxicity, pharmacokinetics, and/or other clinical properties.

In some embodiments, inventive multispecific antibody analogs disclosed herein may be assessed for efficacy in clinically relevant animal models of various human diseases. In many cases, relevant models include various transgenic animals for specific antigens and receptors.

In certain embodiments, the testing of inventive multispecific antibody analogs may include study of efficacy in primates (e.g. cynomolgus monkey model) to facilitate the evaluation of depletion of specific target cells harboring the target antigen. Additional primate models include but are not limited to use of the rhesus monkey to assess inventive multispecific antibody analogs in therapeutic studies of autoimmune, transplantation and cancer.

Toxicity studies are performed to determine drug related-effects that cannot be evaluated in standard pharmacology profiles, or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated, is evaluated for cross-reactivity with normal tissues, immunogenicity/antibody production, conjugate or linker toxicity and "bystander" toxicity of radiolabelled species. Nonetheless, such studies may have to be individualized to address specific concerns and following the guidance set by ICH S6 (Safety studies for biotechnological products, also noted above). As such, the general principles are that the products are sufficiently well characterized, impurities/contaminants have been removed, that the test material is comparable throughout development, and that GLP compliance is maintained.

The pharmacokinetics (PK) of the inventive multispecific antibody analogs disclosed herein may be studied in a variety of animal systems, with the most relevant being non-human primates such as the cynomolgus and rhesus monkeys. Single or repeated i.v./s.c. administrations over a dose range of 6000-fold (0.05-300 mg/kg) can be evaluated for half-life (days to weeks) using plasma concentration and clearance. Volume of distribution at a steady state and level of systemic absorbance can also be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T½). Additional measured parameters could include compartmental analysis of concentration-time data obtained following i.v. administration and bioavailability.

Pharmacodynamic studies may include, but are not limited to, targeting specific cells or blocking signaling mechanisms, measuring inhibition of antigen-specific antibodies etc. The inventive multispecific antibody analogs disclosed herein may target particular effector cell populations and thereby be direct drugs to induce certain activities to improve potency or to increase penetration into a particularly favorable physiological compartment. Such pharmacodynamic effects may be demonstrated in animal models or in humans.

The inventive multispecific antibody analogs disclosed herein may find use in a wide range of products. In one embodiment an inventive multispecific antibody analog disclosed herein comprise a therapeutic, a diagnostic, or a research reagent. The inventive multispecific antibody analogs may find use in a composition that is monoclonal or polyclonal. The inventive multispecific antibody analogs disclosed herein may be used for therapeutic purposes. As will be appreciated by those in the art, the inventive multispecific antibody analogs disclosed herein may be used for any therapeutic purpose that antibodies, Fc fusions, and the like may be used for. The inventive multispecific antibody analogs may be administered to a patient to treat disorders including but not limited to cancer, infectious diseases, autoimmune and inflammatory diseases.

A "patient" for the purposes disclosed herein includes both humans and other animals, e.g., other mammals. Thus the inventive multispecific antibody analogs disclosed herein have both human therapy and veterinary applications. The term "treatment" or "treating" as disclosed herein is meant to include therapeutic treatment, as well as prophylactic, or suppressive measures for a disease or disorder. Thus, for example, successful administration of an inventive multispecific antibody analog prior to onset of the disease results in treatment of the disease. As another example, successful administration of an optimized inventive multispecific antibody analog after clinical manifestation of the disease to combat the symptoms of the disease comprises treatment of the disease. "Treatment" and "treating" also encompasses administration of an optimized inventive multispecific antibody analog after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, the inventive multispecific antibody analogs disclosed herein are administered to a patient having a disease involving inappropriate expression of a protein or other molecule. Within the scope disclosed herein this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the inventive multispecific antibody analogs disclosed herein.

The inventive multispecific antibody analogs herein may be used to treat cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non- Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (e.g. nasopharyngeal cancer, salivary gland carcinoma, and esophagael cancer), lung (e.g. small-cell lung cancer, non-small cell lung cancer, adenocarcinoma of the lung and squamous carcinoma of the lung), digestive system (e.g. gastric or stomach cancer including gastrointestinal cancer, cancer of the bile duct or biliary tract, colon cancer, rectal cancer, colorectal cancer, and anal carcinoma), reproductive system (e.g. testicular, penile, or prostate cancer, uterine, vaginal, vulval, cervical, ovarian, and endometrial cancer), skin (e.g. melanoma, basal cell carcinoma, squamous cell cancer, actinic keratosis), liver (e.g. liver cancer, hepatic carcinoma, hepatocellular cancer, and hepatoma), bone (e.g. osteoclastoma, and osteolytic bone cancers) additional tissues and organs (e.g. pancreatic cancer, bladder cancer, kidney or renal cancer, thyroid cancer, breast cancer, cancer of the peritoneum, and Kaposi's sarcoma), and tumors of the vascular system (e.g. angiosarcoma and hemagiopericytoma).

The inventive multispecific antibody analogs disclosed herein may be used to treat autoimmune diseases. By "autoimmune diseases" herein include allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune dysfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

The inventive multispecific antibody analogs disclosed herein may be used to treat inflammatory disorders. By "inflammatory disorders" herein include acute respiratory distress syndrome (ARDS), acute septic arthritis, adjuvant arthritis, juvenile idiopathic arthritis, allergic encephalomyelitis, allergic rhinitis, allergic vasculitis, allergy, asthma, atherosclerosis, chronic inflammation due to chronic bacterial or viral infections, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

Some autoimmune and inflammatory diseases that may be targeted by the inventive multispecific antibody analogs disclosed herein include Systemic Lupus Erythematosus, Rheumatoid arthritis, Sjogren's syndrome, Multiple sclerosis, Idiopathic thrombocytopenic purpura (ITP), Graves disease, Inflammatory bowel disease, Psoriasis, Type I diabetes, and Asthma.

The inventive multispecific antibody analogs herein may be used to treat infectious diseases. By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infectious diseases may also be caused by bacteria including *Bacillus antracis, Borrelia burgdorferi, Campylobacter jejuni, Chlamydia trachomatis, Clostridium botulinum, Clostridium tetani*, Diptheria, *E. coli, Legionella, Helicobacter pylori, Mycobacterium rickettsia, Mycoplasma nesisseria*, Pertussis, *Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, leishmania, malaria, rickettsia, trypanosoma, and the like.

Furthermore, inventive multispecific antibody analogs disclosed herein may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological and neurodegenerative conditions such as Alzheimer's disease.

Pharmaceutical compositions are contemplated wherein an inventive multispecific antibody analog disclosed herein and one or more therapeutically active agents are formulated. Formulations of the inventive multispecific antibody analogs disclosed herein are prepared for storage by mixing said inventive multispecific antibody analog having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN®, PLURONICS® or polyethylene glycol (PEG). In one embodiment, the pharmaceutical composition that comprises the inventive multispecific antibody analog disclosed herein may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Some embodiments include at least one of the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration may be sterile. This is readily accomplished by filtration through sterile filtration membranes or other methods.

The inventive multispecific antibody analogs disclosed herein may also be formulated as immunoliposomes. A liposome is a small vesicle comprising various types of lipids, phospholipids and/or surfactant that is useful for delivery of a therapeutic agent to a mammal. Liposomes containing the inventive multispecific antibody analog are prepared by methods known in the art. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

An inventive multispecific antibody analog and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(−)-3-hydroxybutyric acid, and PROLEASE™ (commercially available from ALKERMES®), which is a microsphere-based delivery system composed of the desired bioactive molecule incorporated into a matrix of poly-DL-lactide-co-glycolide (PLG).

Administration of the pharmaceutical composition comprising an inventive multispecific antibody analog disclosed herein, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the inventive multispecific antibody analog may be directly applied as a solution or spray. As is known in the art, the pharmaceutical composition may be formulated accordingly depending upon the manner of introduction.

Subcutaneous administration may be used in circumstances where the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate. Inventive multispecific antibody analogs disclosed herein may be more amenable to subcutaneous administration due to, for example, increased potency, improved serum half-life, or enhanced solubility. As is known in the art, protein therapeutics are often delivered by IV infusion or bolus. The inventive multispecific antibody analogs disclosed herein may also be delivered using such methods. For example, administration may be by intravenous infusion with 0.9% sodium chloride as an infusion vehicle.

Pulmonary delivery may be accomplished using an inhaler or nebulizer and a formulation comprising an aerosolizing agent. For example, AERX® inhalable technology commercially available from ARADIGM®, or INHANCE™ pulmonary delivery system commercially available from NEKTAR® Therapeutics may be used. Furthermore, inventive multispecific antibody analogs disclosed herein may be amenable to oral delivery.

In addition, any of a number of delivery systems are known in the art and may be used to administer the inventive multispecific antibody analogs disclosed herein. Examples include, but are not limited to, encapsulation in liposomes, microparticles, microspheres (e.g., PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-glutamate, ethylene-vinyl acetate, lactic acid-glycolic acid copolymers such as the LUPRON DEPOT®, and poly-D-(−)-3-hydroxyburyric acid. It is also possible to administer a nucleic acid encoding an inventive multispecific antibody analog disclosed herein, for example by retroviral infection, direct injection, or coating with lipids, cell surface receptors, or other transfection agents. In all cases, controlled release systems may be used to release the inventive multispecific antibody analog at or close to the desired location of action.

The dosing amounts and frequencies of administration are, in one embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active inventive multispecific antibody analog in the formulation may vary from about 0.1 to 100 weight %. In one embodiment, the concentration of the inventive multispecific antibody analog is in the range of 0.003 to 1.0 molar. In order to treat a patient, a therapeutically effective dose of the inventive multispecific antibody analog disclosed herein may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight. In one embodiment, dosages range from 1 to 10 mg/kg.

In some embodiments, only a single dose of the inventive multispecific antibody analogs is used. In other embodiments, multiple doses of the inventive multispecific antibody analog are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the inventive multispecific antibody analogs disclosed herein are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the inventive multispecific antibody analogs disclosed herein and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

The inventive multispecific antibody analogs disclosed herein may be administered concomitantly with one or more other therapeutic regimens or agents. The additional therapeutic regimes or agents may be used to improve the efficacy or safety of the inventive multispecific antibody analog. Also, the additional therapeutic regimes or agents may be used to treat the same disease or a comorbidity rather than to alter the action of the inventive multispecific antibody analog. For example, an inventive multispecific antibody analog disclosed herein may be administered to the patient along with chemotherapy, radiation therapy, or both chemotherapy and radiation therapy.

The terms "in combination with" and "co-administration" are not limited to the administration of said prophylactic or therapeutic agents at exactly the same time. Instead, it is meant that the inventive multispecific antibody analog disclosed herein and the other agent or agents are administered in a sequence and within a time interval such that they may act together to provide a benefit that is increased versus treatment with only either the inventive multispecific antibody analog disclosed herein or the other agent or agents. In some embodiments, inventive multispecific antibody analogs disclosed herein and the other agent or agents act additively, and sometimes synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

The inventive multispecific antibody analogs disclosed herein may be administered in combination with one or more other prophylactic or therapeutic agents, including but not limited to cytotoxic agents, chemotherapeutic agents, antibiotics, antifungal agents, antiviral agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, other antibodies, Fc fusions, or immunoglobulins, or other therapeutic agents. The therapies of the invention may be combined with other immunotherapies. The therapies of the invention may be combined with antagonists of chemokines or cytokines, including but not limited to antibodies and Fc fusions.

The inventive multispecific antibody analogs disclosed herein may be combined with other therapeutic regimens. For example, in one embodiment, the patient to be treated with an inventive multispecific antibody analog disclosed herein may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Optionally, the radiation therapy may be administered as a single dose or as multiple, sequential doses. The skilled medical practitioner can determine empirically the appropriate dose or doses of radiation therapy useful herein. In accordance with another, an inventive multispecific antibody analog disclosed herein and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with an inventive multispecific antibody analog and one or more other anti-cancer therapies, such as described above, can be employed to deplete or substantially deplete the cancer cells prior to transplantation in a recipient patient. It is of course contemplated that the inventive multispecific antibody analogs disclosed herein may employ in combination with still other therapeutic techniques such as surgery.

EXAMPLES

Example 1: Enrichment of Antibody Population from Naïve Libraries Against Human Epidermal Growth Factor Receptor 2 (HER2) and Human Epidermal Growth Factor Receptor 3 (HER3)

Eight naïve human synthetic yeast libraries each of ~$10^9$ diversity (~$10^{10}$ total diversity of all libraries combined) were prepared and propagated in selective media. Design and generation of libraries, transformation of such libraries into host cells, for example yeast cells, MACS® and FACS selections and reagents for performing such, and the like are described in, for example, WO2009036379, WO2010105256, and WO2012009568.

For discovery of antibodies having specificity for HER2 yeast cells (~$10^{10}$ cells/library) were incubated with 3 ml of 20 nM b-HER2-Fc or 200 nM biotinylated HER2 (B-HER2) for 20 min at room temperature in PBSF (phosphate-buffered saline (PBS) containing 0.1% bovine serum albumin (BSA)) and magnetic bead assisted cell sorting (MACS®) was employed utilizing the Miltenyi® MACs® system (Siegel et al., 2004) for two rounds of enrichment.

For HER3 IgG selections, eight naïve libraries were pulled together to yield two master libraries of four naïve libraries each. Yeast cells (~$10^{10}$ cells/library) were incubated with 3 ml of 25 nM biotinylated HER3 (b-HER3) or 10 nM b-HER3-Fc were incubated for 20 min at room temperature in PBSF.

Figure 3:
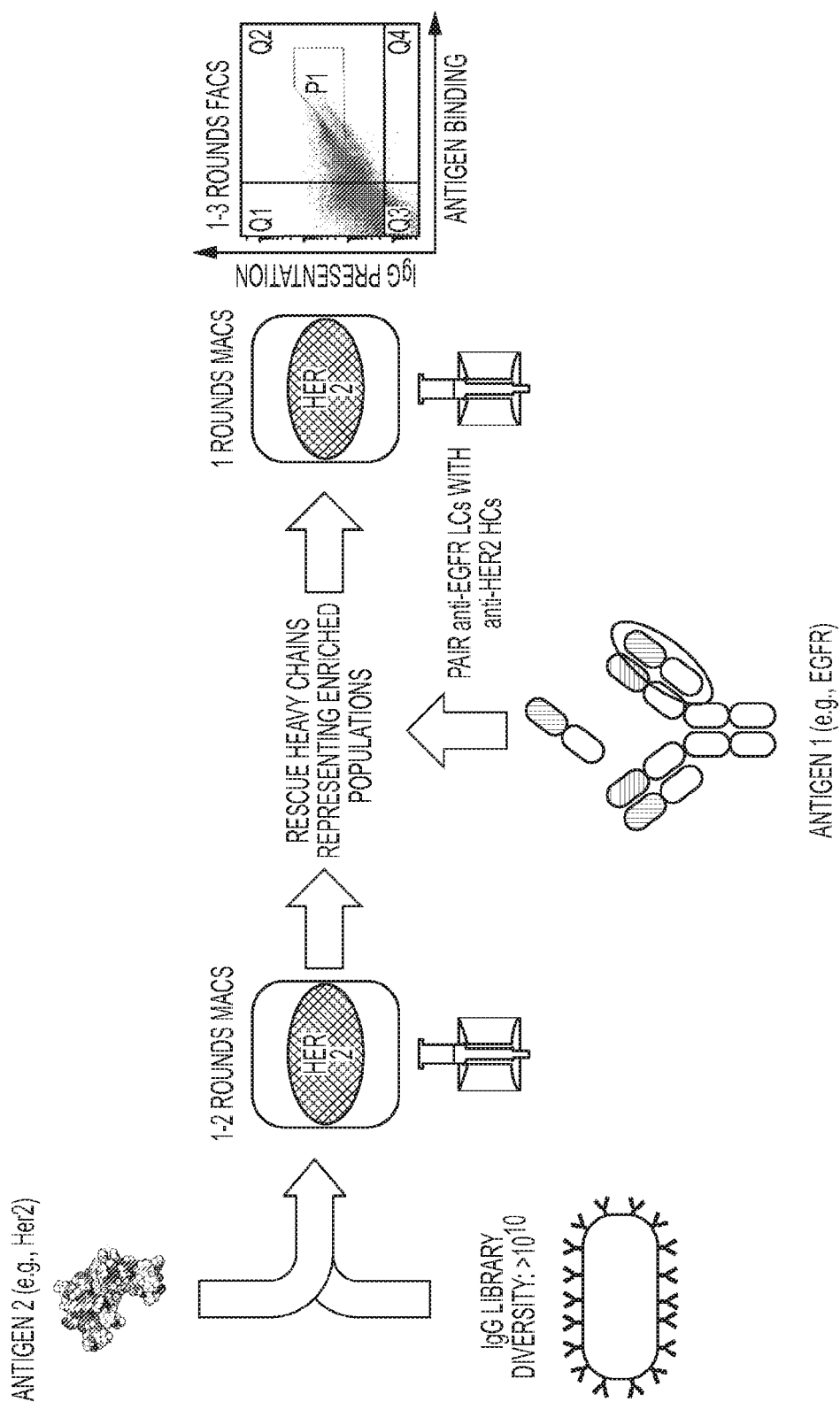
FIG. 3 illustrates and exemplary selection scheme for identifying one or more light chains that can pair with a first heavy chain having specificity for an Antigen 1 as well as a second heavy chain having specificity for an Antigen 2 (i.e., a "common light chain"). A first selection using a naïve library is performed against an Antigen 1 (e.g., EGFR), and one or more light chains from one or more IgGs is isolated from the first selection. A second selection using a naïve library is performed against Antigen 2 (e.g., HER2), and heavy chains are obtained ("rescued") from the output of binders having specificity for Antigen 2 isolated from the second selection. The heavy chains (or a subset of such heavy chains) are added with the one or more light chains from the first selection, generating a restricted library that is enriched for heavy chains having selectivity for Antigen 2 and light chains having specificity for Antigen 1. The total diversity of this restricted library is typically about: $10^9$, or less, $10^8$, or less, or $10^7$ or less; and in each case, the vast majority of the diversity is comprised of the heavy chains. A subsequent selection is performed against Antigen 2 using this restricted library, and the binders having specificity for Antigen 2 are obtained.

Following incubation with antigen (either HER2 or HER3) cells were washed with 50 ml ice-cold wash buffer, and cell pellets were re-suspended in 40 ml wash buffer. Approximately 500 µl streptavidin MicroBeads were added to the re-suspended yeast and subsequently incubated for 15 min at 4° C. Yeast cells were washed and resuspended in 5 ml PBSF buffer, and loaded onto a Miltenyi® LS column. The column was washed 3 times with 3 ml PBSF and then removed from the magnetic field, and the yeast cell of interest were eluted with 5 ml of growth media and then grown overnight. The heavy chains of this enriched population served as the input for generation of restricted libraries that further included predetermined light chains (See, e.g., FIGS. 1, 3, 4 and Brief Description of these Figures). Extraction of Plasmid DNA Encoding Heavy and Light Chain from the Enriched HER2 and HER3 Binding Population After 2 rounds of magnetic activated cell sorting (MACS®), enriched HER2 and HER3 binding yeast population were independently subjected to the smash and grab procedure using ZYMOPREP™ II Yeast Plasmid Miniprep Kit (ZYMO RESEARCH®). DNA extraction was performed with slight modification from manufacturer's protocol. Briefly, 0.5-1 OD of freshly grown yeast were incubated with 6 µL of ZYMOLASE™ enzyme in 200 µL solution 1 and incubated in a shaker at 37° C. for an hour. Following ZYMOLASE™ enzyme treatment, 200 µL of solution 2 was added and mixed thoroughly to lyse the cells and then immediately added 400 µL of solution 3 to neutralize the lysate mixture. Cell lysate was discarded by spinning the centrifuge tube for 10 mins at 21K g on a table top centrifuge (EPPENDORF® Centrifuge 5224). The supernatant was transferred to a ZYMO® spin-I column and spin at 10K g for 30 seconds. 550 µL was added to the column and spin down for 60 seconds. DNA was eluted with either 10 µL of water or TE buffer.
Amplification of Heavy Chain and Light Chain Plasmid in *E. coli*

Approximately 3 µL of DNA extracted from smash and grab procedure was electroporated into 25 µL of *E. coli* (NEB® Turbo Electrocompetent C2986K). The cell/DNA mix was transferred into a chilled 2 mm cuvette and electroporated under the following conditions, voltage: 2100 V, capacitance: 25 µF, resistance: 100Ω. Immediately, following electroporation, cells were rescued by adding 970 µL of SOC media to the cuvette and transferred to a 15 ml culture tube followed by incubation for 45 minutes with shaking at 37° C. Cells were then pelleted by centrifuging at 2400 g and re-suspended in 10 ml LB media+50 µG/ml carbenicillin and grown overnight. For each sample 2 minipreps were performed using standard QIAGEN® miniprep kit. Typical yield from the minipreps were in the range of 10-15 µg of DNA.

Example 2: Generation of HC Chain Dominant Libraries with Five Preselected Light Chains from EGFR Binders Plasmid DNA obtained from the *E. coli*. minipreps obtained in Example 1 was subjected to digestion with restriction enzymes Nco1-HF and Sbf1-HF (unique restriction sites in light chain (LC) plasmid) and HindIII-HF (unique restriction sites in heavy chain (VH) plasmid). Briefly, around 8-10 µg of DNA was digested in cut smart buffer with 200 units of Nco1-HF, Sbf1-HF and HindIII-HF for 4 hours at 37° C. Digested DNA was combined with a PCR amplified DNA fragment that has homology to a portion of the HC plasmid that coincides with the intended recombination site, such that the VH will recombine in-frame with the remainder of the coding region of full heavy chain (VH+hinge+Fc) and thus give rise to an open reading frame that affords expression of the full length IgG heavy chain. This DNA mixture was electroporated into yeast containing the desired light chain plasmids (5 light chains obtained from 5 EGFR-binding IgGs). HC plasmid was repaired in yeast via homologous recombination. The electroporated yeast library with HC diversities and fixed light chains were grown in selective media. Using this procedure, 4 libraries for HER2 and 2 libraries for HER3 were generated. The realized diversity of the libraries were in the range of $10^6$ to $10^7$.

Example 3: Discovery of HER2 and HER3 IgGs from HC Dominant (Biased) Libraries Paired with 5 Predefined Light Chains from EGFR Binders Identification of Parent IgGs Having Common Light Chain Magnetic bead sorting technique utilizing the Miltenyi® MAC® system was performed (Siegel et al., 2004) for the first round of selections (see, e.g., FIGS. 3 and 11).

Briefly, 1.5 ml of 20 nM b-HER2-Fc or 20 nM b-HER3-Fc were incubated with restricted (also known as biased) yeast libraries (as generated above) for 20 min at room temperature in PBSF. Magnetic activated cell sorting (MACS®) was carried out as described above. Following the first round of MACS® selection, three rounds of Fluorescence Activated Cell Sorting (FACS) were performed. For FACS selection, libraries were incubated with decreasing concentrations of antigens (5 nM b-HER2-HIS or 10 nM b-HER3-HIS) and subsequently stained with LC-FITC (diluted 1:100) and either SA-633 (diluted 1:500) or EA-PE (diluted 1:50) for 15 min at 4° C. Cells were washed twice and re-suspended in 0.4 ml wash buffer and transferred to strainer-capped sort tubes. Sorting was performed using a BD FACSARIA® sorter (BD Biosciences) and sort gates were determined to select for high affinity binders with good expression. After the final round of sorting, yeast were plated and individual colonies were picked for characterization.

Affinity Maturation by Introducing CDRH1 and CDRH2 Diversities into Naive HER2 and HER3 Parent IgGs Having Common Light Chain A pool of gapped HC vector with diversity in CDRH1 and CDRH2 was co-transformed with the CDRH3s obtained from the parent IgGs isolated as described above into a yeast strain containing a light chain plasmid harboring the light chain from the parent IgG. The result was a combinatorial library containing the same LC and CDRH3 from each parent IgG, but with diversity in CDRH1, CDRH2 or CDRH1 and CDRH2. The theoretical diversity of this newly built library was in the range of $10^8$. The libraries were propagated in selective media and were subsequently subjected to MACS® and FACS selections.

HER2 IgG optimization: For the $1^{st}$ round of selection libraries were incubated with 1.5 ml of 20 nM b-HER2-Fc in PBSF for 20 mins at room temperature and subsequently performed MACS® selection as mentioned above. For later rounds of selection affinity pressure was applied by competing off IgG bound biotinylated antigen with excess of unlabeled free antigen for appropriate amount of time and subsequently FACS sorting the best affinity yeast clones with high expression. After the final round of sorting, yeast were plated and individual colonies were picked for characterization.

HER3 IgG optimization: For the $1^{st}$ round of selection libraries were incubated with 1.5 ml of 25 nM b-HER3-HIS in PBSF for 20 mins at room temperature and subsequently followed MACS® selection as mentioned above. For later rounds of selection affinity pressure was applied by competing off IgG bound biotinylated antigen with excess of unlabeled free antigen for appropriate amount of time and subsequently FACS sorting the best affinity yeast clones with high expression. After the final round of sorting, yeast were plated and individual colonies were picked for characterization.

Selection of Improved Progenies by Introducing Stochastic Mutations in the Variable Region of Heavy Chain (VH) of Parent HER2

Affinity maturation of the parent HER2 IgG was performed by stochastically mutagenizing the variable region (VH) by using nucleotide analogue mutagenesis. Briefly, mutated VH segments of the HC were co transformed with gapped HC plasmid into a yeast strain containing the light chain plasmid of the parent HER2 IgG. The HC plasmid was repaired by homologous recombination in the yeast, such that the mutagenized VH regions recombined in-frame with gapped HC vector such that open reading frames afforded expression of full length IgGs. The theoretical diversity of this newly built library was in the range of $5 \times 10^6$.

The libraries were propagated and were subsequently subjected to MACS® and FACS selection. Briefly, for the $1^{st}$ round of selection yeast cells (~$10^8$ cells/library) were incubated with 1.5 ml of 10 nM b-HER2-His for 20 min at room temperature in PBSF. Following antigen incubation, cells were labeled with LC-FITC and EAPE and sorted the binders on FACS. For subsequent selections, to yield the best binders either antigen concentration was tittered down to 500 pM or $K_{off}$ pressure was applied by incubating the biotinylated antigen bound library with excess of unlabeled antigen. After the final round of sorting, yeast were plated and individual colonies were picked for characterization.

High Throughput Expression and Purification of Yeast Derived IgGs Having Common Light Chain After successful completion of FACS selection sorted yeast were plated on selective media and individual colonies were picked and sequenced confirmed. Yeast clones expressing a specific IgG were cultivated in 24-well plates by means such as those available in the art (see, e.g., WO2009036379, WO2010105256, and WO2012009568). IgGs were expressed and recovered from the supernatant by a single step of Protein A resin (MABSELECT SURE®, GE HEALTHCARE®) purification executed on a liquid handling robot (BIOMEK® FX Liquid Handler).

OCTET® RED384 Surface Based Binding Assessments

FORTEBIO® KD measurements were performed as previously described (see, e.g., Estep et al., MAbs, Vol. 5(2), pp. 270-278 (2013). Briefly, ligand (antibody or antigen) was loaded to the sensor followed by a short baseline in PBSF, the sensors were exposed to analyte at a single concentration in PBSF for an association step. Dissociation was monitored in PBSF. For dual binding assessment sensors were exposed to $2^{nd}$ analyte instead of PBSF. FORTEBIO®'s data analysis software was used to fit the data to a 1:1 binding model to extract an association rate and dissociation rate. The $K_D$ was calculated using the ratio $k_d/k_a$.

OCTET® RED384 Epitope Binning Assay

Epitope binning assays were performed as previously described (Estep et al 2013). Briefly, control antibodies were loaded onto AHQ sensors and remaining Fc-binding sites on the sensor were blocked with a human IgG1 antibody. Sensors were exposed to antigen followed by the second antibody. Additional binding by the second antibody indicates an unoccupied epitope (non-competitor), while no binding indicates epitope blocking (competitor).

Cloning of IgGs and Multispecific Antibody Analogs for Expression in Human Embryonic Kidney (HEK) Cell Line A mammalian expression vector containing suitable unique restriction sites and harboring the coding sequence for CH1, hinge, CH2, and CH3 regions of human IgG1 was used as the template vector for all variable heavy chain (VH) related cloning. For variable light chain (VK) cloning, a vector containing suitable unique restriction sites and harboring the coding sequence for CK region was used as the template vector.

Variable heavy chain (VH) regions of IgG1 from EGFR-binding IgGs, HER2-binding IgGs, and HER3 IgGs were independently amplified with a forward primer that contains flanking Nhe1 restriction site and a reverse primer that contains flanking Xho1 site. The amplified VH regions and the vector were each digested with Nhe1 and Xho1, and subsequently teach VH region was independently inserted into the vector via ligation using T4 DNA ligase.

Variable light chain (VK) regions of IgG1 from HER 2 IgGs and HER3 IgGs were independently amplified with a forward primer that contains flanking Xho1 restriction site and a reverse primer that contains flanking BSiW1 restriction site. Each amplified VK region and the vector were digested with Xho1 and BSiW1 subsequently the VK region was inserted into the vector via ligation using T4 DNA ligase.

Cloning of the C-terminal Fab regions (see, e.g., FIGS. 5, 6, 7, 8, 9, 12, 13, and 14 for depictions of exemplary multispecific antibody analogs and position of Fab regions therein) were accomplished by ligation of synthetic double stranded Fab-encoding DNA to the vector containing the desired full length IgG1. The Fab-encoding DNA contains a HindIII restriction site at 5'end followed by a 15-mer ((Gly$_4$S)$_3$) linker (SEQ ID NO: 97), followed by VH region and finally the CH1 region followed by a Not1 restriction site at 3'end. Following digestion of the vector and the insert with HindIII and Not1, the Fab-encoding insert was subsequently ligated to the vector.

*E. coli* cells were then transformed with ligated vector via electroporation, and grown on selective plates. Colonies were picked from the plates, grown up, and plasmid DNA extracted and sequence-confirmed.

As indicated above and in the, e.g., FIGS. 7, 8, 9, 12, 13, and 14, exemplary multispecific antibody analogs prepared in accordance with the inventive methods are comprised of two copies of a first polypeptide and four copies of a second polypeptide, wherein:

the first polypeptide comprises, in the following N-terminus to C-terminus order: N-term-Antigen 1 (e.g., EGFR) VH-CH1-Hinge region-CH2-CH3-Antigen 2 (e.g., HER2) VH-CH1-C-term; and the second polypeptide comprises, in the following N-terminus to C-terminus order: N-term-VL-CK-C-term;

wherein the second polypeptide comprises a common light chain that is compatible with VH for Antigen 1 and VH for Antigen 2.

As described above and illustrated in FIGS. 7, 8, 9, 12, 13, and 14, four exemplary multispecific antibody analogs were prepared:

an N-terminal-EGFR::C-terminal-HER2 multispecific antibody analog ("Analog 1");

an N-terminal HER2::C-terminal EGFR multispecific antibody analog ("Analog 2");

an N-terminal EGFR::C-terminal HER3 multispecific antibody analog ("Analog 3"); and an N-terminal HER3::C-terminal EGFR multispecific antibody analog ("Analog 4").

Exemplary such first polypeptide amino acid sequences are as follows:

Analog 1: N-term-EGFR::C-term-HER2 (see, e.g., FIGS. 7, 8, and 9)

First polypeptide amino acid sequence (N-term-EGFR VH-CH1-hinge region-CH2-CH3-HER2 VH-CH1-C-term):

```
                                            (SEQ ID NO: 98)
QVQLQESGPGLVKPSETLSLTCTVSGGSVSSGSYYWSWIRQPPGKGLEWIG

YIYYSGSTNYNPSLKSRVTISVDTSKNQFSLKLSSVTAADTAVYYCARTNL

YSTPFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGKGGGGSGGGG

SGGGGSQVQLQESGPGLVKPSETLSLTCTVSGGSISSGGYYWSWIRQPPGK

GLEWIGIIYYSGWTNYNPSLKSVTISVDASRNQFSLKLSSVTAADTAVYYC

ARGVGPDFWSGYSYSSYFDLWGRGTLVTVSSASTKGPSVFPLAPSSKSTSG

GTAALGCLVKDYFPEPVTVSWNSGALTSGVHTFPAVLQSSGLYSLSSVVTV

PSSSLGTQTYICNVNHKPSNTKVDKKVEPKSC
```

Second polypeptide amino acid sequence (N-term-VL-CK-C-term):

```
                                            (SEQ ID NO: 79)
DIQLTQSPSTLSASVGDRVTITCRASQAISSWLAWYQQKPGKAPKLLIYDA

SSLESGVPSRFSGSGSGTEFTLTISSLQPDDFATYYCHQYQSYSWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC
```

Analog 2: N-term-HER2::C-term-EGFR (see, e.g., FIGS. 7, 8, and 9)

First polypeptide amino acid sequence (N-term-HER2 VH-CH1-hinge region-CH2-CH3-EGFR VH-CH1-C-term):

```
                                            (SEQ ID NO: 76)
QVQLQESGPGLVKPSETLSLTCTVSGGSISSGGYYWSWIRQPPGKGLEWIG

IIYYSGWTNYNPSLKSRVTISVDASRNQFSLKLSSVTAADTAVYYCARGVG

PDFWSGYSYSSYFDLWGRGTLVTVSSASTKGPSVFPLAPSSKSTSGGTAAL

GCLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGKG
```

-continued

GGGSGGGGSGGGGSQVQLQESGPGLVKPSETLSLTCTVSGGSVSSGSYYWS

WIRQPPGKGLEWIGYIYYSGSTNYNPSLKSRVTISVDTSKNQFSLKLSSVT

AADTAVYYCARTNLYSTPFDIWGQGTMVTVSSASTKGPSVFPLAPSSKSTS

GGTAALGCLVKDYFPEPVTVSWNSGALTSGVHTFPAVLQSSGLYSLSSVVT

VPSSSLGTQTYICNVNHKPSNTKVDKKVEPKSC

Second polypeptide amino acid sequence (N-term-VL-CK-C-term):

(SEQ ID NO: 79)
DIQLTQSPSTLSASVGDRVTITCRASQAISSWLAWYQQKPGKAPKLLIYDA

SSLESGVPSRFSGSGSGTEFTLTISSLQPDDFATYYCHQYQSYSWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Analog 3: N-term-EGFR::C-term-HER3 (see. e.g., FIGS. 12, 13, and 14)

First polypeptide amino acid sequence (N-term-EGFR VH-CH1-hinge region-CH2-CH3-HER3 VH-CH1-C-term):

(SEQ ID NO: 74)
QVQLQESGPGLVKPSETLSLTCTVSGGSVSSGSYYWSWIRQPPGKGLEWIG

YIYYSGSTNYNPSLKSRVTISVDTSKNQFSLKLSSVTAADTAVYYCARTNL

YSTPFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGKGGGGSGGGG

SGGGGSQLQLQESGPGLVKPSETLSLTCTVSGGSINSSSYYWQWIRQPPGK

GLEWIGEIAYSGSTYYNPSLKSRVTISVDTSKNQFSLKLSSVTAADTAVYY

CARGQQWAAFDIWGQGTMVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKKVEPKSC

Second polypeptide amino acid sequence (N-term-VL-CK-C-term):

(SEQ ID NO: 78)
DIQLTQSPSSVSASVGDRVTITCRASQDISSWLAWYQQKPGKAPKLLIYAA

SSLQSGVPSRFSGSGSGTDFTLTISSLQPEDFATYYCQQEHDFPWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Analog 4: N-term-HER3::C-term-EGFR (see, e.g., FIGS. 12, 13 and 14)

First polypeptide amino acid sequence (N-term-HER3 VH-CH1-hinge region-CH2-CH3-EGFR VH-CH1-C-term):

(SEQ ID NO: 77)
QLQLQESGPGLVKPSETLSLTCTVSGGSINSSSYYWQWIRQPPGKGLEWIG

EIAYSGSTYYNPSLKSRVTISVDTSKNQFSLKLSSVTAAGTAVYYCARGQQ

WAAFDIWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQPWLNGKEYKCKVSNKALPAPIEKTISKAKGQPREPQVYTLPPSR

DELTKNQVSLTCLVKGFYPSDIAVEWESNGQPENNYKTTPPVLDSDGSFFL

YSKLTVDKSRWQQGNVFSCSVMHEALHNHYTQKSLSLSPGKGGGGSGGGGS

GGGGSQVQLQESGPGLVKPSETLSLTCTVSGGSVSSGSYYWSWIRQPPGKG

LEWIGYIYYSGSTNYNPSLKSRVTISVDTSKNQFSLKLSSVTAADTAVYYC

ARTNLYSTPFDIWGQGTMVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKKVEPKSC

Second polypeptide amino acid sequence (N-term-VL-CK-C-term):

(SEQ ID NO: 78)
DIQLTQSPSSVSASVGDRVTITCRASQDISSWLAWYQQKPGKAPKLLIYAA

SSLQSGVPSRFSGSGSGTDFTLTISSLQPEDFATYYCQQEHDFPWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC

Mammalian expression and purification of IgGs and Multispecific Antibody Analogs Following 7 days of HEK transfection with appropriate vectors, IgGs or multispecific antibody analogs as described above and as depicted in the Figures were harvested and purified by a single step of protein A purification. Protein A resin (MABSELECT SURE®, GE HEALTHCARE®) was first equilibrated in wash buffer (phosphate buffered saline, pH 7.4) and then IgG or bispecific samples were applied to the column. Samples were eluted from the column by the addition of elution buffer (200 mM Acetic Acid, pH 2.0). Once eluted, the samples were neutralized with 2 M HEPES, pH 8.0.

Cell labeling of IgGs and Multispecific Antibody Analogs

IgG and multispecific antibody analogs were incubated with EGFR-overexpressing A431 cells, HER2-overexpressing BT474 cells, and HER3-overexpressing MDA-MB-453 cells. CHO-S cells were used as a negative control.

Around $5 \times 10^4$ cells were incubated with 100 µL of 100 nM of either IgG or multispecific antibody analogs for 30 mins at 4° C. Cells were subsequently washed and stained with goat anti-human IgG-RPE for 15 mins at 4C. Samples were run on BD FACSCanto® II instrument.

MSD®-SET $K_D$ Measurements

Equilibrium affinity measurements performed as previously described (Estep et al., 2013). Solution equilibrium titrations (SET) were performed in PBS+0.1% IgG-Free BSA (PBSF) with antigen held constant at 50 pM and incubated with 3- to 5-fold serial dilutions of antibody starting at around 50 nM. Antibodies (20 nM in PBS) were coated onto standard bind MSD®-ECL plates overnight at 4° C. or at room temperature for 30 min. Plates were then blocked for 30 min with shaking at 700 rpm, followed by three washes with wash buffer (PBSF+0.05% TWEEN®20 surfactant). SET samples were applied and incubated on the plates for 150s with shaking at 700 rpm followed by one wash. Antigen captured on a plate was detected with 250 ng/ml sulfotag-labeled streptavidin in PBSF by incubation on the plate for 3 min. The plates were washed three times with wash buffer and then read on the MSD® SECTOR® Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD®-SET experiments, including SET sample preparation.

Melting Temperature (Tm) Measurement by Differential Scanning Fluorometry (DSF)

Briefly, 10 μL of 20× sypro orange dye was added to 20 μL of 0.5 mg/ml Fab, IgG or bispecific solution and were mixed thoroughly. DSF Tm were performed on a BIO-RAD® CFX96™ RT PCR instrument by ramping temperature at 0.5° C. increment from 40 to 95° C. At each temperature point it was allowed to equilibrate for 2 mins. The melting point of the protein was obtained as the lowest point of first derivative plot, as calculated by the software included with the RT-PCR machine.

Size Exclusion Chromatography (SEC)

SEC chromatogram were acquired by running samples through a TSKGEL® Super SW3000 column (TOSOH BIOSCIENCE® LLC) on an AGILENT® 1100 HPLC system. Briefly, 5 μG of samples were injected with PBS as running buffer at a flow rate of 0.4 ml/min.

Figure 4:
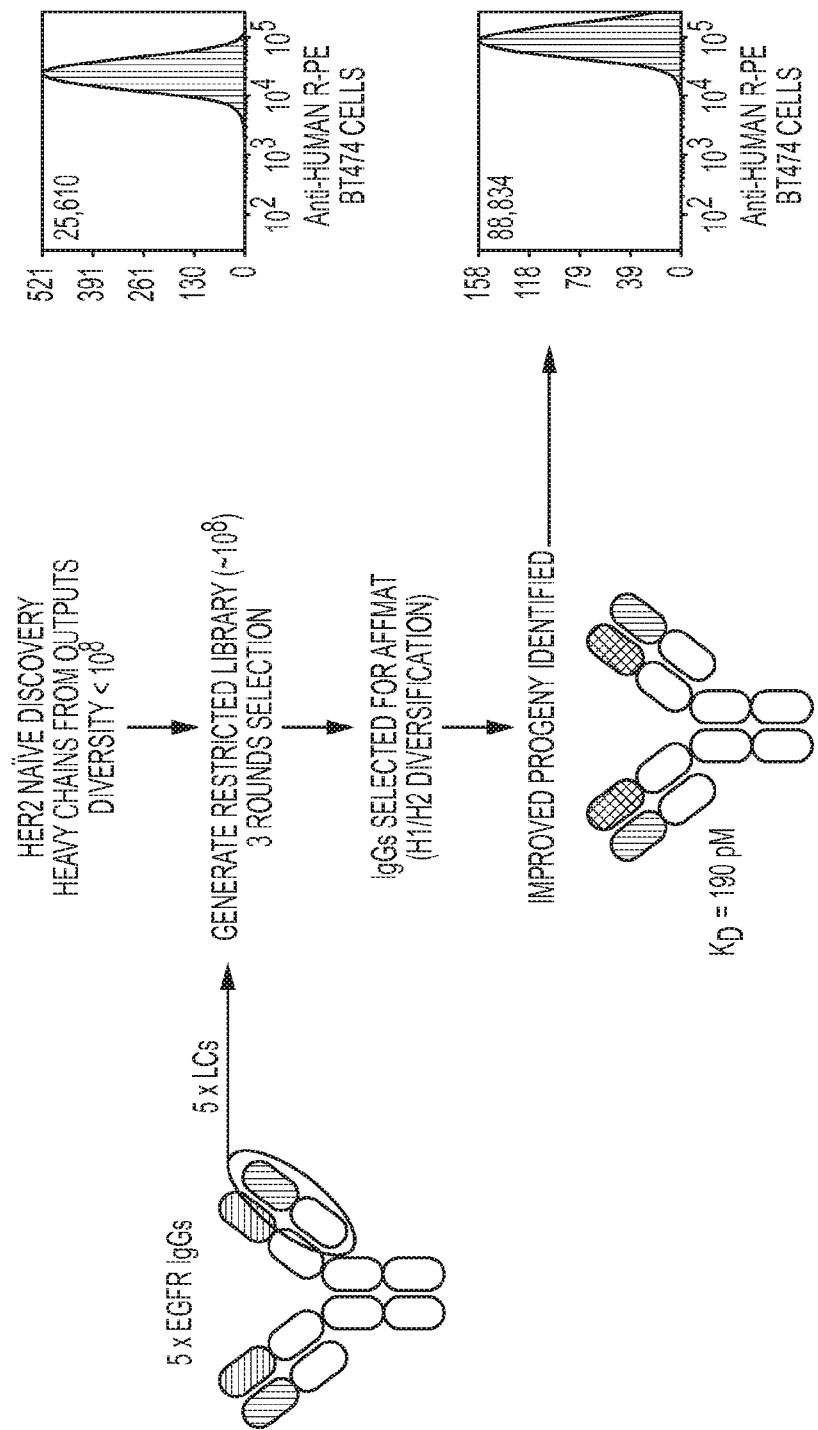
FIG. 4 illustrates an exemplary selection scheme in which a common light chain (common LC) was identified that is compatible with heavy chains identified in naïve selections against EGFR and HER2, respectively. The affinities of the EGFR-binding IgGs from which the 5 denoted light chains were obtained were as illustrated in FIG. 2. The affinity of the progeny obtained by performing the subsequent selections against HER2 using the restricted library is provided (KD=190 pM). Results of experiments to determine whether such progeny could effectively bind to native HER2 antigen expressed on BT474 cells is provided, and was found to be significantly greater than that obtained by using HERCEPTIN® IgG (88,834 MFI vs., 25,610 MFI, respectively).
Figure 5:
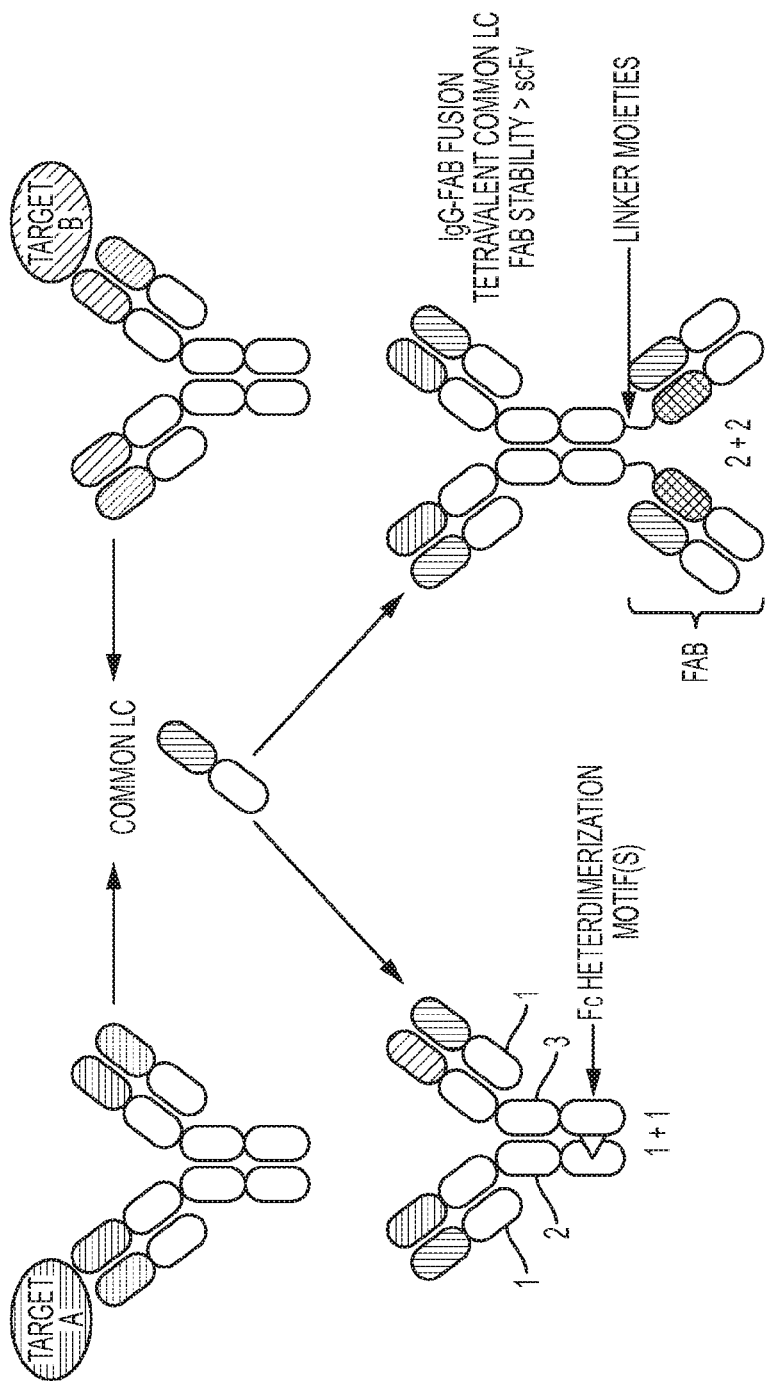
FIG. 5 illustrates alternative approaches and formats that may be employed in which common light chains identified in accordance with the disclosed methods may be applied in order to generate multispecific analogs as disclosed and claimed. Fab=antibody-binding fragment.
Figure 6:
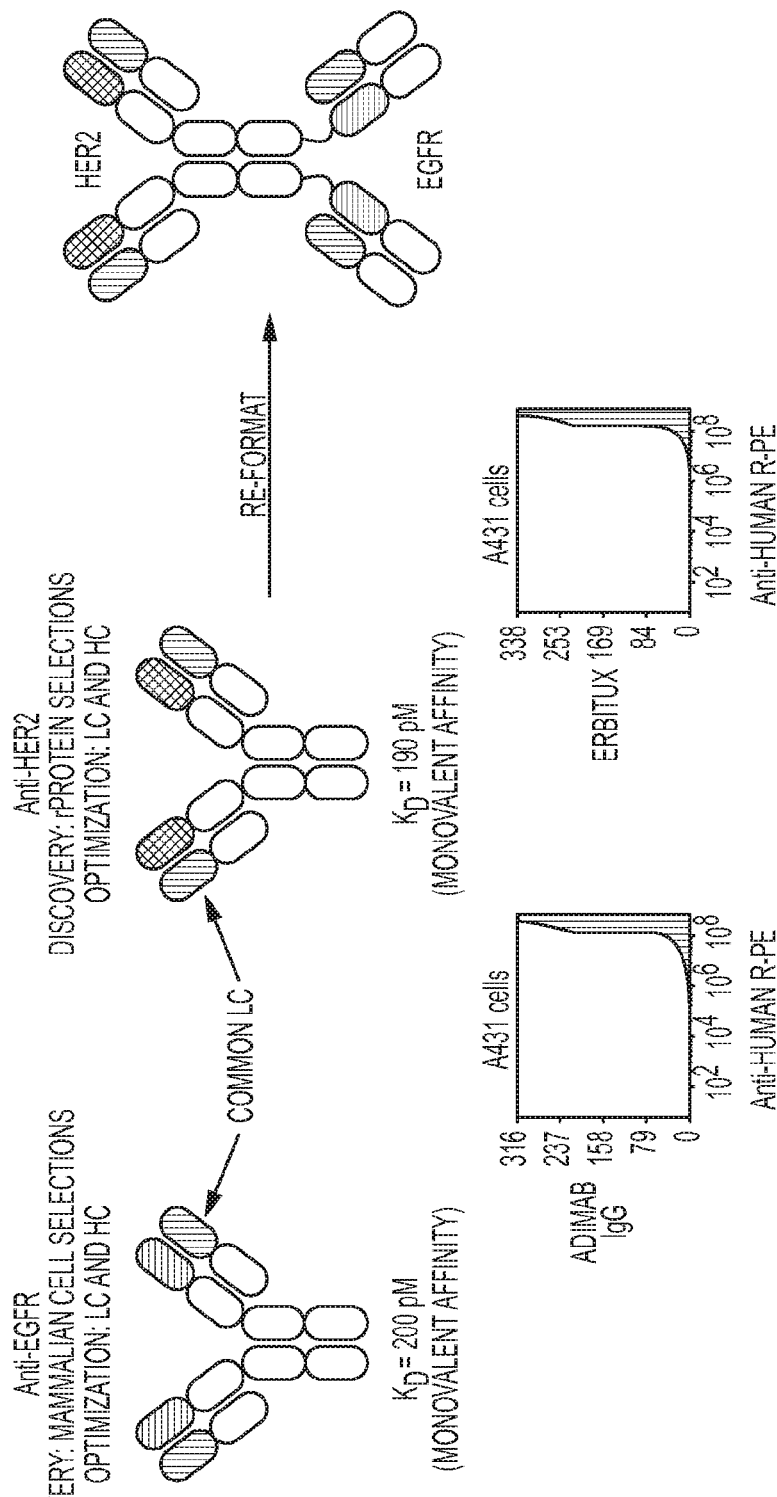
FIG. 6 depicts the affinities of anti-EGFR and HER2 binders each comprising a common light chain and each identified in accordance with methods illustrated in FIGS. 1 through 3, as well as the IgG-Fab 2+2 format was generated therewith, as disclosed in the Examples.
Figure 7:
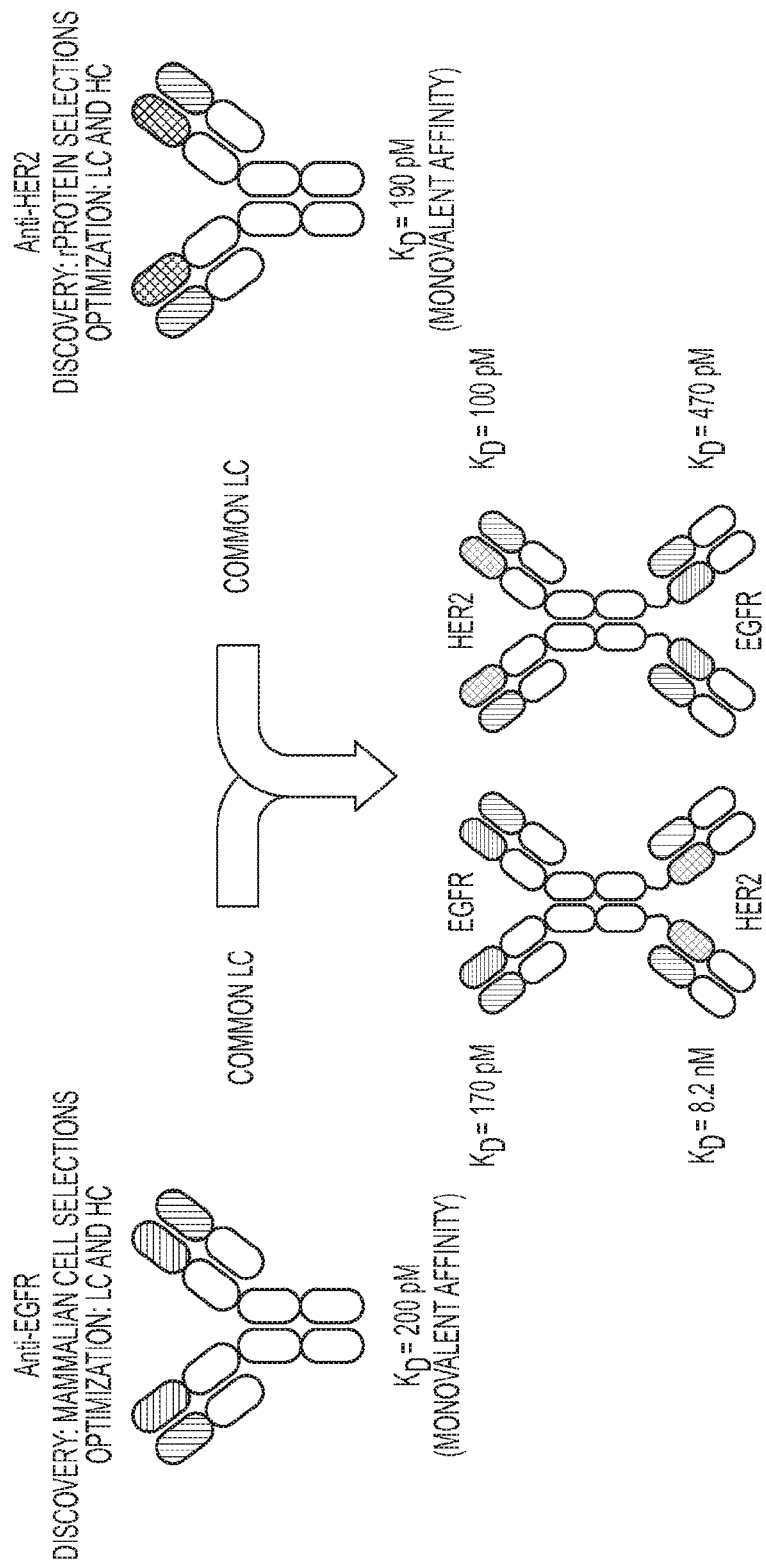
FIG. 7 provides a comparison between the binding affinities of each EGFR binding region and HER2 binding region in the context of the individual IgGs, as provided in FIG. 6, and the binding affinities of each antigen binding region in the context of the illustrated multispecific antibody analogs (bottom two IgG-Fab constructs), as disclosed, e.g., in the Examples.
Figure 11:
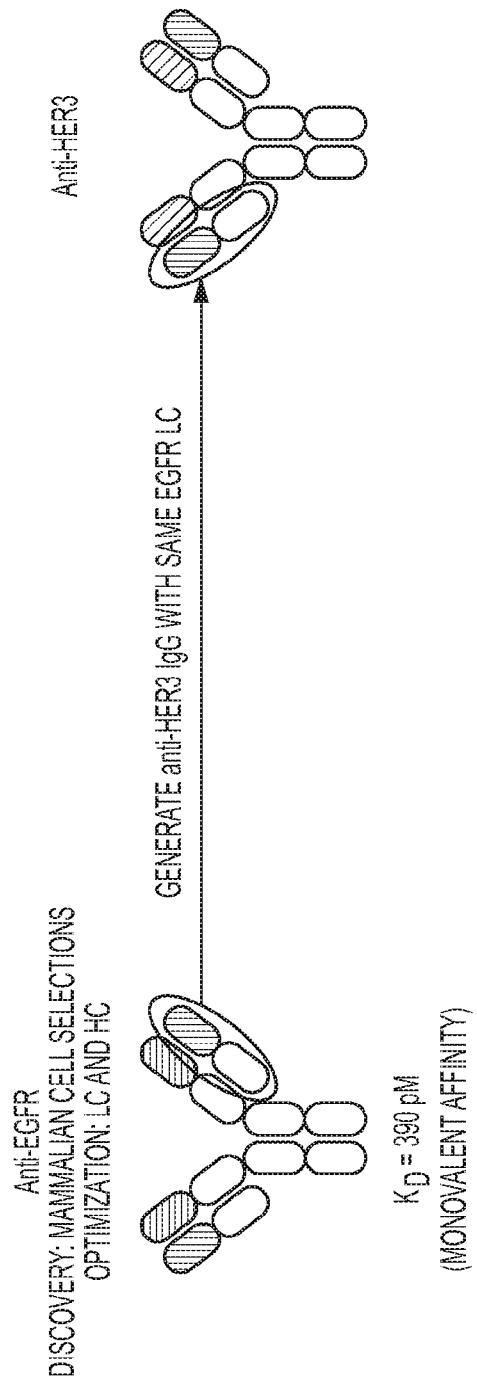
FIG. 11 depicts the affinity of the Anti-EGFR from which the common light chain was isolated in order to identify an anti-HER3-binding IgG in accordance with the methods disclosed herein.
Figure 12:
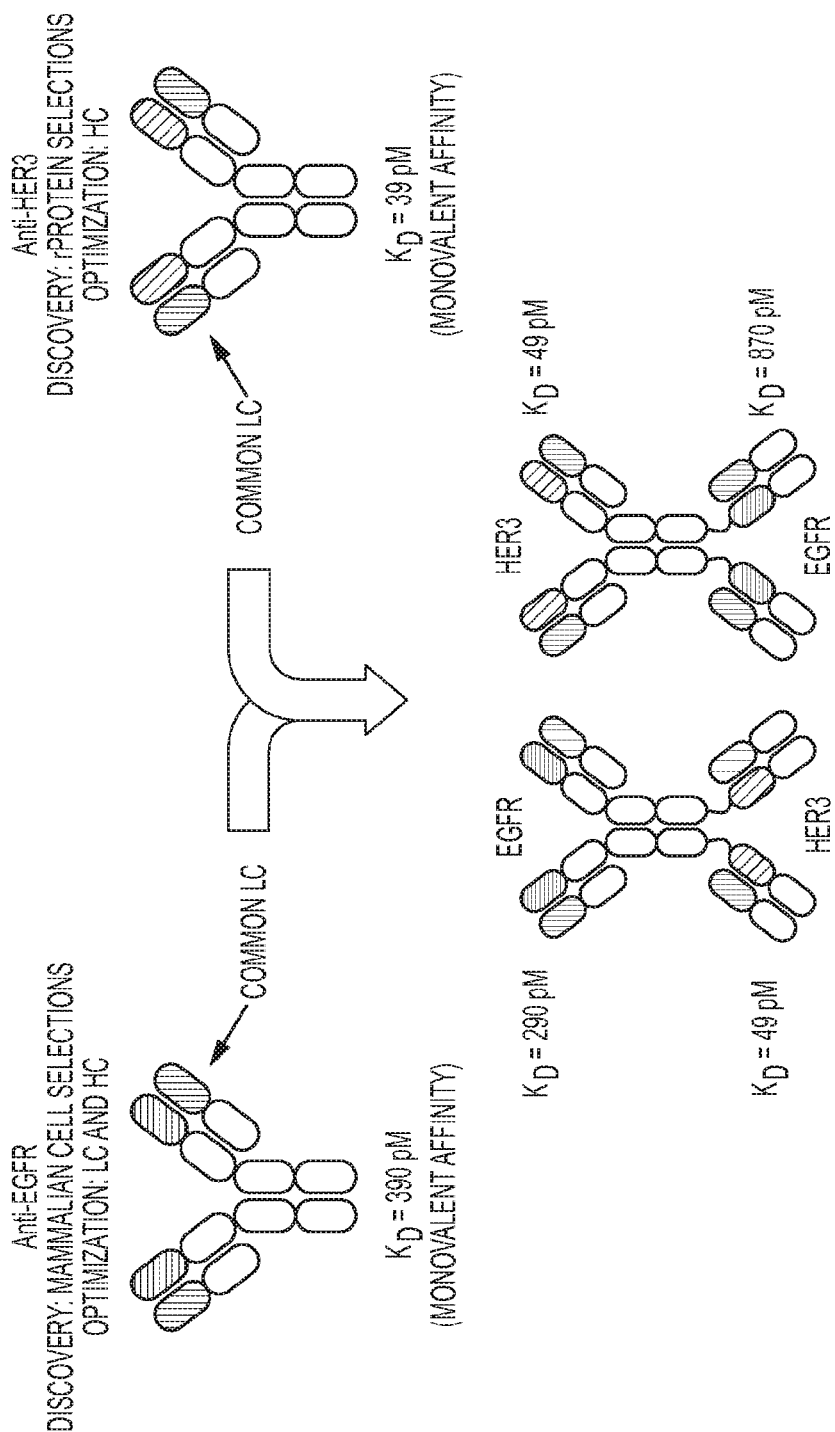
FIG. 12 provides a comparison between the binding affinities of each EGFR binding region and HER3 binding region, identified in accordance with the disclosed methods (see, e.g., FIG. 3 and the Examples) in the context of the individual IgGs, and the binding affinities of each antigen binding region in the context of the illustrated multispecific antibody analogs (bottom two IgG-Fab constructs), as disclosed, e.g., in the Examples.

The results, collectively depicted in, e.g., FIGS. 4 and 7, (for EGFR and HER2 IgGs having common light chains) and FIGS. 11 and 12 (for EGFR and HER3 IgG having common light chains, demonstrate that the methods generating restricted libraries (also known as biased libraries and enriched libraries) as described above, which include: isolating light chains from IgGs identified from selections using naïve libraries interrogated with a first antigen (e.g., EGFR); isolating heavy chains from IgGs isolated from selections using naïve libraries interrogated with a second antigen (e.g., HER2 or HER3); combining the light chains and heavy chains to generate the restricted library; afford libraries from which IgGs can be identified having specificity to both antigen 1 and antigen 2 (e.g., EGFR and, respectively, HER2 or HER3), and which share a common light chain.

The results also demonstrate that when the antigen binding regions are reformatted as IgG-Fab multispecific antibody analogs having common light chains, either as: EGFR-HER2; EGFR-HER2; HER2-EGFR; or HER3-EGFR; IgG-Fabs, such analogs retain specificity for the respective antigen with affinities comparable, or even superior to, the affinities observed for the antigen binding regions in the context of IgGs (See, e.g., FIGS. 7 and 12).

Figure 8:
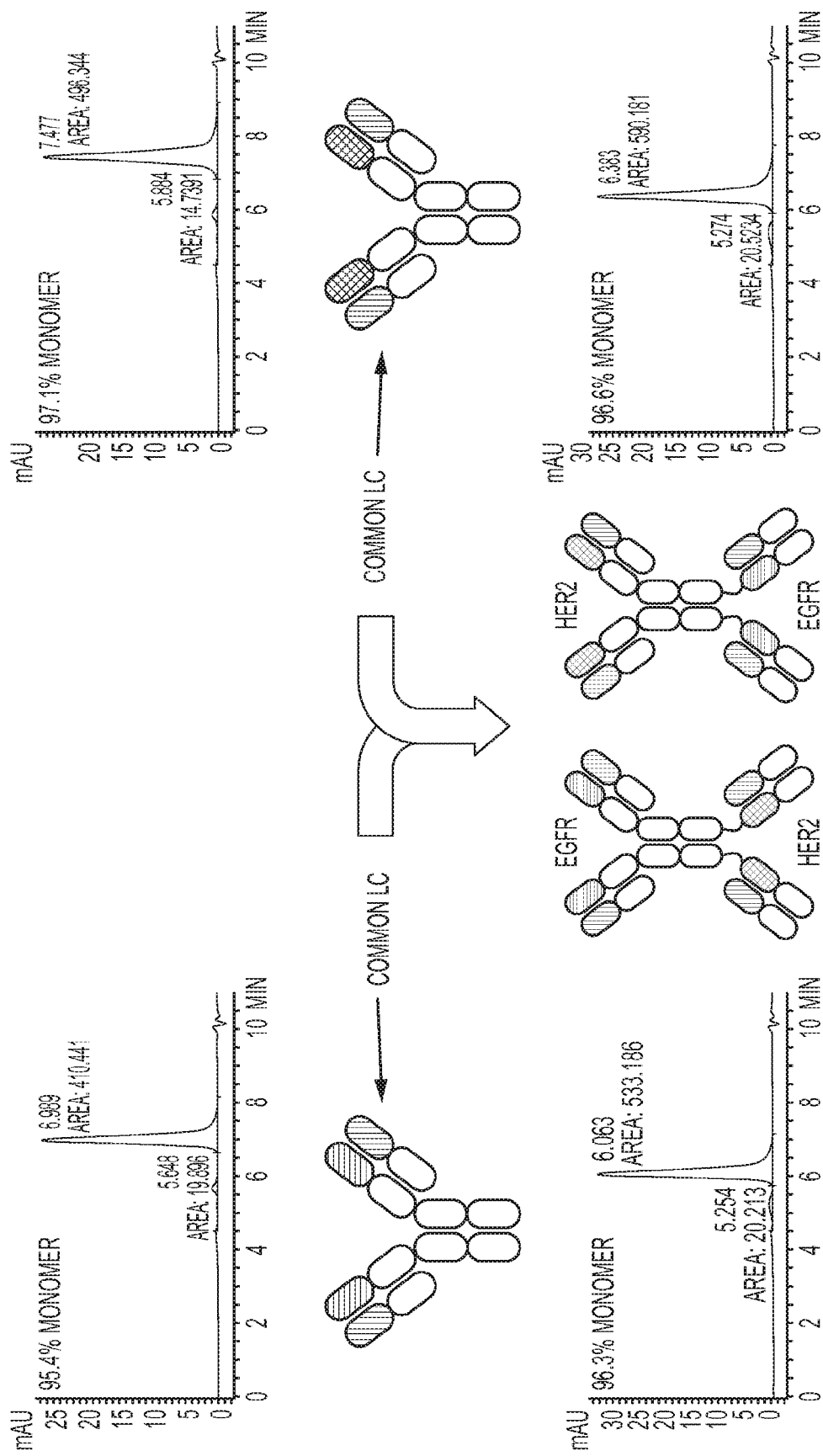
FIG. 8 provides size exclusion chromatographic (SEC) profiles obtained of the individual EGFR- and HER2-binding IgGs depicted in FIGS. 5 and 6 in comparison with the SEC profiles obtained for the multispecific antibody analogs that are depicted in FIG. 6.
Figure 9:
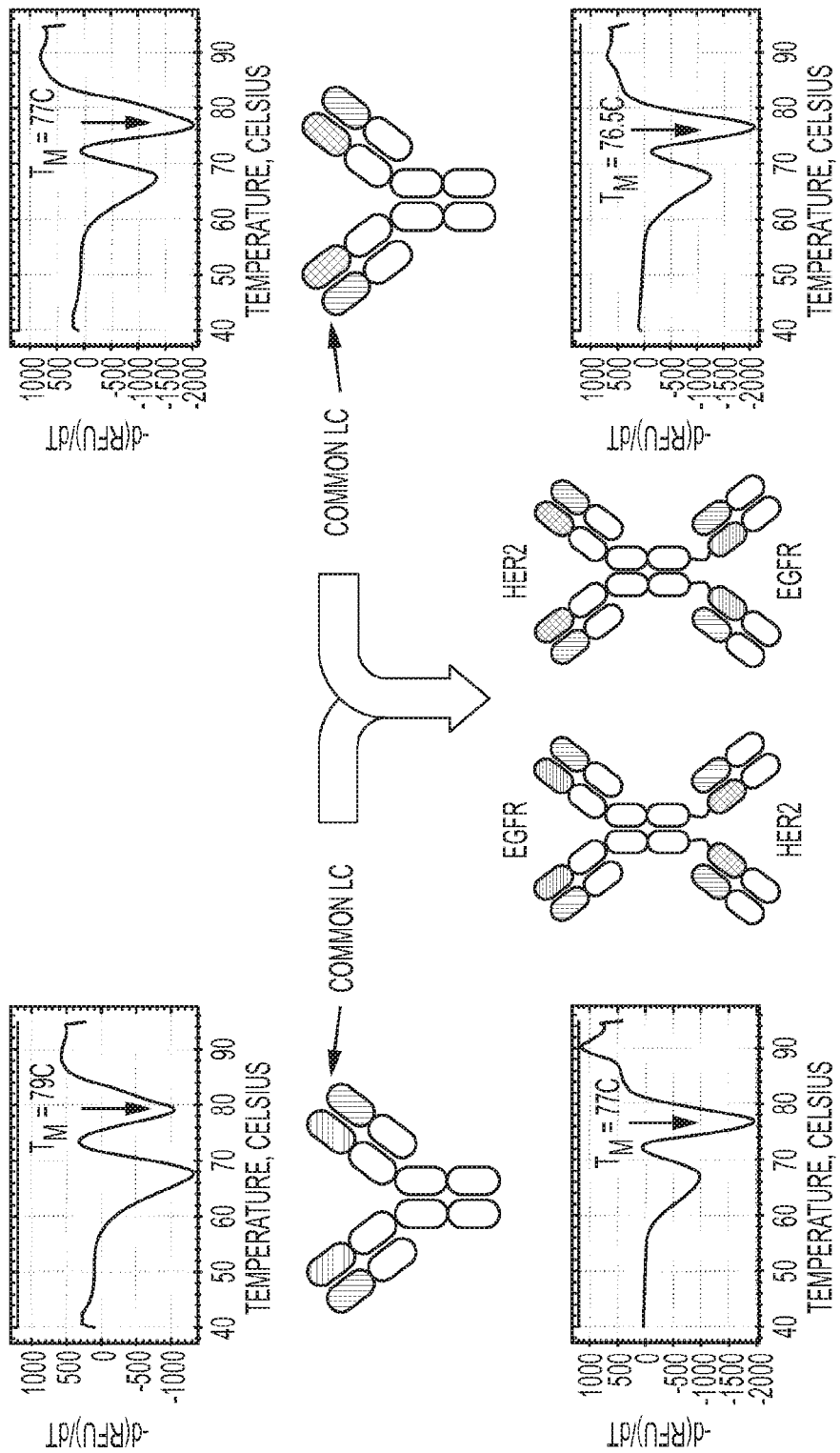
FIG. 9 provides an assessment of the melting temperature ($T_M$) obtained for each of the individual EGFR- and HER2-IgGs depicted in FIGS. 5 and 6 in and the multispecific antibody analogs that are depicted in FIG. 6.
Figure 10:
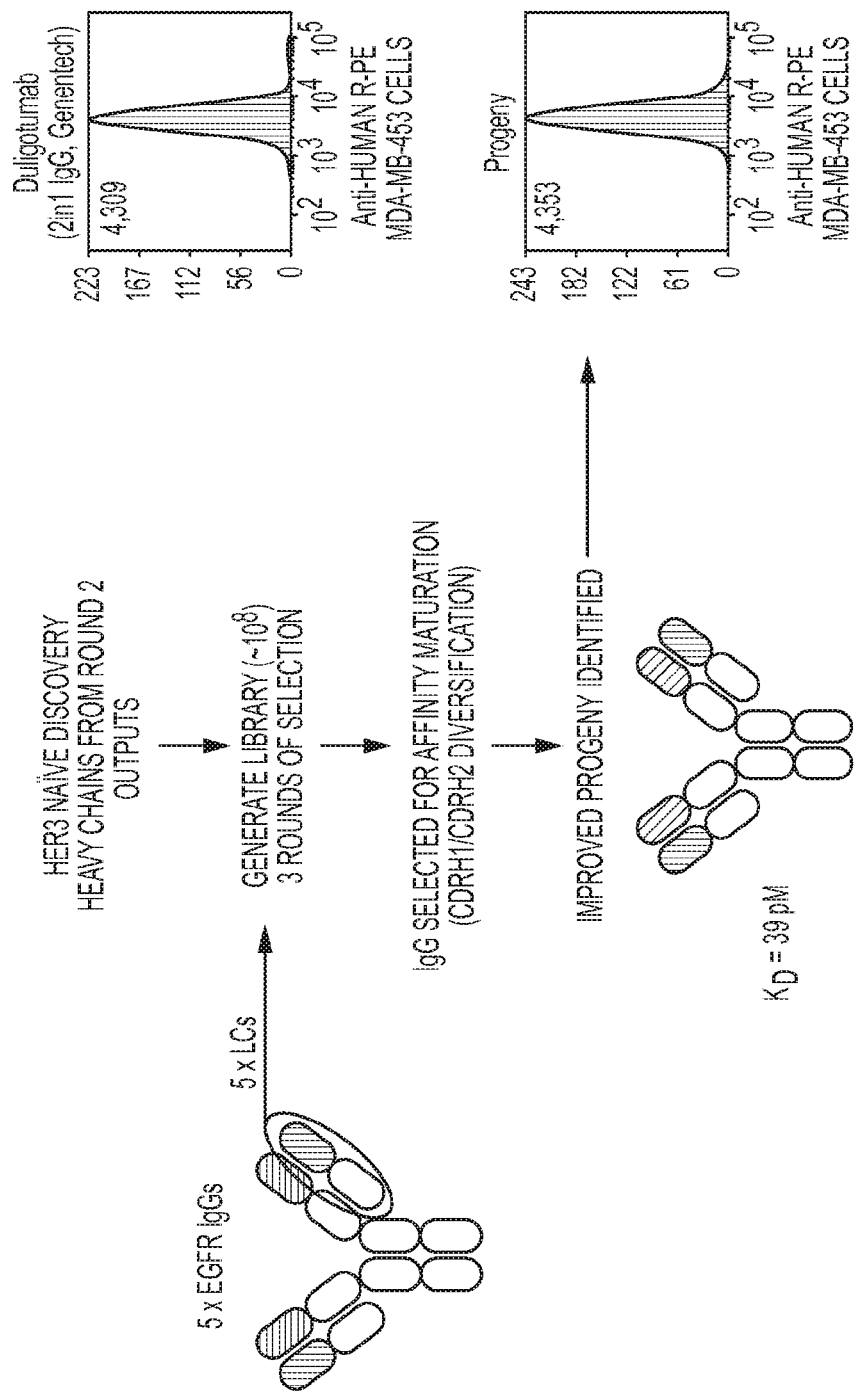
FIG. 10 illustrates an exemplary selection scheme in which a common light chain (common LC) was identified that is compatible with heavy chains identified in naïve selections against EGFR and HER3, respectively. The affinities of the EGFR-binding IgGs from which the 5 denoted light chains were obtained were as illustrated in FIG. 2. The affinity of the progeny obtained by performing the subsequent selections against HER3 using the restricted library is provided (KD=39 pM). Results of experiments to determine whether such progeny could effectively bind to native HER3 antigen expressed on MDA-mb-453 cells is provided, and was found to be comparable to that obtained by using Duligotumab (Genentech) (4,353 MFI vs., 4,309 MFI, respectively).
Figure 13:
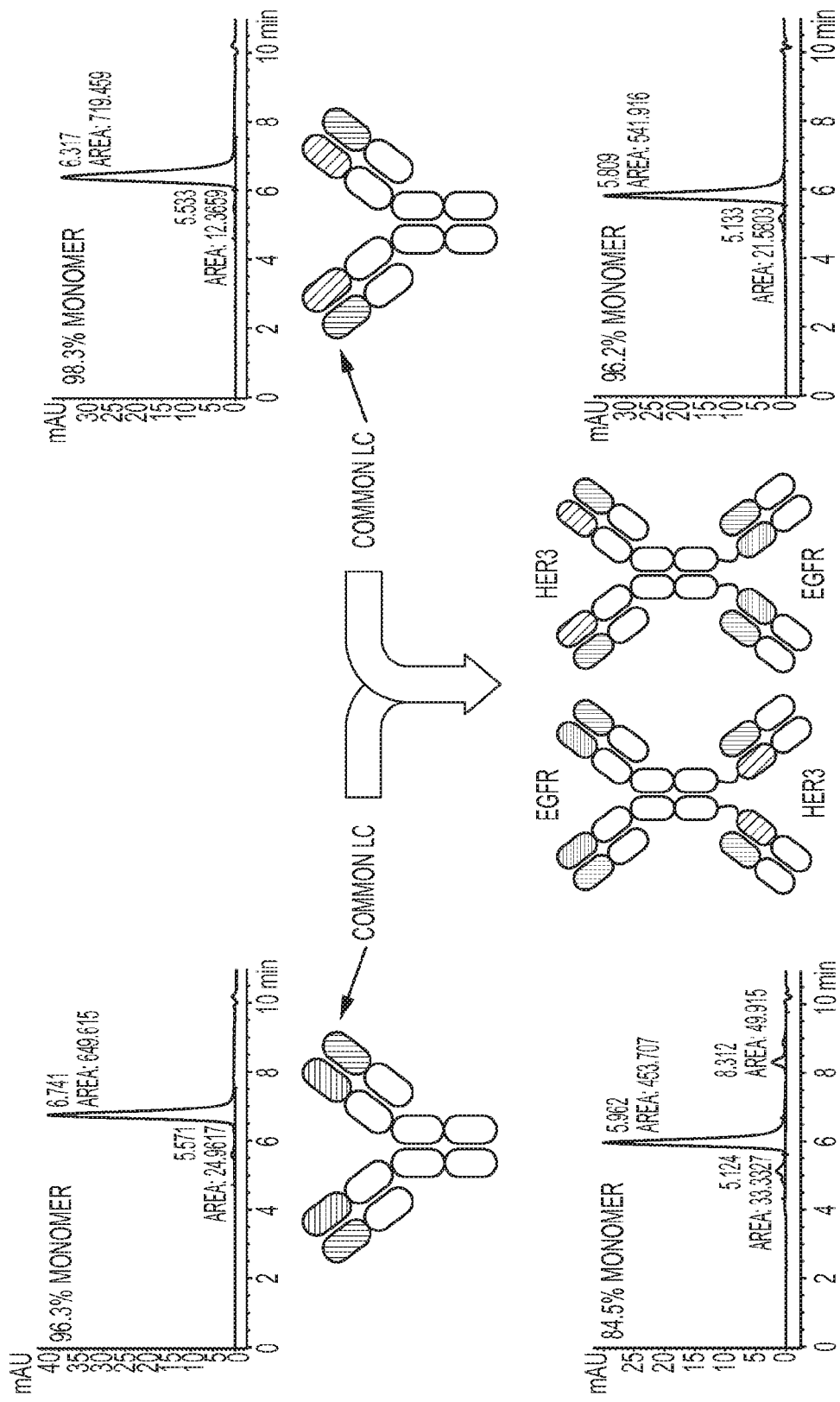
FIG. 13 provides size exclusion chromatographic (SEC) profiles obtained of the individual EGFR- and HER3-binding IgGs depicted in FIGS. 10 through 12, in comparison with the SEC profiles obtained for the multispecific antibody analogs that are depicted in FIG. 12.
Figure 14:
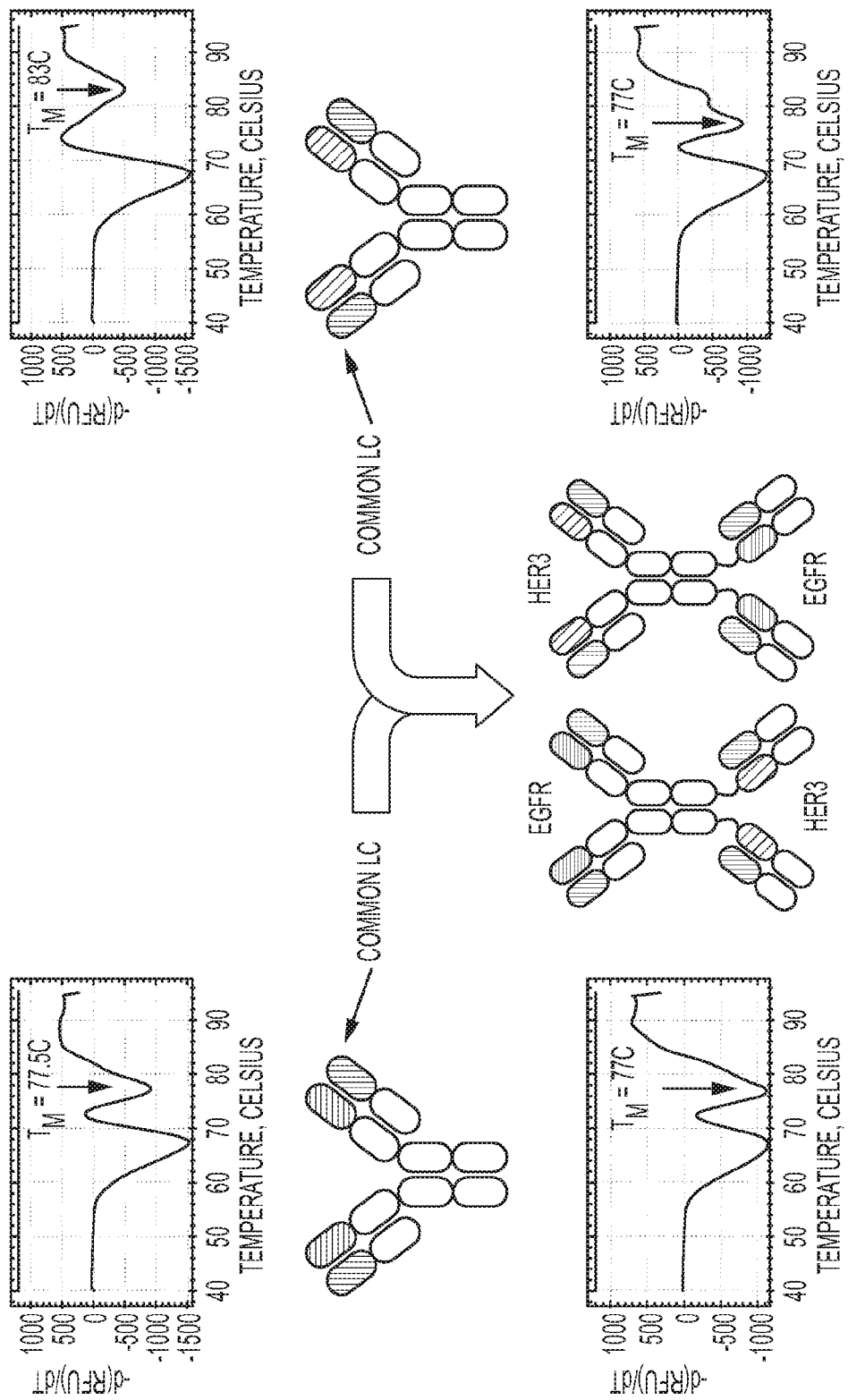
FIG. 14 provides an assessment of the melting temperature ($T_M$) obtained for each of the individual EGFR- and HER2-IgGs depicted in FIGS. 10 through 12 in and the multispecific antibody analogs that are depicted in FIG. 12.
Figure 15:
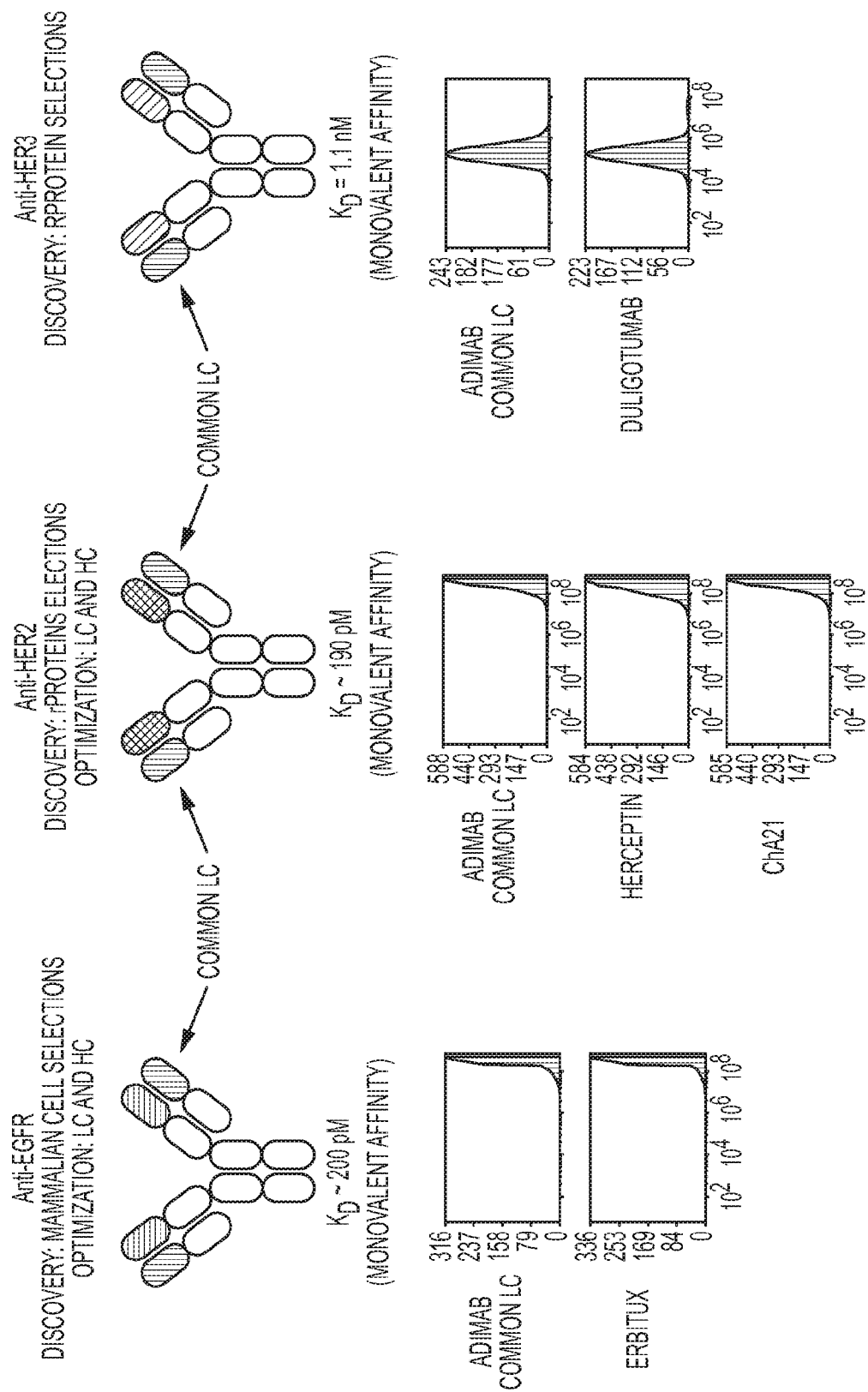
FIG. 15 depicts the identification of a common light chain (common LC) that is able to pair with heavy chains identified from separate naïve library selections against EGFR, HER2, and HER3, respectively, in accordance with the methods disclosed throughout (e.g., in the Examples), and as illustrated in FIGS. 2, 3, 10, and 11.

Such multispecific antibody analogs were also observed to elute from SEC columns as largely monomeric species at percentages comparable to that observed for corresponding IgGs (see, e.g., FIGS. 8 and 13). Additionally, such multispecific antibody analogs were observed to possess melting temperatures comparable to those observed for corresponding IgGs (see, e.g., FIGS. 9 and 14). Accordingly, such multispecific antibody analogs having common light chains demonstrate favorable stability and conformation profiles comparable to full length IgGs.

Additional exemplary Embodiments of certain aspects of the invention are as follows:

Embodiment 1. A method of making a multispecific antibody analog comprising at least two first antigen binding regions and at least two second antigen binding regions, said first and second antigen binding regions having a common light chain, wherein first antigen binding regions have a different antigen specificity than the second antigen binding regions, the method comprising;

i) obtaining at least one light chain from a first antigen binding region having specificity for the first antigen, wherein the first antigen binding region comprises said at least one light chain and a heavy chain;

ii) obtaining heavy chains from the output of a selection performed from a naïve library against a second antigen;

iii) preparing a restricted library comprising heavy chains obtained in step ii) and the at least one light chain obtained in step i);

iv) performing a second selection against the second antigen from the library prepared in step iii);

v) obtaining an multispecific antibody comprising the second antigen binding region from the selection performed in step iv), wherein the second antigen binding region comprises the at least one light chain obtained in step i);

vi) incorporating the first antigen binding region and the second antigen binding region into a multispecific antibody format, wherein the format comprises: an IgG moiety comprising either:
 a) the first antigen binding region; or
 b) the second antigen binding region; and
 two Fab moieties, wherein each Fab moiety comprises either:
 a) the second antigen binding region; or
 b) the first antigen binding region;

wherein the N-terminus of the heavy chain of one Fab moiety is linked to the C-terminus of the Fc region of one heavy chain of the IgG moiety via a linker moiety, and the N-terminus of the heavy chain of the other Fab moiety is linked to the C-terminus of the Fc region of the other heavy chain of the IgG moiety via a linker moiety;

thereby generating the multispecific antibody analog.

Embodiment 2. The method according to Embodiment 1, wherein each linker moiety independently comprises a peptide from 1 to 75 amino acids in length, inclusive.

Embodiment 3. The method according to any one of Embodiments 1 and 2, wherein one or more of the linker moieties independently comprises at least one of the 20 naturally occurring amino acids.

Embodiment 4. The method according to any one of Embodiments 1 through 3, wherein the one or more of the linker moieties independently comprises at least one non-natural amino acid incorporated by chemical synthesis, post-translational chemical modification or by in vivo incorporation by recombinant expression in a host cell.

Embodiment 5. The method according to any one Embodiments of 1 through 4, wherein the one or more of the linker moieties independently comprises one or more amino acids selected from the group consisting of serine, glycine, alanine, proline, asparagine, glutamine, glutamate, aspartate, and lysine.

Embodiment 6. The method according to any one of Embodiments 1 through 5, wherein the one or more of the linker moieties independently comprises a majority of amino acids that are sterically unhindered.

Embodiment 7. The method according to any one of Embodiments 1 through 6, wherein the one or more of the linker moieties independently comprises one or more of the following: an acidic linker, a basic linker, and a structural motif.

Embodiment 8. The method according to any one of Embodiments 1 through 7, wherein one or more of the linker moieties independently comprises: polyglycine, polyalanine, poly(Gly-Ala), or poly(Gly-Ser).

Embodiment 9. The method according to any one of Embodiments 1 through 8, wherein one or more of the linker moieties independently comprises: a polyglycine selected from the group consisting of: (Gly)3 (SEQ ID NO: 1), (Gly)4 (SEQ ID NO: 2), and (Gly)5 (SEQ ID NO: 3).

Embodiment 10. The method according to any one of Embodiments 1 through 9 wherein one or more of the linker moieties independently comprises (Gly)$_3$Lys(Gly)$_4$ (SEQ ID NO: 4); (Gly)$_3$AsnGlySer(Gly)$_2$ (SEQ ID NO: 5); (Gly)$_3$Cys(Gly)$_4$ (SEQ ID NO: 6); and GlyProAsnGlyGly (SEQ ID NO: 7).

Embodiment 11. The method according to any one of Embodiments 1 through 10, wherein one or more of the linker moieties independently comprises a combination of Gly and Ala.

Embodiment 12. The method according to any one of Embodiments 1 through 11, wherein one or more of the linker moieties independently comprises a combination of Gly and Ser.

Embodiment 13. The method according to any one of Embodiments 1 through 12, wherein one or more of the linker moieties independently comprises a combination of:
Gly and Glu; or
Gly and Asp.

Embodiment 14. The method according to any one of Embodiments 1 through 13, wherein one or more of the linker moieties independently comprises a combination of Gly and Lys.

Embodiment 15. The method according to any one of Embodiments 1 through 14, wherein one or more of the linker moieties independently comprises a sequence selected from group consisting of: [Gly-Ser]$_n$ (SEQ ID NO: 8); [Gly-Gly-Ser]$_n$ (SEQ ID NO: 9); [Gly-Gly-Gly-Ser]$_n$ (SEQ ID NO: 10); [Gly-Gly-Gly-Gly-Ser]$_n$ (SEQ ID NO: 11); [Gly-Gly-Gly-Gly-Ser-Gly-Gly-Gly-Gly]n (SEQ ID NO: 12); [Gly-Gly-Gly-Gly-Ser-Gly-Gly-Gly-Gly-Ser-Gly-Gly-Gly-Gly]n (SEQ ID NO: 13); [Gly-Gly-Gly-Gly-Ser Gly-Gly-Gly-Gly-Ser-Gly-Gly-Gly-Gly-Ser-Gly-Gly-Gly-Gly]n (SEQ ID NO: 14); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 15); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 16); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]n (SEQ ID NO: 17); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Embodiment 16. The method according to any one of Embodiments 1 through 15, wherein one or more of the linker moieties independently comprises a sequence selected from the group consisting of: [Gly-Glu]n (SEQ ID NO: 18); [Gly-Gly-Glu]n (SEQ ID NO: 19); [Gly-Gly-Gly-Glu]n (SEQ ID NO: 20); [Gly-Gly-Gly-Gly-Glu]n (SEQ ID NO: 21); [Gly-Asp]n (SEQ ID NO: 22); [Gly-Gly-Asp]$_n$ (SEQ ID NO: 23); [Gly-Gly-Gly-Asp]$_n$ (SEQ ID NO: 24); [Gly-Gly-Gly-Gly-Asp]$_n$ (SEQ ID NO: 25); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Embodiment 17. The method according to any one of Embodiments 1 through 16, wherein at least one of the first and second antigen binding regions comprises at least one humanized variable heavy domain or at least one humanized variable light domain.

Embodiment 18. The method according to any one of Embodiments 1 through 17, wherein at least one of the first and second antigen binding regions comprises at least one complimentary determining region CDR that is derived from a non-human multispecific antibody or multispecific antibody fragment.

Embodiment 19. The method according to any one of Embodiments 1 through 18, wherein at least one of the first and second antigen binding regions binds an epitope from a tumor associated antigen, a hormone receptor, a cytokine receptor, chemokine receptor, a growth factor receptor, an immune activating receptor, a hormone, a cytokine, a chemokine, a growth factor, a G protein-coupled receptor, or a transmembrane receptor.

Embodiment 20. The method according to any one of Embodiments 1 through 19, wherein at least one of the first and second antigen binding regions binds a target associated with an autoimmune disorder, an inflammatory disorder, an oncological disorder, neuromuscular disorder, a neurodegenerative disorder, a metabolic disorder, or an infectious disease.

Embodiment 21. The method according to any one of Embodiments 1 through 20, wherein the multispecific antibody analog binds at least two different targets.

Embodiment 22. The method according to any one of Embodiments 1 through 21, wherein the multispecific analog binds at least three different targets.

Embodiment 23. The method according to any one of Embodiments 1 through 22, wherein the multispecific antibody analog binds at least four different targets.

Embodiment 24. The method according to any one of Embodiments 1 through 23, wherein the multispecific antibody analog binds at least one target monovalently.

Embodiment 25. The method according to any one of Embodiments 1 through 24, wherein the multispecific antibody analog binds at least two targets monovalently.

Embodiment 26. The multivalent multispecific antibody analog according to any one of Embodiments 1 through 72, wherein the multispecific antibody analog binds at least three targets monovalently.

Embodiment 27. The method according to any one of Embodiments 1 through 26, wherein the multispecific antibody analog binds at least four targets monovalently.

Embodiment 28. The method according to any one of Embodiments 1 through 27, wherein at least one of the antigen binding regions comprises or is derived from a non-human species.

Embodiment 29. The method according to any one of Embodiments 1 through 28, wherein at least one of the antigen binding sites comprises a humanized variable domain or a humanized CDR.

Embodiment 30. The method according to any one of Embodiments 1 through 29, wherein at least one VH comprises a VH CDR1, a VH CDR2, and a VH CDR3 each independently selected from the following:

a VH CDR1 amino acid sequence selected from the group consisting of:

```
                                        (SEQ ID NO: 26)
            GSVSSGSYYWS;

(SEQ ID NO: 27)
            GSISSGGYYWS;

(SEQ ID NO: 28)
            GSINSSSYYWQ;

(SEQ ID NO: 29)
            FTLSGDWIH;

(SEQ ID NO: 30)
            FNIKDTYIH;

(SEQ ID NO: 31)
            FSLTNYGVH;

(SEQ ID NO: 32)
            GSISSGGDYWQ;
``` a VH CDR2 amino acid sequence selected from the group consisting of:

```
                                        (SEQ ID NO: 33)
            YIYYSGSTNYNPSLKS;

(SEQ ID NO: 34)
            IIYYSGWTNYNPSLKS;

(SEQ ID NO: 35)
            EIAYSGSTYYNPSLKS;

(SEQ ID NO: 36)
            EISAAGGYTDYADSVKG;

(SEQ ID NO: 37)
            RIYPTNGYTRYADSVKG;

(SEQ ID NO: 38)
            VIWSGGNTDYNTPFTSR;
``` and
a VH CDR3 selected from the group consisting of:

```
                                        (SEQ ID NO: 39)
            ARTNLYSTPFDI;

(SEQ ID NO: 40)
            ARGVGPDFWSGYSYSSYFDL;

(SEQ ID NO: 41)
            ARGQQWAAFDI;

(SEQ ID NO: 42)
            ARESRVSFEAAMDY;

(SEQ ID NO: 43)
            SRWGGDGFYAMDY;

(SEQ ID NO: 44)
            RALTYYDYEFAYW.
```

Embodiment 31. The method according to any one of Embodiments 1 through 30, wherein at least one VL comprises a VL CDR1, a VL CDR2, and a VL CDR3 each independently selected from the following:

a VL CDR1 amino acid sequence selected from the group consisting of:

```
                                        (SEQ ID NO: 45)
            RASQDISSWLA;

(SEQ ID NO: 46)
            RASQAISSWLA;

(SEQ ID NO: 47)
            RASQNIATDVA;

(SEQ ID NO: 48)
            RASQDVNTAVA;

(SEQ ID NO: 49)
            RASQSIGTNIH;
``` a VL CDR2 amino acid sequence selected from the group consisting of:

```
                                        (SEQ ID NO: 50)
            AASSLQS;

(SEQ ID NO: 51)
            DASSLES;

(SEQ ID NO: 52)
            AASSLQS;

(SEQ ID NO: 53)
            SASFLYS;

(SEQ ID NO: 54)
            YASESIS;
``` and
a VL CDR3 amino acid sequence selected from the group consisting of:

```
                                        (SEQ ID NO: 55)
            QQEHDFPWT;

(SEQ ID NO: 56)
            HQYQSYSWT;

(SEQ ID NO: 57)
            QQEHDFPWT;

(SEQ ID NO: 58)
            QQSEPEPYT;

(SEQ ID NO: 59)
            QQHYTTPPT;

(SEQ ID NO: 60)
            QQNNNWPTT.
```

Embodiment 32. The method according to any one of Embodiments 1 through 31, wherein the multispecific antibody analog comprises at least one heavy chain framework region that corresponds to or is derived from VH1-46, VH3-23, VH4-39, or VH4-61, and wherein at least one light chain framework region that corresponds to or is derived from VK1-05, VK1-12, or VK3-11.

Embodiment 33. The method according to any one of Embodiments 1 through 32, wherein the multispecific antibody analog comprises a VH region that comprises an amino acid sequence selected from the group consisting of:

(SEQ ID NO: 99)
QVQLQESGPGLVKPSETLSLTCTVSGGSVSSGSYYWSWIRQPPGKGLEWIG
YIYYSGSTNYNPSLKSRVTISVDTSKNQFSLKLSSVTAADTAVYYCARTNL
YSTPFDIWGQGTMVTVSS;

(SEQ ID NO: 62)
QVQLQESGPGLVKPSETLSLTCTVSGGSISSGGYYWSWIRQPPGKGLEWIG
IIYYSGWTNYNPSLKSRVTISVDASRNQFSLKLSSVTAADTAVYYCARGVG
PDFWSGYSYSSYFDLWGRGTLVTVSS;

(SEW ID NO: 63)
QVQLQESGPGLVKPSETLSLTCTVSGGSINSSSYYWQWIRQPPGKGLEWIG
EIAYSGSTYYNPSLKSRVTISVDTSKNQFSLKLSSVTAADTAVYYCARGQQ
WAAFDIWGQGTMVTVSS;

(SEQ ID NO: 64)
EVQLVESGGGLVQPGGSLRLSCAASGFTLSGDWIHWVRQAPGKGLEWVGEI
SAAGGYTDYADSVKGRFTISADTSKNTAYLQMNSLRAEDTAVYYCAREASR
VSFEAAMDYWGQGTLVTVSS;

(SEQ ID NO: 65)
EVQLVESGGGLVQPGGSLRLSCAASGFNIKDTYIHWVRQAPGKGLEWVARI
YPTNGYTRYADSVKGRFTISADTSKNTAYLQMNSLRAEDTAVYYCSRWGGD
GFYAMDYWGQGTLVTVSS;

(SEQ ID NO: 66)
QVQLKQSGPGLVQPSQSLSITCTVSGFSLTNYGVHWVRQSPGKGLEWLGVI
WSGGNTDYNTPFTSRLSINKDNSKSQVFFKMNSLQSDDTAIYYCARALTYY
DYEFAYWGQGTLVTVSS;
and (SEQ ID NO: 67)
QLQLQESGPGLVKPSETLSLTCTVSGGSISSGGDYWQWIRQPPGKGLEWIG
EIAYSGSTYYNPSLKSRVTISVDTSKNQFSLKLSSVTAADTAVYYCARGQQ
WAAFDIWGQGTMVTVSS.

Embodiment 34. The method according to any one of Embodiments 1 through 33, wherein the multispecific antibody analog comprises a VL region that comprises an amino acid sequence selected from the group consisting of:

(SEQ ID NO: 68)
DIQLTQSPSSVSASVGDRVTITCRASQDISSWLAWYQQKPGKAPKLLIYAA
SSLQSGVPSRFSGSGSGTDFTLTISSLQPEDFATYYCQQEHDFPWTFGGGT
KVEIK;

(SEQ ID NO: 69)
DIQLTQSPSTLSASVGDRVTITCRASQAISSWLAWYQQKPGKAPKLLIYDA
SSLESGVPSRFSGSGSGTEFTLTISSLQPDDFATYYCHQYQSYSWTFGGGT
KVEIK;

(SEQ ID NO: 70)
DIQLTQSPSSVSASVGDRVTITCRASQDISSWLAWYQQKPGKAPKLLIYAA
SSLQSGVPSRFSGSGSGTDFTLTISSLQPEDFATYYCQQEHDFPWTFGGGT
KVEIK;

(SEQ ID NO: 71)
DISMTQSPSSLSASVGDRVTITCRASQNIATDVAWYQQKPGKAPKLLIYSA
SFLYSGVPSRFSGSGSGTDFTLTISSLQPEDFATYYCQQSEPEPYTFGQGT
KVEIK;

(SEQ ID NO: 72)
DIQMTQSPSSLSASVGDRVTITCRASQDVNTAVAWYQQKPGKAPKLLIYSA
SFLYSGVPSRFSGSRSGTDFTLTISSLQPEDFATYYCQQHYTTPPTFGQGT
KVEIK;
and (SEQ ID NO: 73)
DILLTQSPVILSVSPGERVSFSCRASQSIGTNIHWYQQRTHGSPRLLIKYA
SESISGIPSRFSGSGSGTDFTLSINSVESEDIADYYCQQNNNWPTTFGAGT
KLELK.

Embodiment 35. The method according to any one of Embodiments 1 through 34, wherein the multispecific antibody analog comprises a polypeptide comprising, from N-terminus to C-terminus, a first VH region, a CH1, a hinge region, a CH2 region, a CH3 region, a second VH region, and a CH1 region, the amino acid sequence of which comprises an amino acid sequence selected from the group consisting of:

(SEQ ID NO: 74)
QVQLQESGPGLVKPSETLSLTCTVSGGSVSSGSYYWSWIRQPPGKGLEWIG
YIYYSGSTNYNPSLKSRVTISVDTSKNQFSLKLSSVTAADTAVYYCARTNL
YSTPFDIWGQGTMVTVSSASTKGPSVFTLATSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCTAPELLGGPSVFLFPPKPKDTLM
ISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFF
LYSKLTVDKSRWQQGNVFSCSVMHEALHNHYTQKSLSLSPGKGGGGSGGGG
SGGGGSQLQLQESGPGLVKPSETLSLTCTVSGGSINSSSYYWQWIRQPPGK
GLEWIGEIAYSGSTYYNPSLKSRVTISVDTSKNQFSLKLSSVTAADTAVYY
CARGQQWAAFDIWGQGTMVTVSSASTKGPSVFPLAPSSKSTSGGTAALGCL
VKDYFPEPVTVSWNSGALTSGVHTFPAVLQSSGLYSLSSVVTVPSSSLGTQ
TYICNVNHKPSNTKVDKKVEPKSC;

(SEQ ID NO: 75)
QVQLQESGPGLVKPSETLSLTCTVSGGSVSSGSYYWSWIRQPPGKGLEWIG
YIYYSGSTNYNPSLKSRVTISVDTSKNQFSLKLSSVTAADTAVYYCARTNL
YSTPFDIWGQGTMVTVSSASTKGPSVFPLAPSSKSTSGGTAALGCLVKDYF
PEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFF

-continued

LYSKLYVDKSRWQQGNVFSCSVMHEALHNHYTQKSLSLSPGKGGGGSGGGG

SGGGGSQVQLQESGPGLVKPSETLSLTCTVSGGSISSGGYYWSWIRQPPGK

GLEWIGIIYYSGWTNYNPSLKSRVTISVDASRNQFSLKLSSVTAADTAVYY

CARGVGPDFWSGYSYSSYFDLWGRGTLVTVSSASTKGPSVFPLAPSSKSTS

GGTAALGCLVKDYFPEPVTVSWNSGALTSGVHTFPAVLQSSGLYSLSSVVT

VPSSSLGTQTYICNVNHKPSNTKVDKKVEPKSC;

(SEQ ID NO: 76)
QVQLQESGPGLVKPSETLSLTCTVSGGSISSGGYYWSWIRQPPGKGLEWIG

IIYYSGWTNYNPSLKSRVTISVDASRNQFSLKLSSVTAADTAVYYCARGVG

PDFWSGYSYSSYFDLWGRGTLVTVSSASTKGPSVFPLAPSSKSTSGGTALG

CLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKGG

GGSGGGGSGGGGSQVQLQESGPGLVKPSETLSLTCTVSGGSVSSGSYYWSW

IRQPPGKGLEWIGYIYYSGSTNYNPSLKSRVTISVDTSKNQFSLKLSSVTA

ADTAVYYCARTNLYSTPFDIWGQGTMVTVSSASTKGPSVFPLAPSSKSTSG

GTAALGCLVKDYFPEPVTVSWNSGALTSGVHTFPAVLQSSGLYSLSSVVTV

PSSSLGTQTYICNVNHKPSNTKVDKKVEPKSC;

(SEQ ID NO: 77)
QLQLQESGPGLVKPSETLSLTCTVSGGSINSSSYYWQWIRQPPGKGLEWIG

EIAYSGSTYYNPSLKSRVTISVDTSKNQFSLKLSSVTAADTAVYYCARGQQ

WAAFDIWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVS

VLTVLHQDWLNGKEYKCKVSNKALPARIEKTISKAKGQPREPQVYTLPPSR

DELTKNQVSLTCLVKGFYPSDIAVEWESNGQPENNYKTTPPVLDSDGSFFL

YSKLTVDKSRWQQGNVFSCSVMHEALHNHYTQKSLSLSPGKGGGSGGGGS

GGGGSQVQLQESGPGLVKPSETLSLTCTVSGGSVSSGSYYWSWIRQPPGKG

LEWIGYIYYSGSTNYNPSLKSRVTISVDTSKNQFSLKLSSVTAADTAVYYC

ARTNLYSTPFDIWGQGTMVTVSSASTKGPSVFPLAPSSKSTSGGTAALGCL

VKDYFPEPVTVSWNSGALTSGVHTFPAVLQSSGLYSLSSVVTVPSSSLGTQ

TYICNVNHKPSNTKVDKKVEPKSC.

Embodiment 36. The method according to any one of Embodiments 1 through 35, wherein the multispecific antibody analog comprises four copies of a polypeptide comprising, from N-terminus to C-terminus, a VL region, and a CK region, and wherein said polypeptide heterodimerizes with compatible VH regions of the multispecific antibody analog, the amino acid sequence of which comprises an amino acid sequence selected from the group consisting of:

(SEQ ID NO: 78)
DIQLTQSPSSVSASVGDRVTITCRASQDISSWLAWYQQKPGKAPKILIYAA

SSLQSGVPSRFSGSGSGTDFTLTISSLQPEDFATYYCQQEHDFPWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 79)
DIQLTQSPSTLSASVGDRVTITCRASQAISSWLAWYQQKPGKAPKLLIYDA

SSLESGVPSRFSGSGSGTEFTLTISSLQPDDFATYYCHQYQSYSWTFGGGT

KVEIKRTVSSPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 80)
DIQMTQSPSSLSASVGDRVTITCRASQNIATDVAWYQQKPGKAPKLLIYSA

SFLYSGVPSRFSGSGSGTDFTLTISSLQPEDFATYYCQQSEPEPYTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;

(SEQ ID NO: 81)
DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC;
and (SEQ ID NO: 82)
DILLTQSPVILSVSPGERVSFSCRASQSIGTNIHWYQQRTHGSPRLLIKYA

SESISGIPSRFSGSGSGTDFTLSINSVESEDIADYYCQQNNNWPTTFGAGT

KLELKRTVAAPSVFIYPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.

Embodiment 37. The method according to any one of Embodiments 1 through 36 wherein the multispecific antibody analog has binding specificity for an oncology target.

Embodiment 38. The method according to any one of Embodiments 1 through 37, wherein the multispecific antibody analog has binding specificity for one or more targets selected from the group consisting of: EGFR, HER2, and HER3.

Embodiment 39. The method according to any one of Embodiments 1 through 38, wherein the multispecific antibody analog has binding specificity for EGFR and HER2.

Embodiment 40. The method according to any one of Embodiments 1 through 39, wherein the polypeptide multispecific antibody analog has binding specificity for EGFR and HER3.

Embodiment 41. The method according to any one of Embodiments 1 through 40, wherein the multispecific antibody analog has binding specificity for EGFR, HER2, and HER3.

Embodiment 42. The method according to any one of Embodiments 1 through 41, wherein the multispecific antibody analog is selected from the group consisting of the multispecific antibody analogs described in the Examples.

Embodiment 43. The method according to any one of Embodiments 1 through 42, wherein the multispecific antibody analog is expressed by a prokaryotic host cell or a eukaryotic host cell.

Embodiment 44. The method according to any one of Embodiments 1 through 43, wherein the multispecific antibody analog is expressed by a eukaryotic host cell.

Embodiment 45. The method according to any one of Embodiments 1 through 44, wherein the multispecific antibody analog is expressed by a eukaryotic host cell selected from the group consisting of: yeast cells; *Saccharomyces cerevisiae* cells; *Pichia* cells; mammalian cells; Chinese hamster ovary (CHO) cells; human embryonic kidney (HEK) cells; insect cells; Sf9 cells; and Sf21 cells.

Embodiment 46. A multispecific antibody analog prepared by performing a method according to any one of Embodiments 1 through 44.

Embodiment 47. A multispecific antibody analog comprising at least two first antigen binding regions and at least two second antigen binding regions, said first and second antigen binding regions having a common light chain, wherein first antigen binding regions have a different antigen specificity than the second antigen binding regions.

Embodiment 48. A multispecific antibody analog comprising at least two first antigen binding regions and at least two second antigen binding regions, said first and second antigen binding regions having a common light chain, wherein first antigen binding regions have a different antigen specificity than the second antigen binding regions, wherein the analog prepared by a method comprising:

i) obtaining at least one light chain from a first antigen binding region having specificity for the first antigen, wherein the first antigen binding region comprises said at least one light chain and a heavy chain;

ii) obtaining heavy chains from the output of a selection performed from a naïve library against a second antigen;

iii) preparing an multispecific antibody library comprising heavy chains obtained in step ii) and the at least one light chain obtained in step i);

iv) performing a second selection against the second antigen from the library prepared in step iii);

v) obtaining an multispecific antibody comprising the second antigen binding region from the selection performed in step iv);

vi) incorporating the first antigen binding region and the second antigen binding region into a multispecific antibody format, wherein the format comprises:

an IgG moiety comprising either:

a) the first antigen binding region; or b) the second antigen binding region; and two Fab moieties, wherein each Fab moiety comprises either:

a) the second antigen binding region; or b) the first antigen binding region;

wherein the N-terminus of the heavy chain of one Fab moiety is linked to the C-terminus of the Fc region of one heavy chain of the IgG moiety via a linker moiety, and the N-terminus of the heavy chain of the other Fab moiety is linked to the C-terminus of the Fc region of the other heavy chain of the IgG moiety via a linker moiety;

thereby generating the multispecific antibody analog.

Embodiment 49. The multispecific antibody analog to Embodiment 48, wherein each linker moiety independently comprises a peptide from 1 to 75 amino acids in length, inclusive.

Embodiment 50. The multispecific antibody analog according to any one of Embodiments 48 through 49, wherein one or more of the linker moieties independently comprises at least one of the 20 naturally occurring amino acids.

Embodiment 51. The multispecific antibody analog according to any one of Embodiments 48 through 50, wherein the one or more of the linker moieties independently comprises at least one non-natural amino acid incorporated by chemical synthesis, post-translational chemical modification or by in vivo incorporation by recombinant expression in a host cell.

Embodiment 52. The multispecific antibody analog according to any one Embodiments of 48 through 51, wherein the one or more of the linker moieties independently comprises one or more amino acids selected from the group consisting of serine, glycine, alanine, proline, asparagine, glutamine, glutamate, aspartate, and lysine.

Embodiment 53. The multispecific antibody analog according to any one of Embodiments 48 through 52, wherein the one or more of the linker moieties independently comprises a majority of amino acids that are sterically unhindered.

Embodiment 54. The multispecific antibody analog according to any one of Embodiments 48 through 53, wherein the one or more of the linker moieties independently comprises one or more of the following: an acidic linker, a basic linker, and a structural motif.

Embodiment 55. The multispecific antibody analog according to any one of Embodiments 48 through 54, wherein one or more of the linker moieties independently comprises: polyglycine, polyalanine, poly(Gly-Ala), or poly(Gly-Ser).

Embodiment 56. The multispecific antibody analog according to any one of Embodiments 48 through 55, wherein one or more of the linker moieties independently comprises: a polyglycine selected from the group consisting of: $(Gly)_3$ (SEQ ID NO: 1), $(Gly)_4$ (SEQ ID NO: 2), and $(Gly)_5$ (SEQ ID NO: 3).

Embodiment 57. The multispecific antibody analog according to any one of Embodiments 48 through 56 wherein one or more of the linker moieties independently comprises $(Gly)_3Lys(Gly)_4$ (SEQ ID NO: 4); $(Gly)_3AsnGlySer(Gly)_2$ (SEQ ID NO: 5); $(Gly)_3Cys(Gly)_4$ (SEQ ID NO: 6); and GlyProAsnGlyGly (SEQ ID NO: 7).

Embodiment 58. The multispecific antibody analog according to any one of Embodiments 48 through 57, wherein one or more of the linker moieties independently comprises a combination of Gly and Ala.

Embodiment 59. The multispecific antibody analog according to any one of Embodiments 48 through 58, wherein one or more of the linker moieties independently comprises a combination of Gly and Ser.

Embodiment 60. The multispecific antibody analog according to any one of Embodiments 48 through 59, wherein one or more of the linker moieties independently comprises a combination of:

Gly and Glu; or

Gly and Asp.

Embodiment 61. The multispecific antibody analog according to any one of 48 through 60, wherein one or more of the linker moieties independently comprises a combination of Gly and Lys.

Embodiment 62. The multispecific antibody analog according to any one of Embodiments 48 through 61, wherein one or more of the linker moieties independently comprises a sequence selected from group consisting of: [Gly-Ser], (SEQ ID NO: 8); [Gly-Gly-Ser], (SEQ ID NO: 9); [Gly-Gly-Gly-Ser], (SEQ ID NO: 10); [Gly-Gly-Gly-Gly-Ser], (SEQ ID NO: 11); [Gly-Gly-Gly-Gly-Ser-Gly-Gly-Gly-Gly], (SEQ ID NO: 12); [Gly-Gly-Gly-Gly-Ser-Gly-Gly-Gly-Gly-Ser-Gly-Gly-Gly-Gly]$_n$ (SEQ ID NO: 13); [Gly-Gly-Gly-Gly-Ser Gly-Gly-Gly-Gly-Ser-Gly-Gly-Gly-Gly-Ser-Gly-Gly-Gly-Gly]$_n$ (SEQ ID NO: 14); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 15); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 16); [Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly-Ser-Gly-Gly-Gly-Gly]$_n$ (SEQ ID NO: 17); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Embodiment 63. The multispecific antibody analog according to any one of Embodiments 48 through 62, wherein one or more of the linker moieties independently comprises a sequence selected from the group consisting of: [Gly-Glu]n (SEQ ID NO: 18); [Gly-Gly-Glu]n (SEQ ID NO: 19); [Gly-Gly-Gly-Glu]n (SEQ ID NO: 20); [Gly-Gly-Gly-Gly-Glu]n (SEQ ID NO: 21); [Gly-Asp]n (SEQ ID NO: 22); [Gly-Gly-Asp]$_n$ (SEQ ID NO: 23); [Gly-Gly-Gly-Asp]$_n$ (SEQ ID NO: 24); [Gly-Gly-Gly-Gly-Asp]$_n$ (SEQ ID NO: 25); and combinations thereof; where n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, and 75.

Embodiment 64. The multispecific antibody analog according to any one of Embodiments 48 through 63, wherein at least one of the first and second antigen binding regions comprises at least one humanized variable heavy domain or at least one humanized variable light domain.

Embodiment 65. The multispecific antibody analog according to any one of Embodiments 48 through 64, wherein at least one of the first and second antigen binding regions comprises at least one complimentary determining region CDR that is derived from a non-human multispecific antibody or multispecific antibody fragment.

Embodiment 66. The method according to any one of Embodiments 1 through 45, or the multispecific antibody analog according to any one of Embodiments 46 through 65, wherein at least one of the first and second antigen binding regions binds an epitope from a tumor associated antigen, a hormone receptor, a cytokine receptor, chemokine receptor, a growth factor receptor, an immune activating receptor, a hormone, a cytokine, a chemokine, a growth factor, a G protein-coupled receptor, or a transmembrane receptor.

Embodiment 67. The method according to any one of Embodiments 1 through 45, or the multispecific antibody analog according to any one of Embodiments 46 through 66, wherein at least one of the first and second antigen binding regions binds a target associated with an autoimmune disorder, an inflammatory disorder, an oncological disorder, neuromuscular disorder, a neurodegenerative disorder, a metabolic disorder, or an infectious disease.

Embodiment 68. The method according to any one of Embodiments 1 through 45, or the multispecific antibody analog according to any one of Embodiments 46 through 67, wherein the multispecific antibody analog binds at least two different targets.

Embodiment 69. The method according to any one of Embodiments 1 through 45, or the multispecific antibody analog according to any one of Embodiments 46 through 68, wherein the multispecific analog binds at least three different targets.

Embodiment 70. The method according to any one of Embodiments 1 through 45, or the multispecific antibody analog according to any one of Embodiments 46 through 69, wherein the multispecific antibody analog binds at least four different targets.

Embodiment 71. The method according to any one of Embodiments 1 through 45, or the multispecific antibody analog according to any one of Embodiments 46 through 70, wherein the multispecific antibody analog binds at least one target monovalently.

Embodiment 72. The method according to any one of Embodiments 1 through 45, or the multispecific antibody analog according to any one of Embodiments 46 through 71, wherein the multispecific antibody analog binds at least two targets monovalently.

Embodiment 73. The method according to any one of Embodiments 1 through 45, or the multispecific antibody analog according to any one of Embodiments 46 through 72, wherein the multispecific antibody analog binds at least three targets monovalently.

Embodiment 74. The method according to any one of Embodiments 1 through 45, or the multispecific antibody analog according to any one of Embodiments 46 through 73, wherein the multispecific antibody analog binds at least four targets monovalently.

Embodiment 75. The method according to any one of Embodiments 1 through 45, or the multispecific antibody analog according to any one of Embodiments 46 through 74, wherein at least one of the antigen binding regions comprises or is derived from a non-human species.

Embodiment 76. The method according to any one of Embodiments 1 through 45, or the multispecific antibody analog according to any one of Embodiments 46 through 75, wherein at least one of the antigen binding sites comprises a humanized variable domain or a humanized CDR.

Embodiment 77. A method if obtaining or identifying one or more common light chains for use in preparing a multispecific antibody or multispecific antibody analog, the method comprising:
  i) performing a first selection against a first antigen from a first library and obtaining one or more light chains from the output that has specificity for the first antigen;
  ii) performing a second selection against a second antigen from a second library and obtaining heavy chains from the output that has specificity for the second antigen;
  iii) generating a restricted library comprising the one or more light chains obtained in step i) and the heavy chains obtained in step ii);
  iv) performing a third selection against the first antigen from the restricted library generated in step iii) and obtaining one or more antibodies form the output of the third selection, wherein the one or more antibodies comprise one or more light chains that each have specificity for the first antigen and the second antigen;

thereby obtaining or identifying the one or more common light chains.

Embodiment 78. The method according to Embodiment 77, wherein:
a) the first library comprises a naïve library;
b) the second library comprises a naïve library; or
c) the first library comprises a naïve library and the second library comprises a naïve library.

Embodiment 79. The method according to Embodiment 77 or Embodiment 78, wherein the method further comprises:
a) performing a subsequent selection against the first antigen from a maturation library;
b) performing a subsequent selection against the second antigen from a maturation library; or
c) performing a subsequent selection against the first antigen from a maturation library and performing a subsequent selection against the second antigen from a maturation library;
after performing:
a) step i;
b) step ii
c) step iii; and/or
d) step iv.

Embodiment 80. A method of making a multispecific antibody analog comprising contacting the one or more common light chains obtained or identified according to any one of Embodiment 77 Embodiment 79 with:
i) a first polypeptide comprising a heavy chain that has specificity for the first antigen; and
ii) A second polypeptide comprising a heavy chain that has specificity for the second antigen.

Embodiment 81. The method according to Embodiment 81, wherein the one or more common light chains, the first polypeptide, and the second polypeptide are expressed by host cells.

Embodiment 82. The method according to Embodiment 81 or Embodiment 82, wherein the one or more common light chains, the first polypeptide, and the second polypeptide are expressed by the same host cell.

Embodiment 83. A multispecific antibody analog comprising a common light chain obtained or identified by performing a method according to any one of Embodiments 77 through 81.

Whereas particular embodiments of the invention have been described above for purposes of illustration, it will be appreciated by those skilled in the art that numerous variations of the details may be made without departing from the invention as described in the appended claims.

REFERENCES

Estep P., Reid F., Nauman C., Liu Y., Sun T., Sun J. and Xu Y. (2013) *mAbs*, 5, 270-278. First published on 2013 Apr. 12, doi: 10.4161/mabs.23049.

Xu Y., Roach W., Sun T., Jain T., Prinz B., Yu T. Y., Torrey J., Thomas J., Bobrowicz P., Vasquez M. et al. (2013) *Protein engineering, design & selection: PEDS*, 26, 663-670. First published on 2013 Sep. 21, doi: 10.1093/protein/gzt047.

Siegel R. W., Coleman J. R., Miller K. D. and Feldhaus M. J. (2004) *Journal of immunological methods*, 286, 141-153. First published on 2004 Apr. 17, doi: 10.1016/j.jim.2004.01.005.

Horlick R. A., Macomber J. L., Bowers P. M., Neben T. Y., Tomlinson G. L., Krapf I. P., Dalton J. L., Verdino P. and King D. J. (2013) *The Journal of biological chemistry*. First published on 2013 May 22, doi: 10.1074/jbc.M113.452482

Mazor Y., Van Blarcom T., Mabry R., Iverson B. L. and Georgiou G. (2007) *Nature biotechnology*, 25, 563-565. First published on 2007 Apr. 17, doi: 10.1038/nbt1296.

Nett J. H., Cook W. J., Chen M. T., Davidson R. C., Bobrowicz P., Kett W., Brevnova E., Potgieter T. I., Mellon M. T., Prinz B. et al. (2013) *PloS one*, 8, e68325. First published on 2013 Jul. 11, doi: 10.1371/journal.pone.0068325.

Rakestraw J. A., Aird D., Aha P. M., Baynes B. M. and Lipovsek D. (2011) *Protein engineering, design & selection: PEDS*, 24, 525-530. First published on 2011 Mar. 16, doi: 10.1093/protein/gzr008.

Doerner A., Rhiel L., Zielonka S. and Kolmar H. (2013) *FEBS letters*. First published on 2013 Dec. 3, doi: 10.1016/j.febslet.2013.11.025.

What is claimed is:

1. A method of identifying a common VL for use in the synthesis of a multispecific antibody, wherein:
   (A) at least one first antigen binding region comprises a first VH and the common VL; and
   (B) at least one second antigen binding region comprises a second VH and the common VL,
   wherein:
   (A) the first antigen binding region has specificity for a first antigen; and
   (B) the second antigen binding region has specificity for a second antigen different from the first antigen,
   and the method comprises the steps of:
   (i) identifying one or more antigen binding regions having specificity for the first antigen, each of the antigen binding regions comprising: a first-antigen specific human VH; and a first-antigen specific human VL comprising a framework region of VK1-05, VK1-12, or VK3-11,
   (ii) obtaining one or more of the first-antigen specific human VLs from (i),
   (iii) identifying antigen binding regions having specificity for the second antigen, each of the antigen binding regions comprising a second-antigen specific human VH and a second-antigen specific human VL,
   (iv) obtaining two or more of the second-antigen specific human VHs from (iii),
   (v) preparing a restricted library comprising the two or more second-antigen specific human VHs obtained from (iv) and the one or more first-antigen specific human VLs obtained from (ii), wherein the restricted library does not comprise a first-antigen specific human VH from (i), and wherein the restricted library is a human IgG1 antibody library comprising at least $10^5$ different human VHs and 1 to 2910 different human VLs,
   (vi) performing a selection against the second antigen using the restricted library prepared in (v), and
   (vii) identifying from the selection performed in (vi) at least one antigen binding region having specificity for the second antigen, the at least one antigen binding region comprising: a second-antigen specific human VH; and a human VL identical to a first-antigen specific human VL obtained in (ii), thereby identifying a common VL, wherein the common VL:
   (a) has specificity for the first antigen when associated with at least one first-antigen specific human VH from (i), and
   (b) has specificity for the second antigen when associated with at least one second-antigen specific human VH identified in (vii).

2. The method of claim 1, wherein:
   (a) the identifying in (i) is from a selection performed using a naïve library,
   (b) the identifying in (iii) is from a selection performed using a naïve library, or
   (c) the identifying in (i) is from a selection performed using a naïve library and the identifying in (iii) is from a selection performed using a naïve library.

3. A method of identifying a common VL, wherein the common VL:
   (a) has specificity for a first antigen, when associated with at least one VH, and
   (b) has specificity for a second antigen, when associated with at least one VH different from the VH in (a),
   and wherein the first antigen is different from the second antigen and the method comprises the steps of:
   (i) obtaining one or more first-antigen specific human VLs from one or more antigen binding regions having specificity for the first antigen, each of the antigen binding regions comprising: a first-antigen specific human VH; and a first-antigen specific human VL comprising a framework region of VK1-05, VK1-12, or VK3-11,
   (ii) identifying antigen binding regions having specificity for the second antigen, each of the antigen binding regions comprising a second-antigen specific human VH and a second-antigen specific human VL,
   (iii) obtaining two or more of the second-antigen specific human VHs from (ii), (iv) preparing a restricted library comprising the two or more second-antigen specific human VHs obtained from (iii) and the one or more first-antigen specific human VLs obtained from (i), wherein the restricted library does not comprise a first-antigen specific human VH according to (i), and wherein the restricted library is a human IgG1 library comprising at least $10^5$ different human VHs and 1 to 10 different human VLs, (v) performing a selection against the second antigen using the restricted library prepared in (iv), and (vi) identifying from the selection performed in (v) at least one antigen binding region having specificity for the second antigen, the at least one antigen binding region comprising: a second-antigen specific human VH; and a human VL identical to a first-antigen specific human VL obtained in (i), thereby identifying a common VL from the selection performed in (v), wherein the common VL:

(a) has specificity for the first antigen when associated with at least one first-antigen specific human VH according to (i), and (b) has specificity for the second antigen when associated with at least one second-antigen specific human VH identified in (vi).

4. The method of claim 3, wherein the identifying in (ii) is from a selection performed using a naïve library.

5. The method of claim 1, wherein, in (ii), at least one of the one or more first-antigen specific human VLs comprises a framework region of VK1-05.

6. The method of claim 1, wherein, in (ii), at least one of the one or more first-antigen specific human VLs comprises a framework region of VK1-12.

7. The method of claim 1, wherein, in (ii), at least one of the one or more first-antigen specific human VLs comprises a framework region of VK3-11.

8. The method of claim 3, wherein, in (i), at least one of the one or more first-antigen specific human VLs comprises a framework region of VK1-05.

9. The method of claim 3, wherein, in (i), at least one of the one or more first-antigen specific human VLs comprises a framework region of VK1-12.

10. The method of claim 3, wherein, in (i), at least one of the one or more first-antigen specific human VLs comprises a framework region of VK3-11.

* * * * *

SEQUENCE LISTING

```
<160> NUMBER OF SEQ ID NOS: 99

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Gly Gly Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Lys Gly Gly Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Asn Gly Ser Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Cys Gly Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Pro Asn Gly Gly
1               5

<210> SEQ ID NO 8
<211> LENGTH: 150
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(150)
<223> OTHER INFORMATION: This sequence may encompass 1-75 "Gly Ser"
      repeating units, wherein some positions may be absent

<400> SEQUENCE: 8

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

Gly Ser Gly Ser Gly Ser Gly Ser Gly Ser Gly Ser Gly Ser Gly Ser
        35                  40                  45

Gly Ser Gly Ser Gly Ser Gly Ser Gly Ser Gly Ser Gly Ser Gly Ser
    50                  55                  60

Gly Ser Gly Ser Gly Ser Gly Ser Gly Ser Gly Ser Gly Ser Gly Ser
65                  70                  75                  80

Gly Ser Gly Ser Gly Ser Gly Ser Gly Ser Gly Ser Gly Ser Gly Ser
                85                  90                  95

Gly Ser Gly Ser Gly Ser Gly Ser Gly Ser Gly Ser Gly Ser Gly Ser
            100                 105                 110

Gly Ser Gly Ser Gly Ser Gly Ser Gly Ser Gly Ser Gly Ser Gly Ser
        115                 120                 125

Gly Ser Gly Ser Gly Ser Gly Ser Gly Ser Gly Ser Gly Ser Gly Ser
    130                 135                 140

Gly Ser Gly Ser Gly Ser
145                 150

<210> SEQ ID NO 9
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(225)
<223> OTHER INFORMATION: This sequence may encompass 1-75 "Gly Gly Ser"
      repeating units, wherein some positions may be absent

<400> SEQUENCE: 9

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
```

```
                    115                 120                 125
Ser Gly Gly Ser Gly Gly Ser Gly Gly Ser Gly Gly Ser Gly Gly Ser
            130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
                165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
        195                 200                 205

Gly Ser Gly Gly Ser Gly Gly Ser Gly Gly Ser Gly Gly Ser Gly Gly
    210                 215                 220

Ser
225

<210> SEQ ID NO 10
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(300)
<223> OTHER INFORMATION: This sequence may encompass 1-75 "Gly Gly Gly
      Ser" repeating units, wherein some positions may be absent

<400> SEQUENCE: 10

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser Gly Gly Gly Ser Gly Gly Gly Ser
        115                 120                 125

Gly Gly Gly Ser Gly Gly Gly Ser Gly Gly Gly Ser Gly Gly Gly Ser
    130                 135                 140

Gly Gly Gly Ser Gly Gly Gly Ser Gly Gly Gly Ser Gly Gly Gly Ser
145                 150                 155                 160

Gly Gly Gly Ser Gly Gly Gly Ser Gly Gly Gly Ser Gly Gly Gly Ser
                165                 170                 175

Gly Gly Gly Ser Gly Gly Gly Ser Gly Gly Gly Ser Gly Gly Gly Ser
            180                 185                 190

Gly Gly Gly Ser Gly Gly Gly Ser Gly Gly Gly Ser Gly Gly Gly Ser
        195                 200                 205

Gly Gly Gly Ser Gly Gly Gly Ser Gly Gly Gly Ser Gly Gly Gly Ser
```

```
               210                 215                 220
Gly Gly Gly Ser Gly Gly Gly Ser Gly Gly Gly Ser Gly Gly Gly Ser
225                 230                 235                 240

Gly Gly Gly Ser Gly Gly Gly Ser Gly Gly Gly Ser Gly Gly Gly Ser
            245                 250                 255

Gly Gly Gly Ser Gly Gly Gly Ser Gly Gly Gly Ser Gly Gly Gly Ser
            260                 265                 270

Gly Gly Gly Ser Gly Gly Gly Ser Gly Gly Gly Ser Gly Gly Gly Ser
        275                 280                 285

Gly Gly Gly Ser Gly Gly Gly Ser Gly Gly Gly Ser
        290                 295                 300

<210> SEQ ID NO 11
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Gly Gly Gly
      Gly Ser" repeating units, wherein some positions may be absent

<400> SEQUENCE: 11

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
```

```
                        245                 250                 255
Gly Gly Gly Ser Gly Gly Gly Ser Gly Gly Gly Ser Gly Gly
            260                 265                 270
Gly Gly Ser Gly Gly Gly Gly Ser Gly Gly Gly Ser Gly Gly
        275                 280                 285
Gly Ser Gly Gly Gly Gly Ser Gly Gly Gly Ser Gly Gly Gly
    290                 295                 300
Ser Gly Gly Gly Gly Ser Gly Gly Gly Ser Gly Gly Gly Ser
305                 310                 315                 320
Gly Gly Gly Gly Ser Gly Gly Gly Ser Gly Gly Gly Ser Gly
            325                 330                 335
Gly Gly Gly Ser Gly Gly Gly Ser Gly Gly Gly Ser Gly Gly
        340                 345                 350
Gly Gly Ser Gly Gly Gly Ser Gly Gly Gly Ser Gly Gly Gly
    355                 360                 365
Gly Ser Gly Gly Gly Gly Ser
    370                 375

<210> SEQ ID NO 12
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(675)
<223> OTHER INFORMATION: This sequence may encompass 1-75 "Gly Gly Gly
      Gly Ser Gly Gly Gly Gly" repeating units, wherein some positions
      may be absent

<400> SEQUENCE: 12

Gly Gly Gly Gly Ser Gly Gly Gly Gly Gly Gly Ser Gly Gly
1               5                   10                  15
Gly Gly Gly Gly Gly Gly Ser Gly Gly Gly Gly Gly Gly Ser
            20                  25                  30
Gly Gly Gly Gly Gly Gly Gly Ser Gly Gly Gly Gly Gly Gly
        35                  40                  45
Gly Ser Gly Gly Gly Gly Gly Gly Gly Ser Gly Gly Gly Gly
    50                  55                  60
Gly Gly Gly Ser Gly Gly Gly Gly Gly Ser Gly Gly Gly Gly
65                  70                  75                  80
Gly Gly Gly Gly Gly Ser Gly Gly Gly Gly Gly Gly Ser Gly
            85                  90                  95
Gly Gly Gly Gly Gly Gly Ser Gly Gly Gly Gly Gly Gly Gly
        100                 105                 110
Ser Gly Gly Gly Gly Gly Gly Gly Ser Gly Gly Gly Gly Gly
    115                 120                 125
Gly Ser Gly Gly Gly Gly Gly Gly Gly Ser Gly Gly Gly Gly
    130                 135                 140
Gly Gly Gly Gly Ser Gly Gly Gly Gly Gly Gly Ser Gly Gly
145                 150                 155                 160
Gly Gly Gly Gly Gly Ser Gly Gly Gly Gly Gly Gly Gly Ser
            165                 170                 175
Gly Gly Gly Gly Gly Gly Gly Ser Gly Gly Gly Gly Gly Gly
        180                 185                 190
```

```
Gly Ser Gly Gly Gly Gly Gly Gly Gly Ser Gly Gly Gly
        195                 200                 205
Gly Gly Gly Ser Gly Gly Gly Gly Gly Gly Ser Gly Gly
        210                 215                 220
Gly Gly Gly Gly Gly Ser Gly Gly Gly Gly Gly Gly Ser Gly
225                 230                 235                 240
Gly Gly Gly Gly Gly Gly Ser Gly Gly Gly Gly Gly Gly
                245                 250                 255
Ser Gly Gly Gly Gly Gly Gly Ser Gly Gly Gly Gly Gly
                260                 265                 270
Gly Gly Ser Gly Gly Gly Gly Gly Gly Ser Gly Gly Gly
        275                 280                 285
Gly Gly Gly Gly Ser Gly Gly Gly Gly Gly Gly Ser Gly Gly
        290                 295                 300
Gly Gly Gly Gly Gly Ser Gly Gly Gly Gly Gly Gly Ser
305                 310                 315                 320
Gly Gly Gly Gly Gly Gly Gly Ser Gly Gly Gly Gly Gly
                325                 330                 335
Gly Ser Gly Gly Gly Gly Gly Gly Gly Ser Gly Gly Gly
        340                 345                 350
Gly Gly Gly Ser Gly Gly Gly Gly Gly Gly Ser Gly Gly
        355                 360                 365
Gly Gly Gly Gly Ser Gly Gly Gly Gly Gly Gly Ser Gly
        370                 375                 380
Gly Gly Gly Gly Gly Gly Ser Gly Gly Gly Gly Gly Gly
385                 390                 395                 400
Ser Gly Gly Gly Gly Gly Gly Ser Gly Gly Gly Gly Gly
                405                 410                 415
Gly Gly Ser Gly Gly Gly Gly Gly Gly Ser Gly Gly Gly
        420                 425                 430
Gly Gly Gly Gly Ser Gly Gly Gly Gly Gly Gly Ser Gly Gly
        435                 440                 445
Gly Gly Gly Gly Gly Ser Gly Gly Gly Gly Gly Gly Ser
450                 455                 460
Gly Gly Gly Gly Gly Gly Gly Ser Gly Gly Gly Gly Gly
465                 470                 475                 480
Gly Ser Gly Gly Gly Gly Gly Gly Gly Ser Gly Gly Gly
                485                 490                 495
Gly Gly Gly Ser Gly Gly Gly Gly Gly Gly Ser Gly Gly
                500                 505                 510
Gly Gly Gly Gly Ser Gly Gly Gly Gly Gly Gly Ser Gly
                515                 520                 525
Gly Gly Gly Gly Gly Gly Ser Gly Gly Gly Gly Gly Gly
        530                 535                 540
Ser Gly Gly Gly Gly Gly Gly Ser Gly Gly Gly Gly Gly
545                 550                 555                 560
Gly Gly Ser Gly Gly Gly Gly Gly Gly Ser Gly Gly Gly
                565                 570                 575
Gly Gly Gly Ser Gly Gly Gly Gly Gly Gly Ser Gly Gly
                580                 585                 590
Gly Gly Gly Gly Gly Ser Gly Gly Gly Gly Gly Gly Ser
                595                 600                 605
Gly Gly Gly Gly Gly Gly Gly Gly Ser Gly Gly Gly Gly Gly Gly
```

```
                610                 615                 620
Gly Ser Gly Gly Gly Gly Gly Gly Gly Ser Gly Gly Gly Gly
625                 630                 635                 640

Gly Gly Gly Ser Gly Gly Gly Gly Gly Gly Gly Ser Gly Gly
                645                 650                 655

Gly Gly Gly Gly Ser Gly Gly Gly Gly Gly Gly Ser Gly
            660                 665                 670

Gly Gly Gly
        675

<210> SEQ ID NO 13
<211> LENGTH: 1050
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(1050)
<223> OTHER INFORMATION: This sequence may encompass 1-75 "Gly Gly Gly
      Gly Ser Gly Gly Gly Gly Ser Gly Gly Gly Gly" repeating units,
      wherein some positions may be absent

<400> SEQUENCE: 13

Gly Gly Gly Gly Ser Gly Gly Gly Ser Gly Gly Gly Gly Gly
1               5                   10                  15

Gly Gly Ser Gly Gly Gly Gly Ser Gly Gly Gly Gly Gly Gly
            20                  25                  30

Ser Gly Gly Gly Gly Ser Gly Gly Gly Gly Gly Gly Ser Gly
        35                  40                  45

Gly Gly Gly Ser Gly Gly Gly Gly Gly Gly Gly Ser Gly Gly
    50                  55                  60

Gly Ser Gly Gly Gly Gly Gly Gly Ser Gly Gly Gly Gly Ser
65                  70                  75                  80

Gly Gly Gly Gly Gly Gly Gly Ser Gly Gly Gly Ser Gly Gly
            85                  90                  95

Gly Gly Gly Gly Gly Ser Gly Gly Gly Ser Gly Gly Gly Gly
            100                 105                 110

Gly Gly Gly Gly Ser Gly Gly Gly Ser Gly Gly Gly Gly Gly
        115                 120                 125

Gly Gly Ser Gly Gly Gly Gly Ser Gly Gly Gly Gly Gly Gly
    130                 135                 140

Ser Gly Gly Gly Gly Ser Gly Gly Gly Gly Gly Gly Ser Gly
145                 150                 155                 160

Gly Gly Gly Ser Gly Gly Gly Gly Gly Gly Gly Ser Gly Gly
            165                 170                 175

Gly Ser Gly Gly Gly Gly Gly Gly Gly Ser Gly Gly Gly Ser
            180                 185                 190

Gly Gly Gly Gly Gly Gly Gly Ser Gly Gly Gly Gly Ser Gly Gly
        195                 200                 205

Gly Gly Gly Gly Gly Ser Gly Gly Gly Ser Gly Gly Gly Gly
    210                 215                 220

Gly Gly Gly Ser Gly Gly Gly Ser Gly Gly Gly Gly Gly Gly
225                 230                 235                 240

Gly Gly Ser Gly Gly Gly Gly Ser Gly Gly Gly Gly Gly Gly
            245                 250                 255
```

-continued

Ser Gly Gly Gly Gly Ser Gly Gly Gly Gly Gly Gly Ser Gly
              260                 265                 270

Gly Gly Gly Ser Gly Gly Gly Gly Gly Gly Ser Gly Gly Gly
          275                 280                 285

Gly Ser Gly Gly Gly Gly Gly Gly Ser Gly Gly Gly Gly Ser
      290                 295                 300

Gly Gly Gly Gly Gly Gly Ser Gly Gly Gly Ser Gly Gly
305                 310                 315                 320

Gly Gly Gly Gly Gly Ser Gly Gly Gly Ser Gly Gly Gly Gly
                  325                 330                 335

Gly Gly Gly Gly Ser Gly Gly Gly Ser Gly Gly Gly Gly Gly
              340                 345                 350

Gly Gly Ser Gly Gly Gly Ser Gly Gly Gly Gly Gly Gly Gly
          355                 360                 365

Ser Gly Gly Gly Gly Ser Gly Gly Gly Gly Gly Gly Ser Gly
      370                 375                 380

Gly Gly Gly Ser Gly Gly Gly Gly Gly Gly Ser Gly Gly Gly
385                 390                 395                 400

Gly Ser Gly Gly Gly Gly Gly Gly Ser Gly Gly Gly Gly Ser
                  405                 410                 415

Gly Gly Gly Gly Gly Gly Gly Ser Gly Gly Gly Ser Gly Gly
              420                 425                 430

Gly Gly Gly Gly Gly Ser Gly Gly Gly Ser Gly Gly Gly Gly
          435                 440                 445

Gly Gly Gly Gly Ser Gly Gly Gly Ser Gly Gly Gly Gly Gly
      450                 455                 460

Gly Gly Ser Gly Gly Gly Ser Gly Gly Gly Gly Gly Gly Gly
465                 470                 475                 480

Ser Gly Gly Gly Gly Ser Gly Gly Gly Gly Gly Gly Ser Gly
                  485                 490                 495

Gly Gly Gly Ser Gly Gly Gly Gly Gly Gly Ser Gly Gly Gly
              500                 505                 510

Gly Ser Gly Gly Gly Gly Gly Gly Ser Gly Gly Gly Gly Ser
          515                 520                 525

Gly Gly Gly Gly Gly Gly Gly Ser Gly Gly Gly Ser Gly Gly
      530                 535                 540

Gly Gly Gly Gly Gly Ser Gly Gly Gly Ser Gly Gly Gly Gly
545                 550                 555                 560

Gly Gly Gly Gly Ser Gly Gly Gly Ser Gly Gly Gly Gly Gly
                  565                 570                 575

Gly Gly Ser Gly Gly Gly Ser Gly Gly Gly Gly Gly Gly Gly
              580                 585                 590

Ser Gly Gly Gly Gly Ser Gly Gly Gly Gly Gly Gly Ser Gly
          595                 600                 605

Gly Gly Gly Ser Gly Gly Gly Gly Gly Gly Ser Gly Gly Gly
      610                 615                 620

Gly Ser Gly Gly Gly Gly Gly Gly Ser Gly Gly Gly Gly Ser
625                 630                 635                 640

Gly Gly Gly Gly Gly Gly Gly Ser Gly Gly Gly Ser Gly Gly
                  645                 650                 655

Gly Gly Gly Gly Gly Ser Gly Gly Gly Ser Gly Gly Gly Gly
              660                 665                 670

Gly Gly Gly Gly Ser Gly Gly Gly Gly Ser Gly Gly Gly Gly Gly Gly

```
            675                 680                 685
Gly Gly Ser Gly Gly Gly Ser Gly Gly Gly Gly Gly Gly
    690                 695                 700
Ser Gly Gly Gly Gly Ser Gly Gly Gly Gly Gly Gly Ser Gly
705                 710                 715                 720
Gly Gly Gly Ser Gly Gly Gly Gly Gly Gly Ser Gly Gly Gly
                725                 730                 735
Gly Ser Gly Gly Gly Gly Gly Gly Ser Gly Gly Gly Ser
            740                 745                 750
Gly Gly Gly Gly Gly Gly Gly Ser Gly Gly Gly Ser Gly Gly
        755                 760                 765
Gly Gly Gly Gly Gly Ser Gly Gly Gly Ser Gly Gly Gly
    770                 775                 780
Gly Gly Gly Gly Ser Gly Gly Gly Ser Gly Gly Gly Gly Gly
785                 790                 795                 800
Gly Gly Ser Gly Gly Gly Ser Gly Gly Gly Gly Gly Gly
            805                 810                 815
Ser Gly Gly Gly Gly Ser Gly Gly Gly Gly Gly Gly Ser Gly
        820                 825                 830
Gly Gly Gly Ser Gly Gly Gly Gly Gly Gly Ser Gly Gly Gly
        835                 840                 845
Gly Ser Gly Gly Gly Gly Gly Gly Ser Gly Gly Gly Ser
    850                 855                 860
Gly Gly Gly Gly Gly Gly Gly Ser Gly Gly Gly Ser Gly Gly
865                 870                 875                 880
Gly Gly Gly Gly Gly Ser Gly Gly Gly Ser Gly Gly Gly Gly
                885                 890                 895
Gly Gly Gly Gly Ser Gly Gly Gly Gly Ser Gly Gly Gly Gly
            900                 905                 910
Gly Gly Ser Gly Gly Gly Gly Ser Gly Gly Gly Gly Gly Gly
        915                 920                 925
Ser Gly Gly Gly Gly Ser Gly Gly Gly Gly Gly Gly Ser Gly
    930                 935                 940
Gly Gly Ser Gly Gly Gly Gly Gly Gly Ser Gly Gly Gly
945                 950                 955                 960
Gly Ser Gly Gly Gly Gly Gly Gly Ser Gly Gly Gly Ser
                965                 970                 975
Gly Gly Gly Gly Gly Gly Ser Gly Gly Gly Ser Gly Gly
            980                 985                 990
Gly Gly Gly Gly Gly Ser Gly  Gly Gly Gly Ser Gly  Gly Gly Gly
            995                 1000                1005
Gly Gly  Gly Gly Ser Gly Gly  Gly Gly Ser Gly Gly  Gly Gly Gly
        1010                1015                1020
Gly Gly  Gly Ser Gly Gly Gly  Gly Ser Gly Gly Gly  Gly Gly Gly
        1025                1030                1035
Gly Gly  Ser Gly Gly Gly Gly  Ser Gly Gly Gly Gly
        1040                1045                1050

<210> SEQ ID NO 14
<211> LENGTH: 1425
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<220> FEATURE:
<221> NAME/KEY: misc_feature
<222> LOCATION: (1)..(1425)
<223> OTHER INFORMATION: This sequence may encompass 1-75 "Gly Gly Gly
      Gly Ser Gly Gly Gly Gly Ser Gly Gly Gly Gly Ser Gly Gly Gly Gly"
      repeating units, wherein some positions may be absent

<400> SEQUENCE: 14

Gly Gly Gly Gly Ser Gly Gly Gly Ser Gly Gly Gly Ser Gly
1               5                   10                  15

Gly Gly Gly Gly Gly Gly Ser Gly Gly Gly Ser Gly Gly Gly
                20                  25                  30

Gly Ser Gly Gly Gly Gly Gly Gly Ser Gly Gly Gly Gly Ser
        35                  40                  45

Gly Gly Gly Gly Ser Gly Gly Gly Gly Gly Gly Ser Gly Gly
        50                  55                  60

Gly Gly Ser Gly Gly Gly Ser Gly Gly Gly Gly Gly Gly Gly
65              70                  75                  80

Ser Gly Gly Gly Gly Ser Gly Gly Gly Ser Gly Gly Gly Gly
                85                  90                  95

Gly Gly Gly Ser Gly Gly Gly Gly Ser Gly Gly Gly Ser Gly Gly
            100                 105                 110

Gly Gly Gly Gly Gly Ser Gly Gly Gly Ser Gly Gly Gly Gly
            115                 120                 125

Ser Gly Gly Gly Gly Gly Gly Gly Ser Gly Gly Gly Gly Ser Gly
            130                 135                 140

Gly Gly Gly Ser Gly Gly Gly Gly Gly Gly Ser Gly Gly Gly
145             150                 155                 160

Gly Ser Gly Gly Gly Ser Gly Gly Gly Gly Gly Gly Gly Ser
            165                 170                 175

Gly Gly Gly Gly Ser Gly Gly Gly Ser Gly Gly Gly Gly Gly
            180                 185                 190

Gly Gly Ser Gly Gly Gly Ser Gly Gly Gly Ser Gly Gly Gly
            195                 200                 205

Gly Gly Gly Gly Gly Ser Gly Gly Gly Ser Gly Gly Gly Ser
210             215                 220

Gly Gly Gly Gly Gly Gly Gly Ser Gly Gly Gly Ser Gly Gly
225             230                 235                 240

Gly Gly Ser Gly Gly Gly Gly Gly Gly Ser Gly Gly Gly Gly
            245                 250                 255

Ser Gly Gly Gly Ser Gly Gly Gly Gly Gly Gly Gly Ser Gly
            260                 265                 270

Gly Gly Gly Ser Gly Gly Gly Ser Gly Gly Gly Gly Gly Gly
            275                 280                 285

Gly Ser Gly Gly Gly Ser Gly Gly Gly Gly Ser Gly Gly Gly Gly
            290                 295                 300

Gly Gly Gly Gly Ser Gly Gly Gly Gly Gly Gly Gly Ser Gly
305             310                 315                 320

Gly Gly Gly Gly Gly Gly Ser Gly Gly Gly Ser Gly Gly Gly
            325                 330                 335

Gly Ser Gly Gly Gly Gly Gly Gly Gly Ser Gly Gly Gly Ser
            340                 345                 350

Gly Gly Gly Gly Ser Gly Gly Gly Gly Gly Gly Ser Gly Gly
            355                 360                 365

Gly Gly Ser Gly Gly Gly Gly Gly Gly Gly Gly Gly Gly Gly
```

```
                370                 375                 380
Ser Gly Gly Gly Ser Gly Gly Gly Ser Gly Gly Gly
385                 390                 395                 400

Gly Gly Gly Ser Gly Gly Gly Ser Gly Gly Ser Gly Gly
                405                 410                 415

Gly Gly Gly Gly Gly Gly Ser Gly Gly Gly Ser Gly Gly Gly
                420                 425                 430

Ser Gly Gly Gly Gly Gly Gly Ser Gly Gly Gly Ser Gly
435                 440                 445

Gly Gly Gly Ser Gly Gly Gly Gly Gly Ser Gly Gly Gly
                450                 455                 460

Gly Ser Gly Gly Gly Ser Gly Gly Gly Gly Gly Gly Ser
465                 470                 475                 480

Gly Gly Gly Gly Ser Gly Gly Gly Ser Gly Gly Gly Gly
                485                 490                 495

Gly Gly Ser Gly Gly Gly Ser Gly Gly Gly Ser Gly Gly Gly
                500                 505                 510

Gly Gly Gly Gly Gly Ser Gly Gly Gly Ser Gly Gly Gly Ser
                515                 520                 525

Gly Gly Gly Gly Gly Gly Gly Ser Gly Gly Gly Ser Gly Gly
530                 535                 540

Gly Gly Ser Gly Gly Gly Gly Gly Gly Ser Gly Gly Gly
545                 550                 555                 560

Ser Gly Gly Gly Ser Gly Gly Gly Gly Gly Gly Ser Gly
                565                 570                 575

Gly Gly Gly Ser Gly Gly Gly Ser Gly Gly Gly Gly Gly
                580                 585                 590

Gly Ser Gly Gly Gly Gly Ser Gly Gly Gly Ser Gly Gly Gly
                595                 600                 605

Gly Gly Gly Gly Ser Gly Gly Gly Ser Gly Gly Gly Ser Gly
                610                 615                 620

Gly Gly Gly Gly Gly Gly Ser Gly Gly Gly Ser Gly Gly Gly
625                 630                 635                 640

Gly Ser Gly Gly Gly Gly Gly Gly Gly Ser Gly Gly Gly Ser
                645                 650                 655

Gly Gly Gly Gly Ser Gly Gly Gly Gly Gly Gly Ser Gly Gly
                660                 665                 670

Gly Gly Ser Gly Gly Gly Gly Ser Gly Gly Gly Gly Gly Gly
                675                 680                 685

Ser Gly Gly Gly Gly Ser Gly Gly Gly Ser Gly Gly Gly Gly
                690                 695                 700

Gly Gly Gly Ser Gly Gly Gly Gly Ser Gly Gly Ser Gly Gly
705                 710                 715                 720

Gly Gly Gly Gly Gly Ser Gly Gly Gly Ser Gly Gly Gly Gly
                725                 730                 735

Ser Gly Gly Gly Gly Gly Gly Gly Ser Gly Gly Gly Ser Gly
                740                 745                 750

Gly Gly Gly Ser Gly Gly Gly Gly Gly Gly Gly Ser Gly Gly
                755                 760                 765

Gly Ser Gly Gly Gly Ser Gly Gly Gly Gly Gly Gly Ser
                770                 775                 780

Gly Gly Gly Gly Ser Gly Gly Gly Gly Ser Gly Gly Gly Gly Gly
785                 790                 795                 800
```

```
Gly Gly Ser Gly Gly Gly Ser Gly Gly Gly Ser Gly Gly
            805             810             815
Gly Gly Gly Gly Gly Ser Gly Gly Gly Ser Gly Gly Gly Ser
            820             825             830
Gly Gly Gly Gly Gly Gly Gly Ser Gly Gly Gly Ser Gly Gly
            835             840             845
Gly Gly Ser Gly Gly Gly Gly Gly Gly Ser Gly Gly Gly Gly
    850             855             860
Ser Gly Gly Gly Gly Ser Gly Gly Gly Gly Gly Gly Ser Gly
865             870             875             880
Gly Gly Gly Ser Gly Gly Gly Ser Gly Gly Gly Gly Gly Gly
            885             890             895
Gly Ser Gly Gly Gly Gly Ser Gly Gly Gly Ser Gly Gly Gly
            900             905             910
Gly Gly Gly Gly Ser Gly Gly Gly Ser Gly Gly Gly Ser Gly
            915             920             925
Gly Gly Gly Gly Gly Gly Ser Gly Gly Gly Ser Gly Gly Gly
    930             935             940
Gly Ser Gly Gly Gly Gly Gly Gly Ser Gly Gly Gly Ser
945             950             955             960
Gly Gly Gly Gly Ser Gly Gly Gly Gly Gly Gly Ser Gly Gly
            965             970             975
Gly Gly Ser Gly Gly Gly Gly Ser Gly Gly Gly Gly Gly Gly
            980             985             990
Ser Gly Gly Gly Gly Ser Gly Gly  Gly Gly Ser Gly Gly  Gly Gly Gly
            995             1000             1005
Gly Gly  Gly Ser Gly Gly Gly  Gly Ser Gly Gly Gly  Gly Ser Gly
            1010             1015             1020
Gly Gly  Gly Gly Gly Gly Gly  Ser Gly Gly Gly Gly  Ser Gly Gly
            1025             1030             1035
Gly Gly  Ser Gly Gly Gly Gly  Gly Gly Gly Gly Ser  Gly Gly Gly
            1040             1045             1050
Gly Ser  Gly Gly Gly Gly Ser  Gly Gly Gly Gly Gly  Gly Gly Gly
            1055             1060             1065
Ser Gly  Gly Gly Gly Ser Gly  Gly Gly Ser Gly  Gly Gly Gly
            1070             1075             1080
Gly Gly  Gly Gly Ser Gly Gly  Gly Gly Ser Gly Gly  Gly Gly Ser
            1085             1090             1095
Gly Gly  Gly Gly Gly Gly Gly  Ser Gly Gly Gly Gly  Gly Ser Gly
            1100             1105             1110
Gly Gly  Gly Ser Gly Gly Gly  Gly Gly Gly Gly Gly  Ser Gly Gly
            1115             1120             1125
Gly Gly  Ser Gly Gly Gly Gly  Ser Gly Gly Gly Gly  Gly Gly Gly
            1130             1135             1140
Gly Ser  Gly Gly Gly Gly Ser  Gly Gly Gly Gly Ser  Gly Gly Gly
            1145             1150             1155
Gly Gly  Gly Gly Gly Ser Gly  Gly Gly Gly Ser Gly  Gly Gly Gly
            1160             1165             1170
Ser Gly  Gly Gly Gly Gly Gly  Gly Gly Ser Gly Gly  Gly Gly Ser
            1175             1180             1185
Gly Gly  Gly Gly Ser Gly Gly  Gly Gly Gly Gly Gly  Gly Ser Gly
            1190             1195             1200
```

Gly Gly Gly Ser Gly Gly Gly Ser Gly Gly Gly Gly Gly
        1205                1210                1215

Gly Gly Ser Gly Gly Gly Ser Gly Gly Gly Ser Gly Gly
        1220                1225                1230

Gly Gly Gly Gly Gly Ser Gly Gly Gly Ser Gly Gly Gly
        1235                1240                1245

Gly Ser Gly Gly Gly Gly Gly Gly Ser Gly Gly Gly Gly
        1250                1255                1260

Ser Gly Gly Gly Ser Gly Gly Gly Gly Gly Gly Gly Ser
        1265                1270                1275

Gly Gly Gly Gly Ser Gly Gly Gly Ser Gly Gly Gly Gly
        1280                1285                1290

Gly Gly Gly Ser Gly Gly Gly Ser Gly Gly Gly Ser Gly
        1295                1300                1305

Gly Gly Gly Gly Gly Gly Ser Gly Gly Gly Ser Gly Gly
        1310                1315                1320

Gly Gly Ser Gly Gly Gly Gly Gly Gly Gly Ser Gly Gly
        1325                1330                1335

Gly Ser Gly Gly Gly Gly Ser Gly Gly Gly Gly Gly Gly
        1340                1345                1350

Ser Gly Gly Gly Ser Gly Gly Gly Ser Gly Gly Gly Gly
        1355                1360                1365

Gly Gly Gly Gly Ser Gly Gly Gly Ser Gly Gly Gly Ser
        1370                1375                1380

Gly Gly Gly Gly Gly Gly Gly Ser Gly Gly Gly Ser Gly
        1385                1390                1395

Gly Gly Gly Ser Gly Gly Gly Gly Gly Gly Ser Gly Gly
        1400                1405                1410

Gly Gly Ser Gly Gly Gly Gly Ser Gly Gly Gly Gly
        1415                1420                1425

<210> SEQ ID NO 15
<211> LENGTH: 1800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(1800)
<223> OTHER INFORMATION: This sequence may encompass 1-75 "Gly Gly Gly
      Gly Ser Gly Gly Gly Gly Ser Gly Gly Gly Gly Ser Gly Gly Gly Gly
      Ser Gly Gly Gly Gly" repeating units, wherein some positions may
      be absent

<400> SEQUENCE: 15

Gly Gly Gly Gly Ser Gly Gly Gly Ser Gly Gly Gly Gly Ser Gly
1               5                   10                  15

Gly Gly Gly Ser Gly Gly Gly Gly Gly Gly Gly Ser Gly Gly Gly
                20                  25                  30

Gly Ser Gly Gly Gly Gly Ser Gly Gly Gly Ser Gly Gly Gly Gly
        35                  40                  45

Gly Gly Gly Gly Ser Gly Gly Gly Gly Gly Gly Gly Ser Gly Gly
        50                  55                  60

Gly Gly Gly Ser Gly Gly Gly Gly Gly Gly Gly Ser Gly Gly Gly
65                  70                  75                  80

Gly Ser Gly Gly Gly Gly Ser Gly Gly Gly Gly Ser Gly Gly Gly Gly

```
                         85                  90                  95
Gly Gly Gly Gly Ser Gly Gly Gly Ser Gly Gly Gly Ser Gly
                100                 105                 110
Gly Gly Gly Ser Gly Gly Gly Gly Gly Gly Ser Gly Gly Gly
                115                 120                 125
Gly Ser Gly Gly Gly Ser Gly Gly Gly Ser Gly Gly Gly Gly
    130                 135                 140
Gly Gly Gly Gly Ser Gly Gly Gly Ser Gly Gly Gly Ser Gly
145                 150                 155                 160
Gly Gly Ser Gly Gly Gly Gly Gly Gly Ser Gly Gly Gly
                165                 170                 175
Gly Ser Gly Gly Gly Ser Gly Gly Gly Ser Gly Gly Gly Gly
    180                 185                 190
Gly Gly Gly Gly Ser Gly Gly Gly Ser Gly Gly Gly Ser Gly
                195                 200                 205
Gly Gly Gly Ser Gly Gly Gly Gly Gly Gly Ser Gly Gly Gly
                210                 215                 220
Gly Ser Gly Gly Gly Ser Gly Gly Gly Ser Gly Gly Gly Gly
225                 230                 235                 240
Gly Gly Gly Gly Ser Gly Gly Gly Ser Gly Gly Gly Ser Gly
                245                 250                 255
Gly Gly Gly Ser Gly Gly Gly Gly Gly Gly Ser Gly Gly Gly
                260                 265                 270
Gly Ser Gly Gly Gly Ser Gly Gly Gly Ser Gly Gly Gly Gly
    275                 280                 285
Gly Gly Gly Gly Ser Gly Gly Gly Ser Gly Gly Gly Ser Gly
                290                 295                 300
Gly Gly Gly Ser Gly Gly Gly Gly Gly Gly Ser Gly Gly Gly
                305                 310                 315                 320
Gly Ser Gly Gly Gly Ser Gly Gly Gly Ser Gly Gly Gly Gly
    325                 330                 335
Gly Gly Gly Gly Ser Gly Gly Gly Ser Gly Gly Gly Ser Gly
                340                 345                 350
Gly Gly Gly Ser Gly Gly Gly Gly Gly Gly Ser Gly Gly Gly
                355                 360                 365
Gly Ser Gly Gly Gly Ser Gly Gly Gly Ser Gly Gly Gly Gly
    370                 375                 380
Gly Gly Gly Gly Ser Gly Gly Gly Ser Gly Gly Gly Ser Gly
385                 390                 395                 400
Gly Gly Gly Ser Gly Gly Gly Gly Gly Gly Ser Gly Gly Gly
                405                 410                 415
Gly Ser Gly Gly Gly Ser Gly Gly Gly Ser Gly Gly Gly Gly
    420                 425                 430
Gly Gly Gly Gly Ser Gly Gly Gly Ser Gly Gly Gly Ser Gly
                435                 440                 445
Gly Gly Gly Ser Gly Gly Gly Gly Gly Gly Ser Gly Gly Gly
                450                 455                 460
Gly Ser Gly Gly Gly Ser Gly Gly Gly Ser Gly Gly Gly Gly
465                 470                 475                 480
Gly Gly Gly Gly Ser Gly Gly Gly Ser Gly Gly Gly Ser Gly
                485                 490                 495
Gly Gly Gly Ser Gly Gly Gly Gly Gly Gly Gly Ser Gly Gly Gly
                500                 505                 510
```

```
Gly Ser Gly Gly Gly Ser Gly Gly Gly Ser Gly Gly Gly
        515                 520                 525
Gly Gly Gly Gly Ser Gly Gly Gly Ser Gly Gly Gly Ser Gly
530                 535                 540
Gly Gly Gly Ser Gly Gly Gly Gly Gly Gly Ser Gly Gly Gly
545                 550                 555                 560
Gly Ser Gly Gly Gly Ser Gly Gly Gly Ser Gly Gly Gly Gly
        565                 570                 575
Gly Gly Gly Gly Ser Gly Gly Gly Ser Gly Gly Gly Ser Gly
                580                 585                 590
Gly Gly Gly Ser Gly Gly Gly Gly Gly Gly Ser Gly Gly Gly
        595                 600                 605
Gly Ser Gly Gly Gly Ser Gly Gly Gly Ser Gly Gly Gly Gly
        610                 615                 620
Gly Gly Gly Gly Ser Gly Gly Gly Ser Gly Gly Gly Ser Gly
625                 630                 635                 640
Gly Gly Gly Ser Gly Gly Gly Gly Gly Gly Ser Gly Gly Gly
                645                 650                 655
Gly Ser Gly Gly Gly Ser Gly Gly Gly Ser Gly Gly Gly Gly
        660                 665                 670
Gly Gly Gly Gly Ser Gly Gly Gly Ser Gly Gly Gly Ser Gly
        675                 680                 685
Gly Gly Gly Ser Gly Gly Gly Gly Gly Gly Ser Gly Gly Gly
        690                 695                 700
Gly Ser Gly Gly Gly Ser Gly Gly Gly Ser Gly Gly Gly Gly
705                 710                 715                 720
Gly Gly Gly Gly Ser Gly Gly Gly Ser Gly Gly Gly Ser Gly
                725                 730                 735
Gly Gly Gly Ser Gly Gly Gly Gly Gly Gly Ser Gly Gly Gly
                740                 745                 750
Gly Ser Gly Gly Gly Ser Gly Gly Gly Ser Gly Gly Gly Gly
        755                 760                 765
Gly Gly Gly Gly Ser Gly Gly Gly Ser Gly Gly Gly Ser Gly
770                 775                 780
Gly Gly Gly Ser Gly Gly Gly Gly Gly Gly Ser Gly Gly Gly
785                 790                 795                 800
Gly Ser Gly Gly Gly Ser Gly Gly Gly Ser Gly Gly Gly Gly
                805                 810                 815
Gly Gly Gly Gly Ser Gly Gly Gly Ser Gly Gly Gly Ser Gly
                820                 825                 830
Gly Gly Gly Ser Gly Gly Gly Gly Gly Gly Ser Gly Gly Gly
        835                 840                 845
Gly Ser Gly Gly Gly Ser Gly Gly Gly Ser Gly Gly Gly Gly
850                 855                 860
Gly Gly Gly Gly Ser Gly Gly Gly Ser Gly Gly Gly Ser Gly
865                 870                 875                 880
Gly Gly Gly Ser Gly Gly Gly Gly Gly Gly Ser Gly Gly Gly
                885                 890                 895
Gly Ser Gly Gly Gly Ser Gly Gly Gly Ser Gly Gly Gly Gly
        900                 905                 910
Gly Gly Gly Gly Ser Gly Gly Gly Gly Gly Gly Ser Gly Gly
        915                 920                 925
```

Gly Gly Gly Ser Gly Gly Gly Gly Gly Ser Gly Gly Gly
930             935                 940

Gly Ser Gly Gly Gly Gly Ser Gly Gly Gly Ser Gly Gly Gly Gly
945                 950                 955                 960

Gly Gly Gly Gly Ser Gly Gly Gly Gly Ser Gly Gly Gly Gly Ser Gly
                965                 970                 975

Gly Gly Gly Ser Gly Gly Gly Gly Gly Gly Gly Ser Gly Gly Gly
        980                 985                 990

Gly Ser Gly Gly Gly Gly Ser Gly Gly Gly Gly Ser Gly Gly Gly Gly
            995                 1000                1005

Gly Gly Gly Gly Ser Gly Gly Gly Gly Ser Gly Gly Gly Gly Ser
    1010                1015                1020

Gly Gly Gly Gly Ser Gly Gly Gly Gly Gly Gly Gly Ser Gly
    1025                1030                1035

Gly Gly Gly Ser Gly Gly Gly Gly Ser Gly Gly Gly Gly Ser Gly
    1040                1045                1050

Gly Gly Gly Gly Gly Gly Ser Gly Gly Gly Gly Ser Gly Gly
    1055                1060                1065

Gly Gly Ser Gly Gly Gly Gly Ser Gly Gly Gly Gly Gly Gly Gly
    1070                1075                1080

Gly Ser Gly Gly Gly Gly Ser Gly Gly Gly Gly Ser Gly Gly Gly
    1085                1090                1095

Gly Ser Gly Gly Gly Gly Gly Gly Gly Gly Ser Gly Gly Gly Gly
    1100                1105                1110

Ser Gly Gly Gly Gly Ser Gly Gly Gly Gly Ser Gly Gly Gly Gly
    1115                1120                1125

Gly Gly Gly Gly Ser Gly Gly Gly Gly Ser Gly Gly Gly Gly Ser
    1130                1135                1140

Gly Gly Gly Gly Ser Gly Gly Gly Gly Gly Gly Gly Ser Gly
    1145                1150                1155

Gly Gly Gly Ser Gly Gly Gly Gly Ser Gly Gly Gly Gly Ser Gly
    1160                1165                1170

Gly Gly Gly Gly Gly Gly Ser Gly Gly Gly Gly Ser Gly Gly
    1175                1180                1185

Gly Gly Ser Gly Gly Gly Gly Ser Gly Gly Gly Gly Gly Gly Gly
    1190                1195                1200

Gly Ser Gly Gly Gly Gly Ser Gly Gly Gly Gly Ser Gly Gly Gly
    1205                1210                1215

Gly Ser Gly Gly Gly Gly Gly Gly Gly Gly Ser Gly Gly Gly Gly
    1220                1225                1230

Ser Gly Gly Gly Gly Ser Gly Gly Gly Gly Ser Gly Gly Gly Gly
    1235                1240                1245

Gly Gly Gly Gly Ser Gly Gly Gly Gly Ser Gly Gly Gly Gly Ser
    1250                1255                1260

Gly Gly Gly Gly Ser Gly Gly Gly Gly Gly Gly Gly Ser Gly
    1265                1270                1275

Gly Gly Gly Ser Gly Gly Gly Gly Ser Gly Gly Gly Gly Ser Gly
    1280                1285                1290

Gly Gly Gly Gly Gly Gly Gly Ser Gly Gly Gly Gly Ser Gly Gly
    1295                1300                1305

Gly Gly Ser Gly Gly Gly Gly Ser Gly Gly Gly Gly Gly Gly Gly
    1310                1315                1320

Gly Ser Gly Gly Gly Gly Ser Gly Gly Gly Gly Ser Gly Gly Gly

-continued 1325                1330                1335

Gly Ser Gly Gly Gly Gly Gly  Gly Gly Gly Ser  Gly Gly Gly
        1340                1345                1350

Ser Gly Gly Gly Gly Ser Gly  Gly Gly Gly Ser  Gly Gly Gly
        1355                1360                1365

Gly Gly Gly Gly Ser Gly Gly  Gly Gly Ser Gly  Gly Gly Ser
        1370                1375                1380

Gly Gly Gly Gly Ser Gly Gly  Gly Gly Gly Gly  Gly Ser Gly
        1385                1390                1395

Gly Gly Gly Ser Gly Gly Gly  Gly Ser Gly Gly  Gly Ser Gly
        1400                1405                1410

Gly Gly Gly Gly Gly Gly Gly  Ser Gly Gly Gly  Ser Gly Gly
        1415                1420                1425

Gly Gly Ser Gly Gly Gly Gly  Ser Gly Gly Gly  Gly Gly Gly
        1430                1435                1440

Gly Ser Gly Gly Gly Gly Ser  Gly Gly Gly Ser  Gly Gly Gly
        1445                1450                1455

Gly Ser Gly Gly Gly Gly Gly  Gly Gly Ser Gly  Gly Gly Gly
        1460                1465                1470

Ser Gly Gly Gly Gly Ser Gly  Gly Gly Gly Ser  Gly Gly Gly Gly
        1475                1480                1485

Gly Gly Gly Gly Ser Gly Gly  Gly Gly Ser Gly  Gly Gly Ser
        1490                1495                1500

Gly Gly Gly Gly Ser Gly Gly  Gly Gly Gly Gly  Gly Ser Gly
        1505                1510                1515

Gly Gly Gly Ser Gly Gly Gly  Gly Ser Gly Gly  Gly Ser Gly
        1520                1525                1530

Gly Gly Gly Gly Gly Gly Gly  Ser Gly Gly Gly  Ser Gly Gly
        1535                1540                1545

Gly Gly Ser Gly Gly Gly Gly  Ser Gly Gly Gly  Gly Gly Gly
        1550                1555                1560

Gly Ser Gly Gly Gly Gly Ser  Gly Gly Gly Ser  Gly Gly Gly
        1565                1570                1575

Gly Ser Gly Gly Gly Gly Gly  Gly Gly Ser Gly  Gly Gly Gly
        1580                1585                1590

Ser Gly Gly Gly Gly Ser Gly  Gly Gly Gly Ser  Gly Gly Gly
        1595                1600                1605

Gly Gly Gly Gly Ser Gly Gly  Gly Gly Ser Gly  Gly Gly Ser
        1610                1615                1620

Gly Gly Gly Gly Ser Gly Gly  Gly Gly Gly Gly  Gly Ser Gly
        1625                1630                1635

Gly Gly Gly Ser Gly Gly Gly  Gly Ser Gly Gly  Gly Ser Gly
        1640                1645                1650

Gly Gly Gly Gly Gly Gly Gly  Ser Gly Gly Gly  Ser Gly Gly
        1655                1660                1665

Gly Gly Ser Gly Gly Gly Gly  Ser Gly Gly Gly  Gly Gly Gly
        1670                1675                1680

Gly Ser Gly Gly Gly Gly Ser  Gly Gly Gly Ser  Gly Gly Gly
        1685                1690                1695

Gly Ser Gly Gly Gly Gly Gly  Gly Gly Ser Gly  Gly Gly Gly
        1700                1705                1710

Ser Gly Gly Gly Gly Ser Gly  Gly Gly Gly Ser  Gly Gly Gly
        1715                1720                1725

```
Gly Gly  Gly Gly Ser Gly Gly  Gly Gly Ser Gly  Gly Gly Ser
         1730                 1735             1740

Gly Gly  Gly Gly Ser Gly Gly  Gly Gly Gly Gly  Gly Ser Gly
         1745                 1750             1755

Gly Gly  Gly Ser Gly Gly Gly  Gly Ser Gly Gly  Gly Ser Gly
         1760                 1765             1770

Gly Gly  Gly Gly Gly Gly Gly  Ser Gly Gly Gly  Ser Gly Gly
         1775                 1780             1785

Gly Gly  Ser Gly Gly Gly Gly  Ser Gly Gly Gly
         1790                 1795             1800

<210> SEQ ID NO 16
<211> LENGTH: 2175
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2175)
<223> OTHER INFORMATION: This sequence may encompass 1-75 "Gly Gly Gly
      Gly Ser Gly Gly Gly Gly Ser Gly Gly Gly Gly Ser Gly Gly Gly Gly
      Ser Gly Gly Gly Gly Ser Gly Gly Gly Gly" repeating units, wherein
      some positions may be absent

<400> SEQUENCE: 16

Gly Gly  Gly Gly Ser Gly Gly  Gly Ser Gly Gly  Gly Ser Gly
1        5                    10              15

Gly Gly  Gly Ser Gly Gly Gly  Ser Gly Gly Gly  Gly Gly Gly
         20                   25              30

Gly Ser  Gly Gly Gly Ser Gly  Gly Gly Gly Ser  Gly Gly Gly
         35                   40              45

Ser Gly  Gly Gly Gly Ser Gly  Gly Gly Gly Gly  Gly Ser Gly
         50                   55              60

Gly Gly  Gly Ser Gly Gly Gly  Ser Gly Gly Gly  Gly Ser Gly
65       70                   75              80

Gly Gly  Ser Gly Gly Gly Gly  Gly Gly Ser Gly  Gly Gly Gly
         85                   90              95

Ser Gly  Gly Gly Gly Ser Gly  Gly Gly Ser Gly  Gly Gly Ser
         100                  105             110

Gly Gly  Gly Gly Gly Gly Gly  Ser Gly Gly Gly  Ser Gly Gly
         115                  120             125

Gly Gly  Ser Gly Gly Gly Ser  Gly Gly Gly Ser  Gly Gly Gly
         130                  135             140

Gly Gly  Gly Gly Ser Gly Gly  Gly Ser Gly Gly  Gly Gly Ser
145                  150              155              160

Gly Gly  Gly Gly Ser Gly Gly  Gly Ser Gly Gly  Gly Gly Gly
         165                  170             175

Gly Gly  Ser Gly Gly Gly Ser  Gly Gly Gly Gly  Gly Gly Gly
         180                  185             190

Gly Ser  Gly Gly Gly Ser Gly  Gly Gly Gly Gly  Gly Gly Ser
         195                  200             205

Gly Gly  Gly Gly Ser Gly Gly  Gly Ser Gly Gly  Gly Ser Gly
         210                  215             220

Gly Gly  Gly Ser Gly Gly Gly  Gly Gly Gly Gly  Ser Gly Gly Gly
225                  230              235              240
```

-continued

```
Gly Ser Gly Gly Gly Gly Ser Gly Gly Gly Ser Gly Gly Gly
            245                 250                 255

Ser Gly Gly Gly Gly Gly Gly Ser Gly Gly Gly Ser Gly
        260                 265                 270

Gly Gly Gly Ser Gly Gly Gly Ser Gly Gly Gly Ser Gly Gly
        275                 280                 285

Gly Gly Gly Gly Gly Ser Gly Gly Gly Ser Gly Gly Gly Gly
        290                 295                 300

Ser Gly Gly Gly Gly Ser Gly Gly Gly Ser Gly Gly Gly Gly
305                 310                 315                 320

Gly Gly Gly Ser Gly Gly Gly Ser Gly Gly Gly Ser Gly Gly
        325                 330                 335

Gly Gly Ser Gly Gly Gly Gly Ser Gly Gly Gly Gly Gly Gly
        340                 345                 350

Ser Gly Gly Gly Gly Ser Gly Gly Gly Ser Gly Gly Gly Ser
        355                 360                 365

Gly Gly Gly Gly Ser Gly Gly Gly Gly Gly Gly Ser Gly Gly
        370                 375                 380

Gly Gly Ser Gly Gly Gly Gly Ser Gly Gly Gly Ser Gly Gly
385                 390                 395                 400

Gly Ser Gly Gly Gly Gly Gly Gly Gly Ser Gly Gly Gly Ser
        405                 410                 415

Gly Gly Gly Gly Ser Gly Gly Gly Ser Gly Gly Gly Ser Gly
        420                 425                 430

Gly Gly Gly Gly Gly Gly Ser Gly Gly Gly Ser Gly Gly Gly
        435                 440                 445

Gly Ser Gly Gly Gly Ser Gly Gly Gly Ser Gly Gly Gly Gly
        450                 455                 460

Gly Gly Gly Gly Ser Gly Gly Gly Ser Gly Gly Gly Ser Gly
465                 470                 475                 480

Gly Gly Gly Ser Gly Gly Gly Gly Ser Gly Gly Gly Gly Gly
        485                 490                 495

Gly Ser Gly Gly Gly Gly Ser Gly Gly Gly Ser Gly Gly Gly
        500                 505                 510

Ser Gly Gly Gly Gly Ser Gly Gly Gly Gly Gly Gly Ser Gly
        515                 520                 525

Gly Gly Gly Ser Gly Gly Gly Gly Ser Gly Gly Gly Ser Gly Gly
        530                 535                 540

Gly Gly Ser Gly Gly Gly Gly Gly Gly Gly Ser Gly Gly Gly Gly
545                 550                 555                 560

Ser Gly Gly Gly Gly Ser Gly Gly Gly Gly Ser Gly Gly Gly Ser
        565                 570                 575

Gly Gly Gly Gly Gly Gly Gly Ser Gly Gly Gly Ser Gly Gly
        580                 585                 590

Gly Gly Ser Gly Gly Gly Gly Ser Gly Gly Gly Ser Gly Gly Gly
        595                 600                 605

Gly Gly Gly Gly Gly Ser Gly Gly Gly Ser Gly Gly Gly Ser
        610                 615                 620

Gly Gly Gly Gly Ser Gly Gly Gly Ser Gly Gly Gly Gly Gly
625                 630                 635                 640

Gly Gly Ser Gly Gly Gly Gly Ser Gly Gly Gly Ser Gly Gly
        645                 650                 655

Gly Ser Gly Gly Gly Gly Ser Gly Gly Gly Gly Gly Gly Gly Ser
```

```
                660                 665                 670
Gly Gly Gly Gly Ser Gly Gly Gly Ser Gly Gly Gly Ser Gly
            675                 680                 685
Gly Gly Gly Ser Gly Gly Gly Gly Gly Gly Ser Gly Gly Gly
        690                 695                 700
Gly Ser Gly Gly Gly Ser Gly Gly Gly Ser Gly Gly Gly Gly
705                 710                 715                 720
Ser Gly Gly Gly Gly Gly Gly Ser Gly Gly Gly Ser Gly
                725                 730                 735
Gly Gly Ser Gly Gly Gly Ser Gly Gly Gly Ser Gly Gly
            740                 745                 750
Gly Gly Gly Gly Gly Ser Gly Gly Gly Ser Gly Gly Gly
        755                 760                 765
Ser Gly Gly Gly Gly Ser Gly Gly Gly Ser Gly Gly Gly Gly
    770                 775                 780
Gly Gly Gly Ser Gly Gly Gly Ser Gly Gly Gly Ser Gly Gly
785                 790                 795                 800
Gly Gly Ser Gly Gly Gly Ser Gly Gly Gly Gly Gly Gly
                805                 810                 815
Ser Gly Gly Gly Gly Ser Gly Gly Gly Ser Gly Gly Gly Ser
            820                 825                 830
Gly Gly Gly Gly Ser Gly Gly Gly Gly Gly Gly Ser Gly Gly
        835                 840                 845
Gly Gly Ser Gly Gly Gly Ser Gly Gly Gly Ser Gly Gly Gly
    850                 855                 860
Gly Ser Gly Gly Gly Gly Gly Gly Ser Gly Gly Gly Gly Ser
865                 870                 875                 880
Gly Gly Gly Gly Ser Gly Gly Gly Ser Gly Gly Gly Ser Gly
                885                 890                 895
Gly Gly Gly Gly Gly Gly Ser Gly Gly Gly Ser Gly Gly Gly
            900                 905                 910
Gly Ser Gly Gly Gly Ser Gly Gly Gly Ser Gly Gly Gly Gly
        915                 920                 925
Gly Gly Gly Ser Gly Gly Gly Ser Gly Gly Gly Gly Ser Gly
    930                 935                 940
Gly Gly Gly Ser Gly Gly Gly Ser Gly Gly Gly Gly Gly
945                 950                 955                 960
Gly Ser Gly Gly Gly Ser Gly Gly Gly Ser Gly Gly Gly
                965                 970                 975
Ser Gly Gly Gly Gly Ser Gly Gly Gly Gly Gly Gly Ser Gly
            980                 985                 990
Gly Gly Gly Ser Gly Gly Gly Gly Ser Gly Gly Gly Ser Gly Gly
        995                 1000                1005
Gly Gly Ser Gly Gly Gly Gly Gly Gly Gly Ser Gly Gly Gly
    1010                1015                1020
Gly Ser Gly Gly Gly Gly Ser Gly Gly Gly Gly Ser Gly Gly Gly
    1025                1030                1035
Gly Ser Gly Gly Gly Gly Gly Gly Gly Ser Gly Gly Gly Gly
    1040                1045                1050
Ser Gly Gly Gly Gly Ser Gly Gly Gly Ser Gly Gly Gly Gly
    1055                1060                1065
Ser Gly Gly Gly Gly Gly Gly Gly Gly Ser Gly Gly Gly Gly Ser
    1070                1075                1080
```

```
Gly Gly Gly Gly Ser Gly Gly Gly Ser Gly Gly Gly Ser
    1085            1090            1095

Gly Gly Gly Gly Gly Gly Ser Gly Gly Gly Ser Gly
    1100            1105            1110

Gly Gly Gly Ser Gly Gly Gly Ser Gly Gly Gly Ser Gly
    1115            1120            1125

Gly Gly Gly Gly Gly Gly Ser Gly Gly Gly Ser Gly Gly
    1130            1135            1140

Gly Gly Ser Gly Gly Gly Gly Ser Gly Gly Gly Ser Gly Gly
    1145            1150            1155

Gly Gly Gly Gly Gly Gly Ser Gly Gly Gly Ser Gly Gly Gly
    1160            1165            1170

Gly Ser Gly Gly Gly Gly Ser Gly Gly Gly Gly Ser Gly Gly Gly
    1175            1180            1185

Gly Gly Gly Gly Gly Ser Gly Gly Gly Ser Gly Gly Gly Gly
    1190            1195            1200

Ser Gly Gly Gly Gly Ser Gly Gly Gly Ser Gly Gly Gly Gly
    1205            1210            1215

Gly Gly Gly Gly Ser Gly Gly Gly Gly Ser Gly Gly Gly Ser
    1220            1225            1230

Gly Gly Gly Gly Ser Gly Gly Gly Gly Ser Gly Gly Gly Gly
    1235            1240            1245

Gly Gly Gly Ser Gly Gly Gly Gly Ser Gly Gly Gly Ser Gly
    1250            1255            1260

Gly Gly Gly Ser Gly Gly Gly Gly Ser Gly Gly Gly Gly Gly
    1265            1270            1275

Gly Gly Ser Gly Gly Gly Gly Ser Gly Gly Gly Gly Ser Gly Gly
    1280            1285            1290

Gly Gly Ser Gly Gly Gly Gly Ser Gly Gly Gly Gly Gly Gly
    1295            1300            1305

Gly Ser Gly Gly Gly Gly Ser Gly Gly Gly Gly Ser Gly Gly Gly
    1310            1315            1320

Gly Ser Gly Gly Gly Gly Ser Gly Gly Gly Gly Gly Gly Gly Gly
    1325            1330            1335

Ser Gly Gly Gly Gly Ser Gly Gly Gly Ser Gly Gly Gly Gly
    1340            1345            1350

Ser Gly Gly Gly Gly Ser Gly Gly Gly Gly Gly Gly Gly Ser
    1355            1360            1365

Gly Gly Gly Gly Ser Gly Gly Gly Gly Ser Gly Gly Gly Gly Ser
    1370            1375            1380

Gly Gly Gly Gly Ser Gly Gly Gly Gly Gly Gly Gly Ser Gly
    1385            1390            1395

Gly Gly Gly Ser Gly Gly Gly Gly Ser Gly Gly Gly Ser Gly
    1400            1405            1410

Gly Gly Gly Ser Gly Gly Gly Gly Gly Gly Gly Ser Gly Gly
    1415            1420            1425

Gly Gly Ser Gly Gly Gly Gly Ser Gly Gly Gly Gly Ser Gly Gly
    1430            1435            1440

Gly Gly Ser Gly Gly Gly Gly Gly Gly Gly Gly Ser Gly Gly Gly
    1445            1450            1455

Gly Ser Gly Gly Gly Gly Ser Gly Gly Gly Gly Ser Gly Gly Gly
    1460            1465            1470
```

Gly Ser Gly Gly Gly Gly Gly Gly Gly Gly Ser Gly Gly Gly Gly
1475               1480                1485

Ser Gly Gly Gly Gly Ser Gly Gly Gly Gly Ser Gly Gly Gly Gly
1490               1495                1500

Ser Gly Gly Gly Gly Gly Gly Gly Gly Ser Gly Gly Gly Gly Ser
1505               1510                1515

Gly Gly Gly Gly Ser Gly Gly Gly Gly Ser Gly Gly Gly Gly Ser
1520               1525                1530

Gly Gly Gly Gly Gly Gly Gly Ser Gly Gly Gly Gly Gly Ser Gly
1535               1540                1545

Gly Gly Gly Ser Gly Gly Gly Ser Gly Gly Gly Gly Ser Gly Gly
1550               1555                1560

Gly Gly Gly Gly Gly Gly Gly Ser Gly Gly Gly Gly Ser Gly Gly
1565               1570                1575

Gly Gly Ser Gly Gly Gly Gly Ser Gly Gly Gly Gly Ser Gly Gly
1580               1585                1590

Gly Gly Gly Gly Gly Gly Ser Gly Gly Gly Gly Ser Gly Gly Gly
1595               1600                1605

Gly Ser Gly Gly Gly Gly Ser Gly Gly Gly Gly Ser Gly Gly Gly
1610               1615                1620

Gly Gly Gly Gly Gly Gly Ser Gly Gly Gly Gly Ser Gly Gly Gly
1625               1630                1635

Ser Gly Gly Gly Gly Ser Gly Gly Gly Gly Ser Gly Gly Gly Gly
1640               1645                1650

Gly Gly Gly Gly Ser Gly Gly Gly Gly Ser Gly Gly Gly Gly Ser
1655               1660                1665

Gly Gly Gly Gly Ser Gly Gly Gly Gly Ser Gly Gly Gly Gly Gly
1670               1675                1680

Gly Gly Gly Ser Gly Gly Gly Gly Ser Gly Gly Gly Gly Ser Gly
1685               1690                1695

Gly Gly Gly Ser Gly Gly Gly Gly Ser Gly Gly Gly Gly Gly Gly
1700               1705                1710

Gly Gly Ser Gly Gly Gly Gly Ser Gly Gly Gly Gly Ser Gly Gly
1715               1720                1725

Gly Gly Ser Gly Gly Gly Gly Ser Gly Gly Gly Gly Gly Gly Gly
1730               1735                1740

Gly Ser Gly Gly Gly Gly Ser Gly Gly Gly Gly Ser Gly Gly Gly
1745               1750                1755

Gly Ser Gly Gly Gly Gly Ser Gly Gly Gly Gly Gly Gly Gly Gly
1760               1765                1770

Ser Gly Gly Gly Gly Ser Gly Gly Gly Gly Ser Gly Gly Gly Gly
1775               1780                1785

Ser Gly Gly Gly Gly Ser Gly Gly Gly Gly Gly Gly Gly Gly Ser
1790               1795                1800

Gly Gly Gly Gly Ser Gly Gly Gly Gly Ser Gly Gly Gly Gly Ser
1805               1810                1815

Gly Gly Gly Gly Ser Gly Gly Gly Gly Gly Gly Gly Gly Ser Gly
1820               1825                1830

Gly Gly Gly Ser Gly Gly Gly Gly Ser Gly Gly Gly Gly Ser Gly
1835               1840                1845

Gly Gly Gly Ser Gly Gly Gly Gly Gly Gly Gly Gly Ser Gly Gly
1850               1855                1860

Gly Gly Ser Gly Gly Gly Gly Ser Gly Gly Gly Gly Gly Ser Gly Gly

```
                    1865                1870                1875

Gly Gly  Ser Gly Gly Gly  Gly Gly Gly Gly  Ser Gly Gly
        1880                1885                1890

Gly Ser  Gly Gly Gly Gly  Ser Gly Gly Gly  Ser Gly Gly
        1895                1900                1905

Gly Ser  Gly Gly Gly Gly  Gly Gly Gly Ser  Gly Gly Gly
        1910                1915                1920

Ser Gly  Gly Gly Gly Ser  Gly Gly Gly Ser  Gly Gly Gly
        1925                1930                1935

Ser Gly  Gly Gly Gly Gly  Gly Gly Ser Gly  Gly Gly Gly Ser
        1940                1945                1950

Gly Gly  Gly Gly Ser Gly  Gly Gly Gly Ser  Gly Gly Gly Ser
        1955                1960                1965

Gly Gly  Gly Gly Gly Gly  Gly Ser Gly Gly  Gly Ser Gly
        1970                1975                1980

Gly Gly  Gly Ser Gly Gly  Gly Ser Gly Gly  Gly Ser Gly
        1985                1990                1995

Gly Gly  Gly Gly Gly Gly  Ser Gly Gly Gly  Ser Gly Gly
        2000                2005                2010

Gly Gly  Ser Gly Gly Gly  Ser Gly Gly Gly  Ser Gly Gly
        2015                2020                2025

Gly Gly  Gly Gly Gly Ser  Gly Gly Gly Ser  Gly Gly Gly
        2030                2035                2040

Gly Ser  Gly Gly Gly Ser  Gly Gly Gly Ser  Gly Gly Gly
        2045                2050                2055

Gly Gly  Gly Gly Gly Ser Gly  Gly Gly Gly Ser Gly  Gly Gly Gly
        2060                2065                2070

Ser Gly  Gly Gly Gly Ser  Gly Gly Gly Ser  Gly Gly Gly
        2075                2080                2085

Gly Gly  Gly Gly Ser Gly  Gly Gly Gly Ser Gly Gly  Gly Ser
        2090                2095                2100

Gly Gly  Gly Gly Ser Gly  Gly Gly Gly Ser  Gly Gly Gly
        2105                2110                2115

Gly Gly  Gly Ser Gly Gly  Gly Gly Ser Gly  Gly Gly Ser Gly
        2120                2125                2130

Gly Gly  Gly Ser Gly Gly  Gly Ser Gly Gly  Gly Gly Gly
        2135                2140                2145

Gly Gly  Ser Gly Gly Gly Gly  Ser Gly Gly Gly Gly  Ser Gly Gly
        2150                2155                2160

Gly Gly  Ser Gly Gly Gly Gly  Ser Gly Gly Gly
        2165                2170                2175

<210> SEQ ID NO 17
<211> LENGTH: 2550
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(2550)
<223> OTHER INFORMATION: This sequence may encompass 1-75 "Gly Gly Gly
      Gly Ser Gly Gly Gly Gly Ser Gly Gly Gly Gly Ser Gly Gly Gly Gly
      Ser Gly Gly Gly Ser Gly Gly Gly Gly Ser Gly Gly Gly Gly"
      repeating units, wherein some positions may be absent

<400> SEQUENCE: 17
```

```
Gly Gly Gly Gly Ser Gly Gly Gly Ser Gly Gly Gly Ser Gly
1               5                   10                  15
Gly Gly Gly Ser Gly Gly Gly Gly Ser Gly Gly Gly Ser Gly Gly
                20                  25                  30
Gly Gly Gly Gly Gly Ser Gly Gly Gly Ser Gly Gly Gly
        35                  40                  45
Ser Gly Gly Gly Ser Gly Gly Gly Ser Gly Gly Gly Ser
    50                  55                  60
Gly Gly Gly Gly Gly Gly Gly Ser Gly Gly Gly Ser Gly Gly
65                  70                  75                  80
Gly Gly Ser Gly Gly Gly Ser Gly Gly Gly Ser Gly Gly Gly
            85                  90                  95
Gly Ser Gly Gly Gly Gly Gly Gly Ser Gly Gly Gly Ser
        100                 105                 110
Gly Gly Gly Gly Ser Gly Gly Gly Ser Gly Gly Gly Ser Gly
                115                 120                 125
Gly Gly Gly Ser Gly Gly Gly Gly Gly Gly Ser Gly Gly Gly
            130                 135                 140
Gly Ser Gly Gly Gly Ser Gly Gly Gly Ser Gly Gly Gly Gly
145                 150                 155                 160
Ser Gly Gly Gly Ser Gly Gly Gly Gly Gly Gly Ser Gly
                165                 170                 175
Gly Gly Gly Ser Gly Gly Gly Ser Gly Gly Gly Ser Gly Gly
                180                 185                 190
Gly Gly Ser Gly Gly Gly Ser Gly Gly Gly Gly Gly Gly
            195                 200                 205
Ser Gly Gly Gly Ser Gly Gly Gly Ser Gly Gly Gly Ser
210                 215                 220
Gly Gly Gly Gly Ser Gly Gly Gly Ser Gly Gly Gly Gly Gly
225                 230                 235                 240
Gly Gly Ser Gly Gly Gly Ser Gly Gly Gly Ser Gly Gly Gly
            245                 250                 255
Gly Ser Gly Gly Gly Gly Ser Gly Gly Gly Ser Gly Gly Gly
        260                 265                 270
Gly Gly Gly Gly Ser Gly Gly Gly Ser Gly Gly Gly Ser Gly
275                 280                 285
Gly Gly Gly Ser Gly Gly Gly Gly Ser Gly Gly Gly Ser Gly Gly
        290                 295                 300
Gly Gly Gly Gly Gly Ser Gly Gly Gly Ser Gly Gly Gly Gly
305                 310                 315                 320
Ser Gly Gly Gly Ser Gly Gly Gly Gly Gly Gly Ser
                325                 330                 335
Gly Gly Gly Gly Gly Gly Gly Ser Gly Gly Gly Ser Gly Gly
            340                 345                 350
Gly Gly Ser Gly Gly Gly Gly Ser Gly Gly Gly Ser Gly Gly
            355                 360                 365
Gly Ser Gly Gly Gly Gly Gly Gly Ser Gly Gly Gly Ser
        370                 375                 380
Gly Gly Gly Gly Ser Gly Gly Gly Gly Ser Gly Gly Ser Gly
385                 390                 395                 400
Gly Gly Gly Ser Gly Gly Gly Gly Gly Gly Gly Ser Gly Gly Gly
                405                 410                 415
```

Gly Ser Gly Gly Gly Gly Ser Gly Gly Gly Ser Gly Gly
            420                 425                 430

Ser Gly Gly Gly Ser Gly Gly Gly Gly Gly Gly Ser Gly
            435                 440                 445

Gly Gly Gly Ser Gly Gly Gly Gly Ser Gly Gly Gly Ser Gly Gly
        450                 455                 460

Gly Gly Ser Gly Gly Gly Gly Ser Gly Gly Gly Gly Gly Gly Gly
465                 470                 475                 480

Ser Gly Gly Gly Gly Ser Gly Gly Gly Gly Ser Gly Gly Gly Ser
                485                 490                 495

Gly Gly Gly Gly Ser Gly Gly Gly Ser Gly Gly Gly Gly Gly
            500                 505                 510

Gly Gly Ser Gly Gly Gly Gly Ser Gly Gly Gly Ser Gly Gly Gly
            515                 520                 525

Gly Ser Gly Gly Gly Ser Gly Gly Gly Ser Gly Gly Gly Gly
            530                 535                 540

Gly Gly Gly Gly Ser Gly Gly Gly Gly Ser Gly Gly Gly Ser Gly
545                 550                 555                 560

Gly Gly Gly Ser Gly Gly Gly Gly Ser Gly Gly Gly Ser Gly Gly
                565                 570                 575

Gly Gly Gly Gly Gly Gly Ser Gly Gly Gly Ser Gly Gly Gly
            580                 585                 590

Ser Gly Gly Gly Ser Gly Gly Gly Gly Ser Gly Gly Gly Ser
            595                 600                 605

Gly Gly Gly Gly Gly Gly Gly Ser Gly Gly Gly Ser Gly Gly
            610                 615                 620

Gly Gly Ser Gly Gly Gly Ser Gly Gly Gly Gly Ser Gly Gly Gly
625                 630                 635                 640

Gly Ser Gly Gly Gly Gly Gly Gly Gly Ser Gly Gly Gly Ser
                645                 650                 655

Gly Gly Gly Gly Ser Gly Gly Gly Gly Ser Gly Gly Gly Ser Gly
            660                 665                 670

Gly Gly Gly Ser Gly Gly Gly Gly Gly Gly Ser Gly Gly Gly
            675                 680                 685

Gly Ser Gly Gly Gly Gly Ser Gly Gly Gly Ser Gly Gly Gly Gly
            690                 695                 700

Ser Gly Gly Gly Gly Ser Gly Gly Gly Gly Gly Gly Ser Gly
705                 710                 715                 720

Gly Gly Gly Ser Gly Gly Gly Gly Ser Gly Gly Gly Ser Gly Gly
                725                 730                 735

Gly Gly Ser Gly Gly Gly Gly Ser Gly Gly Gly Gly Gly Gly Gly
            740                 745                 750

Ser Gly Gly Gly Gly Ser Gly Gly Gly Gly Ser Gly Gly Gly Ser
            755                 760                 765

Gly Gly Gly Gly Ser Gly Gly Gly Gly Ser Gly Gly Gly Gly
            770                 775                 780

Gly Gly Ser Gly Gly Gly Gly Ser Gly Gly Gly Ser Gly Gly
785                 790                 795                 800

Gly Ser Gly Gly Gly Gly Ser Gly Gly Gly Gly Ser Gly Gly Gly
                805                 810                 815

Gly Gly Gly Gly Ser Gly Gly Gly Gly Ser Gly Gly Gly Ser Gly
            820                 825                 830

Gly Gly Gly Ser Gly Gly Gly Gly Ser Gly Gly Gly Gly Ser Gly Gly

```
                835                 840                 845
Gly Gly Gly Gly Gly Gly Ser Gly Gly Gly Ser Gly Gly Gly
            850                 855                 860

Ser Gly Gly Gly Gly Ser Gly Gly Gly Ser Gly Gly Gly Ser
865                 870                 875                 880

Gly Gly Gly Gly Gly Gly Gly Ser Gly Gly Gly Ser Gly Gly
                885                 890                 895

Gly Gly Ser Gly Gly Gly Ser Gly Gly Gly Ser Gly Gly Gly
            900                 905                 910

Gly Ser Gly Gly Gly Gly Gly Gly Ser Gly Gly Gly Gly Ser
        915                 920                 925

Gly Gly Gly Ser Gly Gly Gly Ser Gly Gly Gly Ser Gly
    930                 935                 940

Gly Gly Gly Ser Gly Gly Gly Gly Gly Gly Ser Gly Gly Gly
945                 950                 955                 960

Gly Ser Gly Gly Gly Ser Gly Gly Gly Ser Gly Gly Gly
        965                 970                 975

Ser Gly Gly Gly Gly Ser Gly Gly Gly Gly Gly Gly Ser Gly
            980                 985                 990

Gly Gly Gly Ser Gly Gly Gly Gly Ser Gly Gly Gly Gly Ser Gly Gly
            995                 1000                1005

Gly Gly Ser Gly Gly Gly Gly Ser Gly Gly Gly Gly Gly Gly
        1010                1015                1020

Gly Ser Gly Gly Gly Gly Ser Gly Gly Gly Gly Ser Gly Gly Gly
    1025                1030                1035

Gly Ser Gly Gly Gly Gly Ser Gly Gly Gly Gly Ser Gly Gly Gly
    1040                1045                1050

Gly Gly Gly Gly Gly Ser Gly Gly Gly Gly Ser Gly Gly Gly Gly
        1055                1060                1065

Ser Gly Gly Gly Gly Ser Gly Gly Gly Gly Ser Gly Gly Gly Gly
    1070                1075                1080

Ser Gly Gly Gly Gly Gly Gly Gly Ser Gly Gly Gly Gly Ser
    1085                1090                1095

Gly Gly Gly Gly Ser Gly Gly Gly Gly Ser Gly Gly Gly Ser
        1100                1105                1110

Gly Gly Gly Gly Ser Gly Gly Gly Gly Gly Gly Gly Ser Gly
        1115                1120                1125

Gly Gly Gly Ser Gly Gly Gly Gly Ser Gly Gly Gly Gly Ser Gly
    1130                1135                1140

Gly Gly Gly Ser Gly Gly Gly Gly Ser Gly Gly Gly Gly Gly Gly
    1145                1150                1155

Gly Gly Ser Gly Gly Gly Gly Ser Gly Gly Gly Gly Ser Gly Gly
        1160                1165                1170

Gly Gly Ser Gly Gly Gly Gly Ser Gly Gly Gly Gly Ser Gly Gly
        1175                1180                1185

Gly Gly Gly Gly Gly Gly Ser Gly Gly Gly Gly Ser Gly Gly Gly
            1190                1195                1200

Gly Ser Gly Gly Gly Gly Ser Gly Gly Gly Gly Ser Gly Gly Gly
    1205                1210                1215

Gly Ser Gly Gly Gly Gly Gly Gly Gly Ser Gly Gly Gly Gly
    1220                1225                1230

Ser Gly Gly Gly Gly Ser Gly Gly Gly Gly Ser Gly Gly Gly Gly
    1235                1240                1245
```

Ser Gly Gly Gly Gly Ser Gly Gly Gly Gly Gly Gly Ser
1250                    1255                1260

Gly Gly Gly Gly Ser Gly Gly Gly Ser Gly Gly Gly Ser
1265                1270            1275

Gly Gly Gly Gly Ser Gly Gly Gly Gly Ser Gly Gly Gly Gly
1280                1285                1290

Gly Gly Gly Ser Gly Gly Gly Ser Gly Gly Gly Ser Gly
1295            1300            1305

Gly Gly Gly Ser Gly Gly Gly Ser Gly Gly Gly Ser Gly
1310            1315            1320

Gly Gly Gly Gly Gly Gly Ser Gly Gly Gly Gly Ser Gly Gly
1325                1330                1335

Gly Gly Ser Gly Gly Gly Gly Ser Gly Gly Gly Gly Ser Gly Gly
1340            1345                1350

Gly Gly Ser Gly Gly Gly Gly Gly Gly Gly Ser Gly Gly Gly
1355            1360                1365

Gly Ser Gly Gly Gly Gly Ser Gly Gly Gly Gly Ser Gly Gly Gly
1370            1375            1380

Gly Ser Gly Gly Gly Gly Ser Gly Gly Gly Gly Gly Gly Gly
1385            1390            1395

Ser Gly Gly Gly Gly Ser Gly Gly Gly Gly Ser Gly Gly Gly Gly
1400                1405            1410

Ser Gly Gly Gly Gly Ser Gly Gly Gly Gly Ser Gly Gly Gly Gly
1415                1420            1425

Gly Gly Gly Gly Ser Gly Gly Gly Gly Ser Gly Gly Gly Gly Ser
1430            1435                1440

Gly Gly Gly Gly Ser Gly Gly Gly Gly Ser Gly Gly Gly Gly Ser
1445            1450                1455

Gly Gly Gly Gly Gly Gly Gly Gly Ser Gly Gly Gly Gly Ser Gly
1460                1465                1470

Gly Gly Gly Ser Gly Gly Gly Ser Gly Gly Gly Gly Ser Gly
1475            1480            1485

Gly Gly Gly Ser Gly Gly Gly Gly Gly Gly Gly Ser Gly Gly
1490                1495                1500

Gly Gly Ser Gly Gly Gly Gly Ser Gly Gly Gly Gly Ser Gly Gly
1505            1510            1515

Gly Gly Ser Gly Gly Gly Gly Ser Gly Gly Gly Gly Gly Gly Gly
1520            1525                1530

Gly Ser Gly Gly Gly Gly Ser Gly Gly Gly Gly Ser Gly Gly Gly
1535            1540            1545

Gly Ser Gly Gly Gly Gly Ser Gly Gly Gly Gly Ser Gly Gly Gly
1550            1555            1560

Gly Gly Gly Gly Gly Ser Gly Gly Gly Ser Gly Gly Gly Gly
1565                1570                1575

Ser Gly Gly Gly Gly Ser Gly Gly Gly Gly Ser Gly Gly Gly Gly
1580                1585                1590

Ser Gly Gly Gly Gly Gly Gly Gly Ser Gly Gly Gly Ser
1595                1600            1605

Gly Gly Gly Gly Ser Gly Gly Gly Gly Ser Gly Gly Gly Ser
1610            1615            1620

Gly Gly Gly Gly Ser Gly Gly Gly Gly Gly Gly Gly Ser Gly
1625                1630            1635

```
Gly Gly Gly Ser Gly Gly Gly  Ser Gly Gly  Gly Ser Gly
    1640             1645              1650

Gly Gly Gly Ser Gly Gly Gly  Ser Gly Gly  Gly Gly Gly
    1655             1660              1665

Gly Gly Ser Gly Gly Gly Gly  Ser Gly Gly  Gly Ser Gly Gly
    1670             1675              1680

Gly Gly Ser Gly Gly Gly Gly  Ser Gly Gly  Gly Ser Gly Gly
    1685             1690              1695

Gly Gly Gly Gly Gly Gly Ser  Gly Gly Gly  Ser Gly Gly Gly
    1700             1705              1710

Gly Ser Gly Gly Gly Gly Ser  Gly Gly Gly  Ser Gly Gly Gly
    1715             1720              1725

Gly Ser Gly Gly Gly Gly Gly  Gly Gly Ser  Gly Gly Gly Gly
    1730             1735              1740

Ser Gly Gly Gly Gly Ser Gly  Gly Gly Ser  Gly Gly Gly Gly
    1745             1750              1755

Ser Gly Gly Gly Gly Ser Gly  Gly Gly Gly  Gly Gly Ser
    1760             1765              1770

Gly Gly Gly Gly Ser Gly Gly  Gly Gly Ser  Gly Gly Gly Ser
    1775             1780              1785

Gly Gly Gly Gly Ser Gly Gly  Gly Gly Ser  Gly Gly Gly Gly
    1790             1795              1800

Gly Gly Gly Ser Gly Gly Gly  Gly Ser Gly  Gly Gly Ser Gly
    1805             1810              1815

Gly Gly Gly Ser Gly Gly Gly  Gly Ser Gly  Gly Gly Ser Gly
    1820             1825              1830

Gly Gly Gly Gly Gly Gly Gly  Ser Gly Gly  Gly Ser Gly Gly
    1835             1840              1845

Gly Gly Ser Gly Gly Gly Gly  Ser Gly Gly  Gly Ser Gly Gly
    1850             1855              1860

Gly Gly Ser Gly Gly Gly Gly  Gly Gly Gly  Ser Gly Gly Gly
    1865             1870              1875

Gly Ser Gly Gly Gly Gly Ser  Gly Gly Gly  Ser Gly Gly Gly
    1880             1885              1890

Gly Ser Gly Gly Gly Gly Ser  Gly Gly Gly  Gly Gly Gly Gly
    1895             1900              1905

Ser Gly Gly Gly Gly Ser Gly  Gly Gly Ser  Gly Gly Gly Gly
    1910             1915              1920

Ser Gly Gly Gly Gly Ser Gly  Gly Gly Gly  Ser Gly Gly Gly
    1925             1930              1935

Gly Gly Gly Gly Ser Gly Gly  Gly Gly Ser  Gly Gly Gly Ser
    1940             1945              1950

Gly Gly Gly Gly Ser Gly Gly  Gly Gly Ser  Gly Gly Gly Ser
    1955             1960              1965

Gly Gly Gly Gly Gly Gly Gly  Ser Gly Gly  Gly Gly Ser Gly
    1970             1975              1980

Gly Gly Gly Ser Gly Gly Gly  Ser Gly Gly  Gly Gly Ser Gly
    1985             1990              1995

Gly Gly Gly Ser Gly Gly Gly  Gly Gly Gly  Gly Ser Gly Gly
    2000             2005              2010

Gly Gly Ser Gly Gly Gly Gly  Ser Gly Gly  Gly Ser Gly Gly
    2015             2020              2025

Gly Gly Ser Gly Gly Gly Gly  Ser Gly Gly  Gly Gly Gly Gly
```

-continued

```
            2030                2035                2040

Gly Ser Gly Gly Gly Gly Ser Gly Gly Gly Ser Gly Gly Gly
        2045                2050                2055

Gly Ser Gly Gly Gly Gly Ser Gly Gly Gly Ser Gly Gly Gly
        2060                2065                2070

Gly Gly Gly Gly Gly Ser Gly Gly Gly Ser Gly Gly Gly
        2075                2080                2085

Ser Gly Gly Gly Gly Ser Gly Gly Gly Ser Gly Gly Gly Gly
        2090                2095                2100

Ser Gly Gly Gly Gly Gly Gly Gly Ser Gly Gly Gly Gly Ser
        2105                2110                2115

Gly Gly Gly Gly Ser Gly Gly Gly Gly Ser Gly Gly Gly Ser
        2120                2125                2130

Gly Gly Gly Gly Ser Gly Gly Gly Gly Gly Gly Gly Ser Gly
        2135                2140                2145

Gly Gly Gly Ser Gly Gly Gly Gly Ser Gly Gly Gly Ser Gly
        2150                2155                2160

Gly Gly Gly Ser Gly Gly Gly Gly Ser Gly Gly Gly Gly Gly
        2165                2170                2175

Gly Gly Ser Gly Gly Gly Gly Ser Gly Gly Gly Gly Ser Gly Gly
        2180                2185                2190

Gly Gly Ser Gly Gly Gly Gly Ser Gly Gly Gly Gly Ser Gly Gly
        2195                2200                2205

Gly Gly Gly Gly Gly Gly Ser Gly Gly Gly Gly Ser Gly Gly Gly
        2210                2215                2220

Gly Ser Gly Gly Gly Gly Ser Gly Gly Gly Gly Ser Gly Gly Gly
        2225                2230                2235

Gly Ser Gly Gly Gly Gly Gly Gly Gly Gly Ser Gly Gly Gly Gly
        2240                2245                2250

Ser Gly Gly Gly Gly Ser Gly Gly Gly Gly Ser Gly Gly Gly Gly
        2255                2260                2265

Ser Gly Gly Gly Gly Ser Gly Gly Gly Gly Gly Gly Gly Gly Ser
        2270                2275                2280

Gly Gly Gly Gly Ser Gly Gly Gly Gly Ser Gly Gly Gly Gly Ser
        2285                2290                2295

Gly Gly Gly Gly Ser Gly Gly Gly Gly Ser Gly Gly Gly Gly Gly
        2300                2305                2310

Gly Gly Gly Ser Gly Gly Gly Gly Ser Gly Gly Gly Gly Ser Gly
        2315                2320                2325

Gly Gly Gly Ser Gly Gly Gly Gly Ser Gly Gly Gly Gly Ser Gly
        2330                2335                2340

Gly Gly Gly Gly Gly Gly Gly Ser Gly Gly Gly Gly Ser Gly Gly
        2345                2350                2355

Gly Gly Ser Gly Gly Gly Gly Ser Gly Gly Gly Gly Ser Gly Gly
        2360                2365                2370

Gly Gly Ser Gly Gly Gly Gly Gly Gly Gly Gly Ser Gly Gly Gly
        2375                2380                2385

Gly Ser Gly Gly Gly Gly Ser Gly Gly Gly Gly Ser Gly Gly Gly
        2390                2395                2400

Gly Ser Gly Gly Gly Gly Ser Gly Gly Gly Gly Gly Gly Gly Gly
        2405                2410                2415

Ser Gly Gly Gly Gly Ser Gly Gly Gly Gly Ser Gly Gly Gly Gly
        2420                2425                2430
```

```
Ser Gly Gly Gly Ser Gly  Gly Gly Ser Gly  Gly Gly Gly
    2435            2440            2445

Gly Gly Gly Gly Ser Gly  Gly Gly Ser Gly  Gly Gly Ser
    2450            2455            2460

Gly Gly Gly Gly Ser Gly  Gly Gly Ser Gly  Gly Gly Ser
    2465            2470            2475

Gly Gly Gly Gly Gly Gly  Gly Ser Gly Gly  Gly Ser Gly
    2480            2485            2490

Gly Gly Gly Ser Gly Gly  Gly Ser Gly Gly  Gly Ser Gly
    2495            2500            2505

Gly Gly Gly Ser Gly Gly  Gly Gly Gly Gly  Ser Gly Gly
    2510            2515            2520

Gly Gly Ser Gly Gly Gly  Ser Gly Gly Gly  Ser Gly Gly
    2525            2530            2535

Gly Gly Ser Gly Gly Gly  Ser Gly Gly Gly Gly
    2540            2545            2550

<210> SEQ ID NO 18
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(150)
<223> OTHER INFORMATION: This sequence may encompass 1-75 "Gly Glu"
      repeating units, wherein some positions may be absent

<400> SEQUENCE: 18

Gly Glu Gly Glu Gly Glu Gly Glu Gly Glu Gly Glu Gly Glu Gly Glu
1               5                   10                  15

Gly Glu Gly Glu Gly Glu Gly Glu Gly Glu Gly Glu Gly Glu Gly Glu
            20                  25                  30

Gly Glu Gly Glu Gly Glu Gly Glu Gly Glu Gly Glu Gly Glu Gly Glu
        35                  40                  45

Gly Glu Gly Glu Gly Glu Gly Glu Gly Glu Gly Glu Gly Glu Gly Glu
    50                  55                  60

Gly Glu Gly Glu Gly Glu Gly Glu Gly Glu Gly Glu Gly Glu Gly Glu
65                  70                  75                  80

Gly Glu Gly Glu Gly Glu Gly Glu Gly Glu Gly Glu Gly Glu Gly Glu
                85                  90                  95

Gly Glu Gly Glu Gly Glu Gly Glu Gly Glu Gly Glu Gly Glu Gly Glu
            100                 105                 110

Gly Glu Gly Glu Gly Glu Gly Glu Gly Glu Gly Glu Gly Glu Gly Glu
        115                 120                 125

Gly Glu Gly Glu Gly Glu Gly Glu Gly Glu Gly Glu Gly Glu Gly Glu
    130                 135                 140

Gly Glu Gly Glu Gly Glu
145                 150

<210> SEQ ID NO 19
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<221> NAME/KEY: misc_feature
<222> LOCATION: (1)..(225)
<223> OTHER INFORMATION: This sequence may encompass 1-75 "Gly Gly Glu"
    repeating units, wherein some positions may be absent

<400> SEQUENCE: 19

```
Gly Gly Glu Gly Gly Glu Gly Gly Glu Gly Gly Glu Gly Gly Gly
1               5                   10                  15

Gly Glu Gly Gly Glu Gly Gly Glu Gly Gly Glu Gly Gly Gly Gly
            20                  25                  30

Glu Gly Gly Glu Gly Gly Glu Gly Gly Glu Gly Gly Gly Gly Glu
        35                  40                  45

Gly Gly Glu Gly Gly Glu Gly Gly Glu Gly Gly Gly Gly Glu Gly
    50                  55                  60

Gly Glu Gly Gly Glu Gly Gly Glu Gly Gly Gly Gly Glu Gly Gly
65                  70                  75                  80

Glu Gly Gly Glu Gly Gly Glu Gly Gly Gly Gly Glu Gly Gly Glu
            85                  90                  95

Gly Gly Glu Gly Gly Glu Gly Gly Gly Gly Glu Gly Gly Glu Gly
            100                 105                 110

Gly Glu Gly Gly Glu Gly Gly Gly Gly Glu Gly Gly Glu Gly Gly
        115                 120                 125

Glu Gly Gly Glu Gly Gly Gly Gly Glu Gly Gly Glu Gly Gly Glu
    130                 135                 140

Gly Gly Glu Gly Gly Gly Gly Glu Gly Gly Glu Gly Gly Glu Gly
145                 150                 155                 160

Gly Glu Gly Gly Gly Gly Glu Gly Gly Glu Gly Gly Glu Gly Gly
            165                 170                 175

Glu Gly Gly Gly Gly Glu Gly Gly Glu Gly Gly Glu Gly Gly Glu
            180                 185                 190

Gly Gly Gly Gly Glu Gly Gly Glu Gly Gly Glu Gly Gly Glu Gly
            195                 200                 205

Gly Glu Gly Gly Glu Gly Gly Glu Gly Gly Glu Gly Gly Gly Gly
    210                 215                 220

Glu
225
```

<210> SEQ ID NO 20
<211> LENGTH: 300
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: misc_feature
<222> LOCATION: (1)..(300)
<223> OTHER INFORMATION: This sequence may encompass 1-75 "Gly Gly Gly
    Glu" repeating units, wherein some positions may be absent

<400> SEQUENCE: 20

```
Gly Gly Gly Glu Gly Gly Gly Glu Gly Gly Gly Glu Gly Gly Gly Glu
1               5                   10                  15

Gly Gly Gly Glu Gly Gly Gly Glu Gly Gly Gly Glu Gly Gly Gly Glu
            20                  25                  30

Gly Gly Gly Glu Gly Gly Gly Glu Gly Gly Gly Glu Gly Gly Gly Glu
        35                  40                  45

Gly Gly Gly Glu Gly Gly Gly Glu Gly Gly Gly Glu Gly Gly Gly Glu
```

Gly Gly Gly Glu Gly Gly Gly Glu Gly Gly Gly Glu
65                  70                  75                  80

Gly Gly Gly Glu Gly Gly Gly Glu Gly Gly Gly Glu
            85                  90                  95

Gly Gly Gly Glu Gly Gly Gly Glu Gly Gly Gly Glu
            100                 105                 110

Gly Gly Gly Glu Gly Gly Gly Glu Gly Gly Gly Glu
        115                 120                 125

Gly Gly Gly Glu Gly Gly Gly Glu Gly Gly Gly Glu
    130                 135                 140

Gly Gly Gly Glu Gly Gly Gly Glu Gly Gly Gly Glu
145                 150                 155                 160

Gly Gly Gly Glu Gly Gly Gly Glu Gly Gly Gly Glu
            165                 170                 175

Gly Gly Gly Glu Gly Gly Gly Glu Gly Gly Gly Glu
            180                 185                 190

Gly Gly Gly Glu Gly Gly Gly Glu Gly Gly Gly Glu
        195                 200                 205

Gly Gly Gly Glu Gly Gly Gly Glu Gly Gly Gly Glu
    210                 215                 220

Gly Gly Gly Glu Gly Gly Gly Glu Gly Gly Gly Glu
225                 230                 235                 240

Gly Gly Gly Glu Gly Gly Gly Glu Gly Gly Gly Glu
            245                 250                 255

Gly Gly Gly Glu Gly Gly Gly Glu Gly Gly Gly Glu
            260                 265                 270

Gly Gly Gly Glu Gly Gly Gly Glu Gly Gly Gly Glu
        275                 280                 285

Gly Gly Gly Glu Gly Gly Gly Glu Gly Gly Gly Glu
    290                 295                 300

<210> SEQ ID NO 21
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Gly Gly Gly
      Gly Glu" repeating units, wherein some positions may be absent

<400> SEQUENCE: 21

Gly Gly Gly Gly Glu Gly Gly Gly Glu Gly Gly Gly Gly Glu Gly
1               5                   10                  15

Gly Gly Gly Glu Gly Gly Gly Glu Gly Gly Gly Glu Gly Gly
            20                  25                  30

Gly Gly Glu Gly Gly Gly Glu Gly Gly Gly Glu Gly Gly Gly
        35                  40                  45

Gly Glu Gly Gly Gly Gly Glu Gly Gly Gly Gly Glu Gly Gly Gly
    50                  55                  60

Glu Gly Gly Gly Glu Gly Gly Gly Glu Gly Gly Gly Glu
65                  70                  75                  80

Gly Gly Gly Gly Glu Gly Gly Gly Gly Glu Gly Gly Gly Glu Gly

```
                    85                  90                  95
Gly Gly Gly Glu Gly Gly Gly Glu Gly Gly Gly Glu Gly Gly
                100                 105                 110
Gly Gly Glu Gly Gly Gly Gly Glu Gly Gly Gly Glu Gly Gly
                115                 120                 125
Gly Gly Glu Gly Gly Gly Glu Gly Gly Gly Glu Gly Gly Gly
            130                 135                 140
Glu Gly Gly Gly Glu Gly Gly Gly Glu Gly Gly Gly Gly Glu
145                 150                 155                 160
Gly Gly Gly Gly Glu Gly Gly Gly Glu Gly Gly Gly Glu Gly
                165                 170                 175
Gly Gly Gly Glu Gly Gly Gly Glu Gly Gly Gly Glu Gly Gly
                180                 185                 190
Gly Gly Glu Gly Gly Gly Glu Gly Gly Gly Glu Gly Gly Gly
                195                 200                 205
Gly Glu Gly Gly Gly Glu Gly Gly Gly Glu Gly Gly Gly Gly
            210                 215                 220
Glu Gly Gly Gly Glu Gly Gly Gly Glu Gly Gly Gly Gly Glu
225                 230                 235                 240
Gly Gly Gly Gly Glu Gly Gly Gly Glu Gly Gly Gly Glu Gly
                245                 250                 255
Gly Gly Gly Glu Gly Gly Gly Glu Gly Gly Gly Glu Gly Gly
                260                 265                 270
Gly Gly Glu Gly Gly Gly Glu Gly Gly Gly Glu Gly Gly Gly
                275                 280                 285
Gly Glu Gly Gly Gly Glu Gly Gly Gly Glu Gly Gly Gly Gly
            290                 295                 300
Glu Gly Gly Gly Glu Gly Gly Gly Glu Gly Gly Gly Gly Glu
305                 310                 315                 320
Gly Gly Gly Gly Glu Gly Gly Gly Glu Gly Gly Gly Glu Gly
                325                 330                 335
Gly Gly Gly Glu Gly Gly Gly Glu Gly Gly Gly Glu Gly Gly
                340                 345                 350
Gly Gly Glu Gly Gly Gly Glu Gly Gly Gly Glu Gly Gly Gly
                355                 360                 365
Gly Glu Gly Gly Gly Gly Glu
            370                 375

<210> SEQ ID NO 22
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(150)
<223> OTHER INFORMATION: This sequence may encompass 1-75 "Gly Asp"
      repeating units, wherein some positions may be absent

<400> SEQUENCE: 22

Gly Asp Gly Asp Gly Asp Gly Asp Gly Asp Gly Asp Gly Asp Gly Asp
1               5                   10                  15
Gly Asp Gly Asp Gly Asp Gly Asp Gly Asp Gly Asp Gly Asp
            20                  25                  30
Gly Asp Gly Asp Gly Asp Gly Asp Gly Asp Gly Asp Gly Asp Gly Asp
```

```
            35                  40                  45
Gly Asp Gly Asp Gly Asp Gly Asp Gly Asp Gly Asp Gly Asp
 50                  55                  60

Gly Asp Gly Asp Gly Asp Gly Asp Gly Asp Gly Asp Gly Asp
65                  70                  75                  80

Gly Asp Gly Asp Gly Asp Gly Asp Gly Asp Gly Asp Gly Asp
                85                  90                  95

Gly Asp Gly Asp Gly Asp Gly Asp Gly Asp Gly Asp Gly Asp
            100                 105                 110

Gly Asp Gly Asp Gly Asp Gly Asp Gly Asp Gly Asp Gly Asp
        115                 120                 125

Gly Asp Gly Asp Gly Asp Gly Asp Gly Asp Gly Asp Gly Asp
    130                 135                 140

Gly Asp Gly Asp Gly Asp
145                 150

<210> SEQ ID NO 23
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(225)
<223> OTHER INFORMATION: This sequence may encompass 1-75 "Gly Gly Asp"
      repeating units, wherein some positions may be absent

<400> SEQUENCE: 23

Gly Gly Asp Gly Gly Asp Gly Gly Asp Gly Gly Asp Gly Gly Asp Gly
1               5                   10                  15

Asp Gly Gly Asp Gly Gly Asp Gly Gly Asp Gly Gly Asp Gly Gly
            20                  25                  30

Asp Gly Gly Asp Gly Gly Asp Gly Gly Asp Gly Gly Asp Gly Asp
        35                  40                  45

Gly Gly Asp Gly Gly Asp Gly Gly Asp Gly Gly Asp Gly Gly Asp Gly
50                  55                  60

Gly Asp Gly Gly Asp Gly Gly Asp Gly Gly Asp Gly Gly Asp Gly Gly
65                  70                  75                  80

Asp Gly Gly Asp Gly Gly Asp Gly Gly Asp Gly Gly Asp Gly Gly Asp
                85                  90                  95

Gly Gly Asp Gly Gly Asp Gly Gly Asp Gly Gly Asp Gly Gly Asp Gly
            100                 105                 110

Gly Asp Gly Gly Asp Gly Gly Asp Gly Gly Asp Gly Gly Asp Gly Gly
        115                 120                 125

Asp Gly Gly Asp Gly Gly Asp Gly Gly Asp Gly Gly Asp Gly Gly Asp
    130                 135                 140

Gly Gly Asp Gly Gly Asp Gly Gly Asp Gly Gly Asp Gly Gly Asp Gly
145                 150                 155                 160

Gly Asp Gly Gly Asp Gly Gly Asp Gly Gly Asp Gly Gly Asp Gly Gly
                165                 170                 175

Asp Gly Gly Asp Gly Gly Asp Gly Gly Asp Gly Gly Asp Gly Gly Asp
            180                 185                 190

Gly Gly Asp Gly Gly Asp Gly Gly Asp Gly Gly Asp Gly Gly Asp Gly
        195                 200                 205

Gly Asp Gly Gly Asp Gly Gly Asp Gly Gly Asp Gly Gly Asp Gly Gly
```

```
                     210                 215                 220
Asp
225

<210> SEQ ID NO 24
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(300)
<223> OTHER INFORMATION: This sequence may encompass 1-75 "Gly Gly Gly
      Asp" repeating units, wherein some positions may be absent

<400> SEQUENCE: 24

Gly Gly Gly Asp Gly Gly Gly Asp Gly Gly Gly Asp Gly Gly Gly Asp
1               5                   10                  15

Gly Gly Gly Asp Gly Gly Gly Asp Gly Gly Gly Asp Gly Gly Gly Asp
            20                  25                  30

Gly Gly Gly Asp Gly Gly Gly Asp Gly Gly Gly Asp Gly Gly Gly Asp
        35                  40                  45

Gly Gly Gly Asp Gly Gly Gly Asp Gly Gly Gly Asp Gly Gly Gly Asp
    50                  55                  60

Gly Gly Gly Asp Gly Gly Gly Asp Gly Gly Gly Asp Gly Gly Gly Asp
65                  70                  75                  80

Gly Gly Gly Asp Gly Gly Gly Asp Gly Gly Gly Asp Gly Gly Gly Asp
                85                  90                  95

Gly Gly Gly Asp Gly Gly Gly Asp Gly Gly Gly Asp Gly Gly Gly Asp
            100                 105                 110

Gly Gly Gly Asp Gly Gly Gly Asp Gly Gly Gly Asp Gly Gly Gly Asp
        115                 120                 125

Gly Gly Gly Asp Gly Gly Gly Asp Gly Gly Gly Asp Gly Gly Gly Asp
    130                 135                 140

Gly Gly Gly Asp Gly Gly Gly Asp Gly Gly Gly Asp Gly Gly Gly Asp
145                 150                 155                 160

Gly Gly Gly Asp Gly Gly Gly Asp Gly Gly Gly Asp Gly Gly Gly Asp
                165                 170                 175

Gly Gly Gly Asp Gly Gly Gly Asp Gly Gly Gly Asp Gly Gly Gly Asp
            180                 185                 190

Gly Gly Gly Asp Gly Gly Gly Asp Gly Gly Gly Asp Gly Gly Gly Asp
        195                 200                 205

Gly Gly Gly Asp Gly Gly Gly Asp Gly Gly Gly Asp Gly Gly Gly Asp
    210                 215                 220

Gly Gly Gly Asp Gly Gly Gly Asp Gly Gly Gly Asp Gly Gly Gly Asp
225                 230                 235                 240

Gly Gly Gly Asp Gly Gly Gly Asp Gly Gly Gly Asp Gly Gly Gly Asp
                245                 250                 255

Gly Gly Gly Asp Gly Gly Gly Asp Gly Gly Gly Asp Gly Gly Gly Asp
            260                 265                 270

Gly Gly Gly Asp Gly Gly Gly Asp Gly Gly Gly Asp Gly Gly Gly Asp
        275                 280                 285

Gly Gly Gly Asp Gly Gly Gly Asp Gly Gly Gly Asp
    290                 295                 300
```

```
<210> SEQ ID NO 25
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Gly Gly Gly
      Gly Asp" repeating units, wherein some positions may be absent

<400> SEQUENCE: 25

Gly Gly Gly Gly Asp Gly Gly Gly Gly Asp Gly Gly Gly Gly Asp Gly
1               5                   10                  15

Gly Gly Gly Asp Gly Gly Gly Gly Asp Gly Gly Gly Gly Asp Gly Gly
            20                  25                  30

Gly Gly Asp Gly Gly Gly Gly Asp Gly Gly Gly Gly Asp Gly Gly Gly
        35                  40                  45

Gly Asp Gly Gly Gly Gly Asp Gly Gly Gly Gly Asp Gly Gly Gly Gly
    50                  55                  60

Asp Gly Gly Gly Gly Asp Gly Gly Gly Gly Asp Gly Gly Gly Gly Asp
65                  70                  75                  80

Gly Gly Gly Gly Asp Gly Gly Gly Gly Asp Gly Gly Gly Gly Asp Gly
                85                  90                  95

Gly Gly Gly Asp Gly Gly Gly Gly Asp Gly Gly Gly Gly Asp Gly Gly
            100                 105                 110

Gly Gly Asp Gly Gly Gly Gly Asp Gly Gly Gly Gly Asp Gly Gly Gly
        115                 120                 125

Gly Asp Gly Gly Gly Gly Asp Gly Gly Gly Gly Asp Gly Gly Gly Gly
    130                 135                 140

Asp Gly Gly Gly Gly Asp Gly Gly Gly Gly Asp Gly Gly Gly Gly Asp
145                 150                 155                 160

Gly Gly Gly Gly Asp Gly Gly Gly Gly Asp Gly Gly Gly Gly Asp Gly
                165                 170                 175

Gly Gly Gly Asp Gly Gly Gly Gly Asp Gly Gly Gly Gly Asp Gly Gly
            180                 185                 190

Gly Gly Asp Gly Gly Gly Gly Asp Gly Gly Gly Gly Asp Gly Gly Gly
        195                 200                 205

Gly Asp Gly Gly Gly Gly Asp Gly Gly Gly Gly Asp Gly Gly Gly Gly
    210                 215                 220

Asp Gly Gly Gly Gly Asp Gly Gly Gly Gly Asp Gly Gly Gly Gly Asp
225                 230                 235                 240

Gly Gly Gly Gly Asp Gly Gly Gly Gly Asp Gly Gly Gly Gly Asp Gly
                245                 250                 255

Gly Gly Gly Asp Gly Gly Gly Gly Asp Gly Gly Gly Gly Asp Gly Gly
            260                 265                 270

Gly Gly Asp Gly Gly Gly Gly Asp Gly Gly Gly Gly Asp Gly Gly Gly
        275                 280                 285

Gly Asp Gly Gly Gly Gly Asp Gly Gly Gly Gly Asp Gly Gly Gly Gly
    290                 295                 300

Asp Gly Gly Gly Gly Asp Gly Gly Gly Gly Asp Gly Gly Gly Gly Asp
305                 310                 315                 320

Gly Gly Gly Gly Asp Gly Gly Gly Gly Asp Gly Gly Gly Gly Asp Gly
                325                 330                 335

Gly Gly Gly Asp Gly Gly Gly Gly Asp Gly Gly Gly Gly Asp Gly Gly
```

```
                    340                 345                 350
Gly Gly Asp Gly Gly Gly Gly Asp Gly Gly Gly Asp Gly Gly Gly
                355                 360                 365
Gly Asp Gly Gly Gly Gly Asp
        370                 375
```

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Gly Ser Val Ser Ser Gly Ser Tyr Tyr Trp Ser
1               5                   10
```

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Gly Ser Ile Ser Ser Gly Gly Tyr Tyr Trp Ser
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gly Ser Ile Asn Ser Ser Ser Tyr Tyr Trp Gln
1               5                   10
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Phe Thr Leu Ser Gly Asp Trp Ile His
1               5
```

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Phe Asn Ile Lys Asp Thr Tyr Ile His
1               5
```

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Ser Leu Thr Asn Tyr Gly Val His
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Ile Ser Ser Gly Gly Asp Tyr Trp Gln
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Ile Tyr Tyr Ser Gly Ser Thr Asn Tyr Asn Pro Ser Leu Lys Ser
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Ile Tyr Tyr Ser Gly Trp Thr Asn Tyr Asn Pro Ser Leu Lys Ser
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Ile Ala Tyr Ser Gly Ser Thr Tyr Tyr Asn Pro Ser Leu Lys Ser
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Glu Ile Ser Ala Ala Gly Gly Tyr Thr Asp Tyr Ala Asp Ser Val Lys
1               5                   10                  15
Gly

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ile Tyr Pro Thr Asn Gly Tyr Thr Arg Tyr Ala Asp Ser Val Lys
1               5                   10                  15
Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ile Trp Ser Gly Gly Asn Thr Asp Tyr Asn Thr Pro Phe Thr Ser
1               5                   10                  15
Arg

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Thr Asn Leu Tyr Ser Thr Pro Phe Asp Ile
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Gly Val Gly Pro Asp Phe Trp Ser Gly Tyr Ser Tyr Ser Ser
1               5                   10                  15
Tyr Phe Asp Leu
            20

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Ala Arg Gly Gln Gln Trp Ala Ala Phe Asp Ile
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Arg Glu Ser Arg Val Ser Phe Glu Ala Ala Met Asp Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Arg Trp Gly Gly Asp Gly Phe Tyr Ala Met Asp Tyr
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ala Leu Thr Tyr Tyr Asp Tyr Glu Phe Ala Tyr Trp
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ala Ser Gln Asp Ile Ser Ser Trp Leu Ala
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Gln Ala Ile Ser Ser Trp Leu Ala
1               5                   10

<210> SEQ ID NO 47
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

Arg Ala Ser Gln Asn Ile Ala Thr Asp Val Ala
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Asp Val Asn Thr Ala Val Ala
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Ser Gln Ser Ile Gly Thr Asn Ile His
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ala Ser Ser Leu Gln Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ala Ser Ser Leu Glu Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Ala Ser Ser Leu Gln Ser
1               5
```

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Ala Ser Phe Leu Tyr Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Ala Ser Glu Ser Ile Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gln Glu His Asp Phe Pro Trp Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Gln Tyr Gln Ser Tyr Ser Trp Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Glu His Asp Phe Pro Trp Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 58

Gln Gln Ser Glu Pro Glu Pro Tyr Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln His Tyr Thr Thr Pro Pro Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Asn Asn Asn Trp Pro Thr Thr
1               5

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Val Gln Leu Gln Glu Ser Gly Pro Gly Leu Val Lys Pro Ser Glu Thr
1               5                   10                  15

Leu Ser Leu Thr Cys Thr Val Ser Gly Gly Ser Val Ser Ser Gly Ser
                20                  25                  30

Tyr Tyr Trp Ser Trp Ile Arg Gln Pro Pro Gly Lys Gly Leu Glu Trp
            35                  40                  45

Ile Gly Tyr Ile Tyr Tyr Ser Gly Ser Thr Asn Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Thr Asn Leu Tyr Ser Thr Pro Phe Asp Ile Trp Gly Gln Gly
            100                 105                 110

Thr Met Val Thr Val Ser Ser
        115

<210> SEQ ID NO 62
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ile Ile Tyr Tyr Ser Gly Trp Thr Asn Tyr Asn Pro Ser
    50                  55                  60

Leu Lys Ser Arg Val Thr Ile Ser Val Asp Ala Ser Arg Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Val Gly Pro Asp Phe Trp Ser Gly Tyr Ser Tyr Ser
            100                 105                 110

Ser Tyr Phe Asp Leu Trp Gly Arg Gly Thr Leu Val Thr Val Ser Ser
            115                 120                 125
```

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Ser
            20                  25                  30

Ser Tyr Tyr Trp Gln Trp Ile Arg Gln Pro Pro Gly Lys Gly Leu Glu
        35                  40                  45

Trp Ile Gly Glu Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Gln Trp Ala Ala Phe Asp Ile Trp Gly Gln Gly
            100                 105                 110

Thr Met Val Thr Val Ser Ser
        115
```

<210> SEQ ID NO 64
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45
```

```
Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120

<210> SEQ ID NO 65
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asp Asp Thr Ala Ile Tyr Tyr Cys Ala
                 85                  90                  95
```

```
Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Asp Tyr Trp Gln Trp Ile Arg Gln Pro Pro Gly Lys Gly Leu Glu
        35                  40                  45

Trp Ile Gly Glu Ile Ala Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Gln Gln Trp Ala Ala Phe Asp Ile Trp Gly Gln Gly
            100                 105                 110

Thr Met Val Thr Val Ser Ser
        115

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Asp Phe Pro Trp
            85                  90                  95

Thr Phe Gly Gly Gly Thr Lys Val Glu Ile Lys
            100                 105

<210> SEQ ID NO 69
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 69

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ala Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Gln Ser Tyr Ser Trp
                85                  90                  95

Thr Phe Gly Gly Gly Thr Lys Val Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Asp Phe Pro Trp
                85                  90                  95

Thr Phe Gly Gly Gly Thr Lys Val Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Glu Pro Glu Pro Tyr
                 85                  90                  95

Thr Phe Gly Gln Gly Thr Lys Val Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                 20                  25                  30

Ile His Trp Tyr Gln Gln Arg Thr His Gly Ser Pro Arg Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys
            100                 105

<210> SEQ ID NO 74
<211> LENGTH: 687
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 74

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Thr Asn Leu Tyr Ser Thr Pro Phe Asp Ile Trp Gly Gln
        100                 105                 110

Gly Thr Met Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Ser Gly Gly Gly Gly
450                 455                 460

Ser Gln Leu Gln Leu Gln Glu Ser Gly Pro Gly Leu Val Lys Pro Ser
465                 470                 475                 480

Glu Thr Leu Ser Leu Thr Cys Thr Val Ser Gly Gly Ser Ile Asn Ser
            485                 490                 495

Ser Ser Tyr Tyr Trp Gln Trp Ile Arg Gln Pro Pro Gly Lys Gly Leu
            500                 505                 510

Glu Trp Ile Gly Glu Ile Ala Tyr Ser Gly Ser Thr Tyr Tyr Asn Pro
            515                 520                 525

Ser Leu Lys Ser Arg Val Thr Ile Ser Val Asp Thr Ser Lys Asn Gln
530                 535                 540

Phe Ser Leu Lys Leu Ser Ser Val Thr Ala Ala Asp Thr Ala Val Tyr
545                 550                 555                 560

Tyr Cys Ala Arg Gly Gln Trp Ala Ala Phe Asp Ile Trp Gly Gln
            565                 570                 575

Gly Thr Met Val Thr Val Ser Ser Ala Ser Thr Lys Gly Pro Ser Val
            580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
            610                 615                 620

Trp Asn Ser Gly Ala Leu Thr Ser Gly Val His Thr Phe Pro Ala Val
625                 630                 635                 640

Leu Gln Ser Ser Gly Leu Tyr Ser Leu Ser Ser Val Val Thr Val Pro
            645                 650                 655

Ser Ser Ser Leu Gly Thr Gln Thr Tyr Ile Cys Asn Val Asn His Lys
            660                 665                 670

Pro Ser Asn Thr Lys Val Asp Lys Lys Val Glu Pro Lys Ser Cys
            675                 680                 685

<210> SEQ ID NO 75
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Thr Asn Leu Tyr Ser Thr Pro Phe Asp Ile Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Ser Gly Gly Gly Gly
            450                 455                 460

Ser Gln Val Gln Leu Gln Glu Ser Gly Pro Gly Leu Val Lys Pro Ser
465                 470                 475                 480
```

```
Glu Thr Leu Ser Leu Thr Cys Thr Val Ser Gly Gly Ser Ile Ser Ser
                485                 490                 495

Gly Gly Tyr Tyr Trp Ser Trp Ile Arg Gln Pro Pro Gly Lys Gly Leu
            500                 505                 510

Glu Trp Ile Gly Ile Ile Tyr Tyr Ser Gly Trp Thr Asn Tyr Asn Pro
            515                 520                 525

Ser Leu Lys Ser Arg Val Thr Ile Ser Val Asp Ala Ser Arg Asn Gln
    530                 535                 540

Phe Ser Leu Lys Leu Ser Ser Val Thr Ala Ala Asp Thr Ala Val Tyr
545                 550                 555                 560

Tyr Cys Ala Arg Gly Val Gly Pro Asp Phe Trp Ser Gly Tyr Ser Tyr
                565                 570                 575

Ser Ser Tyr Phe Asp Leu Trp Gly Arg Gly Thr Leu Val Thr Val Ser
            580                 585                 590

Ser Ala Ser Thr Lys Gly Pro Ser Val Phe Pro Leu Ala Pro Ser Ser
            595                 600                 605

Lys Ser Thr Ser Gly Gly Thr Ala Ala Leu Gly Cys Leu Val Lys Asp
    610                 615                 620

Tyr Phe Pro Glu Pro Val Thr Val Ser Trp Asn Ser Gly Ala Leu Thr
625                 630                 635                 640

Ser Gly Val His Thr Phe Pro Ala Val Leu Gln Ser Ser Gly Leu Tyr
                645                 650                 655

Ser Leu Ser Ser Val Val Thr Val Pro Ser Ser Ser Leu Gly Thr Gln
            660                 665                 670

Thr Tyr Ile Cys Asn Val Asn His Lys Pro Ser Asn Thr Lys Val Asp
            675                 680                 685

Lys Lys Val Glu Pro Lys Ser Cys
690                 695

<210> SEQ ID NO 76
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Ile Ile Tyr Tyr Ser Gly Trp Thr Asn Tyr Asn Pro Ser
    50                  55                  60

Leu Lys Ser Arg Val Thr Ile Ser Val Asp Ala Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Gly Pro Asp Phe Trp Ser Gly Tyr Ser Tyr Ser
            100                 105                 110

Ser Tyr Phe Asp Leu Trp Gly Arg Gly Thr Leu Val Thr Val Ser Ser
        115                 120                 125

Ala Ser Thr Lys Gly Pro Ser Val Phe Pro Leu Ala Pro Ser Ser Lys
    130                 135                 140
```

```
Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
    195                 200                 205

Tyr Ile Cys Asn Val Asn His Lys Pro Ser Asn Thr Lys Val Asp Lys
210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys Gly Gly Gly Gly Ser Gly
    450                 455                 460

Gly Gly Gly Ser Gly Gly Gly Ser Gln Val Gln Leu Gln Glu Ser
465                 470                 475                 480

Gly Pro Gly Leu Val Lys Pro Ser Glu Thr Leu Ser Leu Thr Cys Thr
                485                 490                 495

Val Ser Gly Gly Ser Val Ser Ser Gly Ser Tyr Tyr Trp Ser Trp Ile
            500                 505                 510

Arg Gln Pro Pro Gly Lys Gly Leu Glu Trp Ile Gly Tyr Ile Tyr Tyr
        515                 520                 525

Ser Gly Ser Thr Asn Tyr Asn Pro Ser Leu Lys Ser Arg Val Thr Ile
    530                 535                 540

Ser Val Asp Thr Ser Lys Asn Gln Phe Ser Leu Lys Leu Ser Ser Val
545                 550                 555                 560
```

```
Thr Ala Ala Asp Thr Ala Val Tyr Tyr Cys Ala Arg Thr Asn Leu Tyr
                565                 570                 575

Ser Thr Pro Phe Asp Ile Trp Gly Gln Gly Thr Met Val Thr Val Ser
            580                 585                 590

Ser Ala Ser Thr Lys Gly Pro Ser Val Phe Pro Leu Ala Pro Ser Ser
        595                 600                 605

Lys Ser Thr Ser Gly Gly Thr Ala Ala Leu Gly Cys Leu Val Lys Asp
    610                 615                 620

Tyr Phe Pro Glu Pro Val Thr Val Ser Trp Asn Ser Gly Ala Leu Thr
625                 630                 635                 640

Ser Gly Val His Thr Phe Pro Ala Val Leu Gln Ser Ser Gly Leu Tyr
                645                 650                 655

Ser Leu Ser Ser Val Val Thr Val Pro Ser Ser Ser Leu Gly Thr Gln
            660                 665                 670

Thr Tyr Ile Cys Asn Val Asn His Lys Pro Ser Asn Thr Lys Val Asp
        675                 680                 685

Lys Lys Val Glu Pro Lys Ser Cys
    690                 695

<210> SEQ ID NO 77
<211> LENGTH: 687
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Ser
            20                  25                  30

Ser Tyr Tyr Trp Gln Trp Ile Arg Gln Pro Pro Gly Lys Gly Leu Glu
        35                  40                  45

Trp Ile Gly Glu Ile Ala Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Gln Trp Ala Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
    450                 455                 460

Gln Val Gln Leu Gln Glu Ser Gly Pro Gly Leu Val Lys Pro Ser Glu
465                 470                 475                 480

Thr Leu Ser Leu Thr Cys Thr Val Ser Gly Gly Ser Val Ser Ser Gly
                485                 490                 495

Ser Tyr Tyr Trp Ser Trp Ile Arg Gln Pro Pro Gly Lys Gly Leu Glu
            500                 505                 510

Trp Ile Gly Tyr Ile Tyr Tyr Ser Gly Ser Thr Asn Tyr Asn Pro Ser
            515                 520                 525

Leu Lys Ser Arg Val Thr Ile Ser Val Asp Thr Ser Lys Asn Gln Phe
            530                 535                 540

Ser Leu Lys Leu Ser Ser Val Thr Ala Ala Asp Thr Ala Val Tyr Tyr
545                 550                 555                 560

Cys Ala Arg Thr Asn Leu Tyr Ser Thr Pro Phe Asp Ile Trp Gly Gln
            565                 570                 575

Gly Thr Met Val Thr Val Ser Ser Ala Ser Thr Lys Gly Pro Ser Val
            580                 585                 590

Phe Pro Leu Ala Pro Ser Ser Lys Ser Thr Ser Gly Gly Thr Ala Ala
            595                 600                 605

Leu Gly Cys Leu Val Lys Asp Tyr Phe Pro Glu Pro Val Thr Val Ser
            610                 615                 620

Trp Asn Ser Gly Ala Leu Thr Ser Gly Val His Thr Phe Pro Ala Val
625                 630                 635                 640
```

Leu Gln Ser Ser Gly Leu Tyr Ser Leu Ser Ser Val Val Thr Val Pro
                645                 650                 655

Ser Ser Ser Leu Gly Thr Gln Thr Tyr Ile Cys Asn Val Asn His Lys
            660                 665                 670

Pro Ser Asn Thr Lys Val Asp Lys Lys Val Glu Pro Lys Ser Cys
        675                 680                 685

<210> SEQ ID NO 78
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu His Asp Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 79
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ala Ile Ser Ser Trp
            20                  25                  30

```
Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys His Gln Tyr Gln Ser Tyr Ser Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 80
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Glu Pro Glu Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 82
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30
```

```
Ile His Trp Tyr Gln Gln Arg Thr His Gly Ser Pro Arg Leu Leu Ile
         35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 83
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(225)
<223> OTHER INFORMATION: This sequence may encompass 1-75 "Gly Gly Lys"
      repeating units, wherein some positions may be absent

<400> SEQUENCE: 83

Gly Gly Lys Gly Gly Lys Gly Gly Lys Gly Gly Lys Gly Gly Lys Gly
 1               5                  10                  15

Gly Lys Gly Gly Lys Gly Gly Lys Gly Gly Lys Gly Gly Lys Gly Gly
                 20                  25                  30

Lys Gly Gly Lys Gly Gly Lys Gly Gly Lys Gly Gly Lys Gly Gly Lys
         35                  40                  45

Gly Gly Lys Gly Gly Lys Gly Gly Lys Gly Gly Lys Gly Gly Lys Gly
 50                  55                  60

Gly Lys Gly Gly Lys Gly Gly Lys Gly Gly Lys Gly Gly Lys Gly Gly
 65                  70                  75                  80

Lys Gly Gly Lys Gly Gly Lys Gly Gly Lys Gly Gly Lys Gly Gly Lys
                 85                  90                  95

Gly Gly Lys Gly Gly Lys Gly Gly Lys Gly Gly Lys Gly Gly Lys Gly
            100                 105                 110

Gly Lys Gly Gly Lys Gly Gly Lys Gly Gly Lys Gly Gly Lys Gly Gly
            115                 120                 125

Lys Gly Gly Lys Gly Gly Lys Gly Gly Lys Gly Gly Lys Gly Gly Lys
        130                 135                 140
```

Gly Gly Lys Gly Gly Lys Gly Gly Lys Gly Gly Lys Gly
145                 150                 155                 160

Gly Lys Gly Gly Lys Gly Gly Lys Gly Gly Lys Gly Gly
            165                 170                 175

Lys Gly Gly Lys Gly Gly Lys Gly Gly Lys Gly Gly Lys
        180                 185                 190

Gly Gly Lys Gly Gly Lys Gly Gly Lys Gly Gly Lys Gly
    195                 200                 205

Gly Lys Gly Gly Lys Gly Gly Lys Gly Gly Lys Gly Gly
210                 215                 220

Lys
225

<210> SEQ ID NO 84
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(300)
<223> OTHER INFORMATION: This sequence may encompass 1-75 "Gly Gly Gly
      Lys" repeating units, wherein some positions may be absent

<400> SEQUENCE: 84

Gly Gly Gly Lys Gly Gly Gly Lys Gly Gly Gly Lys Gly Gly Gly Lys
1               5                   10                  15

Gly Gly Gly Lys Gly Gly Gly Lys Gly Gly Gly Lys Gly Gly Gly Lys
            20                  25                  30

Gly Gly Gly Lys Gly Gly Gly Lys Gly Gly Gly Lys Gly Gly Gly Lys
        35                  40                  45

Gly Gly Gly Lys Gly Gly Gly Lys Gly Gly Gly Lys Gly Gly Gly Lys
    50                  55                  60

Gly Gly Gly Lys Gly Gly Gly Lys Gly Gly Gly Lys Gly Gly Gly Lys
65                  70                  75                  80

Gly Gly Gly Lys Gly Gly Gly Lys Gly Gly Gly Lys Gly Gly Gly Lys
            85                  90                  95

Gly Gly Gly Lys Gly Gly Gly Lys Gly Gly Gly Lys Gly Gly Gly Lys
        100                 105                 110

Gly Gly Gly Lys Gly Gly Gly Lys Gly Gly Gly Lys Gly Gly Gly Lys
    115                 120                 125

Gly Gly Gly Lys Gly Gly Gly Lys Gly Gly Gly Lys Gly Gly Gly Lys
130                 135                 140

Gly Gly Gly Lys Gly Gly Gly Lys Gly Gly Gly Lys Gly Gly Gly Lys
145                 150                 155                 160

Gly Gly Gly Lys Gly Gly Gly Lys Gly Gly Gly Lys Gly Gly Gly Lys
            165                 170                 175

Gly Gly Gly Lys Gly Gly Gly Lys Gly Gly Gly Lys Gly Gly Gly Lys
        180                 185                 190

Gly Gly Gly Lys Gly Gly Gly Lys Gly Gly Gly Lys Gly Gly Gly Lys
    195                 200                 205

Gly Gly Gly Lys Gly Gly Gly Lys Gly Gly Gly Lys Gly Gly Gly Lys
210                 215                 220

Gly Gly Gly Lys Gly Gly Gly Lys Gly Gly Gly Lys Gly Gly Gly Lys
225                 230                 235                 240

```
Gly Gly Gly Lys Gly Gly Gly Lys Gly Gly Gly Lys
            245             250             255

Gly Gly Gly Lys Gly Gly Gly Lys Gly Gly Gly Lys
            260             265             270

Gly Gly Gly Lys Gly Gly Gly Lys Gly Gly Gly Lys
            275             280             285

Gly Gly Gly Lys Gly Gly Gly Lys Gly Gly Gly Lys
            290             295             300

<210> SEQ ID NO 85
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Gly Gly Gly
      Gly Lys" repeating units, wherein some positions may be absent

<400> SEQUENCE: 85

Gly Gly Gly Gly Lys Gly Gly Gly Lys Gly Gly Gly Lys Gly
1               5                   10                  15

Gly Gly Gly Lys Gly Gly Gly Gly Lys Gly Gly Gly Lys Gly Gly
                20                  25                  30

Gly Gly Lys Gly Gly Gly Gly Lys Gly Gly Gly Lys Gly Gly Gly
        35                  40                  45

Gly Lys Gly Gly Gly Lys Gly Gly Gly Lys Gly Gly Gly Gly
    50                  55                  60

Lys Gly Gly Gly Lys Gly Gly Gly Lys Gly Gly Gly Gly Lys
65                  70                  75                  80

Gly Gly Gly Lys Gly Gly Gly Gly Lys Gly Gly Gly Lys Gly
            85                  90                  95

Gly Gly Gly Lys Gly Gly Gly Gly Lys Gly Gly Gly Lys Gly
            100                 105                 110

Gly Gly Lys Gly Gly Gly Gly Lys Gly Gly Gly Lys Gly Gly
        115                 120                 125

Gly Lys Gly Gly Gly Lys Gly Gly Gly Lys Gly Gly Gly Gly
    130                 135                 140

Lys Gly Gly Gly Lys Gly Gly Gly Lys Gly Gly Gly Gly Lys
145                 150                 155                 160

Gly Gly Gly Gly Lys Gly Gly Gly Lys Gly Gly Gly Lys Gly
            165                 170                 175

Gly Gly Gly Lys Gly Gly Gly Lys Gly Gly Gly Lys Gly Gly
            180                 185                 190

Gly Gly Lys Gly Gly Gly Lys Gly Gly Gly Lys Gly Gly Gly
        195                 200                 205

Gly Lys Gly Gly Gly Lys Gly Gly Gly Lys Gly Gly Gly Gly
    210                 215                 220

Lys Gly Gly Gly Lys Gly Gly Gly Lys Gly Gly Gly Gly Lys
225                 230                 235                 240

Gly Gly Gly Gly Lys Gly Gly Gly Lys Gly Gly Gly Lys Gly
            245                 250                 255

Gly Gly Gly Lys Gly Gly Gly Lys Gly Gly Gly Lys Gly Gly
            260                 265                 270
```

```
Gly Gly Lys Gly Gly Gly Lys Gly Gly Gly Lys Gly Gly Gly
        275                 280                 285

Gly Lys Gly Gly Gly Lys Gly Gly Gly Lys Gly Gly Gly Gly
        290                 295                 300

Lys Gly Gly Gly Lys Gly Gly Gly Lys Gly Gly Gly Gly Lys
305                 310                 315                 320

Gly Gly Gly Lys Gly Gly Gly Lys Gly Gly Gly Lys Gly
                325                 330                 335

Gly Gly Gly Lys Gly Gly Gly Lys Gly Gly Gly Lys Gly Gly
            340                 345                 350

Gly Gly Lys Gly Gly Gly Lys Gly Gly Gly Lys Gly Gly Gly
        355                 360                 365

Gly Lys Gly Gly Gly Lys
    370             375

<210> SEQ ID NO 86
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(150)
<223> OTHER INFORMATION: This sequence may encompass 1-75 "Gly Arg"
      repeating units, wherein some positions may be absent

<400> SEQUENCE: 86

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg Gly Arg
            20                  25                  30

Gly Arg Gly Arg Gly Arg Gly Arg Gly Arg Gly Arg Gly Arg Gly Arg
        35                  40                  45

Gly Arg Gly Arg Gly Arg Gly Arg Gly Arg Gly Arg Gly Arg Gly Arg
    50                  55                  60

Gly Arg Gly Arg Gly Arg Gly Arg Gly Arg Gly Arg Gly Arg Gly Arg
65                  70                  75                  80

Gly Arg Gly Arg Gly Arg Gly Arg Gly Arg Gly Arg Gly Arg Gly Arg
                85                  90                  95

Gly Arg Gly Arg Gly Arg Gly Arg Gly Arg Gly Arg Gly Arg Gly Arg
            100                 105                 110

Gly Arg Gly Arg Gly Arg Gly Arg Gly Arg Gly Arg Gly Arg Gly Arg
        115                 120                 125

Gly Arg Gly Arg Gly Arg Gly Arg Gly Arg Gly Arg Gly Arg Gly Arg
    130                 135                 140

Gly Arg Gly Arg Gly Arg
145             150

<210> SEQ ID NO 87
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(225)
```

<223> OTHER INFORMATION: This sequence may encompass 1-75 "Gly Gly Arg"
      repeating units, wherein some positions may be absent

<400> SEQUENCE: 87

```
Gly Gly Arg Gly Gly Arg Gly Gly Arg Gly Gly Arg Gly Gly Gly
1               5                   10                  15

Gly Arg Gly Gly Arg Gly Gly Arg Gly Gly Arg Gly Gly Arg Gly
                20                  25                  30

Arg Gly Gly Arg Gly Gly Arg Gly Gly Arg Gly Gly Arg Gly Gly Arg
            35                  40                  45

Gly Gly Arg Gly Gly Arg Gly Gly Arg Gly Gly Arg Gly Gly Arg Gly
        50                  55                  60

Gly Arg Gly Gly Arg Gly Gly Arg Gly Gly Arg Gly Gly Arg Gly Gly
65                  70                  75                  80

Arg Gly Gly Arg Gly Gly Arg Gly Gly Arg Gly Gly Arg Gly Gly Arg
                85                  90                  95

Gly Gly Arg Gly Gly Arg Gly Gly Arg Gly Gly Arg Gly Gly Arg Gly
                100                 105                 110

Gly Arg Gly Gly Arg Gly Gly Arg Gly Gly Arg Gly Gly Arg Gly Gly
            115                 120                 125

Arg Gly Gly Arg Gly Gly Arg Gly Gly Arg Gly Gly Arg Gly Gly Arg
        130                 135                 140

Gly Gly Arg Gly Gly Arg Gly Gly Arg Gly Gly Arg Gly Gly Arg Gly
145                 150                 155                 160

Gly Arg Gly Gly Arg Gly Gly Arg Gly Gly Arg Gly Gly Arg Gly Gly
                165                 170                 175

Arg Gly Gly Arg Gly Gly Arg Gly Gly Arg Gly Gly Arg Gly Gly Arg
                180                 185                 190

Gly Gly Arg Gly Gly Arg Gly Gly Arg Gly Gly Arg Gly Gly Arg Gly
            195                 200                 205

Gly Arg Gly Gly Arg Gly Gly Arg Gly Gly Arg Gly Gly Arg Gly Gly
        210                 215                 220

Arg
225
```

<210> SEQ ID NO 88
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(300)
<223> OTHER INFORMATION: This sequence may encompass 1-75 "Gly Gly Gly
      Arg" repeating units, wherein some positions may be absent

<400> SEQUENCE: 88

```
Gly Gly Gly Arg Gly Gly Gly Arg Gly Gly Gly Arg Gly Gly Gly Arg
1               5                   10                  15

Gly Gly Gly Arg Gly Gly Gly Arg Gly Gly Gly Arg Gly Gly Gly Arg
                20                  25                  30

Gly Gly Gly Arg Gly Gly Gly Arg Gly Gly Gly Arg Gly Gly Gly Arg
            35                  40                  45

Gly Gly Gly Arg Gly Gly Gly Arg Gly Gly Gly Arg Gly Gly Gly Arg
        50                  55                  60

Gly Gly Gly Arg Gly Gly Gly Arg Gly Gly Gly Arg Gly Gly Gly Arg
```

-continued

```
                65                  70                  75                  80
Gly Gly Gly Arg Gly Gly Gly Arg Gly Gly Gly Arg Gly Gly Gly Arg
                    85                  90                  95
Gly Gly Gly Arg Gly Gly Gly Arg Gly Gly Gly Arg Gly Gly Gly Arg
                    100                 105                 110
Gly Gly Gly Arg Gly Gly Gly Arg Gly Gly Gly Arg Gly Gly Gly Arg
                    115                 120                 125
Gly Gly Gly Arg Gly Gly Gly Arg Gly Gly Gly Arg Gly Gly Gly Arg
                    130                 135                 140
Gly Gly Gly Arg Gly Gly Gly Arg Gly Gly Gly Arg Gly Gly Gly Arg
145                 150                 155                 160
Gly Gly Gly Arg Gly Gly Gly Arg Gly Gly Gly Arg Gly Gly Gly Arg
                    165                 170                 175
Gly Gly Gly Arg Gly Gly Gly Arg Gly Gly Gly Arg Gly Gly Gly Arg
                    180                 185                 190
Gly Gly Gly Arg Gly Gly Gly Arg Gly Gly Gly Arg Gly Gly Gly Arg
                    195                 200                 205
Gly Gly Gly Arg Gly Gly Gly Arg Gly Gly Gly Arg Gly Gly Gly Arg
                    210                 215                 220
Gly Gly Gly Arg Gly Gly Gly Arg Gly Gly Gly Arg Gly Gly Gly Arg
225                 230                 235                 240
Gly Gly Gly Arg Gly Gly Gly Arg Gly Gly Gly Arg Gly Gly Gly Arg
                    245                 250                 255
Gly Gly Gly Arg Gly Gly Gly Arg Gly Gly Gly Arg Gly Gly Gly Arg
                    260                 265                 270
Gly Gly Gly Arg Gly Gly Gly Arg Gly Gly Gly Arg Gly Gly Gly Arg
                    275                 280                 285
Gly Gly Gly Arg Gly Gly Gly Arg Gly Gly Gly Arg
        290                 295                 300

<210> SEQ ID NO 89
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Gly Gly Gly
      Gly Arg" repeating units, wherein some positions may be absent

<400> SEQUENCE: 89

Gly Gly Gly Gly Arg Gly Gly Gly Gly Arg Gly Gly Gly Gly Arg Gly
1               5                   10                  15
Gly Gly Gly Arg Gly Gly Gly Gly Arg Gly Gly Gly Gly Arg Gly Gly
            20                  25                  30
Gly Gly Arg Gly Gly Gly Gly Arg Gly Gly Gly Gly Arg Gly Gly Gly
        35                  40                  45
Gly Arg Gly Gly Gly Gly Arg Gly Gly Gly Gly Arg Gly Gly Gly Gly
    50                  55                  60
Arg Gly Gly Gly Gly Arg Gly Gly Gly Gly Arg Gly Gly Gly Gly Arg
65                  70                  75                  80
Gly Gly Gly Gly Arg Gly Gly Gly Gly Arg Gly Gly Gly Gly Arg Gly
                85                  90                  95
Gly Gly Gly Arg Gly Gly Gly Gly Arg Gly Gly Gly Gly Arg Gly Gly
```

```
                100                 105                 110
Gly Gly Arg Gly Gly Gly Gly Arg Gly Gly Gly Arg Gly Gly
            115                 120                 125

Gly Arg Gly Gly Gly Gly Arg Gly Gly Gly Arg Gly Gly Gly
        130                 135                 140

Arg Gly Gly Gly Gly Arg Gly Gly Gly Gly Arg Gly Gly Gly Arg
145                 150                 155                 160

Gly Gly Gly Gly Arg Gly Gly Gly Gly Arg Gly Gly Gly Arg Gly
                165                 170                 175

Gly Gly Gly Arg Gly Gly Gly Gly Arg Gly Gly Gly Arg Gly Gly
            180                 185                 190

Gly Gly Arg Gly Gly Gly Gly Arg Gly Gly Gly Arg Gly Gly Gly
        195                 200                 205

Gly Arg Gly Gly Gly Gly Arg Gly Gly Gly Gly Arg Gly Gly Gly Gly
    210                 215                 220

Arg Gly Gly Gly Gly Arg Gly Gly Gly Gly Arg Gly Gly Gly Gly Arg
225                 230                 235                 240

Gly Gly Gly Gly Arg Gly Gly Gly Gly Arg Gly Gly Gly Gly Arg Gly
                245                 250                 255

Gly Gly Gly Arg Gly Gly Gly Gly Arg Gly Gly Gly Gly Arg Gly Gly
            260                 265                 270

Gly Gly Arg Gly Gly Gly Gly Arg Gly Gly Gly Gly Arg Gly Gly Gly
        275                 280                 285

Gly Arg Gly Gly Gly Gly Arg Gly Gly Gly Gly Arg Gly Gly Gly Gly
    290                 295                 300

Arg Gly Gly Gly Gly Arg Gly Gly Gly Gly Arg Gly Gly Gly Gly Arg
305                 310                 315                 320

Gly Gly Gly Gly Arg Gly Gly Gly Gly Arg Gly Gly Gly Gly Arg Gly
                325                 330                 335

Gly Gly Gly Arg Gly Gly Gly Gly Arg Gly Gly Gly Gly Arg Gly Gly
            340                 345                 350

Gly Gly Arg Gly Gly Gly Gly Arg Gly Gly Gly Gly Arg Gly Gly Gly
        355                 360                 365

Gly Arg Gly Gly Gly Gly Arg
    370                 375
```

<210> SEQ ID NO 90
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(375)
<223> OTHER INFORMATION: This sequence may encompass 1-75 "Glu Ala Ala
      Ala Lys" repeating units, wherein some positions may be absent

<400> SEQUENCE: 90

```
Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
                20                  25                  30

Ala Ala Lys Glu Ala Ala Ala Lys Glu Ala Ala Ala Lys Glu Ala Ala
            35                  40                  45

Ala Lys Glu Ala Ala Ala Lys Glu Ala Ala Ala Lys Glu Ala Ala Ala
```

```
                50              55              60
Lys Glu Ala Ala Ala Lys Glu Ala Ala Ala Lys Glu Ala Ala Lys
 65              70              75              80

Glu Ala Ala Ala Lys Glu Ala Ala Lys Glu Ala Ala Ala Lys Glu
                 85              90              95

Ala Ala Ala Lys Glu Ala Ala Ala Lys Glu Ala Ala Ala Lys Glu Ala
            100             105             110

Ala Ala Lys Glu Ala Ala Ala Lys Glu Ala Ala Ala Lys Glu Ala Ala
            115             120             125

Ala Lys Glu Ala Ala Ala Lys Glu Ala Ala Ala Lys Glu Ala Ala Ala
    130             135             140

Lys Glu Ala Ala Ala Lys Glu Ala Ala Ala Lys Glu Ala Ala Ala Lys
145             150             155             160

Glu Ala Ala Ala Lys Glu Ala Ala Ala Lys Glu Ala Ala Ala Lys Glu
                165             170             175

Ala Ala Ala Lys Glu Ala Ala Ala Lys Glu Ala Ala Ala Lys Glu Ala
            180             185             190

Ala Ala Lys Glu Ala Ala Ala Lys Glu Ala Ala Ala Lys Glu Ala Ala
            195             200             205

Ala Lys Glu Ala Ala Ala Lys Glu Ala Ala Ala Lys Glu Ala Ala Ala
    210             215             220

Lys Glu Ala Ala Ala Lys Glu Ala Ala Ala Lys Glu Ala Ala Ala Lys
225             230             235             240

Glu Ala Ala Ala Lys Glu Ala Ala Ala Lys Glu Ala Ala Ala Lys Glu
                245             250             255

Ala Ala Ala Lys Glu Ala Ala Ala Lys Glu Ala Ala Ala Lys Glu Ala
            260             265             270

Ala Ala Lys Glu Ala Ala Ala Lys Glu Ala Ala Ala Lys Glu Ala Ala
            275             280             285

Ala Lys Glu Ala Ala Ala Lys Glu Ala Ala Ala Lys Glu Ala Ala Ala
    290             295             300

Lys Glu Ala Ala Ala Lys Glu Ala Ala Ala Lys Glu Ala Ala Ala Lys
305             310             315             320

Glu Ala Ala Ala Lys Glu Ala Ala Ala Lys Glu Ala Ala Ala Lys Glu
                325             330             335

Ala Ala Ala Lys Glu Ala Ala Ala Lys Glu Ala Ala Ala Lys Glu Ala
            340             345             350

Ala Ala Lys Glu Ala Ala Ala Lys Glu Ala Ala Ala Lys Glu Ala Ala
            355             360             365

Ala Lys Glu Ala Ala Ala Lys
    370             375

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Ala Ala Ala Lys Glu Ala Ala Ala Lys Glu Ala Ala Ala Lys
 1               5                  10                  15

<210> SEQ ID NO 92
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Ala Ala Ala Lys Glu Ala Ala Ala Lys Glu Ala Ala Ala Lys Glu
1               5                   10                  15

Ala Ala Ala Lys
            20

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Gly Gly Ser
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 95

His His His His His His
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 96

His His His His His His His His His His
1               5                   10

<210> SEQ ID NO 97
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 97

Gly Gly Gly Gly Ser Gly Gly Gly Ser Gly Gly Gly Gly Ser
1               5                   10                  15

<210> SEQ ID NO 98
<211> LENGTH: 695
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Asn Leu Tyr Ser Thr Pro Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Gly Gly Gly Gly
    450                 455                 460

Ser Gln Val Gln Leu Gln Glu Ser Gly Pro Gly Leu Val Lys Pro Ser
465                 470                 475                 480

Glu Thr Leu Ser Leu Thr Cys Thr Val Ser Gly Gly Ser Ile Ser Ser
                485                 490                 495

Gly Gly Tyr Tyr Trp Ser Trp Ile Arg Gln Pro Pro Gly Lys Gly Leu
            500                 505                 510

Glu Trp Ile Gly Ile Ile Tyr Tyr Ser Gly Trp Thr Asn Tyr Asn Pro
        515                 520                 525

Ser Leu Lys Ser Val Thr Ile Ser Val Asp Ala Ser Arg Asn Gln Phe
530                 535                 540

Ser Leu Lys Leu Ser Ser Val Thr Ala Ala Asp Thr Ala Val Tyr Tyr
545                 550                 555                 560

Cys Ala Arg Gly Val Gly Pro Asp Phe Trp Ser Gly Tyr Ser Tyr Ser
                565                 570                 575

Ser Tyr Phe Asp Leu Trp Gly Arg Gly Thr Leu Val Thr Val Ser Ser
            580                 585                 590

Ala Ser Thr Lys Gly Pro Ser Val Phe Pro Leu Ala Pro Ser Ser Lys
        595                 600                 605

Ser Thr Ser Gly Gly Thr Ala Ala Leu Gly Cys Leu Val Lys Asp Tyr
610                 615                 620

Phe Pro Glu Pro Val Thr Val Ser Trp Asn Ser Gly Ala Leu Thr Ser
625                 630                 635                 640

Gly Val His Thr Phe Pro Ala Val Leu Gln Ser Ser Gly Leu Tyr Ser
                645                 650                 655

Leu Ser Ser Val Val Thr Val Pro Ser Ser Ser Leu Gly Thr Gln Thr
            660                 665                 670

Tyr Ile Cys Asn Val Asn His Lys Pro Ser Asn Thr Lys Val Asp Lys
        675                 680                 685

Lys Val Glu Pro Lys Ser Cys
690                 695

<210> SEQ ID NO 99
<211> LENGTH: 120
<212> TYPE: PRT
<213> ORGANISM: Artificial Sequence
<220> FEATURE:
<223> OTHER INFORMATION: Description of Artificial Sequence: Synthetic
```

```
    polypeptide

<400> SEQUENCE: 99

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Asn Leu Tyr Ser Thr Pro Phe Asp Ile Trp Gly Gln
            100                 105                 110

Gly Thr Met Val Thr Val Ser Ser
            115                 120
```